US011365259B2

(12) United States Patent
Goetsch et al.

(10) Patent No.: US 11,365,259 B2
(45) Date of Patent: *Jun. 21, 2022

(54) IGF-1R ANTIBODY AND ITS USE AS ADDRESSING VEHICLE FOR THE TREATMENT OF CANCER

(71) Applicant: PIERRE FABRE MEDICAMENT, Boulogne-Billancourt (FR)

(72) Inventors: Liliane Goetsch, Ayze (FR); Matthieu Broussas, Seyssel (FR); Charlotte Beau-Larvor, Jonzier Epagny (FR); Thierry Champion, Saint Julien en Genevois (FR); Alain Robert, Annemasse (FR)

(73) Assignee: PIERRE FABRE MEDICAMENT, Boulogne-Billancourt (FR)

( * ) Notice: Subject to any disclaimer, the term of this patent is extended or adjusted under 35 U.S.C. 154(b) by 603 days.

This patent is subject to a terminal disclaimer.

(21) Appl. No.: 16/223,363

(22) Filed: Dec. 18, 2018

(65) Prior Publication Data

US 2019/0330353 A1    Oct. 31, 2019

Related U.S. Application Data

(63) Continuation of application No. 15/305,157, filed as application No. PCT/EP2015/059050 on Apr. 27, 2015, now Pat. No. 10,202,458.

(60) Provisional application No. 61/984,160, filed on Apr. 25, 2014.

(51) Int. Cl.
| | |
|---|---|
| *A61K 39/395* | (2006.01) |
| *C07K 16/28* | (2006.01) |
| *A61K 47/68* | (2017.01) |
| *G01N 33/68* | (2006.01) |

(52) U.S. Cl.
CPC ...... *C07K 16/2863* (2013.01); *A61K 47/6851* (2017.08); *G01N 33/6854* (2013.01); *C07K 2317/24* (2013.01); *C07K 2317/33* (2013.01); *C07K 2317/565* (2013.01); *C07K 2317/73* (2013.01); *C07K 2317/75* (2013.01); *C07K 2317/76* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,530,101 | A | 6/1996 | Queen et al. |
| 5,585,089 | A | 12/1996 | Queen et al. |
| 5,633,641 | A | 6/1997 | Pedersen et al. |
| 5,639,641 | A | 6/1997 | Pedersen et al. |
| 5,693,761 | A | 12/1997 | Queen et al. |
| 5,877,293 | A | 3/1999 | Adair |
| 5,886,152 | A | 3/1999 | Nakatani et al. |
| 6,054,297 | A | 4/2000 | Carter et al. |
| 6,180,370 | B1 | 1/2001 | Queen et al. |
| 7,521,541 | B2 | 4/2009 | Eigenbrot et al. |
| 7,723,485 | B2 | 5/2010 | Junutula et al. |
| 9,556,274 | B2 * | 1/2017 | Baum .................. C07K 16/468 |

FOREIGN PATENT DOCUMENTS

| | | |
|---|---|---|
| EP | 0452216 B1 | 1/1996 |
| EP | 0682040 B1 | 8/1999 |
| EP | 0566647 B1 | 1/2003 |
| EP | 0939127 B1 | 9/2014 |
| WO | WO 2008/079849 A3 | 7/2008 |
| WO | WO 2009/052249 A1 | 4/2009 |
| WO | WO 2011/117330 A1 | 7/2011 |
| WO | WO 2011/130598 A1 | 10/2011 |

OTHER PUBLICATIONS

Bitelman, C. et al., "IFG1R-Directed Targeted Therapy Enhances The Cytotoxic Effect of Chemotherapy in Endometrial Cancer," Cancer Letters, 335:153-159, (2013).
Dornan, D. et al., "Therapeutic Potential of an Anti-CD796b Antibody-Drug Conjugate, Anti-CD796b-vc-MMAE, For The Treatment of Non-Hodgkin Lymphoma," Blood, 114:2721-2729, (2009).
International Search Report PCT/EP2015/059050 dated Sep. 2, 2015.
Junutula, J.R. et al., "Site-Specific Conjugation of a Cytotoxic Drug to an Antibody Improves The Therapeutic Index," Nature Biotech., 26:925-932, (2008).
Kaas, Q. et al., "IMGT/3Dstructure-DB and IMGT/StructuralQuery, A Database and a Tool for Immunoglobulin, T Cell Receptor and MHC Structural Data," Nucleic Acids Research, 32:D208-D210, (2004).
Kaas, Q. et al., "IMGT Colliers De Perles: Standardized Sequence-Structure Representations of the IgSF and MhcSF Superfamily Domains," Curr. Bioinfor., 2:21-30, (2007).
Kohler, G. et al., "Continuous Cultures of Fused Cells Secreting Antibody of Predefined Specificity," Nature, 256:495-497, (1975).
LeFranc, M., "Unique Database Numbering System for Immunogenetic Analysis," Immunol. Today, 18:509, (1997).

(Continued)

*Primary Examiner* — Meera Natarajan
(74) *Attorney, Agent, or Firm* — Finnegan, Henderson, Farabow, Garrett & Dunner, L.L.P.

(57) ABSTRACT

The present invention relates to an antibody, in particular a monoclonal antibody, capable of binding to IGF-1R, as well as the amino and nucleic acid sequences coding for said antibody. From one aspect, the invention relates to an antibody, or an antigen binding fragment thereof, capable of binding to IGF-1R and, by inducing internalization of IGF-1R, being internalized into the cell. The invention also comprises the use of said antibody as an addressing product or vehicle in conjugation with other anti-cancer compounds such as toxins, radio-elements or drugs, and the use of same for the treatment of certain cancers.

26 Claims, 33 Drawing Sheets

Specification includes a Sequence Listing.

(56) References Cited

OTHER PUBLICATIONS

LeFranc, M., "The IMGT Unique Numbering for Immunogobulins, T-Cell Receptors, and Ig-Like Domains," The Immunol., 7:132-136, (1999).
LeFranc, M., "IMGT Unique Numbering for Immunoglobulin and T Cell Receptor Variable Domains and Ig Superfamily V-Like Domains," Devel. and Comp. Immunol., 27:55-77, (2003).
Needleman, S.B. et al., "A General Method Applicable to the Search for Similarities in the Amino Acid Sequence of Two Proteins," J. Mol. Biol., 48:443-453, (1970).
Ohtani, M. et al., "Mechanisms of Antibody-Mediated Insulin-Like Growth Factor I Receptor (IGF-IR) Down-Regulation in MCF-7 Breast Cancer Cells," BioScience Trends, 3:131-138, (2009).
Pearson, W.R. et al., "Improved Tools for Biological Sequence Comparison," Proc. Natl. Acad. Sci. USA, 85:2444-2448, (1988).
Ruiz, M. et al, "IMGT Gene Identification and Colliers De Perles of Human Immunoglobulins With Known 3D Structures," Immunogenetics, 53:857-883, (2000).
Smith, T.F. et al., "Comparison of Biosequences," Adv. Appl. Math., 2:482-489, (1981).
Tatusova, T.A. et al., "BLAST 2 Sequences, A New Tool for Comparing Protein and Nucleotide Sequences," FEMS Microbiol. Let., 174:247-250, (1999).

\* cited by examiner

FIG. 3A
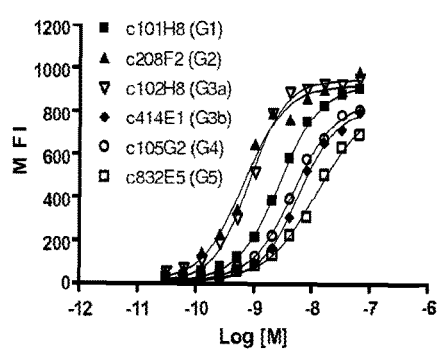
FIG. 3B
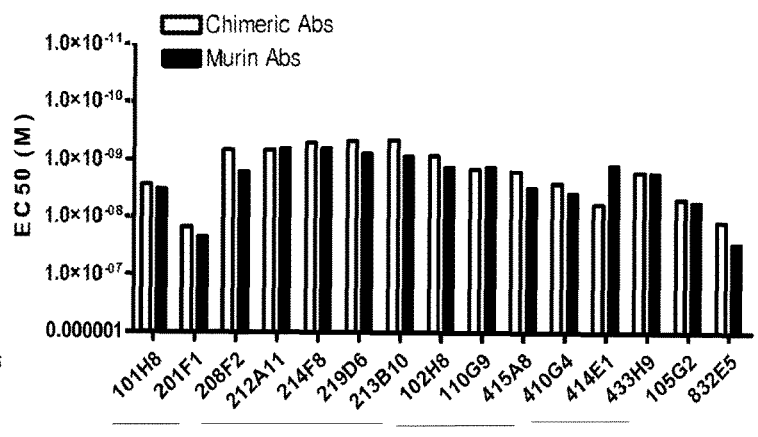
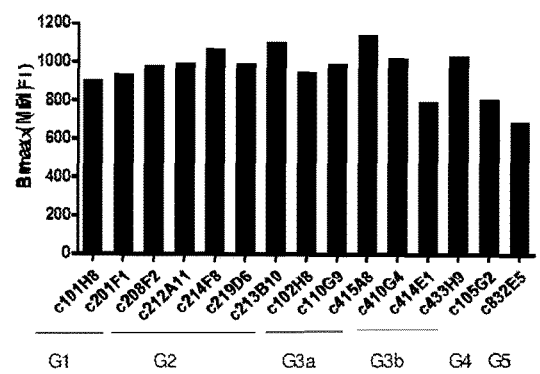
FIG. 3C

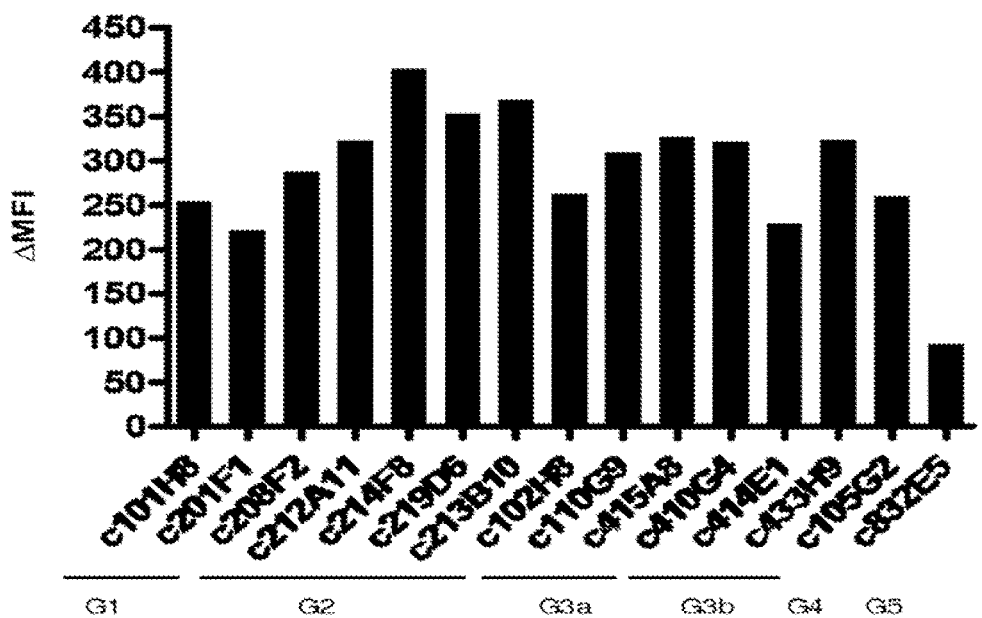
FIG. 11
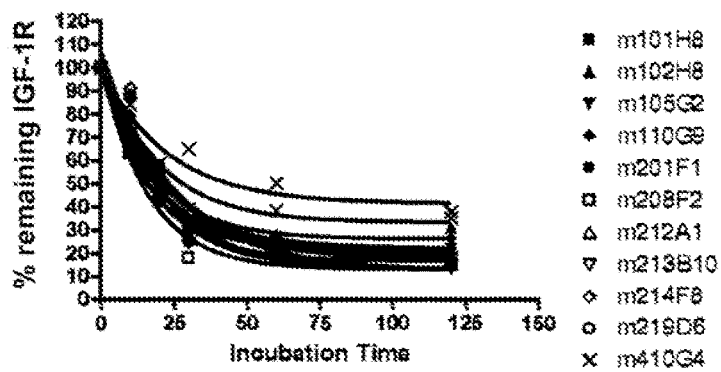
FIG. 12A
FIG. 12B
|  | Abs | HalfLife |
|---|---|---|
| G1 | m101H8 | 11.89 |
| G1 | m201F1 | 14.83 |
| G2 | m208F2 | 11.11 |
| G2 | m212A11 | 14.3 |
| G2 | m214F8 | 16.61 |
| G2 | m219D6 | 17.85 |
| G2 | m213B10 | 12.83 |
| G3a | m102H8 | 12.16 |
| G3a | m110G9 | 13.56 |
| G3a | m415A8 | 12.92 |
| G3b | m410G4 | 13.57 |
| G3b | m414E1 | 13.01 |
| G3b | m433H9 | 14.88 |
| G4 | m105G2 | 10.75 |
| G5 | m832E5 | 15.87 |

FIG. 19A
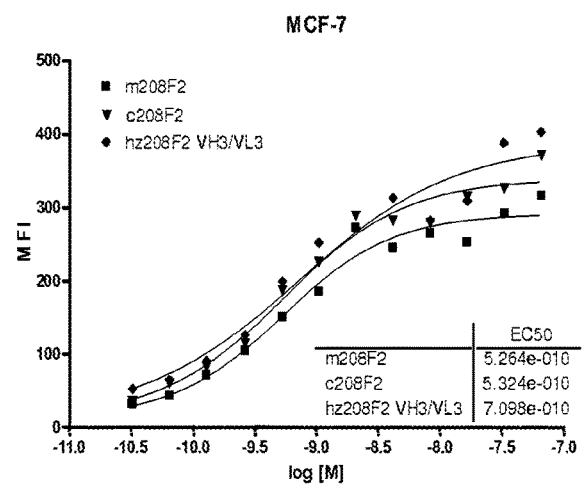
FIG. 19B
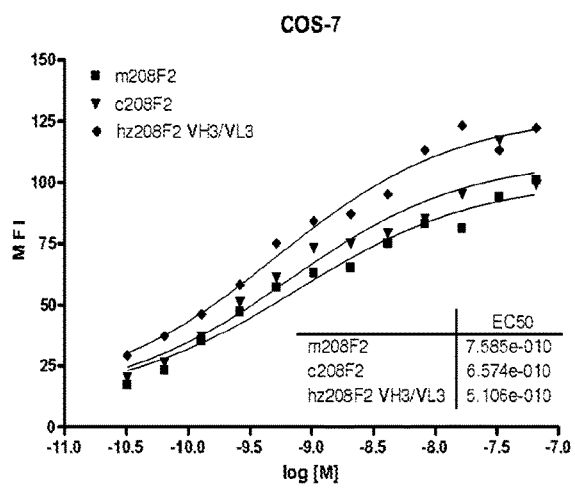
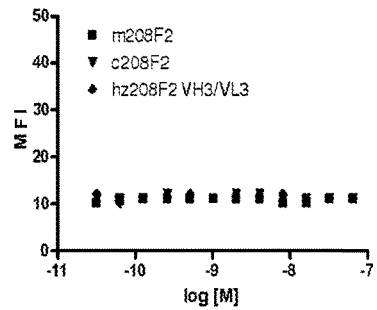
FIG. 19C
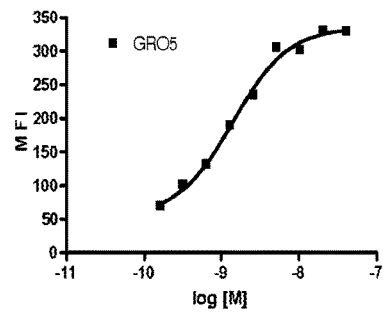
FIG. 19D

SEQUENCE LISTING

```
<160> NUMBER OF SEQ ID NOS: 92

<210> SEQ ID NO 1
<211> LENGTH: 8
<212> TYPE: PRT
<213> ORGANISM: artificial
<220> FEATURE:
<223> OTHER INFORMATION: Consensus CDR -H1
<220> FEATURE:
<221> NAME/KEY: MISC_FEATURE
<222> LOCATION: (3)..(3)
<223> OTHER INFORMATION: Thr may be replaced by Ser
<220> FEATURE:
<221> NAME/KEY: MISC_FEATURE
<222> LOCATION: (8)..(8)
<223> OTHER INFORMATION: Tyr may be replaced by Phe

<400> SEQUENCE: 1

Gly Tyr Thr Phe Thr Ser Tyr Tyr
1               5

<210> SEQ ID NO 2
<211> LENGTH: 8
<212> TYPE: PRT
<213> ORGANISM: artificial
<220> FEATURE:
<223> OTHER INFORMATION: Consensus CDR-H2

<400> SEQUENCE: 2
```

```
Ile Trp Pro Gly Asp Gly Ser Thr
1               5

<210> SEQ ID NO 3
<211> LENGTH: 13
<212> TYPE: PRT
<213> ORGANISM: artificial
<220> FEATURE:
<223> OTHER INFORMATION: Consensus CDR-H3

<400> SEQUENCE: 3

Ala Ser Pro Met Ile Thr Pro Asn Tyr Ala Met Asp Tyr
1               5                   10

<210> SEQ ID NO 4
<211> LENGTH: 6
<212> TYPE: PRT
<213> ORGANISM: artificial
<220> FEATURE:
<223> OTHER INFORMATION: Consensus CDR-L1
<220> FEATURE:
<221> NAME/KEY: MISC_FEATURE
<222> LOCATION: (4)..(4)
<223> OTHER INFORMATION: Ser may be replaced by Asn

<400> SEQUENCE: 4

Gln Asp Ile Ser Lys Tyr
1               5

<210> SEQ ID NO 5
<211> LENGTH: 3
<212> TYPE: PRT
<213> ORGANISM: artificial
<220> FEATURE:
<223> OTHER INFORMATION: Consensus CDR-L2

<400> SEQUENCE: 5

Tyr Thr Ser
1

<210> SEQ ID NO 6
<211> LENGTH: 9
<212> TYPE: PRT
<213> ORGANISM: artificial
<220> FEATURE:
<223> OTHER INFORMATION: Consensus CDR-L3
<220> FEATURE:
<221> NAME/KEY: MISC_FEATURE
<222> LOCATION: (5)..(5)
<223> OTHER INFORMATION: Thr may be replaced by Ala

<400> SEQUENCE: 6

Gln Gln Gly Ser Thr Leu Pro Tyr Thr
1               5

<210> SEQ ID NO 7
<211> LENGTH: 8
<212> TYPE: PRT
<213> ORGANISM: artificial
<220> FEATURE:
<223> OTHER INFORMATION: CDR-H1

<400> SEQUENCE: 7

Gly Tyr Thr Phe Thr Ser Tyr Tyr
1               5

<210> SEQ ID NO 8
```

<211> LENGTH: 8
<212> TYPE: PRT
<213> ORGANISM: artificial
<220> FEATURE:
<223> OTHER INFORMATION: CDR-H1

<400> SEQUENCE: 8

Gly Tyr Ser Phe Thr Ser Tyr Phe
1               5

<210> SEQ ID NO 9
<211> LENGTH: 6
<212> TYPE: PRT
<213> ORGANISM: artificial
<220> FEATURE:
<223> OTHER INFORMATION: CDR-L1

<400> SEQUENCE: 9

Gln Asp Ile Ser Lys Tyr
1               5

<210> SEQ ID NO 10
<211> LENGTH: 6
<212> TYPE: PRT
<213> ORGANISM: artificial
<220> FEATURE:
<223> OTHER INFORMATION: CDR-L1

<400> SEQUENCE: 10

Gln Asp Ile Asn Lys Tyr
1               5

<210> SEQ ID NO 11
<211> LENGTH: 9
<212> TYPE: PRT
<213> ORGANISM: artificial
<220> FEATURE:
<223> OTHER INFORMATION: CDR-L3

<400> SEQUENCE: 11

Gln Gln Gly Ser Thr Leu Pro Tyr Thr
1               5

<210> SEQ ID NO 12
<211> LENGTH: 9
<212> TYPE: PRT
<213> ORGANISM: artificial
<220> FEATURE:
<223> OTHER INFORMATION: CDR-L3

<400> SEQUENCE: 12

Gln Gln Gly Ser Ala Leu Pro Tyr Thr
1               5

<210> SEQ ID NO 13
<211> LENGTH: 120
<212> TYPE: PRT
<213> ORGANISM: artificial
<220> FEATURE:
<223> OTHER INFORMATION: c208F2, heavy chain, VH

<400> SEQUENCE: 13

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

```
Tyr Ile Tyr Trp Val Lys Gln Arg Pro Gly Gln Gly Leu Glu Trp Leu
            35                  40                  45

Gly Trp Ile Trp Pro Gly Asp Gly Ser Thr Lys Tyr Asn Glu Lys Phe
 50                  55                  60

Lys Asp Lys Thr Thr Leu Thr Ala Asp Lys Ser Ser Asn Thr Ala Tyr
 65                  70                  75                  80

Met Phe Leu Ser Ser Leu Thr Ser Glu Asp Ser Ala Val Tyr Phe Cys
                 85                  90                  95

Ala Ser Pro Met Ile Thr Pro Asn Tyr Ala Met Asp Tyr Trp Gly Gln
            100                 105                 110

Gly Ala Ser Val Thr Val Ser Ser
            115                 120
```

<210> SEQ ID NO 14
<211> LENGTH: 120
<212> TYPE: PRT
<213> ORGANISM: artificial
<220> FEATURE:
<223> OTHER INFORMATION: c212A11, heavy chain, VH

<400> SEQUENCE: 14

```
Gln Val Gln Leu Gln Gln Ser Gly Pro Glu Leu Val Lys Pro Gly Ala
 1               5                  10                  15

Ser Val Lys Met Ser Cys Lys Ala Ser Gly Tyr Thr Phe Thr Ser Tyr
                 20                  25                  30

Tyr Ile His Trp Val Lys Gln Arg Pro Gly Gln Gly Leu Glu Trp Ile
            35                  40                  45

Gly Trp Ile Trp Pro Gly Asp Gly Ser Thr Lys Tyr Asn Glu Lys Phe
 50                  55                  60

Lys Gly Lys Thr Thr Leu Thr Ala Asp Lys Ser Ser Ser Thr Ala Tyr
 65                  70                  75                  80

Met Phe Leu Ser Ser Leu Thr Ser Glu Asp Ser Ala Val Tyr Phe Cys
                 85                  90                  95

Ala Ser Pro Met Ile Thr Pro Asn Tyr Ala Met Asp Tyr Trp Gly Gln
            100                 105                 110

Gly Ala Ser Val Thr Val Ser Ser
            115                 120
```

<210> SEQ ID NO 15
<211> LENGTH: 120
<212> TYPE: PRT
<213> ORGANISM: artificial
<220> FEATURE:
<223> OTHER INFORMATION: c214F8, heavy chain, VH

<400> SEQUENCE: 15

```
Gln Val Gln Leu Gln Gln Ser Gly Ser Glu Leu Val Lys Pro Gly Ala
 1               5                  10                  15

Ser Val Lys Leu Ser Cys Lys Ala Ser Gly Tyr Thr Phe Thr Ser Tyr
                 20                  25                  30

Tyr Ile His Trp Val Lys Gln Arg Pro Gly Gln Gly Leu Glu Trp Ile
            35                  40                  45

Gly Trp Ile Trp Pro Gly Asp Gly Ser Thr Lys Tyr Asn Glu Arg Phe
 50                  55                  60

Lys Gly Lys Thr Thr Leu Thr Ala Asp Lys Ser Ser Ser Thr Ala Tyr
 65                  70                  75                  80

Met Phe Leu Ser Ser Leu Thr Ser Glu Asp Ser Ala Val Tyr Phe Cys
                 85                  90                  95
```

Ala Ser Pro Met Ile Thr Pro Asn Tyr Ala Met Asp Tyr Trp Gly Gln
                100                 105                 110

Gly Ala Ser Val Thr Val Ser Ser
        115                 120

<210> SEQ ID NO 16
<211> LENGTH: 120
<212> TYPE: PRT
<213> ORGANISM: artificial
<220> FEATURE:
<223> OTHER INFORMATION: c219D6, heavy chain, VH

<400> SEQUENCE: 16

Gln Val Gln Leu Gln Gln Ser Gly Pro Glu Leu Val Lys Pro Gly Asp
1               5                   10                  15

Ser Val Lys Met Ser Cys Lys Ala Ser Gly Tyr Ser Phe Thr Ser Tyr
                20                  25                  30

Phe Ile His Trp Val Lys Gln Arg Pro Gly Gln Gly Leu Glu Trp Ile
            35                  40                  45

Gly Trp Ile Trp Pro Gly Asp Gly Ser Thr Lys Tyr Asn Glu Lys Phe
    50                  55                  60

Lys Gly Lys Thr Thr Leu Thr Thr Asp Lys Ser Ser Ser Thr Ala Tyr
65                  70                  75                  80

Met Phe Leu Asn Ser Leu Thr Ser Glu Asp Ser Ala Val Tyr Phe Cys
                85                  90                  95

Ala Ser Pro Met Ile Thr Pro Asn Tyr Ala Met Asp Tyr Trp Gly Gln
                100                 105                 110

Gly Ala Ser Val Thr Val Ser Ser
        115                 120

<210> SEQ ID NO 17
<211> LENGTH: 120
<212> TYPE: PRT
<213> ORGANISM: artificial
<220> FEATURE:
<223> OTHER INFORMATION: c213B10, heavy chain, VH

<400> SEQUENCE: 17

Gln Val Gln Leu Gln Gln Ser Gly Ser Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Tyr Ile His Trp Val Lys Gln Arg Pro Gly Gln Gly Leu Glu Trp Ile
            35                  40                  45

Gly Trp Ile Trp Pro Gly Asp Gly Ser Thr Lys Tyr Asn Glu Arg Phe
    50                  55                  60

Lys Gly Lys Thr Thr Leu Thr Ala Asp Lys Ser Ser Ser Thr Ala Tyr
65                  70                  75                  80

Met Phe Leu Ser Ser Leu Thr Ser Glu Asp Ser Ala Val Tyr Phe Cys
                85                  90                  95

Ala Ser Pro Met Ile Thr Pro Asn Tyr Ala Met Asp Tyr Trp Gly Gln
                100                 105                 110

Gly Ala Ser Val Thr Val Ser Ser
        115                 120

<210> SEQ ID NO 18
<211> LENGTH: 107
<212> TYPE: PRT

<213> ORGANISM: artificial
<220> FEATURE:
<223> OTHER INFORMATION: c208F2, light chain, VL

<400> SEQUENCE: 18

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Gln Pro Asp Gly Thr Ile Lys Leu Leu Ile
        35                  40                  45

Tyr Tyr Thr Ser Arg Leu His Ser Gly Val Pro Ser Arg Phe Ser Gly
50                  55                  60

Arg Gly Ser Gly Thr Asp Tyr Ser Leu Thr Ile Ser Asn Val Glu Gln
65                  70                  75                  80

Glu Asp Ile Ala Thr Tyr Phe Cys Gln Gln Gly Ser Thr Leu Pro Tyr
                85                  90                  95

Thr Phe Gly Gly Gly Thr Lys Leu Glu Ile Lys
            100                 105

<210> SEQ ID NO 19
<211> LENGTH: 107
<212> TYPE: PRT
<213> ORGANISM: artificial
<220> FEATURE:
<223> OTHER INFORMATION: c212A11, light chain, VL

<400> SEQUENCE: 19

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Asn Lys Tyr
            20                  25                  30

Leu Asn Trp Tyr Gln Gln Gln Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Arg Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Ser Thr Leu Pro Tyr
                85                  90                  95

Thr Phe Gly Gly Gly Thr Lys Leu Glu Ile Lys
            100                 105

<210> SEQ ID NO 20
<211> LENGTH: 107
<212> TYPE: PRT
<213> ORGANISM: artificial
<220> FEATURE:
<223> OTHER INFORMATION: c214F8, light chain, VL

<400> SEQUENCE: 20

Asp Ile Gln Met Thr Gln Thr Thr Ser Ser Leu Ser Ala Ser Leu Gly
1               5                   10                  15

Asp Arg Val Thr Phe Ser Cys Arg Ala Ser Gln Asp Ile Ser Lys Tyr
            20                  25                  30

Leu Asn Trp Tyr Gln Gln Gln Pro Asp Gly Thr Ile Lys Leu Leu Ile
        35                  40                  45

Tyr Tyr Thr Ser Arg Leu His Ser Gly Val Pro Ser Arg Phe Ser Gly
50                  55                  60

Arg Gly Ser Gly Thr Asp Tyr Ser Leu Thr Ile Thr Asn Leu Glu Gln
65                  70                  75                  80

Glu Asp Ile Ala Thr Tyr Phe Cys Gln Gln Gly Ser Ala Leu Pro Tyr
                85                  90                  95

Thr Phe Gly Gly Gly Thr Lys Leu Glu Ile Lys
            100                 105

<210> SEQ ID NO 21
<211> LENGTH: 107
<212> TYPE: PRT
<213> ORGANISM: artificial
<220> FEATURE:
<223> OTHER INFORMATION: c219D6, light chain, VL

<400> SEQUENCE: 21

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
                20                  25                  30

Leu Asn Trp Tyr Gln Gln Pro Asp Gly Thr Val Lys Leu Leu Ile
            35                  40                  45

Tyr Tyr Thr Ser Arg Leu His Ser Gly Val Pro Ser Arg Phe Ser Gly
    50                  55                  60

Arg Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Ser Thr Leu Pro Tyr
                85                  90                  95

Thr Phe Gly Gly Gly Thr Lys Leu Glu Ile Lys
            100                 105

<210> SEQ ID NO 22
<211> LENGTH: 107
<212> TYPE: PRT
<213> ORGANISM: artificial
<220> FEATURE:
<223> OTHER INFORMATION: c213B10, light chain, VL

<400> SEQUENCE: 22

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
                20                  25                  30

Leu Asn Trp Tyr Gln Gln Pro Asp Gly Thr Ile Lys Leu Leu Ile
            35                  40                  45

Tyr Tyr Thr Ser Arg Leu His Ser Gly Val Pro Ser Arg Phe Ser Gly
    50                  55                  60

Arg Gly Ser Gly Thr Asp Tyr Ser Leu Thr Ile Thr Asn Leu Glu Gln
65                  70                  75                  80

Glu Asp Ile Ala Thr Tyr Phe Cys Gln Gln Gly Ser Ala Leu Pro Tyr
                85                  90                  95

Thr Phe Gly Gly Gly Thr Lys Leu Glu Ile Lys
            100                 105

<210> SEQ ID NO 23
<211> LENGTH: 449
<212> TYPE: PRT
<213> ORGANISM: artificial
<220> FEATURE:
<223> OTHER INFORMATION: c208F2, heavy chain, full length

<400> SEQUENCE: 23

```
Gln Val Gln Leu Gln Gln Ser Gly Pro Glu Leu Val Lys Pro Gly Ala
1               5                   10                  15
Ser Val Lys Met Ser Cys Lys Ala Ser Gly Tyr Thr Phe Thr Ser Tyr
            20                  25                  30
Tyr Ile Tyr Trp Val Lys Gln Arg Pro Gly Gln Gly Leu Glu Trp Leu
        35                  40                  45
Gly Trp Ile Trp Pro Gly Asp Gly Ser Thr Lys Tyr Asn Glu Lys Phe
    50                  55                  60
Lys Asp Lys Thr Thr Leu Thr Ala Asp Lys Ser Ser Asn Thr Ala Tyr
65                  70                  75                  80
Met Phe Leu Ser Ser Leu Thr Ser Glu Asp Ser Ala Val Tyr Phe Cys
                85                  90                  95
Ala Ser Pro Met Ile Thr Pro Asn Tyr Ala Met Asp Tyr Trp Gly Gln
            100                 105                 110
Gly Ala Ser Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Arg Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
```

```
                        405                 410                 415
Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
        435                 440                 445

Gly

<210> SEQ ID NO 24
<211> LENGTH: 449
<212> TYPE: PRT
<213> ORGANISM: artificial
<220> FEATURE:
<223> OTHER INFORMATION: c212A11, heavy chain, full length

<400> SEQUENCE: 24

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Tyr Ile His Trp Val Lys Gln Arg Pro Gly Gln Gly Leu Glu Trp Ile
            35                  40                  45

Gly Trp Ile Trp Pro Gly Asp Gly Ser Thr Lys Tyr Asn Glu Lys Phe
    50                  55                  60

Lys Gly Lys Thr Thr Leu Thr Ala Asp Lys Ser Ser Thr Ala Tyr
65                  70                  75                  80

Met Phe Leu Ser Ser Leu Thr Ser Glu Asp Ser Ala Val Tyr Phe Cys
                85                  90                  95

Ala Ser Pro Met Ile Thr Pro Asn Tyr Ala Met Asp Tyr Trp Gly Gln
            100                 105                 110

Gly Ala Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320
```

-continued

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 25
<211> LENGTH: 449
<212> TYPE: PRT
<213> ORGANISM: artificial
<220> FEATURE:
<223> OTHER INFORMATION: c214F8, heavy chain, full length

<400> SEQUENCE: 25

Gln Val Gln Leu Gln Gln Ser Gly Ser Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Tyr Ile His Trp Val Lys Gln Arg Pro Gly Gln Gly Leu Glu Trp Ile
        35                  40                  45

Gly Trp Ile Trp Pro Gly Asp Gly Ser Thr Lys Tyr Asn Glu Arg Phe
    50                  55                  60

Lys Gly Lys Thr Thr Leu Thr Ala Asp Lys Ser Ser Thr Ala Tyr
65                  70                  75                  80

Met Phe Leu Ser Ser Leu Thr Ser Glu Asp Ser Ala Val Tyr Phe Cys
                85                  90                  95

Ala Ser Pro Met Ile Thr Pro Asn Tyr Ala Met Asp Tyr Trp Gly Gln
            100                 105                 110

Gly Ala Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 26
<211> LENGTH: 449
<212> TYPE: PRT
<213> ORGANISM: artificial
<220> FEATURE:
<223> OTHER INFORMATION: c219D6, heavy chain, full length

<400> SEQUENCE: 26

Gln Val Gln Leu Gln Gln Ser Gly Pro Glu Leu Val Lys Pro Gly Asp
1               5                   10                  15

Ser Val Lys Met Ser Cys Lys Ala Ser Gly Tyr Ser Phe Thr Ser Tyr
            20                  25                  30

Phe Ile His Trp Val Lys Gln Arg Pro Gly Gln Gly Leu Glu Trp Ile
        35                  40                  45

Gly Trp Ile Trp Pro Gly Asp Gly Ser Thr Lys Tyr Asn Glu Lys Phe
    50                  55                  60

Lys Gly Lys Thr Thr Leu Thr Thr Asp Lys Ser Ser Ser Thr Ala Tyr
65                  70                  75                  80

Met Phe Leu Asn Ser Leu Thr Ser Glu Asp Ser Ala Val Tyr Phe Cys
                85                  90                  95

Ala Ser Pro Met Ile Thr Pro Asn Tyr Ala Met Asp Tyr Trp Gly Gln
            100                 105                 110

Gly Ala Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala

```
            130                 135                 140
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly

<210> SEQ ID NO 27
<211> LENGTH: 449
<212> TYPE: PRT
<213> ORGANISM: artificial
<220> FEATURE:
<223> OTHER INFORMATION: c213B10, heavy chain, full length

<400> SEQUENCE: 27

Gln Val Gln Leu Gln Gln Ser Gly Ser Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Val Lys Gln Arg Pro Gly Gln Gly Leu Glu Trp Ile
        35                  40                  45
```

```
Gly Trp Ile Trp Pro Gly Asp Gly Ser Thr Lys Tyr Asn Glu Arg Phe
 50                  55                  60

Lys Gly Lys Thr Thr Leu Thr Ala Asp Lys Ser Ser Thr Ala Tyr
 65                  70                  75                  80

Met Phe Leu Ser Ser Leu Thr Ser Glu Asp Ser Ala Val Tyr Phe Cys
                 85                  90                  95

Ala Ser Pro Met Ile Thr Pro Asn Tyr Ala Met Asp Tyr Trp Gly Gln
             100                 105                 110

Gly Ala Ser Val Thr Val Ser Ser Ala Ser Thr Lys Gly Pro Ser Val
             115                 120                 125

Phe Pro Leu Ala Pro Ser Ser Lys Ser Thr Ser Gly Gly Thr Ala Ala
     130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                 165                 170                 175

Leu Gln Ser Ser Gly Leu Tyr Ser Leu Ser Ser Val Val Thr Val Pro
             180                 185                 190

Ser Ser Ser Leu Gly Thr Gln Thr Tyr Ile Cys Asn Val Asn His Lys
             195                 200                 205

Pro Ser Asn Thr Lys Val Asp Lys Arg Val Glu Pro Lys Ser Cys Asp
     210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                 245                 250                 255

Ser Arg Thr Pro Glu Val Thr Cys Val Val Val Asp Val Ser His Glu
             260                 265                 270

Asp Pro Glu Val Lys Phe Asn Trp Tyr Val Asp Gly Val Glu Val His
     275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                 325                 330                 335

Lys Thr Ile Ser Lys Ala Lys Gly Gln Pro Arg Glu Pro Gln Val Tyr
             340                 345                 350

Thr Leu Pro Pro Ser Arg Glu Glu Met Thr Lys Asn Gln Val Ser Leu
     355                 360                 365

Thr Cys Leu Val Lys Gly Phe Tyr Pro Ser Asp Ile Ala Val Glu Trp
     370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                 405                 410                 415

Lys Ser Arg Trp Gln Gln Gly Asn Val Phe Ser Cys Ser Val Met His
             420                 425                 430

Glu Ala Leu His Asn His Tyr Thr Gln Lys Ser Leu Ser Leu Ser Pro
             435                 440                 445

Gly
```

```
<210> SEQ ID NO 28
<211> LENGTH: 214
<212> TYPE: PRT
<213> ORGANISM: artificial
<220> FEATURE:
<223> OTHER INFORMATION: c208F2, light chain, full length

<400> SEQUENCE: 28
```

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Pro Asp Gly Thr Ile Lys Leu Leu Ile
        35                  40                  45

Tyr Tyr Thr Ser Arg Leu His Ser Gly Val Pro Ser Arg Phe Ser Gly
    50                  55                  60

Arg Gly Ser Gly Thr Asp Tyr Ser Leu Thr Ile Ser Asn Val Glu Gln
65                  70                  75                  80

Glu Asp Ile Ala Thr Tyr Phe Cys Gln Gln Gly Ser Thr Leu Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 29
<211> LENGTH: 214
<212> TYPE: PRT
<213> ORGANISM: artificial
<220> FEATURE:
<223> OTHER INFORMATION: c212A11, light chain, full length

<400> SEQUENCE: 29
```

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Asn Lys Tyr
            20                  25                  30

Leu Asn Trp Tyr Gln Gln Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Arg Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Ser Thr Leu Pro Tyr
                85                  90                  95

```
Thr Phe Gly Gly Gly Thr Lys Leu Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 30
<211> LENGTH: 214
<212> TYPE: PRT
<213> ORGANISM: artificial
<220> FEATURE:
<223> OTHER INFORMATION: c214F8, light chain, full length

<400> SEQUENCE: 30

```
Asp Ile Gln Met Thr Gln Thr Thr Ser Ser Leu Ser Ala Ser Leu Gly
1               5                   10                  15
Asp Arg Val Thr Phe Ser Cys Arg Ala Ser Gln Asp Ile Ser Lys Tyr
            20                  25                  30
Leu Asn Trp Tyr Gln Gln Pro Asp Gly Thr Ile Lys Leu Leu Ile
        35                  40                  45
Tyr Tyr Thr Ser Arg Leu His Ser Gly Val Pro Ser Arg Phe Ser Gly
    50                  55                  60
Arg Gly Ser Gly Thr Asp Tyr Ser Leu Thr Ile Thr Asn Leu Glu Gln
65                  70                  75                  80
Glu Asp Ile Ala Thr Tyr Phe Cys Gln Gln Gly Ser Ala Leu Pro Tyr
                85                  90                  95
Thr Phe Gly Gly Gly Thr Lys Leu Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 31
<211> LENGTH: 214

<212> TYPE: PRT
<213> ORGANISM: artificial
<220> FEATURE:
<223> OTHER INFORMATION: c219D6, light chain, full length

<400> SEQUENCE: 31

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Arg Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Ser Thr Leu Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 32
<211> LENGTH: 214
<212> TYPE: PRT
<213> ORGANISM: artificial
<220> FEATURE:
<223> OTHER INFORMATION: c213B10, light chain, full length

<400> SEQUENCE: 32

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Pro Asp Gly Thr Ile Lys Leu Leu Ile
        35                  40                  45

Tyr Tyr Thr Ser Arg Leu His Ser Gly Val Pro Ser Arg Phe Ser Gly
50                  55                  60

Arg Gly Ser Gly Thr Asp Tyr Ser Leu Thr Ile Thr Asn Leu Glu Gln
65                  70                  75                  80

Glu Asp Ile Ala Thr Tyr Phe Cys Gln Gln Gly Ser Ala Leu Pro Tyr
                85                  90                  95

Thr Phe Gly Gly Gly Thr Lys Leu Glu Ile Lys Arg Thr Val Ala Ala
            100                 105                 110

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 33
<211> LENGTH: 120
<212> TYPE: PRT
<213> ORGANISM: artificial
<220> FEATURE:
<223> OTHER INFORMATION: hz208F2 (var.1) heavy chain, VH

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Trp Pro Gly Asp Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
        115                 120

<210> SEQ ID NO 34
<211> LENGTH: 120
<212> TYPE: PRT
<213> ORGANISM: artificial
<220> FEATURE:
<223> OTHER INFORMATION: hz208F2 (var. 3), VH

<400> SEQUENCE: 34

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Tyr Ile Tyr Trp Val Lys Gln Ala Pro Gly Gln Gly Leu Glu Trp Leu
        35                  40                  45

Gly Trp Ile Trp Pro Gly Asp Gly Ser Thr Lys Tyr Asn Glu Lys Phe
    50                  55                  60

Gln Gly Arg Val Thr Leu Thr Ala Asp Lys Ser Ser Asn Thr Ala Tyr
```

65                  70                  75                  80
Met Phe Leu Ser Ser Leu Arg Ser Glu Asp Thr Ala Val Tyr Phe Cys
                    85                  90                  95

Ala Ser Pro Met Ile Thr Pro Asn Tyr Ala Met Asp Tyr Trp Gly Gln
            100                 105                 110

Gly Thr Leu Val Thr Val Ser Ser
        115                 120

<210> SEQ ID NO 35
<211> LENGTH: 107
<212> TYPE: PRT
<213> ORGANISM: artificial
<220> FEATURE:
<223> OTHER INFORMATION: hz208F2 (var. 1), VL

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ser Thr Leu Pro Tyr
                85                  90                  95

Thr Phe Gly Gly Gly Thr Lys Val Glu Ile Lys
            100                 105

<210> SEQ ID NO 36
<211> LENGTH: 107
<212> TYPE: PRT
<213> ORGANISM: artificial
<220> FEATURE:
<223> OTHER INFORMATION: hz208F2 (var.3), VL

<400> SEQUENCE: 36

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Arg Gly Ser Gly Thr Asp Tyr Ser Leu Thr Ile Ser Asn Leu Gln Pro
65                  70                  75                  80

Glu Asp Phe Ala Thr Tyr Phe Cys Gln Gln Gly Ser Thr Leu Pro Tyr
                85                  90                  95

Thr Phe Gly Gly Gly Thr Lys Val Glu Ile Lys
            100                 105

<210> SEQ ID NO 37
<211> LENGTH: 449
<212> TYPE: PRT
<213> ORGANISM: artificial
<220> FEATURE:

<223> OTHER INFORMATION: hz208F2 (var. 1), heavy chain, full length

<400> SEQUENCE: 37

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Trp Pro Gly Asp Gly Ser Thr Ser Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400
```

```
Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
        435                 440                 445

Gly

<210> SEQ ID NO 38
<211> LENGTH: 449
<212> TYPE: PRT
<213> ORGANISM: artificial
<220> FEATURE:
<223> OTHER INFORMATION: hz208F2 (var.3), heavy chain full length

<400> SEQUENCE: 38

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Tyr Ile Tyr Trp Val Lys Gln Ala Pro Gly Gln Gly Leu Glu Trp Leu
        35                  40                  45

Gly Trp Ile Trp Pro Gly Asp Gly Ser Thr Lys Tyr Asn Glu Lys Phe
    50                  55                  60

Gln Gly Arg Val Thr Leu Thr Ala Asp Lys Ser Ser Asn Thr Ala Tyr
65                  70                  75                  80

Met Phe Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
```

```
                    305                 310                 315                 320
Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly

<210> SEQ ID NO 39
<211> LENGTH: 214
<212> TYPE: PRT
<213> ORGANISM: artificial
<220> FEATURE:
<223> OTHER INFORMATION: hz208F2 (var. 1), light chain, full length

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
                20                  25                  30

Leu Asn Trp Tyr Gln Gln Lys Pro Gly Lys Ala Pro Lys Leu Leu Ile
            35                  40                  45

Tyr Tyr Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ser Thr Leu Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 40
<211> LENGTH: 214
<212> TYPE: PRT
<213> ORGANISM: artificial
<220> FEATURE:
<223> OTHER INFORMATION: hz208F2 (var.3), light chain, full length

<400> SEQUENCE: 40

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Arg Gly Ser Gly Thr Asp Tyr Ser Leu Thr Ile Ser Asn Leu Gln Pro
65                  70                  75                  80

Glu Asp Phe Ala Thr Tyr Phe Cys Gln Gln Gly Ser Thr Leu Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 41
<211> LENGTH: 120
<212> TYPE: PRT
<213> ORGANISM: artificial
<220> FEATURE:
<223> OTHER INFORMATION: hz208F2 (var.2) heavy chain, VH
<220> FEATURE:
<221> NAME/KEY: MISC_FEATURE
<222> LOCATION: (20)..(20)
<223> OTHER INFORMATION: Met may be replaced by Val
<220> FEATURE:
<221> NAME/KEY: MISC_FEATURE
<222> LOCATION: (34)..(34)
<223> OTHER INFORMATION: Ile may be replaced by Met
<220> FEATURE:
<221> NAME/KEY: MISC_FEATURE
<222> LOCATION: (35)..(35)
<223> OTHER INFORMATION: Tyr may be replaced by His
<220> FEATURE:
<221> NAME/KEY: MISC_FEATURE
<222> LOCATION: (38)..(38)
<223> OTHER INFORMATION: Lys may be replaced by Arg
<220> FEATURE:
<221> NAME/KEY: MISC_FEATURE
<222> LOCATION: (48)..(48)

```
<223> OTHER INFORMATION: Leu may be replaced by Met
<220> FEATURE:
<221> NAME/KEY: MISC_FEATURE
<222> LOCATION: (50)..(50)
<223> OTHER INFORMATION: Trp may be replaced by Ile
<220> FEATURE:
<221> NAME/KEY: MISC_FEATURE
<222> LOCATION: (59)..(59)
<223> OTHER INFORMATION: Lys may be replaced by Ser
<220> FEATURE:
<221> NAME/KEY: MISC_FEATURE
<222> LOCATION: (61)..(61)
<223> OTHER INFORMATION: Asn may be replaced by Ala
<220> FEATURE:
<221> NAME/KEY: MISC_FEATURE
<222> LOCATION: (62)..(62)
<223> OTHER INFORMATION: Glu may be replaced by Gln
<220> FEATURE:
<221> NAME/KEY: MISC_FEATURE
<222> LOCATION: (70)..(70)
<223> OTHER INFORMATION: Leu may be replaced by Met
<220> FEATURE:
<221> NAME/KEY: MISC_FEATURE
<222> LOCATION: (72)..(72)
<223> OTHER INFORMATION: Ala may be replaced by Arg
<220> FEATURE:
<221> NAME/KEY: MISC_FEATURE
<222> LOCATION: (74)..(74)
<223> OTHER INFORMATION: Lys may be replaced by Thr
<220> FEATURE:
<221> NAME/KEY: MISC_FEATURE
<222> LOCATION: (76)..(76)
<223> OTHER INFORMATION: Ser may be replaced by Thr
<220> FEATURE:
<221> NAME/KEY: MISC_FEATURE
<222> LOCATION: (77)..(77)
<223> OTHER INFORMATION: Asn may be replaced by Ser
<220> FEATURE:
<221> NAME/KEY: MISC_FEATURE
<222> LOCATION: (79)..(79)
<223> OTHER INFORMATION: Ala may be replaced by Val
<220> FEATURE:
<221> NAME/KEY: MISC_FEATURE
<222> LOCATION: (82)..(82)
<223> OTHER INFORMATION: Phe may be replaced by Glu
<220> FEATURE:
<221> NAME/KEY: MISC_FEATURE
<222> LOCATION: (95)..(95)
<223> OTHER INFORMATION: Phe may be replaced by Tyr

<400> SEQUENCE: 41

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Tyr Ile Tyr Trp Val Lys Gln Ala Pro Gly Gln Gly Leu Glu Trp Leu
        35                  40                  45

Gly Trp Ile Trp Pro Gly Asp Gly Ser Thr Lys Tyr Asn Glu Lys Phe
    50                  55                  60

Gln Gly Arg Val Thr Leu Thr Ala Asp Lys Ser Ser Asn Thr Ala Tyr
65                  70                  75                  80

Met Phe Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
            115                 120

<210> SEQ ID NO 42
<211> LENGTH: 107
```

```
<212> TYPE: PRT
<213> ORGANISM: artificial
<220> FEATURE:
<223> OTHER INFORMATION: hz208F2 (var. 2), light chain, VL
<220> FEATURE:
<221> NAME/KEY: MISC_FEATURE
<222> LOCATION: (22)..(22)
<223> OTHER INFORMATION: Ser may be replaced by Thr
<220> FEATURE:
<221> NAME/KEY: MISC_FEATURE
<222> LOCATION: (53)..(53)
<223> OTHER INFORMATION: Arg may be replaced by Ser
<220> FEATURE:
<221> NAME/KEY: MISC_FEATURE
<222> LOCATION: (55)..(55)
<223> OTHER INFORMATION: His may be replaced by Gln
<220> FEATURE:
<221> NAME/KEY: MISC_FEATURE
<222> LOCATION: (65)..(65)
<223> OTHER INFORMATION: Arg may be replaced by Ser
<220> FEATURE:
<221> NAME/KEY: MISC_FEATURE
<222> LOCATION: (71)..(71)
<223> OTHER INFORMATION: Tyr may be replaced by Phe
<220> FEATURE:
<221> NAME/KEY: MISC_FEATURE
<222> LOCATION: (72)..(72)
<223> OTHER INFORMATION: Ser may be replaced by Thr
<220> FEATURE:
<221> NAME/KEY: MISC_FEATURE
<222> LOCATION: (77)..(77)
<223> OTHER INFORMATION: Asn may be replaced by Ser
<220> FEATURE:
<221> NAME/KEY: MISC_FEATURE
<222> LOCATION: (87)..(87)
<223> OTHER INFORMATION: Phe may be replaced by Tyr

<400> SEQUENCE: 42

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Arg Gly Ser Gly Thr Asp Tyr Ser Leu Thr Ile Ser Asn Leu Gln Pro
65                  70                  75                  80

Glu Asp Phe Ala Thr Tyr Phe Cys Gln Gln Gly Ser Thr Leu Pro Tyr
                85                  90                  95

Thr Phe Gly Gly Gly Thr Lys Val Glu Ile Lys
            100                 105

<210> SEQ ID NO 43
<211> LENGTH: 329
<212> TYPE: PRT
<213> ORGANISM: artificial
<220> FEATURE:
<223> OTHER INFORMATION: Constant domain (VH) IgG1

<400> SEQUENCE: 43

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 44
<211> LENGTH: 326
<212> TYPE: PRT
<213> ORGANISM: artificial
<220> FEATURE:
<223> OTHER INFORMATION: Constant domain (VH) IgG4 (S228P)

<400> SEQUENCE: 44

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Lys Thr
65                  70                  75                  80

```
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Pro Cys Pro Ala Pro
            100                 105                 110
Glu Phe Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
    130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
    210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Glu Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Leu Gly
                325

<210> SEQ ID NO 45
<211> LENGTH: 107
<212> TYPE: PRT
<213> ORGANISM: artificial
<220> FEATURE:
<223> OTHER INFORMATION: Domain kappa (VL)

<400> SEQUENCE: 45

Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105
```

```
<210> SEQ ID NO 46
<211> LENGTH: 98
<212> TYPE: PRT
<213> ORGANISM: artificial
<220> FEATURE:
<223> OTHER INFORMATION: Human germline IGHV1-46*01

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 47
<211> LENGTH: 95
<212> TYPE: PRT
<213> ORGANISM: artificial
<220> FEATURE:
<223> OTHER INFORMATION: Human germline IGKV1-39*01

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 48
<211> LENGTH: 15
<212> TYPE: PRT
<213> ORGANISM: artificial
<220> FEATURE:
<223> OTHER INFORMATION: Human germline IGHJ4*01

<400> SEQUENCE: 48

Tyr Phe Asp Tyr Trp Gly Gln Gly Thr Leu Val Thr Val Ser Ser
1               5                   10                  15

<210> SEQ ID NO 49
<211> LENGTH: 12
<212> TYPE: PRT
<213> ORGANISM: artificial
<220> FEATURE:
<223> OTHER INFORMATION: Human germline IGKJ4*01
```

-continued

```
<400> SEQUENCE: 49

Leu Thr Phe Gly Gly Gly Thr Lys Val Glu Ile Lys
1               5                   10

<210> SEQ ID NO 50
<211> LENGTH: 1367
<212> TYPE: PRT
<213> ORGANISM: artificial
<220> FEATURE:
<223> OTHER INFORMATION: IGF-1R (human)

<400> SEQUENCE: 50

Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
    50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
    210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
        275                 280                 285

Glu Ser Ser Asp Ser Glu Gly Phe Val Ile His Asp Gly Glu Cys Met
    290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
                325                 330                 335

Lys Thr Lys Thr Ile Asp Ser Val Thr Ser Ala Gln Met Leu Gln Gly
```

-continued

```
                340             345             350
Cys Thr Ile Phe Lys Gly Asn Leu Leu Ile Asn Ile Arg Arg Gly Asn
                355             360                 365
Asn Ile Ala Ser Glu Leu Glu Asn Phe Met Gly Leu Ile Glu Val Val
            370             375             380
Thr Gly Tyr Val Lys Ile Arg His Ser His Ala Leu Val Ser Leu Ser
385             390             395                 400
Phe Leu Lys Asn Leu Arg Leu Ile Leu Gly Glu Glu Gln Leu Glu Gly
                405             410                 415
Asn Tyr Ser Phe Tyr Val Leu Asp Asn Gln Asn Leu Gln Gln Leu Trp
            420             425             430
Asp Trp Asp His Arg Asn Leu Thr Ile Lys Ala Gly Lys Met Tyr Phe
            435             440             445
Ala Phe Asn Pro Lys Leu Cys Val Ser Glu Ile Tyr Arg Met Glu Glu
            450             455             460
Val Thr Gly Thr Lys Gly Arg Gln Ser Lys Gly Asp Ile Asn Thr Arg
465             470             475                 480
Asn Asn Gly Glu Arg Ala Ser Cys Glu Ser Asp Val Leu His Phe Thr
                485             490                 495
Ser Thr Thr Thr Ser Lys Asn Arg Ile Ile Thr Trp His Arg Tyr
            500             505             510
Arg Pro Pro Asp Tyr Arg Asp Leu Ile Ser Phe Thr Val Tyr Tyr Lys
        515             520             525
Glu Ala Pro Phe Lys Asn Val Thr Glu Tyr Asp Gly Gln Asp Ala Cys
        530             535             540
Gly Ser Asn Ser Trp Asn Met Val Asp Val Asp Leu Pro Pro Asn Lys
545             550             555                 560
Asp Val Glu Pro Gly Ile Leu Leu His Gly Leu Lys Pro Trp Thr Gln
                565             570                 575
Tyr Ala Val Tyr Val Lys Ala Val Thr Leu Thr Met Val Glu Asn Asp
            580             585             590
His Ile Arg Gly Ala Lys Ser Glu Ile Leu Tyr Ile Arg Thr Asn Ala
            595             600             605
Ser Val Pro Ser Ile Pro Leu Asp Val Leu Ser Ala Ser Asn Ser Ser
        610             615             620
Ser Gln Leu Ile Val Lys Trp Asn Pro Pro Ser Leu Pro Asn Gly Asn
625             630             635                 640
Leu Ser Tyr Tyr Ile Val Arg Trp Gln Arg Gln Pro Gln Asp Gly Tyr
                645             650                 655
Leu Tyr Arg His Asn Tyr Cys Ser Lys Asp Lys Ile Pro Ile Arg Lys
                660             665                 670
Tyr Ala Asp Gly Thr Ile Asp Ile Glu Glu Val Thr Glu Asn Pro Lys
            675             680             685
Thr Glu Val Cys Gly Gly Glu Lys Gly Pro Cys Cys Ala Cys Pro Lys
        690             695             700
Thr Glu Ala Glu Lys Gln Ala Glu Lys Glu Glu Ala Glu Tyr Arg Lys
705             710             715                 720
Val Phe Glu Asn Phe Leu His Asn Ser Ile Phe Val Pro Arg Pro Glu
                725             730                 735
Arg Lys Arg Arg Asp Val Met Gln Val Ala Asn Thr Thr Met Ser Ser
            740             745             750
Arg Ser Arg Asn Thr Thr Ala Ala Asp Thr Tyr Asn Ile Thr Asp Pro
            755             760             765
```

```
Glu Glu Leu Glu Thr Glu Tyr Pro Phe Phe Glu Ser Arg Val Asp Asn
    770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                    805                 810                 815

Ala Ser Asn Phe Val Phe Ala Arg Thr Met Pro Ala Glu Gly Ala Asp
                820                 825                 830

Asp Ile Pro Gly Pro Val Thr Trp Glu Pro Arg Pro Glu Asn Ser Ile
            835                 840                 845

Phe Leu Lys Trp Pro Glu Pro Glu Asn Pro Asn Gly Leu Ile Leu Met
850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                885                 890                 895

Asn Pro Gly Asn Tyr Thr Ala Arg Ile Gln Ala Thr Ser Leu Ser Gly
            900                 905                 910

Asn Gly Ser Trp Thr Asp Pro Val Phe Phe Tyr Val Gln Ala Lys Thr
        915                 920                 925

Gly Tyr Glu Asn Phe Ile His Leu Ile Ile Ala Leu Pro Val Ala Val
930                 935                 940

Leu Leu Ile Val Gly Gly Leu Val Ile Met Leu Tyr Val Phe His Arg
945                 950                 955                 960

Lys Arg Asn Asn Ser Arg Leu Gly Asn Gly Val Leu Tyr Ala Ser Val
                965                 970                 975

Asn Pro Glu Tyr Phe Ser Ala Ala Asp Val Tyr Val Pro Asp Glu Trp
            980                 985                 990

Glu Val Ala Arg Glu Lys Ile Thr  Met Ser Arg Glu Leu Gly Gln Gly
            995                 1000               1005

Ser Phe  Gly Met Val Tyr Glu  Gly Val Ala Lys Gly  Val Val Lys
    1010                1015                1020

Asp Glu  Pro Glu Thr Arg Val  Ala Ile Lys Thr Val  Asn Glu Ala
    1025                1030                1035

Ala Ser  Met Arg Glu Arg Ile  Glu Phe Leu Asn Glu  Ala Ser Val
    1040                1045                1050

Met Lys  Glu Phe Asn Cys His  His Val Val Arg Leu  Leu Gly Val
    1055                1060                1065

Val Ser  Gln Gly Gln Pro Thr  Leu Val Ile Met Glu  Leu Met Thr
    1070                1075                1080

Arg Gly  Asp Leu Lys Ser Tyr  Leu Arg Ser Leu Arg  Pro Glu Met
    1085                1090                1095

Glu Asn  Asn Pro Val Leu Ala  Pro Pro Ser Leu Ser  Lys Met Ile
    1100                1105                1110

Gln Met  Ala Gly Glu Ile Ala  Asp Gly Met Ala Tyr  Leu Asn Ala
    1115                1120                1125

Asn Lys  Phe Val His Arg Asp  Leu Ala Ala Arg Asn  Cys Met Val
    1130                1135                1140

Ala Glu  Asp Phe Thr Val Lys  Ile Gly Asp Phe Gly  Met Thr Arg
    1145                1150                1155

Asp Ile  Tyr Glu Thr Asp Tyr  Tyr Arg Lys Gly Gly  Lys Gly Leu
    1160                1165                1170
```

```
Leu Pro Val Arg Trp Met Ser Pro Glu Ser Leu Lys Asp Gly Val
    1175            1180                1185

Phe Thr Thr Tyr Ser Asp Val Trp Ser Phe Gly Val Val Leu Trp
    1190            1195                1200

Glu Ile Ala Thr Leu Ala Glu Gln Pro Tyr Gln Gly Leu Ser Asn
    1205            1210                1215

Glu Gln Val Leu Arg Phe Val Met Glu Gly Gly Leu Leu Asp Lys
    1220            1225                1230

Pro Asp Asn Cys Pro Asp Met Leu Phe Glu Leu Met Arg Met Cys
    1235            1240                1245

Trp Gln Tyr Asn Pro Lys Met Arg Pro Ser Phe Leu Glu Ile Ile
    1250            1255                1260

Ser Ser Ile Lys Glu Glu Met Glu Pro Gly Phe Arg Glu Val Ser
    1265            1270                1275

Phe Tyr Tyr Ser Glu Glu Asn Lys Leu Pro Glu Pro Glu Glu Leu
    1280            1285                1290

Asp Leu Glu Pro Glu Asn Met Glu Ser Val Pro Leu Asp Pro Ser
    1295            1300                1305

Ala Ser Ser Ser Ser Leu Pro Leu Pro Asp Arg His Ser Gly His
    1310            1315                1320

Lys Ala Glu Asn Gly Pro Gly Pro Gly Val Leu Val Leu Arg Ala
    1325            1330                1335

Ser Phe Asp Glu Arg Gln Pro Tyr Ala His Met Asn Gly Gly Arg
    1340            1345                1350

Lys Asn Glu Arg Ala Leu Pro Leu Pro Gln Ser Ser Thr Cys
    1355            1360                1365

<210> SEQ ID NO 51
<211> LENGTH: 932
<212> TYPE: PRT
<213> ORGANISM: artificial
<220> FEATURE:
<223> OTHER INFORMATION: IGF-1R ECD (human)

<400> SEQUENCE: 51

Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
            115                 120                 125

Gly Leu Tyr Asn Leu Arg Asn Ile Thr Arg Gly Ala Ile Arg Ile Glu
        130                 135                 140

Lys Asn Ala Asp Leu Cys Tyr Leu Ser Thr Val Asp Trp Ser Leu Ile
145                 150                 155                 160
```

-continued

```
Leu Asp Ala Val Ser Asn Asn Tyr Ile Val Gly Asn Lys Pro Pro Lys
                165                 170                 175
Glu Cys Gly Asp Leu Cys Pro Gly Thr Met Glu Glu Lys Pro Met Cys
            180                 185                 190
Glu Lys Thr Thr Ile Asn Asn Glu Tyr Asn Tyr Arg Cys Trp Thr Thr
        195                 200                 205
Asn Arg Cys Gln Lys Met Cys Pro Ser Thr Cys Gly Lys Arg Ala Cys
    210                 215                 220
Thr Glu Asn Asn Glu Cys Cys His Pro Glu Cys Leu Gly Ser Cys Ser
225                 230                 235                 240
Ala Pro Asp Asn Asp Thr Ala Cys Val Ala Cys Arg His Tyr Tyr Tyr
                245                 250                 255
Ala Gly Val Cys Val Pro Ala Cys Pro Pro Asn Thr Tyr Arg Phe Glu
            260                 265                 270
Gly Trp Arg Cys Val Asp Arg Asp Phe Cys Ala Asn Ile Leu Ser Ala
        275                 280                 285
Glu Ser Ser Asp Ser Glu Gly Phe Val Ile His Asp Gly Glu Cys Met
    290                 295                 300
Gln Glu Cys Pro Ser Gly Phe Ile Arg Asn Gly Ser Gln Ser Met Tyr
305                 310                 315                 320
Cys Ile Pro Cys Glu Gly Pro Cys Pro Lys Val Cys Glu Glu Glu Lys
                325                 330                 335
Lys Thr Lys Thr Ile Asp Ser Val Thr Ser Ala Gln Met Leu Gln Gly
            340                 345                 350
Cys Thr Ile Phe Lys Gly Asn Leu Leu Ile Asn Ile Arg Arg Gly Asn
        355                 360                 365
Asn Ile Ala Ser Glu Leu Glu Asn Phe Met Gly Leu Ile Glu Val Val
    370                 375                 380
Thr Gly Tyr Val Lys Ile Arg His Ser His Ala Leu Val Ser Leu Ser
385                 390                 395                 400
Phe Leu Lys Asn Leu Arg Leu Ile Leu Gly Glu Glu Gln Leu Glu Gly
                405                 410                 415
Asn Tyr Ser Phe Tyr Val Leu Asp Asn Gln Asn Leu Gln Gln Leu Trp
            420                 425                 430
Asp Trp Asp His Arg Asn Leu Thr Ile Lys Ala Gly Lys Met Tyr Phe
        435                 440                 445
Ala Phe Asn Pro Lys Leu Cys Val Ser Glu Ile Tyr Arg Met Glu Glu
    450                 455                 460
Val Thr Gly Thr Lys Gly Arg Gln Ser Lys Gly Asp Ile Asn Thr Arg
465                 470                 475                 480
Asn Asn Gly Glu Arg Ala Ser Cys Glu Ser Asp Val Leu His Phe Thr
                485                 490                 495
Ser Thr Thr Thr Ser Lys Asn Arg Ile Ile Ile Thr Trp His Arg Tyr
            500                 505                 510
Arg Pro Pro Asp Tyr Arg Asp Leu Ile Ser Phe Thr Val Tyr Tyr Lys
        515                 520                 525
Glu Ala Pro Phe Lys Asn Val Thr Glu Tyr Asp Gly Gln Asp Ala Cys
    530                 535                 540
Gly Ser Asn Ser Trp Asn Met Val Asp Val Asp Leu Pro Pro Asn Lys
545                 550                 555                 560
Asp Val Glu Pro Gly Ile Leu Leu His Gly Leu Lys Pro Trp Thr Gln
                565                 570                 575
Tyr Ala Val Tyr Val Lys Ala Val Thr Leu Thr Met Val Glu Asn Asp
```

```
                580             585             590
His Ile Arg Gly Ala Lys Ser Glu Ile Leu Tyr Ile Arg Thr Asn Ala
            595                 600                 605
Ser Val Pro Ser Ile Pro Leu Asp Val Leu Ser Ala Ser Asn Ser Ser
        610                 615                 620
Ser Gln Leu Ile Val Lys Trp Asn Pro Ser Leu Pro Asn Gly Asn
625                 630                 635                 640
Leu Ser Tyr Tyr Ile Val Arg Trp Gln Arg Gln Pro Gln Asp Gly Tyr
                645                 650                 655
Leu Tyr Arg His Asn Tyr Cys Ser Lys Asp Lys Ile Pro Ile Arg Lys
            660                 665                 670
Tyr Ala Asp Gly Thr Ile Asp Ile Glu Glu Val Thr Glu Asn Pro Lys
            675                 680                 685
Thr Glu Val Cys Gly Gly Glu Lys Gly Pro Cys Cys Ala Cys Pro Lys
        690                 695                 700
Thr Glu Ala Glu Lys Gln Ala Glu Lys Glu Glu Ala Glu Tyr Arg Lys
705                 710                 715                 720
Val Phe Glu Asn Phe Leu His Asn Ser Ile Phe Val Pro Arg Pro Glu
                725                 730                 735
Arg Lys Arg Arg Asp Val Met Gln Val Ala Asn Thr Thr Met Ser Ser
            740                 745                 750
Arg Ser Arg Asn Thr Thr Ala Ala Asp Thr Tyr Asn Ile Thr Asp Pro
        755                 760                 765
Glu Glu Leu Glu Thr Glu Tyr Pro Phe Phe Glu Ser Arg Val Asp Asn
770                 775                 780
Lys Glu Arg Thr Val Ile Ser Asn Leu Arg Pro Phe Thr Leu Tyr Arg
785                 790                 795                 800
Ile Asp Ile His Ser Cys Asn His Glu Ala Glu Lys Leu Gly Cys Ser
                805                 810                 815
Ala Ser Asn Phe Val Phe Ala Arg Thr Met Pro Ala Glu Gly Ala Asp
            820                 825                 830
Asp Ile Pro Gly Pro Val Thr Trp Glu Pro Arg Pro Glu Asn Ser Ile
            835                 840                 845
Phe Leu Lys Trp Pro Glu Pro Glu Asn Pro Asn Gly Leu Ile Leu Met
        850                 855                 860
Tyr Glu Ile Lys Tyr Gly Ser Gln Val Glu Asp Gln Arg Glu Cys Val
865                 870                 875                 880
Ser Arg Gln Glu Tyr Arg Lys Tyr Gly Gly Ala Lys Leu Asn Arg Leu
                885                 890                 895
Asn Pro Gly Asn Tyr Thr Ala Arg Ile Gln Ala Thr Ser Leu Ser Gly
            900                 905                 910
Asn Gly Ser Trp Thr Asp Pro Val Phe Phe Tyr Val Gln Ala Lys Thr
            915                 920                 925
Gly Tyr Glu Asn
    930

<210> SEQ ID NO 52
<211> LENGTH: 512
<212> TYPE: PRT
<213> ORGANISM: artificial
<220> FEATURE:
<223> OTHER INFORMATION: IGF-1R ECD Nterminal (human)

<400> SEQUENCE: 52

Met Lys Ser Gly Ser Gly Gly Gly Ser Pro Thr Ser Leu Trp Gly Leu
```

-continued

```
1               5                   10                  15
Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
                35                  40                  45

Leu Glu Asn Cys Thr Val Ile Glu Gly Tyr Leu His Ile Leu Leu Ile
                50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
                100                 105                 110

Tyr Asn Tyr Ala Leu Val Ile Phe Glu Met Thr Asn Leu Lys Asp Ile
                115                 120                 125

Gly Leu Tyr Asn Leu Arg Asn Ile Thr Arg Gly Ala Ile Arg Ile Glu
                130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
                180                 185                 190

Glu Lys Thr Thr Ile Asn Asn Glu Tyr Asn Tyr Arg Cys Trp Thr Thr
                195                 200                 205

Asn Arg Cys Gln Lys Met Cys Pro Ser Thr Cys Gly Lys Arg Ala Cys
210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
                260                 265                 270

Gly Trp Arg Cys Val Asp Arg Asp Phe Cys Ala Asn Ile Leu Ser Ala
                275                 280                 285

Glu Ser Ser Asp Ser Glu Gly Phe Val Ile His Asp Gly Glu Cys Met
                290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
                325                 330                 335

Lys Thr Lys Thr Ile Asp Ser Val Thr Ser Ala Gln Met Leu Gln Gly
                340                 345                 350

Cys Thr Ile Phe Lys Gly Asn Leu Leu Ile Asn Ile Arg Arg Gly Asn
                355                 360                 365

Asn Ile Ala Ser Glu Leu Glu Asn Phe Met Gly Leu Ile Glu Val Val
                370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
                405                 410                 415

Asn Tyr Ser Phe Tyr Val Leu Asp Asn Gln Asn Leu Gln Gln Leu Trp
                420                 425                 430
```

Asp Trp Asp His Arg Asn Leu Thr Ile Lys Ala Gly Lys Met Tyr Phe
            435                 440                 445

Ala Phe Asn Pro Lys Leu Cys Val Ser Glu Ile Tyr Arg Met Glu Glu
        450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
                485                 490                 495

Ser Thr Thr Thr Ser Lys Asn Arg Ile Ile Ile Thr Trp His Arg Tyr
                500                 505                 510

<210> SEQ ID NO 53
<211> LENGTH: 4
<212> TYPE: PRT
<213> ORGANISM: artificial
<220> FEATURE:
<223> OTHER INFORMATION: tetrapeptide (linker)

<400> SEQUENCE: 53

Gly Phe Leu Gly
1

<210> SEQ ID NO 54
<211> LENGTH: 4
<212> TYPE: PRT
<213> ORGANISM: artificial
<220> FEATURE:
<223> OTHER INFORMATION: tetrapeptide (linker)

<400> SEQUENCE: 54

Ala Leu Ala Leu
1

<210> SEQ ID NO 55
<211> LENGTH: 5
<212> TYPE: PRT
<213> ORGANISM: artificial
<220> FEATURE:
<223> OTHER INFORMATION: tetrapeptide (linker)

<400> SEQUENCE: 55

Pro Val Gly Val Val
1               5

<210> SEQ ID NO 56
<211> LENGTH: 120
<212> TYPE: PRT
<213> ORGANISM: artificial
<220> FEATURE:
<223> OTHER INFORMATION: hz208F2 heavy chain H037, VH

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Lys Ser Ser Thr Val Tyr
65                  70                  75                  80

Met Glu Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
        115                 120

<210> SEQ ID NO 57
<211> LENGTH: 107
<212> TYPE: PRT
<213> ORGANISM: artificial
<220> FEATURE:
<223> OTHER INFORMATION: hz208F2 light chain L018, VL

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Ser Gly
50                  55                  60

Arg Gly Ser Gly Thr Asp Tyr Ser Leu Thr Ile Ser Ser Leu Gln Pro
65                  70                  75                  80

Glu Asp Phe Ala Thr Tyr Phe Cys Gln Gln Gly Ser Thr Leu Pro Tyr
                85                  90                  95

Thr Phe Gly Gly Gly Thr Lys Val Glu Ile Lys
            100                 105

<210> SEQ ID NO 58
<211> LENGTH: 449
<212> TYPE: PRT
<213> ORGANISM: artificial
<220> FEATURE:
<223> OTHER INFORMATION: hz208F2 heavy chain H037 full length

<400> SEQUENCE: 58

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
50                  55                  60

Gln Gly Arg Val Thr Met Thr Arg Asp Lys Ser Ser Ser Thr Val Tyr
65                  70                  75                  80

Met Glu Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser

-continued

```
            145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Arg Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
        370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
            435                 440                 445
Gly

<210> SEQ ID NO 59
<211> LENGTH: 214
<212> TYPE: PRT
<213> ORGANISM: artificial
<220> FEATURE:
<223> OTHER INFORMATION: hz208F2 light chain L018 full length

<400> SEQUENCE: 59

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Ile Ser Lys Tyr
                20                  25                  30
Leu Asn Trp Tyr Gln Gln Lys Pro Gly Lys Ala Pro Lys Leu Leu Ile
            35                  40                  45
Tyr Tyr Thr Ser Arg Leu Gln Ser Gly Val Pro Ser Arg Phe Ser Gly
        50                  55                  60
```

Arg Gly Ser Gly Thr Asp Tyr Ser Leu Thr Ile Ser Ser Leu Gln Pro
 65                  70                  75                  80

Glu Asp Phe Ala Thr Tyr Phe Cys Gln Gln Gly Ser Thr Leu Pro Tyr
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 60
<211> LENGTH: 107
<212> TYPE: PRT
<213> ORGANISM: artificial
<220> FEATURE:
<223> OTHER INFORMATION: hz208F2 light chain L021, VL

<400> SEQUENCE: 60

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Lys Tyr
             20                  25                  30

Leu Asn Trp Tyr Gln Gln Lys Pro Gly Lys Ala Pro Lys Leu Leu Ile
         35                  40                  45

Tyr Tyr Thr Ser Arg Leu His Ser Gly Val Pro Ser Arg Phe Ser Gly
 50                  55                  60

Arg Gly Ser Gly Thr Asp Phe Ser Leu Thr Ile Ser Ser Leu Gln Pro
 65                  70                  75                  80

Glu Asp Phe Ala Thr Tyr Phe Cys Gln Gln Gly Ser Thr Leu Pro Tyr
                 85                  90                  95

Thr Phe Gly Gly Gly Thr Lys Val Glu Ile Lys
            100                 105

<210> SEQ ID NO 61
<211> LENGTH: 214
<212> TYPE: PRT
<213> ORGANISM: artificial
<220> FEATURE:
<223> OTHER INFORMATION: hz208F2 light chain L021 full length

<400> SEQUENCE: 61

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Lys Tyr
             20                  25                  30

Leu Asn Trp Tyr Gln Gln Lys Pro Gly Lys Ala Pro Lys Leu Leu Ile

```
            35                  40                  45
Tyr Tyr Thr Ser Arg Leu His Ser Gly Val Pro Ser Arg Phe Ser Gly
 50                  55                  60

Arg Gly Ser Gly Thr Asp Phe Ser Leu Thr Ile Ser Ser Leu Gln Pro
 65                  70                  75                  80

Glu Asp Phe Ala Thr Tyr Phe Cys Gln Gln Gly Ser Thr Leu Pro Tyr
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 62
<211> LENGTH: 120
<212> TYPE: PRT
<213> ORGANISM: artificial
<220> FEATURE:
<223> OTHER INFORMATION: hz208F2 heavy chain H047, VH

<400> SEQUENCE: 62

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Tyr Ile His Trp Val Arg Gln Ala Pro Gly Gln Gly Leu Glu Trp Met
         35                  40                  45

Gly Trp Ile Trp Pro Gly Asp Gly Ser Thr Lys Tyr Ala Gln Lys Phe
 50                  55                  60

Gln Gly Arg Val Thr Met Thr Arg Asp Thr Ser Ser Asn Thr Val Tyr
 65                  70                  75                  80

Met Glu Leu Ser Ser Leu Arg Ser Glu Asp Thr Ala Val Tyr Tyr Cys
                 85                  90                  95

Ala Ser Pro Met Ile Thr Pro Asn Tyr Ala Met Asp Tyr Trp Gly Gln
            100                 105                 110

Gly Thr Leu Val Thr Val Ser Ser
            115                 120

<210> SEQ ID NO 63
<211> LENGTH: 449
<212> TYPE: PRT
<213> ORGANISM: artificial
<220> FEATURE:
<223> OTHER INFORMATION: hz208F2 heavy chain H047 full length

<400> SEQUENCE: 63
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Asn Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
```

-continued

```
                    420                 425                 430

Glu Ala Leu His Asn His Tyr Thr Gln Lys Ser Leu Ser Leu Ser Pro
            435                 440                 445

Gly

<210> SEQ ID NO 64
<211> LENGTH: 120
<212> TYPE: PRT
<213> ORGANISM: artificial
<220> FEATURE:
<223> OTHER INFORMATION: hz208F2 heavy chain H049, VH

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Trp Ile Trp Pro Gly Asp Gly Ser Thr Lys Tyr Ala Gln Lys Phe
        50                  55                  60

Gln Gly Arg Val Thr Met Thr Arg Asp Lys Ser Ser Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
                100                 105                 110

Gly Thr Leu Val Thr Val Ser Ser
            115                 120

<210> SEQ ID NO 65
<211> LENGTH: 449
<212> TYPE: PRT
<213> ORGANISM: artificial
<220> FEATURE:
<223> OTHER INFORMATION: hz208F2 heavy chain H049 full length

<400> SEQUENCE: 65

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Trp Ile Trp Pro Gly Asp Gly Ser Thr Lys Tyr Ala Gln Lys Phe
        50                  55                  60

Gln Gly Arg Val Thr Met Thr Arg Asp Lys Ser Ser Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
```

```
                145                 150                 155                 160
Trp Asn Ser Gly Ala Leu Thr Ser Gly Val His Thr Phe Pro Ala Val
                    165                 170                 175
Leu Gln Ser Ser Gly Leu Tyr Ser Leu Ser Val Val Thr Val Pro
                180                 185                 190
Ser Ser Ser Leu Gly Thr Gln Thr Tyr Ile Cys Asn Val Asn His Lys
            195                 200                 205
Pro Ser Asn Thr Lys Val Asp Lys Arg Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
            435                 440                 445
Gly

<210> SEQ ID NO 66
<211> LENGTH: 120
<212> TYPE: PRT
<213> ORGANISM: artificial
<220> FEATURE:
<223> OTHER INFORMATION: hz208F2 heavy chain H051, VH

<400> SEQUENCE: 66

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
                20                  25                  30
Tyr Met His Trp Val Arg Gln Ala Pro Gly Gln Gly Leu Glu Trp Met
            35                  40                  45
Gly Trp Ile Trp Pro Gly Asp Gly Ser Thr Lys Tyr Ala Gln Lys Phe
    50                  55                  60
```

```
Gln Gly Arg Val Thr Met Thr Arg Asp Thr Ser Ser Asn Thr Val Tyr
 65                  70                  75                  80

Met Glu Leu Ser Ser Leu Arg Ser Glu Asp Thr Ala Val Tyr Phe Cys
                 85                  90                  95

Ala Ser Pro Met Ile Thr Pro Asn Tyr Ala Met Asp Tyr Trp Gly Gln
            100                 105                 110

Gly Thr Leu Val Thr Val Ser Ser
        115                 120

<210> SEQ ID NO 67
<211> LENGTH: 449
<212> TYPE: PRT
<213> ORGANISM: artificial
<220> FEATURE:
<223> OTHER INFORMATION: hz208F2 heavy chain H051 full length

<400> SEQUENCE: 67

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
             20                  25                  30

Tyr Met His Trp Val Arg Gln Ala Pro Gly Gln Gly Leu Glu Trp Met
         35                  40                  45

Gly Trp Ile Trp Pro Gly Asp Gly Ser Thr Lys Tyr Ala Gln Lys Phe
     50                  55                  60

Gln Gly Arg Val Thr Met Thr Arg Asp Thr Ser Ser Asn Thr Val Tyr
 65                  70                  75                  80

Met Glu Leu Ser Ser Leu Arg Ser Glu Asp Thr Ala Val Tyr Phe Cys
                 85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300
```

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 68
<211> LENGTH: 120
<212> TYPE: PRT
<213> ORGANISM: artificial
<220> FEATURE:
<223> OTHER INFORMATION: hz208F2 heavy chain H052, VH

<400> SEQUENCE: 68

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
        115                 120

<210> SEQ ID NO 69
<211> LENGTH: 449
<212> TYPE: PRT
<213> ORGANISM: artificial
<220> FEATURE:
<223> OTHER INFORMATION: hz208F2 heavy chain H052 full length

<400> SEQUENCE: 69

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

```
Tyr Met His Trp Val Arg Gln Ala Pro Gly Gln Gly Leu Glu Trp Met
    35                  40                  45

Gly Trp Ile Trp Pro Gly Asp Gly Ser Thr Lys Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445
```

-continued

Gly

<210> SEQ ID NO 70
<211> LENGTH: 120
<212> TYPE: PRT
<213> ORGANISM: artificial
<220> FEATURE:
<223> OTHER INFORMATION: hz208F2 heavy chain H057, VH

<400> SEQUENCE: 70

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Lys Ser Thr Asn Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
        115                 120
```

<210> SEQ ID NO 71
<211> LENGTH: 449
<212> TYPE: PRT
<213> ORGANISM: artificial
<220> FEATURE:
<223> OTHER INFORMATION: hz208F2 heavy chain H057 full length

<400> SEQUENCE: 71

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Lys Ser Thr Asn Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 72
<211> LENGTH: 120
<212> TYPE: PRT
<213> ORGANISM: artificial
<220> FEATURE:
<223> OTHER INFORMATION: hz208F2 heavy chain H068, VH

<400> SEQUENCE: 72

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Thr Asn Thr Val Tyr
65                  70                  75                  80

Met Glu Leu Ser Ser Leu Arg Ser Glu Asp Thr Ala Val Tyr Phe Cys
```

```
                    85                  90                  95
Ala Ser Pro Met Ile Thr Pro Asn Tyr Ala Met Asp Tyr Trp Gly Gln
            100                 105                 110

Gly Thr Leu Val Thr Val Ser Ser
            115                 120
```

<210> SEQ ID NO 73
<211> LENGTH: 449
<212> TYPE: PRT
<213> ORGANISM: artificial
<220> FEATURE:
<223> OTHER INFORMATION: hz208F2 heavy chain H068 full length

<400> SEQUENCE: 73

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
50                  55                  60

Gln Gly Arg Val Thr Met Thr Arg Asp Thr Ser Thr Asn Thr Val Tyr
65                  70                  75                  80

Met Glu Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
```

```
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 74
<211> LENGTH: 120
<212> TYPE: PRT
<213> ORGANISM: artificial
<220> FEATURE:
<223> OTHER INFORMATION: hz208F2 heavy chain H070, VH

<400> SEQUENCE: 74

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
        115                 120

<210> SEQ ID NO 75
<211> LENGTH: 449
<212> TYPE: PRT
<213> ORGANISM: artificial
<220> FEATURE:
<223> OTHER INFORMATION: hz208F2 heavy chain H070 full length

<400> SEQUENCE: 75

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
```

```
                     50                  55                  60
    Gln Gly Arg Val Thr Met Thr Arg Asp Thr Ser Thr Ser Thr Val Tyr
     65                  70                  75                  80
    Met Glu Leu Ser Ser Leu Arg Ser Glu Asp Thr Ala Val Tyr Tyr Cys
                         85                  90                  95
    Ala Ser Pro Met Ile Thr Pro Asn Tyr Ala Met Asp Tyr Trp Gly Gln
                    100                 105                 110
    Gly Thr Leu Val Thr Val Ser Ser Ala Ser Thr Lys Gly Pro Ser Val
                115                 120                 125
    Phe Pro Leu Ala Pro Ser Ser Lys Ser Thr Ser Gly Gly Thr Ala Ala
    130                 135                 140
    Leu Gly Cys Leu Val Lys Asp Tyr Phe Pro Glu Pro Val Thr Val Ser
    145                 150                 155                 160
    Trp Asn Ser Gly Ala Leu Thr Ser Gly Val His Thr Phe Pro Ala Val
                    165                 170                 175
    Leu Gln Ser Ser Gly Leu Tyr Ser Leu Ser Ser Val Val Thr Val Pro
                180                 185                 190
    Ser Ser Ser Leu Gly Thr Gln Thr Tyr Ile Cys Asn Val Asn His Lys
                195                 200                 205
    Pro Ser Asn Thr Lys Val Asp Lys Arg Val Glu Pro Lys Ser Cys Asp
    210                 215                 220
    Lys Thr His Thr Cys Pro Pro Cys Pro Ala Pro Glu Leu Leu Gly Gly
    225                 230                 235                 240
    Pro Ser Val Phe Leu Phe Pro Pro Lys Pro Lys Asp Thr Leu Met Ile
                    245                 250                 255
    Ser Arg Thr Pro Glu Val Thr Cys Val Val Val Asp Val Ser His Glu
                260                 265                 270
    Asp Pro Glu Val Lys Phe Asn Trp Tyr Val Asp Gly Val Glu Val His
                275                 280                 285
    Asn Ala Lys Thr Lys Pro Arg Glu Glu Gln Tyr Asn Ser Thr Tyr Arg
            290                 295                 300
    Val Val Ser Val Leu Thr Val Leu His Gln Asp Trp Leu Asn Gly Lys
    305                 310                 315                 320
    Glu Tyr Lys Cys Lys Val Ser Asn Lys Ala Leu Pro Ala Pro Ile Glu
                    325                 330                 335
    Lys Thr Ile Ser Lys Ala Lys Gly Gln Pro Arg Glu Pro Gln Val Tyr
                340                 345                 350
    Thr Leu Pro Pro Ser Arg Glu Glu Met Thr Lys Asn Gln Val Ser Leu
                355                 360                 365
    Thr Cys Leu Val Lys Gly Phe Tyr Pro Ser Asp Ile Ala Val Glu Trp
    370                 375                 380
    Glu Ser Asn Gly Gln Pro Glu Asn Asn Tyr Lys Thr Thr Pro Pro Val
    385                 390                 395                 400
    Leu Asp Ser Asp Gly Ser Phe Phe Leu Tyr Ser Lys Leu Thr Val Asp
                    405                 410                 415
    Lys Ser Arg Trp Gln Gln Gly Asn Val Phe Ser Cys Ser Val Met His
                420                 425                 430
    Glu Ala Leu His Asn His Tyr Thr Gln Lys Ser Leu Ser Leu Ser Pro
                435                 440                 445
    Gly

<210> SEQ ID NO 76
<211> LENGTH: 120
```

```
<212> TYPE: PRT
<213> ORGANISM: artificial
<220> FEATURE:
<223> OTHER INFORMATION: hz208F2 heavy chain H071, VH

<400> SEQUENCE: 76

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Thr Asn Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
        115                 120

<210> SEQ ID NO 77
<211> LENGTH: 449
<212> TYPE: PRT
<213> ORGANISM: artificial
<220> FEATURE:
<223> OTHER INFORMATION: hz208F2 heavy chain H071 full length

<400> SEQUENCE: 77

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Thr Asn Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 78
<211> LENGTH: 120
<212> TYPE: PRT
<213> ORGANISM: artificial
<220> FEATURE:
<223> OTHER INFORMATION: hz208F2 heavy chain H076, VH

<400> SEQUENCE: 78

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

```
Gly Thr Leu Val Thr Val Ser Ser
        115                 120

<210> SEQ ID NO 79
<211> LENGTH: 449
<212> TYPE: PRT
<213> ORGANISM: artificial
<220> FEATURE:
<223> OTHER INFORMATION: hz208F2 heavy chain H076 full length

<400> SEQUENCE: 79

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350
```

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 80
<211> LENGTH: 120
<212> TYPE: PRT
<213> ORGANISM: artificial
<220> FEATURE:
<223> OTHER INFORMATION: hz208F2 heavy chain H077, VH

<400> SEQUENCE: 80

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
        115                 120

<210> SEQ ID NO 81
<211> LENGTH: 449
<212> TYPE: PRT
<213> ORGANISM: artificial
<220> FEATURE:
<223> OTHER INFORMATION: hz208F2 heavy chain H077 full length

<400> SEQUENCE: 81

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Ser Thr Val Tyr
65                  70                  75                  80

```
Met Glu Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 82
<211> LENGTH: 512
<212> TYPE: PRT
<213> ORGANISM: Artificial
<220> FEATURE:
<223> OTHER INFORMATION: Mutated IGF-1R ECD Nterminal with Arginine at
      position 494
```

<400> SEQUENCE: 82

| | | | | | | | | | | | | | | |
|---|---|---|---|---|---|---|---|---|---|---|---|---|---|---|
|Met|Lys|Ser|Gly|Ser|Gly|Gly|Ser|Pro|Thr|Ser|Leu|Trp|Gly|Leu|
|1| | | |5| | | |10| | | |15| | |
|Leu|Phe|Leu|Ser|Ala|Ala|Leu|Ser|Leu|Trp|Pro|Thr|Ser|Gly|Glu|Ile|
| | | | |20| | | | |25| | | | |30| |
|Cys|Gly|Pro|Gly|Ile|Asp|Ile|Arg|Asn|Asp|Tyr|Gln|Gln|Leu|Lys|Arg|
| | | |35| | | | |40| | | | |45| | |
|Leu|Glu|Asn|Cys|Thr|Val|Ile|Glu|Gly|Tyr|Leu|His|Ile|Leu|Leu|Ile|
| |50| | | | |55| | | | |60| | | | |
|Ser|Lys|Ala|Glu|Asp|Tyr|Arg|Ser|Tyr|Arg|Phe|Pro|Lys|Leu|Thr|Val|
|65| | | | |70| | | | |75| | | | |80|
|Ile|Thr|Glu|Tyr|Leu|Leu|Leu|Phe|Arg|Val|Ala|Gly|Leu|Glu|Ser|Leu|
| | | | |85| | | | |90| | | | |95| |
|Gly|Asp|Leu|Phe|Pro|Asn|Leu|Thr|Val|Ile|Arg|Gly|Trp|Lys|Leu|Phe|
| | | | |100| | | | |105| | | | |110| |
|Tyr|Asn|Tyr|Ala|Leu|Val|Ile|Phe|Glu|Met|Thr|Asn|Leu|Lys|Asp|Ile|
| | | | |115| | | | |120| | | | |125| |
|Gly|Leu|Tyr|Asn|Leu|Arg|Asn|Ile|Thr|Arg|Gly|Ala|Ile|Arg|Ile|Glu|
| |130| | | | |135| | | | |140| | | | |
|Lys|Asn|Ala|Asp|Leu|Cys|Tyr|Leu|Ser|Thr|Val|Asp|Trp|Ser|Leu|Ile|
|145| | | | |150| | | | |155| | | | |160|
|Leu|Asp|Ala|Val|Ser|Asn|Asn|Tyr|Ile|Val|Gly|Asn|Lys|Pro|Pro|Lys|
| | | | |165| | | | |170| | | | |175| |
|Glu|Cys|Gly|Asp|Leu|Cys|Pro|Gly|Thr|Met|Glu|Glu|Lys|Pro|Met|Cys|
| | | |180| | | | |185| | | | |190| | |
|Glu|Lys|Thr|Thr|Ile|Asn|Asn|Glu|Tyr|Asn|Tyr|Arg|Cys|Trp|Thr|Thr|
| | |195| | | | |200| | | | |205| | | |
|Asn|Arg|Cys|Gln|Lys|Met|Cys|Pro|Ser|Thr|Cys|Gly|Lys|Arg|Ala|Cys|
| |210| | | | |215| | | | |220| | | | |
|Thr|Glu|Asn|Asn|Glu|Cys|Cys|His|Pro|Glu|Cys|Leu|Gly|Ser|Cys|Ser|
|225| | | | |230| | | | |235| | | | |240|
|Ala|Pro|Asp|Asn|Asp|Thr|Ala|Cys|Val|Ala|Cys|Arg|His|Tyr|Tyr|Tyr|
| | | | |245| | | | |250| | | | |255| |
|Ala|Gly|Val|Cys|Val|Pro|Ala|Cys|Pro|Pro|Asn|Thr|Tyr|Arg|Phe|Glu|
| | | |260| | | | |265| | | | |270| | |
|Gly|Trp|Arg|Cys|Val|Asp|Arg|Asp|Phe|Cys|Ala|Asn|Ile|Leu|Ser|Ala|
| | |275| | | | |280| | | | |285| | | |
|Glu|Ser|Ser|Asp|Ser|Glu|Gly|Phe|Val|Ile|His|Asp|Gly|Glu|Cys|Met|
| |290| | | | |295| | | | |300| | | | |
|Gln|Glu|Cys|Pro|Ser|Gly|Phe|Ile|Arg|Asn|Gly|Ser|Gln|Ser|Met|Tyr|
|305| | | | |310| | | | |315| | | | |320|
|Cys|Ile|Pro|Cys|Glu|Gly|Pro|Cys|Pro|Lys|Val|Cys|Glu|Glu|Glu|Lys|
| | | | |325| | | | |330| | | | |335| |
|Lys|Thr|Lys|Thr|Ile|Asp|Ser|Val|Thr|Ser|Ala|Gln|Met|Leu|Gln|Gly|
| | |340| | | | |345| | | | |350| | | |
|Cys|Thr|Ile|Phe|Lys|Gly|Asn|Leu|Leu|Ile|Asn|Ile|Arg|Arg|Gly|Asn|
| |355| | | | |360| | | | |365| | | | |
|Asn|Ile|Ala|Ser|Glu|Leu|Glu|Asn|Phe|Met|Gly|Leu|Ile|Glu|Val|Val|
| |370| | | | |375| | | | |380| | | | |
|Thr|Gly|Tyr|Val|Lys|Ile|Arg|His|Ser|His|Ala|Leu|Val|Ser|Leu|Ser|
|385| | | | |390| | | | |395| | | | |400|
|Phe|Leu|Lys|Asn|Leu|Arg|Leu|Ile|Leu|Gly|Glu|Glu|Gln|Leu|Glu|Gly|

-continued

```
                    405                 410                 415
Asn Tyr Ser Phe Tyr Val Leu Asp Asn Gln Asn Leu Gln Gln Leu Trp
                420                 425                 430

Asp Trp Asp His Arg Asn Leu Thr Ile Lys Ala Gly Lys Met Tyr Phe
            435                 440                 445

Ala Phe Asn Pro Lys Leu Cys Val Ser Glu Ile Tyr Arg Met Glu Glu
        450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu Arg Phe Thr
                485                 490                 495

Ser Thr Thr Thr Ser Lys Asn Arg Ile Ile Ile Thr Trp His Arg Tyr
            500                 505                 510

<210> SEQ ID NO 83
<211> LENGTH: 941
<212> TYPE: PRT
<213> ORGANISM: Artificial
<220> FEATURE:
<223> OTHER INFORMATION: C1 fragment with His Tag

<400> SEQUENCE: 83

Met Lys Ser Gly Ser Gly Gly Ser Pro Thr Ser Leu Trp Gly Leu Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
        50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
        130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
        210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
```

```
             260                 265                 270
Gly Trp Arg Cys Val Asp Arg Asp Phe Cys Ala Asn Ile Leu Ser Ala
            275                 280                 285

Glu Ser Ser Asp Ser Glu Gly Phe Val Ile His Asp Gly Glu Cys Met
290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
                325                 330                 335

Lys Thr Lys Thr Ile Asp Ser Val Thr Ser Ala Gln Met Leu Gln Gly
            340                 345                 350

Cys Thr Ile Phe Lys Gly Asn Leu Leu Ile Asn Ile Arg Arg Gly Asn
            355                 360                 365

Asn Ile Ala Ser Glu Leu Glu Asn Phe Met Gly Leu Ile Glu Val Val
            370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Leu Glu Gly
                405                 410                 415

Asn Tyr Ser Phe Tyr Val Leu Asp Asn Gln Asn Leu Gln Gln Leu Trp
                420                 425                 430

Asp Trp Asp His Arg Asn Leu Thr Ile Lys Ala Gly Lys Met Tyr Phe
            435                 440                 445

Ala Phe Asn Pro Lys Leu Cys Val Ser Glu Ile Tyr Arg Met Glu Glu
            450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
                485                 490                 495

Ser Thr Thr Thr Ser Lys Asn Arg Ile Ile Ile Thr Trp His Arg Tyr
                500                 505                 510

Arg Pro Pro Asp Tyr Arg Asp Leu Ile Ser Phe Thr Val Tyr Tyr Lys
            515                 520                 525

Glu Ala Pro Phe Lys Asn Val Thr Glu Tyr Asp Gly Gln Asp Ala Cys
            530                 535                 540

Gly Ser Asn Ser Trp Asn Met Val Asp Val Asp Leu Pro Pro Asn Lys
545                 550                 555                 560

Glu Gly Glu Pro Gly Ile Leu Leu His Gly Leu Lys Pro Trp Thr Gln
                565                 570                 575

Tyr Ala Val Tyr Val Lys Ala Val Thr Leu Thr Met Val Glu Asn Asp
            580                 585                 590

His Ile Arg Gly Ala Lys Ser Glu Ile Leu Tyr Ile Arg Thr Asn Ala
            595                 600                 605

Ser Val Pro Ser Ile Pro Leu Asp Val Leu Ser Ala Ser Asn Ser Ser
            610                 615                 620

Ser Gln Leu Ile Val Lys Trp Asn Pro Pro Thr Leu Pro Asn Gly Asn
625                 630                 635                 640

Leu Ser Tyr Tyr Ile Val Arg Trp Gln Arg Gln Pro Gln Asp Gly Tyr
                645                 650                 655

Leu Tyr Arg His Asn Tyr Cys Ser Lys Asp Lys Ile Pro Ile Arg Lys
                660                 665                 670

Tyr Ala Asp Gly Thr Ile Asp Val Glu Glu Val Thr Glu Asn Pro Lys
            675                 680                 685
```

```
Thr Glu Val Cys Gly Gly Asp Lys Gly Pro Cys Cys Ala Cys Pro Lys
690                 695                 700

Thr Glu Ala Glu Lys Gln Ala Glu Lys Glu Glu Ala Glu Tyr Arg Lys
705                 710                 715                 720

Val Phe Glu Asn Phe Leu His Asn Ser Ile Phe Val Pro Arg Pro Glu
            725                 730                 735

Arg Arg Arg Arg Asp Val Met Gln Val Ala Asn Thr Thr Met Ser Ser
            740                 745                 750

Arg Ser Arg Asn Thr Thr Val Ala Asp Thr Tyr Asn Ile Thr Asp Pro
        755                 760                 765

Glu Glu Phe Glu Thr Glu Tyr Pro Phe Phe Glu Ser Arg Val Asp Asn
770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                805                 810                 815

Ala Ser Asn Phe Val Phe Ala Arg Thr Met Pro Ala Glu Gly Ala Asp
            820                 825                 830

Asp Ile Pro Gly Pro Val Thr Trp Glu Pro Arg Pro Glu Asn Ser Ile
        835                 840                 845

Phe Leu Lys Trp Pro Glu Pro Glu Asn Pro Asn Gly Leu Ile Leu Met
850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                885                 890                 895

Asn Pro Gly Asn Tyr Thr Ala Arg Ile Gln Ala Thr Ser Leu Ser Gly
            900                 905                 910

Asn Gly Ser Trp Thr Asp Pro Val Phe Phe Tyr Val Pro Ala Lys Thr
        915                 920                 925

Thr Tyr Glu Asn Phe Met His His His His His His
930                 935                 940

<210> SEQ ID NO 84
<211> LENGTH: 939
<212> TYPE: PRT
<213> ORGANISM: Artificial
<220> FEATURE:
<223> OTHER INFORMATION: C2 fragment with His Tag

<400> SEQUENCE: 84

Met Lys Ser Gly Ser Gly Gly Ser Pro Thr Ser Leu Trp Gly Leu
1               5                   10                  15

Val Phe Leu Ser Ala Ala Leu Ser Leu Trp Pro Thr Ser Gly Glu Ile
            20                  25                  30

Cys Gly Pro Gly Ile Asp Ile Arg Asn Asp Tyr Gln Gln Leu Lys Arg
        35                  40                  45

Leu Glu Asn Cys Thr Val Ile Glu Gly Phe Leu His Ile Leu Leu Ile
    50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110
```

```
Tyr Asn Tyr Ala Leu Val Ile Phe Glu Met Thr Asn Leu Lys Asp Ile
            115                 120                 125
Gly Leu Tyr Asn Leu Arg Asn Ile Thr Arg Gly Ala Ile Arg Ile Glu
        130                 135                 140
Lys Asn Ala Asp Leu Cys Tyr Leu Ser Thr Ile Asp Trp Ser Leu Ile
145                 150                 155                 160
Leu Asp Ala Val Ser Asn Asn Tyr Ile Val Gly Asn Lys Pro Pro Lys
                165                 170                 175
Glu Cys Gly Asp Leu Cys Pro Gly Thr Leu Glu Lys Pro Met Cys
            180                 185                 190
Glu Lys Thr Thr Ile Asn Asn Glu Tyr Asn Tyr Arg Cys Trp Thr Thr
            195                 200                 205
Asn Arg Cys Gln Lys Met Cys Pro Ser Val Cys Gly Lys Arg Ala Cys
        210                 215                 220
Thr Glu Asn Asn Glu Cys Cys His Pro Glu Cys Leu Gly Ser Cys His
225                 230                 235                 240
Thr Pro Asp Asp Asn Thr Thr Cys Val Ala Cys Arg His Tyr Tyr Tyr
                245                 250                 255
Lys Gly Val Cys Val Pro Ala Cys Pro Pro Gly Thr Tyr Arg Phe Glu
            260                 265                 270
Gly Trp Arg Cys Val Asp Arg Asp Phe Cys Ala Asn Ile Pro Asn Ala
        275                 280                 285
Glu Ser Ser Asp Ser Asp Gly Phe Val Ile His Asp Asp Glu Cys Met
        290                 295                 300
Gln Glu Cys Pro Ser Gly Phe Ile Arg Asn Ser Thr Gln Ser Met Tyr
305                 310                 315                 320
Cys Ile Pro Cys Glu Gly Pro Cys Pro Lys Val Cys Gly Asp Glu Glu
                325                 330                 335
Lys Lys Thr Lys Thr Ile Asp Ser Val Thr Ser Ala Gln Met Leu Gln
            340                 345                 350
Gly Cys Thr Ile Leu Lys Gly Asn Leu Leu Ile Asn Ile Arg Arg Gly
        355                 360                 365
Asn Asn Ile Ala Ser Glu Leu Glu Asn Phe Met Gly Leu Ile Glu Val
        370                 375                 380
Val Thr Gly Tyr Val Lys Ile Arg His Ser His Ala Leu Val Ser Leu
385                 390                 395                 400
Ser Phe Leu Lys Asn Leu Arg Leu Ile Leu Gly Glu Glu Gln Leu Glu
                405                 410                 415
Gly Asn Tyr Ser Phe Tyr Val Leu Asp Asn Gln Asn Leu Gln Gln Leu
            420                 425                 430
Trp Asp Trp Asn His Arg Asn Leu Thr Val Arg Ser Gly Lys Met Tyr
        435                 440                 445
Phe Ala Phe Asn Pro Lys Leu Cys Val Ser Glu Ile Tyr Arg Met Glu
450                 455                 460
Glu Val Thr Gly Thr Lys Gly Arg Gln Ser Lys Gly Asp Ile Asn Thr
465                 470                 475                 480
Arg Asn Asn Gly Glu Arg Ala Ser Cys Glu Ser Asp Val Leu Arg Phe
                485                 490                 495
Thr Ser Thr Thr Thr Trp Lys Asn Arg Ile Ile Ile Thr Trp His Arg
            500                 505                 510
Tyr Arg Pro Pro Asp Tyr Arg Asp Leu Ile Ser Phe Thr Val Tyr Tyr
        515                 520                 525
```

```
Lys Glu Ala Pro Phe Lys Asn Val Thr Glu Tyr Asp Gly Gln Asp Ala
    530                 535                 540

Cys Gly Ser Asn Ser Trp Asn Met Val Asp Val Asp Leu Pro Pro Asn
545                 550                 555                 560

Lys Asp Val Glu Pro Gly Ile Leu Leu His Gly Leu Lys Pro Trp Thr
                565                 570                 575

Gln Tyr Ala Val Tyr Val Lys Ala Val Thr Leu Thr Met Val Glu Asn
            580                 585                 590

Asp His Ile Arg Gly Ala Lys Ser Glu Ile Leu Tyr Ile Arg Thr Asn
        595                 600                 605

Ala Ser Val Pro Ser Ile Pro Leu Asp Val Leu Ser Ala Ser Asn Ser
    610                 615                 620

Ser Ser Gln Leu Ile Val Lys Trp Asn Pro Pro Ser Leu Pro Asn Gly
625                 630                 635                 640

Asn Leu Ser Tyr Tyr Ile Val Arg Trp Gln Arg Gln Pro Gln Asp Gly
                645                 650                 655

Tyr Leu Tyr Arg His Asn Tyr Cys Ser Lys Asp Lys Ile Pro Ile Arg
            660                 665                 670

Lys Tyr Ala Asp Gly Thr Ile Asp Ile Glu Glu Val Thr Glu Asn Pro
        675                 680                 685

Lys Thr Glu Val Cys Gly Gly Glu Lys Gly Pro Cys Cys Ala Cys Pro
    690                 695                 700

Lys Thr Glu Ala Glu Lys Gln Ala Glu Lys Glu Glu Ala Glu Tyr Arg
705                 710                 715                 720

Lys Val Phe Glu Asn Phe Leu His Asn Ser Ile Phe Val Pro Arg Pro
                725                 730                 735

Glu Arg Lys Arg Arg Asp Val Met Gln Val Ala Asn Thr Thr Met Ser
            740                 745                 750

Ser Arg Ser Arg Asn Thr Thr Ala Ala Asp Thr Tyr Asn Ile Thr Asp
        755                 760                 765

Pro Glu Glu Leu Glu Thr Glu Tyr Pro Phe Phe Glu Ser Arg Val Asp
    770                 775                 780

Asn Lys Glu Arg Thr Val Ile Ser Asn Leu Arg Pro Phe Thr Leu Tyr
785                 790                 795                 800

Arg Ile Asp Ile His Ser Cys Asn His Glu Ala Glu Lys Leu Gly Cys
                805                 810                 815

Ser Ala Ser Asn Phe Val Phe Ala Arg Thr Met Pro Ala Glu Gly Ala
            820                 825                 830

Asp Asp Ile Pro Gly Pro Val Thr Trp Glu Pro Arg Pro Glu Asn Ser
        835                 840                 845

Ile Phe Leu Lys Trp Pro Glu Pro Glu Asn Pro Asn Gly Leu Ile Leu
    850                 855                 860

Met Tyr Glu Ile Lys Tyr Gly Ser Gln Val Glu Asp Gln Arg Glu Cys
865                 870                 875                 880

Val Ser Arg Gln Glu Tyr Arg Lys Tyr Gly Gly Ala Lys Leu Asn Arg
                885                 890                 895

Leu Asn Pro Gly Asn Tyr Thr Ala Arg Ile Gln Ala Thr Ser Leu Ser
            900                 905                 910

Gly Asn Gly Ser Trp Thr Asp Pro Val Phe Phe Tyr Val Gln Ala Lys
        915                 920                 925

Thr Gly Tyr Glu Asn His His His His His
    930                 935
```

```
<210> SEQ ID NO 85
<211> LENGTH: 938
<212> TYPE: PRT
<213> ORGANISM: Artificial
<220> FEATURE:
<223> OTHER INFORMATION: C3 fragment with His Tag

<400> SEQUENCE: 85

Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
            115                 120                 125

Gly Leu Tyr Asn Leu Arg Asn Ile Thr Arg Gly Ala Ile Arg Ile Glu
130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Lys Pro Met Cys
            180                 185                 190

Glu Lys Thr Thr Ile Asn Asn Glu Tyr Asn Tyr Arg Cys Trp Thr Thr
            195                 200                 205

Asn Arg Cys Gln Lys Met Cys Pro Ser Thr Cys Gly Lys Arg Ala Cys
210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
            275                 280                 285

Glu Ser Ser Asp Ser Glu Gly Phe Val Ile His Asp Gly Glu Cys Met
290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Lys
                325                 330                 335

Lys Thr Lys Thr Ile Asp Ser Val Thr Ser Ala Gln Met Leu Gln Gly
            340                 345                 350

Cys Thr Ile Phe Lys Gly Asn Leu Leu Ile Asn Ile Arg Arg Gly Asn
            355                 360                 365

Asn Ile Ala Ser Glu Leu Glu Asn Phe Met Gly Leu Ile Glu Val Val
```

```
            370                 375                 380
Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
                405                 410                 415

Asn Tyr Ser Phe Tyr Val Leu Asp Asn Gln Asn Leu Gln Gln Leu Trp
            420                 425                 430

Asp Trp Asp His Arg Asn Leu Thr Ile Lys Ala Gly Lys Met Tyr Phe
            435                 440                 445

Ala Phe Asn Pro Lys Leu Cys Val Ser Glu Ile Tyr Arg Met Glu Glu
            450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu Arg Phe Thr
                485                 490                 495

Ser Thr Thr Thr Ser Lys Asn Arg Ile Ile Thr Trp His Arg Tyr
            500                 505                 510

Arg Pro Pro Asp Tyr Arg Asp Leu Ile Ser Phe Thr Val Tyr Tyr Lys
            515                 520                 525

Glu Ala Pro Phe Lys Asn Val Thr Glu Tyr Asp Gly Gln Asp Ala Cys
            530                 535                 540

Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
                565                 570                 575

Tyr Ala Val Tyr Val Lys Ala Val Thr Leu Thr Met Val Glu Asn Asp
            580                 585                 590

His Ile Arg Gly Ala Lys Ser Glu Ile Leu Tyr Ile Arg Thr Asn Ala
            595                 600                 605

Ser Val Pro Ser Ile Pro Leu Asp Val Leu Ser Ala Ser Asn Ser Ser
            610                 615                 620

Ser Gln Leu Ile Val Lys Trp Asn Pro Pro Ser Leu Pro Asn Gly Asn
625                 630                 635                 640

Leu Ser Tyr Tyr Ile Val Arg Trp Gln Arg Gln Pro Gln Asp Gly Tyr
                645                 650                 655

Leu Tyr Arg His Asn Tyr Cys Ser Lys Asp Lys Ile Pro Ile Arg Lys
            660                 665                 670

Tyr Ala Asp Gly Thr Ile Asp Ile Glu Glu Val Thr Glu Asn Pro Lys
            675                 680                 685

Thr Glu Val Cys Gly Gly Glu Lys Gly Pro Cys Cys Ala Cys Pro Lys
            690                 695                 700

Thr Glu Ala Glu Lys Gln Ala Glu Lys Glu Glu Ala Glu Tyr Arg Lys
705                 710                 715                 720

Val Phe Glu Asn Phe Leu His Asn Ser Ile Phe Val Pro Arg Pro Glu
                725                 730                 735

Arg Lys Arg Arg Asp Val Met Gln Val Ala Asn Thr Thr Met Ser Ser
            740                 745                 750

Arg Ser Arg Asn Thr Thr Ala Ala Asp Thr Tyr Asn Ile Thr Asp Pro
            755                 760                 765

Glu Glu Leu Glu Thr Glu Tyr Pro Phe Phe Glu Ser Arg Val Asp Asn
            770                 775                 780

Lys Glu Arg Thr Val Ile Ser Asn Leu Arg Pro Phe Thr Leu Tyr Arg
785                 790                 795                 800
```

```
Ile Asp Ile His Ser Cys Asn His Glu Ala Glu Lys Leu Gly Cys Ser
            805                 810                 815

Ala Ser Asn Phe Val Phe Ala Arg Thr Met Pro Ala Glu Gly Ala Asp
            820                 825                 830

Asp Ile Pro Gly Pro Val Thr Trp Glu Pro Arg Pro Glu Asn Ser Ile
            835                 840                 845

Phe Leu Lys Trp Pro Glu Pro Glu Asn Pro Asn Gly Leu Ile Leu Met
            850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Ala Lys Leu Asn Arg Leu
            885                 890                 895

Asn Pro Gly Asn Tyr Thr Ala Arg Ile Gln Ala Thr Ser Leu Ser Gly
            900                 905                 910

Asn Gly Ser Trp Thr Asp Pro Val Phe Phe Tyr Val Gln Ala Lys Thr
            915                 920                 925

Gly Tyr Glu Asn His His His His His His
    930                 935

<210> SEQ ID NO 86
<211> LENGTH: 938
<212> TYPE: PRT
<213> ORGANISM: Artificial
<220> FEATURE:
<223> OTHER INFORMATION: C4 fragment with His Tag

<400> SEQUENCE: 86

Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
            20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
    50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
            115                 120                 125

Gly Leu Tyr Asn Leu Arg Asn Ile Thr Arg Gly Ala Ile Arg Ile Glu
        130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
            195                 200                 205

Asn Arg Cys Gln Lys Met Cys Pro Ser Thr Cys Gly Lys Arg Ala Cys
        210                 215                 220
```

-continued

```
Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
            245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
            275                 280                 285

Glu Ser Ser Asp Ser Glu Gly Phe Val Ile His Asp Gly Glu Cys Met
            290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
            325                 330                 335

Lys Thr Lys Thr Ile Asp Ser Val Thr Ser Ala Gln Met Leu Gln Gly
            340                 345                 350

Cys Thr Ile Phe Lys Gly Asn Leu Leu Ile Asn Ile Arg Arg Gly Asn
            355                 360                 365

Asn Ile Ala Ser Glu Leu Glu Asn Phe Met Gly Leu Ile Glu Val Val
370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
            405                 410                 415

Asn Tyr Ser Phe Tyr Val Leu Asp Asn Gln Asn Leu Gln Gln Leu Trp
            420                 425                 430

Asp Trp Asp His Arg Asn Leu Thr Ile Lys Ala Gly Lys Met Tyr Phe
            435                 440                 445

Ala Phe Asn Pro Lys Leu Cys Val Ser Glu Ile Tyr Arg Met Glu Glu
450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
            485                 490                 495

Ser Thr Thr Thr Trp Lys Asn Arg Ile Ile Ile Thr Trp His Arg Tyr
            500                 505                 510

Arg Pro Pro Asp Tyr Arg Asp Leu Ile Ser Phe Thr Val Tyr Tyr Lys
            515                 520                 525

Glu Ala Pro Phe Lys Asn Val Thr Glu Tyr Asp Gly Gln Asp Ala Cys
            530                 535                 540

Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
            565                 570                 575

Tyr Ala Val Tyr Val Lys Ala Val Thr Leu Thr Met Val Glu Asn Asp
            580                 585                 590

His Ile Arg Gly Ala Lys Ser Glu Ile Leu Tyr Ile Arg Thr Asn Ala
            595                 600                 605

Ser Val Pro Ser Ile Pro Leu Asp Val Leu Ser Ala Ser Asn Ser Ser
            610                 615                 620

Ser Gln Leu Ile Val Lys Trp Asn Pro Pro Ser Leu Pro Asn Gly Asn
625                 630                 635                 640
```

Leu Ser Tyr Tyr Ile Val Arg Trp Gln Arg Gln Pro Gln Asp Gly Tyr
            645                 650                 655

Leu Tyr Arg His Asn Tyr Cys Ser Lys Asp Lys Ile Pro Ile Arg Lys
        660                 665                 670

Tyr Ala Asp Gly Thr Ile Asp Ile Glu Glu Val Thr Glu Asn Pro Lys
        675                 680                 685

Thr Glu Val Cys Gly Gly Lys Gly Pro Cys Cys Ala Cys Pro Lys
    690                 695                 700

Thr Glu Ala Glu Lys Gln Ala Glu Lys Glu Glu Ala Glu Tyr Arg Lys
705                 710                 715                 720

Val Phe Glu Asn Phe Leu His Asn Ser Ile Phe Val Pro Arg Pro Glu
            725                 730                 735

Arg Lys Arg Arg Asp Val Met Gln Val Ala Asn Thr Thr Met Ser Ser
                740                 745                 750

Arg Ser Arg Asn Thr Thr Ala Ala Asp Thr Tyr Asn Ile Thr Asp Pro
        755                 760                 765

Glu Glu Leu Glu Thr Glu Tyr Pro Phe Phe Glu Ser Arg Val Asp Asn
    770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
            805                 810                 815

Ala Ser Asn Phe Val Phe Ala Arg Thr Met Pro Ala Glu Gly Ala Asp
                820                 825                 830

Asp Ile Pro Gly Pro Val Thr Trp Glu Pro Arg Pro Glu Asn Ser Ile
        835                 840                 845

Phe Leu Lys Trp Pro Glu Pro Glu Asn Pro Asn Gly Leu Ile Leu Met
    850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
            885                 890                 895

Asn Pro Gly Asn Tyr Thr Ala Arg Ile Gln Ala Thr Ser Leu Ser Gly
                900                 905                 910

Asn Gly Ser Trp Thr Asp Pro Val Phe Phe Tyr Val Gln Ala Lys Thr
        915                 920                 925

Gly Tyr Glu Asn His His His His His
    930                 935

<210> SEQ ID NO 87
<211> LENGTH: 938
<212> TYPE: PRT
<213> ORGANISM: Artificial
<220> FEATURE:
<223> OTHER INFORMATION: C6 fragment with His Tag

<400> SEQUENCE: 87

Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
            20                  25                  30

Cys Gly Pro Gly Ile Asp Ile Arg Asn Asp Tyr Gln Gln Leu Lys Arg
        35                  40                  45

Leu Glu Asn Cys Thr Val Ile Glu Gly Tyr Leu His Ile Leu Leu Ile
    50                  55                  60

```
Ser Lys Ala Glu Asp Tyr Arg Ser Tyr Arg Phe Pro Lys Leu Thr Val
 65                  70                  75                  80

Ile Thr Glu Tyr Leu Leu Leu Phe Arg Val Ala Gly Leu Glu Ser Leu
             85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
            115                 120                 125

Gly Leu Tyr Asn Leu Arg Asn Ile Thr Arg Gly Ala Ile Arg Ile Glu
            130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
            195                 200                 205

Asn Arg Cys Gln Lys Met Cys Pro Ser Thr Cys Gly Lys Arg Ala Cys
210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
            245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
            275                 280                 285

Glu Ser Ser Asp Ser Glu Gly Phe Val Ile His Asp Gly Glu Cys Met
            290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
            325                 330                 335

Lys Thr Lys Thr Ile Asp Ser Val Thr Ser Ala Gln Met Leu Gln Gly
            340                 345                 350

Cys Thr Ile Phe Lys Gly Asn Leu Leu Ile Asn Ile Arg Arg Gly Asn
            355                 360                 365

Asn Ile Ala Ser Glu Leu Glu Asn Phe Met Gly Leu Ile Glu Val Val
            370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Gln Leu Glu Gly
                405                 410                 415

Asn Tyr Ser Phe Tyr Val Leu Asp Asn Gln Asn Leu Gln Gln Leu Trp
            420                 425                 430

Asp Trp Asp His Arg Asn Leu Thr Ile Lys Ala Gly Lys Met Tyr Phe
            435                 440                 445

Ala Phe Asn Pro Lys Leu Cys Val Ser Glu Ile Tyr Arg Met Glu Glu
            450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu Arg Phe Thr
```

```
            485                 490                 495
Ser Thr Thr Thr Trp Lys Asn Arg Ile Ile Thr Trp His Arg Tyr
            500                 505                 510

Arg Pro Pro Asp Tyr Arg Asp Leu Ile Ser Phe Thr Val Tyr Lys
            515                 520                 525

Glu Ala Pro Phe Lys Asn Val Thr Glu Tyr Asp Gly Gln Asp Cys
            530                 535                 540

Gly Ser Asn Ser Trp Asn Met Val Asp Val Asp Leu Pro Pro Asn Lys
545             550                 555                 560

Asp Val Glu Pro Gly Ile Leu Leu His Gly Leu Lys Pro Trp Thr Gln
                565                 570                 575

Tyr Ala Val Tyr Val Lys Ala Val Thr Leu Thr Met Val Glu Asn Asp
            580                 585                 590

His Ile Arg Gly Ala Lys Ser Glu Ile Leu Tyr Ile Arg Thr Asn Ala
            595                 600                 605

Ser Val Pro Ser Ile Pro Leu Asp Val Leu Ser Ala Ser Asn Ser Ser
            610                 615                 620

Ser Gln Leu Ile Val Lys Trp Asn Pro Pro Ser Leu Pro Asn Gly Asn
625             630                 635                 640

Leu Ser Tyr Tyr Ile Val Arg Trp Gln Arg Gln Pro Gln Asp Gly Tyr
                645                 650                 655

Leu Tyr Arg His Asn Tyr Cys Ser Lys Asp Lys Ile Pro Ile Arg Lys
            660                 665                 670

Tyr Ala Asp Gly Thr Ile Asp Ile Glu Glu Val Thr Glu Asn Pro Lys
            675                 680                 685

Thr Glu Val Cys Gly Gly Glu Lys Gly Pro Cys Cys Ala Cys Pro Lys
            690                 695                 700

Thr Glu Ala Glu Lys Gln Ala Glu Lys Glu Glu Ala Glu Tyr Arg Lys
705             710                 715                 720

Val Phe Glu Asn Phe Leu His Asn Ser Ile Phe Val Pro Arg Pro Glu
                725                 730                 735

Arg Lys Arg Arg Asp Val Met Gln Val Ala Asn Thr Thr Met Ser Ser
            740                 745                 750

Arg Ser Arg Asn Thr Thr Ala Ala Asp Thr Tyr Asn Ile Thr Asp Pro
            755                 760                 765

Glu Glu Leu Glu Thr Glu Tyr Pro Phe Phe Glu Ser Arg Val Asp Asn
            770                 775                 780

Lys Glu Arg Thr Val Ile Ser Asn Leu Arg Pro Phe Thr Leu Tyr Arg
785             790                 795                 800

Ile Asp Ile His Ser Cys Asn His Glu Ala Glu Lys Leu Gly Cys Ser
                805                 810                 815

Ala Ser Asn Phe Val Phe Ala Arg Thr Met Pro Ala Glu Gly Ala Asp
            820                 825                 830

Asp Ile Pro Gly Pro Val Thr Trp Glu Pro Arg Pro Glu Asn Ser Ile
            835                 840                 845

Phe Leu Lys Trp Pro Glu Pro Glu Asn Pro Asn Gly Leu Ile Leu Met
850             855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                885                 890                 895

Asn Pro Gly Asn Tyr Thr Ala Arg Ile Gln Ala Thr Ser Leu Ser Gly
            900                 905                 910
```

Asn Gly Ser Trp Thr Asp Pro Val Phe Phe Tyr Val Gln Ala Lys Thr
            915                 920                 925

Gly Tyr Glu Asn His His His His His
        930                 935

<210> SEQ ID NO 88
<211> LENGTH: 939
<212> TYPE: PRT
<213> ORGANISM: Artificial
<220> FEATURE:
<223> OTHER INFORMATION: C7 fragment with His Tag

<400> SEQUENCE: 88

Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Val Cys Gly Lys Arg Ala Cys
    210                 215                 220

Thr Glu Asn Asn Glu Cys Cys His Pro Glu Cys Leu Gly Ser Cys His
225                 230                 235                 240

Thr Pro Asp Asp Asn Thr Thr Cys Val Ala Cys Arg His Tyr Tyr Tyr
                245                 250                 255

Lys Gly Val Cys Val Pro Ala Cys Pro Pro Gly Thr Tyr Arg Phe Glu
            260                 265                 270

Gly Trp Arg Cys Val Asp Arg Asp Phe Cys Ala Asn Ile Pro Asn Ala
        275                 280                 285

Glu Ser Ser Asp Ser Asp Gly Phe Val Ile His Asp Asp Glu Cys Met
    290                 295                 300

Gln Glu Cys Pro Ser Gly Phe Ile Arg Asn Ser Thr Gln Ser Met Tyr
305                 310                 315                 320

Cys Ile Pro Cys Glu Gly Pro Cys Pro Lys Val Cys Gly Asp Glu Glu
                325                 330                 335

```
Lys Lys Thr Lys Thr Ile Asp Ser Val Thr Ser Ala Gln Met Leu Gln
            340                 345                 350

Gly Cys Thr Ile Leu Lys Gly Asn Leu Leu Ile Asn Ile Arg Arg Gly
            355                 360                 365

Asn Asn Ile Ala Ser Glu Leu Glu Asn Phe Met Gly Leu Ile Glu Val
370                 375                 380

Val Thr Gly Tyr Val Lys Ile Arg His Ser His Ala Leu Val Ser Leu
385                 390                 395                 400

Ser Phe Leu Lys Asn Leu Arg Leu Ile Leu Gly Glu Gln Leu Glu
                405                 410                 415

Gly Asn Tyr Ser Phe Tyr Val Leu Asp Asn Gln Asn Leu Gln Gln Leu
            420                 425                 430

Trp Asp Trp Asp His Arg Asn Leu Thr Ile Lys Ala Gly Lys Met Tyr
            435                 440                 445

Phe Ala Phe Asn Pro Lys Leu Cys Val Ser Glu Ile Tyr Arg Met Glu
            450                 455                 460

Glu Val Thr Gly Thr Lys Gly Arg Gln Ser Lys Gly Asp Ile Asn Thr
465                 470                 475                 480

Arg Asn Asn Gly Glu Arg Ala Ser Cys Glu Ser Asp Val Leu His Phe
                485                 490                 495

Thr Ser Thr Thr Thr Ser Lys Asn Arg Ile Ile Ile Thr Trp His Arg
            500                 505                 510

Tyr Arg Pro Pro Asp Tyr Arg Asp Leu Ile Ser Phe Thr Val Tyr Tyr
            515                 520                 525

Lys Glu Ala Pro Phe Lys Asn Val Thr Glu Tyr Asp Gly Gln Asp Ala
            530                 535                 540

Cys Gly Ser Asn Ser Trp Asn Met Val Asp Val Asp Leu Pro Pro Asn
545                 550                 555                 560

Lys Asp Val Glu Pro Gly Ile Leu Leu His Gly Leu Lys Pro Trp Thr
                565                 570                 575

Gln Tyr Ala Val Tyr Val Lys Ala Val Thr Leu Thr Met Val Glu Asn
            580                 585                 590

Asp His Ile Arg Gly Ala Lys Ser Glu Ile Leu Tyr Ile Arg Thr Asn
            595                 600                 605

Ala Ser Val Pro Ser Ile Pro Leu Asp Val Leu Ser Ala Ser Asn Ser
610                 615                 620

Ser Ser Gln Leu Ile Val Lys Trp Asn Pro Pro Ser Leu Pro Asn Gly
625                 630                 635                 640

Asn Leu Ser Tyr Tyr Ile Val Arg Trp Gln Arg Gln Pro Gln Asp Gly
                645                 650                 655

Tyr Leu Tyr Arg His Asn Tyr Cys Ser Lys Asp Lys Ile Pro Ile Arg
            660                 665                 670

Lys Tyr Ala Asp Gly Thr Ile Asp Ile Glu Glu Val Thr Glu Asn Pro
            675                 680                 685

Lys Thr Glu Val Cys Gly Gly Glu Lys Gly Pro Cys Cys Ala Cys Pro
            690                 695                 700

Lys Thr Glu Ala Glu Lys Gln Ala Glu Lys Glu Glu Ala Glu Tyr Arg
705                 710                 715                 720

Lys Val Phe Glu Asn Phe Leu His Asn Ser Ile Phe Val Pro Arg Pro
                725                 730                 735

Glu Arg Lys Arg Arg Asp Val Met Gln Val Ala Asn Thr Thr Met Ser
            740                 745                 750
```

-continued

```
Ser Arg Ser Arg Asn Thr Thr Ala Ala Asp Thr Tyr Asn Ile Thr Asp
            755                 760                 765

Pro Glu Glu Leu Glu Thr Glu Tyr Pro Phe Phe Glu Ser Arg Val Asp
    770                 775                 780

Asn Lys Glu Arg Thr Val Ile Ser Asn Leu Arg Pro Phe Thr Leu Tyr
785                 790                 795                 800

Arg Ile Asp Ile His Ser Cys Asn His Glu Ala Glu Lys Leu Gly Cys
                805                 810                 815

Ser Ala Ser Asn Phe Val Phe Ala Arg Thr Met Pro Ala Glu Gly Ala
            820                 825                 830

Asp Asp Ile Pro Gly Pro Val Thr Trp Glu Pro Arg Pro Glu Asn Ser
            835                 840                 845

Ile Phe Leu Lys Trp Pro Glu Pro Glu Asn Pro Asn Gly Leu Ile Leu
            850                 855                 860

Met Tyr Glu Ile Lys Tyr Gly Ser Gln Val Glu Asp Gln Arg Glu Cys
865                 870                 875                 880

Val Ser Arg Gln Glu Tyr Arg Lys Tyr Gly Gly Ala Lys Leu Asn Arg
                885                 890                 895

Leu Asn Pro Gly Asn Tyr Thr Ala Arg Ile Gln Ala Thr Ser Leu Ser
            900                 905                 910

Gly Asn Gly Ser Trp Thr Asp Pro Val Phe Phe Tyr Val Gln Ala Lys
            915                 920                 925

Thr Gly Tyr Glu Asn His His His His His
            930                 935
```

```
<210> SEQ ID NO 89
<211> LENGTH: 938
<212> TYPE: PRT
<213> ORGANISM: Artificial
<220> FEATURE:
<223> OTHER INFORMATION: C8 fragment with His Tag

<400> SEQUENCE: 89

Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
            20                  25                  30

Cys Gly Pro Gly Ile Asp Ile Arg Asn Asp Tyr Gln Gln Leu Lys Arg
        35                  40                  45

Leu Glu Asn Cys Thr Val Ile Glu Gly Tyr Leu His Ile Leu Leu Ile
    50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175
```

-continued

```
Glu Cys Gly Asp Leu Cys Pro Gly Thr Met Glu Glu Lys Pro Met Cys
            180                 185                 190
Glu Lys Thr Thr Ile Asn Asn Glu Tyr Asn Tyr Arg Cys Trp Thr Thr
        195                 200                 205
Asn Arg Cys Gln Lys Met Cys Pro Ser Thr Cys Gly Lys Arg Ala Cys
    210                 215                 220
Thr Glu Asn Asn Glu Cys Cys His Pro Glu Cys Leu Gly Ser Cys Ser
225                 230                 235                 240
Ala Pro Asp Asn Asp Thr Ala Cys Val Ala Cys Arg His Tyr Tyr Tyr
            245                 250                 255
Ala Gly Val Cys Val Pro Ala Cys Pro Pro Asn Thr Tyr Arg Phe Glu
            260                 265                 270
Gly Trp Arg Cys Val Asp Arg Asp Phe Cys Ala Asn Ile Leu Ser Ala
        275                 280                 285
Glu Ser Ser Asp Ser Glu Gly Phe Val Ile His Asp Gly Glu Cys Met
    290                 295                 300
Gln Glu Cys Pro Ser Gly Phe Ile Arg Asn Gly Ser Gln Ser Met Tyr
305                 310                 315                 320
Cys Ile Pro Cys Glu Gly Pro Cys Pro Lys Val Cys Glu Glu Lys
            325                 330                 335
Lys Thr Lys Thr Ile Asp Ser Val Thr Ser Ala Gln Met Leu Gln Gly
            340                 345                 350
Cys Thr Ile Phe Lys Gly Asn Leu Leu Ile Asn Ile Arg Arg Gly Asn
        355                 360                 365
Asn Ile Ala Ser Glu Leu Glu Asn Phe Met Gly Leu Ile Glu Val Val
    370                 375                 380
Thr Gly Tyr Val Lys Ile Arg His Ser His Ala Leu Val Ser Leu Ser
385                 390                 395                 400
Phe Leu Lys Asn Leu Arg Leu Ile Leu Gly Glu Gln Leu Glu Gly
            405                 410                 415
Asn Tyr Ser Phe Tyr Val Leu Asp Asn Gln Asn Leu Gln Leu Trp
        420                 425                 430
Asp Trp Asn His Arg Asn Leu Thr Val Arg Ser Gly Lys Met Tyr Phe
    435                 440                 445
Ala Phe Asn Pro Lys Leu Cys Val Ser Glu Ile Tyr Arg Met Glu Glu
    450                 455                 460
Val Thr Gly Thr Lys Gly Arg Gln Ser Lys Gly Asp Ile Asn Thr Arg
465                 470                 475                 480
Asn Asn Gly Glu Arg Ala Ser Cys Glu Ser Asp Val Leu His Phe Thr
            485                 490                 495
Ser Thr Thr Thr Ser Lys Asn Arg Ile Ile Ile Thr Trp His Arg Tyr
        500                 505                 510
Arg Pro Pro Asp Tyr Arg Asp Leu Ile Ser Phe Thr Val Tyr Tyr Lys
    515                 520                 525
Glu Ala Pro Phe Lys Asn Val Thr Glu Tyr Asp Gly Gln Asp Ala Cys
    530                 535                 540
Gly Ser Asn Ser Trp Asn Met Val Asp Val Asp Leu Pro Pro Asn Lys
545                 550                 555                 560
Asp Val Glu Pro Gly Ile Leu Leu His Gly Leu Lys Pro Trp Thr Gln
            565                 570                 575
Tyr Ala Val Tyr Val Lys Ala Val Thr Leu Thr Met Val Glu Asn Asp
            580                 585                 590
His Ile Arg Gly Ala Lys Ser Glu Ile Leu Tyr Ile Arg Thr Asn Ala
```

595                 600                 605
Ser Val Pro Ser Ile Pro Leu Asp Val Leu Ser Ala Ser Asn Ser Ser
610                 615                 620

Ser Gln Leu Ile Val Lys Trp Asn Pro Ser Leu Pro Asn Gly Asn
625                 630                 635                 640

Leu Ser Tyr Tyr Ile Val Arg Trp Gln Arg Gln Pro Gln Asp Gly Tyr
                    645                 650                 655

Leu Tyr Arg His Asn Tyr Cys Ser Lys Asp Lys Ile Pro Ile Arg Lys
                660                 665                 670

Tyr Ala Asp Gly Thr Ile Asp Ile Glu Glu Val Thr Glu Asn Pro Lys
            675                 680                 685

Thr Glu Val Cys Gly Gly Glu Lys Gly Pro Cys Cys Ala Cys Pro Lys
690                 695                 700

Thr Glu Ala Glu Lys Gln Ala Glu Lys Glu Glu Ala Glu Tyr Arg Lys
705                 710                 715                 720

Val Phe Glu Asn Phe Leu His Asn Ser Ile Phe Val Pro Arg Pro Glu
                    725                 730                 735

Arg Lys Arg Arg Asp Val Met Gln Val Ala Asn Thr Thr Met Ser Ser
                740                 745                 750

Arg Ser Arg Asn Thr Thr Ala Ala Asp Thr Tyr Asn Ile Thr Asp Pro
            755                 760                 765

Glu Glu Leu Glu Thr Glu Tyr Pro Phe Phe Gly Ser Arg Val Asp Asn
770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                    805                 810                 815

Ala Ser Asn Phe Val Phe Ala Arg Thr Met Pro Ala Glu Gly Ala Asp
                820                 825                 830

Asp Ile Pro Gly Pro Val Thr Trp Glu Pro Arg Pro Glu Asn Ser Ile
            835                 840                 845

Phe Leu Lys Trp Pro Glu Pro Glu Asn Pro Asn Gly Leu Ile Leu Met
850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                    885                 890                 895

Asn Pro Gly Asn Tyr Thr Ala Arg Ile Gln Ala Thr Ser Leu Ser Gly
                900                 905                 910

Asn Gly Ser Trp Thr Asp Pro Val Phe Phe Tyr Val Gln Ala Lys Thr
            915                 920                 925

Gly Tyr Glu Asn His His His His His
930                 935

<210> SEQ ID NO 90
<211> LENGTH: 942
<212> TYPE: PRT
<213> ORGANISM: Artificial
<220> FEATURE:
<223> OTHER INFORMATION: C9 fragment with His Tag

<400> SEQUENCE: 90

Met Lys Ser Gly Ser Gly Gly Ser Pro Thr Ser Leu Trp Gly Leu
1               5                   10                  15

Val Phe Leu Ser Ala Ala Leu Ser Leu Trp Pro Thr Ser Gly Glu Ile

```
                  20                  25                  30
Cys Gly Pro Gly Ile Asp Ile Arg Asn Asp Tyr Gln Gln Leu Lys Arg
             35                  40                  45

Leu Glu Asn Cys Thr Val Ile Glu Gly Phe Leu His Ile Leu Leu Ile
 50                  55                  60

Ser Lys Ala Glu Asp Tyr Arg Ser Tyr Arg Phe Pro Lys Leu Thr Val
 65                  70                  75                  80

Ile Thr Glu Tyr Leu Leu Leu Phe Arg Val Ala Gly Leu Glu Ser Leu
                 85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
            115                 120                 125

Gly Leu Tyr Asn Leu Arg Asn Ile Thr Arg Gly Ala Ile Arg Ile Glu
            130                 135                 140

Lys Asn Ala Asp Leu Cys Tyr Leu Ser Thr Ile Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Leu Glu Glu Lys Pro Met Cys
            180                 185                 190

Glu Lys Thr Thr Ile Asn Asn Glu Tyr Asn Tyr Arg Cys Trp Thr Thr
            195                 200                 205

Asn Arg Cys Gln Lys Met Cys Pro Ser Val Cys Gly Lys Arg Ala Cys
            210                 215                 220

Thr Glu Asn Asn Glu Cys Cys His Pro Glu Cys Leu Gly Ser Cys His
225                 230                 235                 240

Thr Pro Asp Asp Asn Thr Thr Cys Val Ala Cys Arg His Tyr Tyr Tyr
                245                 250                 255

Lys Gly Val Cys Val Pro Ala Cys Pro Pro Gly Thr Tyr Arg Phe Glu
            260                 265                 270

Gly Trp Arg Cys Val Asp Arg Asp Phe Cys Ala Asn Ile Pro Asn Ala
            275                 280                 285

Glu Ser Ser Asp Ser Asp Gly Phe Val Ile His Asp Asp Glu Cys Met
            290                 295                 300

Gln Glu Cys Pro Ser Gly Phe Ile Arg Asn Ser Thr Gln Ser Met Tyr
305                 310                 315                 320

Cys Ile Pro Cys Glu Gly Pro Cys Pro Lys Val Cys Gly Asp Glu Glu
                325                 330                 335

Lys Lys Thr Lys Thr Ile Asp Ser Val Thr Ser Ala Gln Met Leu Gln
            340                 345                 350

Gly Cys Thr Ile Leu Lys Gly Asn Leu Leu Ile Asn Ile Arg Arg Gly
            355                 360                 365

Asn Asn Ile Ala Ser Glu Leu Glu Asn Phe Met Gly Leu Ile Glu Val
            370                 375                 380

Val Thr Gly Tyr Val Lys Ile Arg His Ser His Ala Leu Val Ser Leu
385                 390                 395                 400

Ser Phe Leu Lys Asn Leu Arg Leu Ile Leu Gly Glu Glu Gln Leu Glu
                405                 410                 415

Gly Asn Tyr Ser Phe Tyr Val Leu Asp Asn Gln Asn Leu Gln Gln Leu
            420                 425                 430

Trp Asp Trp Asn His Arg Asn Leu Thr Val Arg Ser Gly Lys Met Tyr
            435                 440                 445
```

```
Phe Ala Phe Asn Pro Lys Leu Cys Val Ser Glu Ile Tyr Arg Met Glu
    450                 455                 460

Glu Val Thr Gly Thr Lys Gly Arg Gln Ser Lys Gly Asp Ile Asn Thr
465                 470                 475                 480

Arg Asn Asn Gly Glu Arg Ala Ser Cys Glu Ser Asp Val Leu His Phe
                485                 490                 495

Thr Ser Thr Thr Thr Trp Lys Asn Arg Ile Ile Ile Thr Trp His Arg
            500                 505                 510

Tyr Arg Pro Pro Asp Tyr Arg Asp Leu Ile Ser Phe Thr Val Tyr Tyr
        515                 520                 525

Lys Glu Ala Pro Phe Lys Asn Val Thr Glu Tyr Asp Gly Gln Asp Ala
530                 535                 540

Cys Gly Ser Asn Ser Trp Asn Met Val Asp Val Asp Leu Pro Pro Asn
545                 550                 555                 560

Lys Glu Gly Glu Pro Gly Ile Leu Leu His Gly Leu Lys Pro Trp Thr
                565                 570                 575

Gln Tyr Ala Val Tyr Val Lys Ala Val Thr Leu Thr Met Val Glu Asn
            580                 585                 590

Asp His Ile Arg Gly Ala Lys Ser Glu Ile Leu Tyr Ile Arg Thr Asn
        595                 600                 605

Ala Ser Val Pro Ser Ile Pro Leu Asp Val Leu Ser Ala Ser Asn Ser
610                 615                 620

Ser Ser Gln Leu Ile Val Lys Trp Asn Pro Pro Thr Leu Pro Asn Gly
625                 630                 635                 640

Asn Leu Ser Tyr Tyr Ile Val Arg Trp Gln Arg Gln Pro Gln Asp Gly
                645                 650                 655

Tyr Leu Tyr Arg His Asn Tyr Cys Ser Lys Asp Lys Ile Pro Ile Arg
            660                 665                 670

Lys Tyr Ala Asp Gly Thr Ile Asp Val Glu Glu Val Thr Glu Asn Pro
        675                 680                 685

Lys Thr Glu Val Cys Gly Gly Asp Lys Gly Pro Cys Cys Ala Cys Pro
690                 695                 700

Lys Thr Glu Ala Glu Lys Gln Ala Glu Lys Glu Glu Ala Glu Tyr Arg
705                 710                 715                 720

Lys Val Phe Glu Asn Phe Leu His Asn Ser Ile Phe Val Pro Arg Pro
                725                 730                 735

Glu Arg Arg Arg Arg Asp Val Met Gln Val Ala Asn Thr Thr Met Ser
            740                 745                 750

Ser Arg Ser Arg Asn Thr Thr Val Ala Asp Thr Tyr Asn Ile Thr Asp
        755                 760                 765

Pro Glu Glu Phe Glu Thr Glu Tyr Pro Phe Phe Glu Ser Arg Val Asp
770                 775                 780

Asn Lys Glu Arg Thr Val Ile Ser Asn Leu Arg Pro Phe Thr Leu Tyr
785                 790                 795                 800

Arg Ile Asp Ile His Ser Cys Asn His Glu Ala Glu Lys Leu Gly Cys
                805                 810                 815

Ser Ala Ser Asn Phe Val Phe Ala Arg Thr Met Pro Ala Glu Gly Ala
            820                 825                 830

Asp Asp Ile Pro Gly Pro Val Thr Trp Glu Pro Arg Pro Glu Asn Ser
        835                 840                 845

Ile Phe Leu Lys Trp Pro Glu Pro Glu Asn Pro Asn Gly Leu Ile Leu
850                 855                 860
```

```
Met Tyr Glu Ile Lys Tyr Gly Ser Gln Val Glu Asp Gln Arg Glu Cys
865                 870                 875                 880

Val Ser Arg Gln Glu Tyr Arg Lys Tyr Gly Gly Ala Lys Leu Asn Arg
                885                 890                 895

Leu Asn Pro Gly Asn Tyr Thr Ala Arg Ile Gln Ala Thr Ser Leu Ser
                900                 905                 910

Gly Asn Gly Ser Trp Thr Asp Pro Val Phe Phe Tyr Val Pro Ala Lys
                915                 920                 925

Thr Thr Tyr Glu Asn Phe Met His His His His His His
930                 935                 940

<210> SEQ ID NO 91
<211> LENGTH: 942
<212> TYPE: PRT
<213> ORGANISM: artificial
<220> FEATURE:
<223> OTHER INFORMATION: IGF-1R (murine), extracellular domain with His
      Tag

<400> SEQUENCE: 91

Met Lys Ser Gly Ser Gly Gly Ser Pro Thr Ser Leu Trp Gly Leu
1               5                   10                  15

Val Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
                35                  40                  45

Leu Glu Asn Cys Thr Val Ile Glu Gly Phe Leu His Ile Leu Leu Ile
                50                  55                  60

Ser Lys Ala Glu Asp Tyr Arg Ser Tyr Arg Phe Pro Lys Leu Thr Val
65              70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
                100                 105                 110

Tyr Asn Tyr Ala Leu Val Ile Phe Glu Met Thr Asn Leu Lys Asp Ile
                115                 120                 125

Gly Leu Tyr Asn Leu Arg Asn Ile Thr Arg Gly Ala Ile Arg Ile Glu
                130                 135                 140

Lys Asn Ala Asp Leu Cys Tyr Leu Ser Thr Ile Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Leu Glu Glu Lys Pro Met Cys
                180                 185                 190

Glu Lys Thr Thr Ile Asn Asn Glu Tyr Asn Tyr Arg Cys Trp Thr Thr
                195                 200                 205

Asn Arg Cys Gln Lys Met Cys Pro Ser Val Cys Gly Lys Arg Ala Cys
                210                 215                 220

Thr Glu Asn Asn Glu Cys Cys His Pro Glu Cys Leu Gly Ser Cys His
225                 230                 235                 240

Thr Pro Asp Asp Asn Thr Thr Cys Val Ala Cys Arg His Tyr Tyr Tyr
                245                 250                 255

Lys Gly Val Cys Val Pro Ala Cys Pro Pro Gly Thr Tyr Arg Phe Glu
                260                 265                 270

Gly Trp Arg Cys Val Asp Arg Asp Phe Cys Ala Asn Ile Pro Asn Ala
                275                 280                 285
```

```
Glu Ser Ser Asp Ser Asp Gly Phe Val Ile His Asp Glu Cys Met
    290                 295                 300
Gln Glu Cys Pro Ser Gly Phe Ile Arg Asn Ser Thr Gln Ser Met Tyr
305                 310                 315                 320
Cys Ile Pro Cys Glu Gly Pro Cys Pro Lys Val Cys Gly Asp Glu Glu
                325                 330                 335
Lys Lys Thr Lys Thr Ile Asp Ser Val Thr Ser Ala Gln Met Leu Gln
            340                 345                 350
Gly Cys Thr Ile Leu Lys Gly Asn Leu Leu Ile Asn Ile Arg Arg Gly
        355                 360                 365
Asn Asn Ile Ala Ser Glu Leu Glu Asn Phe Met Gly Leu Ile Glu Val
    370                 375                 380
Val Thr Gly Tyr Val Lys Ile Arg His Ser His Ala Leu Val Ser Leu
385                 390                 395                 400
Ser Phe Leu Lys Asn Leu Arg Leu Ile Leu Gly Glu Glu Gln Leu Glu
                405                 410                 415
Gly Asn Tyr Ser Phe Tyr Val Leu Asp Asn Gln Asn Leu Gln Gln Leu
            420                 425                 430
Trp Asp Trp Asn His Arg Asn Leu Thr Val Arg Ser Gly Lys Met Tyr
        435                 440                 445
Phe Ala Phe Asn Pro Lys Leu Cys Val Ser Glu Ile Tyr Arg Met Glu
    450                 455                 460
Glu Val Thr Gly Thr Lys Gly Arg Gln Ser Lys Gly Asp Ile Asn Thr
465                 470                 475                 480
Arg Asn Asn Gly Glu Arg Ala Ser Cys Glu Ser Asp Val Leu Arg Phe
                485                 490                 495
Thr Ser Thr Thr Thr Trp Lys Asn Arg Ile Ile Ile Thr Trp His Arg
            500                 505                 510
Tyr Arg Pro Pro Asp Tyr Arg Asp Leu Ile Ser Phe Thr Val Tyr Tyr
        515                 520                 525
Lys Glu Ala Pro Phe Lys Asn Val Thr Glu Tyr Asp Gly Gln Asp Ala
    530                 535                 540
Cys Gly Ser Asn Ser Trp Asn Met Val Asp Val Asp Leu Pro Pro Asn
545                 550                 555                 560
Lys Glu Gly Glu Pro Gly Ile Leu Leu His Gly Leu Lys Pro Trp Thr
                565                 570                 575
Gln Tyr Ala Val Tyr Val Lys Ala Val Thr Leu Thr Met Val Glu Asn
            580                 585                 590
Asp His Ile Arg Gly Ala Lys Ser Glu Ile Leu Tyr Ile Arg Thr Asn
        595                 600                 605
Ala Ser Val Pro Ser Ile Pro Leu Asp Val Leu Ser Ala Ser Asn Ser
    610                 615                 620
Ser Ser Gln Leu Ile Val Lys Trp Asn Pro Pro Thr Leu Pro Asn Gly
625                 630                 635                 640
Asn Leu Ser Tyr Tyr Ile Val Arg Trp Gln Arg Gln Pro Gln Asp Gly
                645                 650                 655
Tyr Leu Tyr Arg His Asn Tyr Cys Ser Lys Asp Lys Ile Pro Ile Arg
            660                 665                 670
Lys Tyr Ala Asp Gly Thr Ile Asp Val Glu Glu Val Thr Glu Asn Pro
        675                 680                 685
Lys Thr Glu Val Cys Gly Gly Asp Lys Gly Pro Cys Cys Ala Cys Pro
    690                 695                 700
```

Lys Thr Glu Ala Glu Lys Gln Ala Glu Lys Glu Ala Glu Tyr Arg
705                 710                 715                 720

Lys Val Phe Glu Asn Phe Leu His Asn Ser Ile Phe Val Pro Arg Pro
            725                 730                 735

Glu Arg Arg Arg Arg Asp Val Met Gln Val Ala Asn Thr Thr Met Ser
            740                 745                 750

Ser Arg Ser Arg Asn Thr Thr Val Ala Asp Thr Tyr Asn Ile Thr Asp
            755                 760                 765

Pro Glu Glu Phe Glu Thr Glu Tyr Pro Phe Phe Glu Ser Arg Val Asp
        770                 775                 780

Asn Lys Glu Arg Thr Val Ile Ser Asn Leu Arg Pro Phe Thr Leu Tyr
785                 790                 795                 800

Arg Ile Asp Ile His Ser Cys Asn His Glu Ala Glu Lys Leu Gly Cys
            805                 810                 815

Ser Ala Ser Asn Phe Val Phe Ala Arg Thr Met Pro Ala Glu Gly Ala
            820                 825                 830

Asp Asp Ile Pro Gly Pro Val Thr Trp Glu Pro Arg Pro Glu Asn Ser
        835                 840                 845

Ile Phe Leu Lys Trp Pro Glu Pro Glu Asn Pro Asn Gly Leu Ile Leu
850                 855                 860

Met Tyr Glu Ile Lys Tyr Gly Ser Gln Val Glu Asp Gln Arg Glu Cys
865                 870                 875                 880

Val Ser Arg Gln Glu Tyr Arg Lys Tyr Gly Gly Ala Lys Leu Asn Arg
            885                 890                 895

Leu Asn Pro Gly Asn Tyr Thr Ala Arg Ile Gln Ala Thr Ser Leu Ser
        900                 905                 910

Gly Asn Gly Ser Trp Thr Asp Pro Val Phe Phe Tyr Val Pro Ala Lys
        915                 920                 925

Thr Thr Tyr Glu Asn Phe Met His His His His His His
        930                 935                 940

<210> SEQ ID NO 92
<211> LENGTH: 512
<212> TYPE: PRT
<213> ORGANISM: Artificial
<220> FEATURE:
<223> OTHER INFORMATION: Mutated IGF-1R ECD Nterminal with Alanine at
      position 491

<400> SEQUENCE: 92

Met Lys Ser Gly Ser Gly Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
            20                  25                  30

Cys Gly Pro Gly Ile Asp Ile Arg Asn Asp Tyr Gln Gln Leu Lys Arg
        35                  40                  45

Leu Glu Asn Cys Thr Val Ile Glu Gly Tyr Leu His Ile Leu Leu Ile
    50                  55                  60

Ser Lys Ala Glu Asp Tyr Arg Ser Tyr Arg Phe Pro Lys Leu Thr Val
65              70                  75                  80

Ile Thr Glu Tyr Leu Leu Leu Phe Arg Val Ala Gly Leu Glu Ser Leu
            85                  90                  95

Gly Asp Leu Phe Pro Asn Leu Thr Val Ile Arg Gly Trp Lys Leu Phe
        100                 105                 110

Tyr Asn Tyr Ala Leu Val Ile Phe Glu Met Thr Asn Leu Lys Asp Ile
    115                 120                 125

```
Gly Leu Tyr Asn Leu Arg Asn Ile Thr Arg Gly Ala Ile Arg Ile Glu
    130                 135                 140
Lys Asn Ala Asp Leu Cys Tyr Leu Ser Thr Val Asp Trp Ser Leu Ile
145                 150                 155                 160
Leu Asp Ala Val Ser Asn Asn Tyr Ile Val Gly Asn Lys Pro Pro Lys
                165                 170                 175
Glu Cys Gly Asp Leu Cys Pro Gly Thr Met Glu Glu Lys Pro Met Cys
                180                 185                 190
Glu Lys Thr Thr Ile Asn Asn Glu Tyr Asn Tyr Arg Cys Trp Thr Thr
                195                 200                 205
Asn Arg Cys Gln Lys Met Cys Pro Ser Thr Cys Gly Lys Arg Ala Cys
    210                 215                 220
Thr Glu Asn Asn Glu Cys Cys His Pro Glu Cys Leu Gly Ser Cys Ser
225                 230                 235                 240
Ala Pro Asp Asn Asp Thr Ala Cys Val Ala Cys Arg His Tyr Tyr Tyr
                245                 250                 255
Ala Gly Val Cys Val Pro Ala Cys Pro Pro Asn Thr Tyr Arg Phe Glu
                260                 265                 270
Gly Trp Arg Cys Val Asp Arg Asp Phe Cys Ala Asn Ile Leu Ser Ala
    275                 280                 285
Glu Ser Ser Asp Ser Glu Gly Phe Val Ile His Asp Gly Glu Cys Met
    290                 295                 300
Gln Glu Cys Pro Ser Gly Phe Ile Arg Asn Gly Ser Gln Ser Met Tyr
305                 310                 315                 320
Cys Ile Pro Cys Glu Gly Pro Cys Pro Lys Val Cys Glu Glu Glu Lys
                325                 330                 335
Lys Thr Lys Thr Ile Asp Ser Val Thr Ser Ala Gln Met Leu Gln Gly
                340                 345                 350
Cys Thr Ile Phe Lys Gly Asn Leu Leu Ile Asn Ile Arg Arg Gly Asn
                355                 360                 365
Asn Ile Ala Ser Glu Leu Glu Asn Phe Met Gly Leu Ile Glu Val Val
    370                 375                 380
Thr Gly Tyr Val Lys Ile Arg His Ser His Ala Leu Val Ser Leu Ser
385                 390                 395                 400
Phe Leu Lys Asn Leu Arg Leu Ile Leu Gly Glu Glu Gln Leu Glu Gly
                405                 410                 415
Asn Tyr Ser Phe Tyr Val Leu Asp Asn Gln Asn Leu Gln Gln Leu Trp
                420                 425                 430
Asp Trp Asp His Arg Asn Leu Thr Ile Lys Ala Gly Lys Met Tyr Phe
                435                 440                 445
Ala Phe Asn Pro Lys Leu Cys Val Ser Glu Ile Tyr Arg Met Glu Glu
    450                 455                 460
Val Thr Gly Thr Lys Gly Arg Gln Ser Lys Gly Asp Ile Asn Thr Arg
465                 470                 475                 480
Asn Asn Gly Glu Arg Ala Ser Cys Glu Ser Ala Val Leu His Phe Thr
                485                 490                 495
Ser Thr Thr Thr Ser Lys Asn Arg Ile Ile Ile Thr Trp His Arg Tyr
                500                 505                 510
```

IGF-1R ANTIBODY AND ITS USE AS ADDRESSING VEHICLE FOR THE TREATMENT OF CANCER

This application is a continuation application of U.S. application Ser. No. 15/305,157, filed on Oct. 19, 2016, which is a national phase application based on PCT/EP2015/059050, filed Apr. 27, 2015, which claims the benefit of priority of U.S. Provisional Application No. 61/984,160, filed Apr. 25, 2014, the contents of each prior application are hereby incorporated by reference in their entireties.

The present invention relates to a novel antibody, in particular a monoclonal antibody, capable of binding to IGF-1R, as well as the amino and nucleic acid sequences coding for said antibody. From one aspect, the invention relates to a novel antibody, or an antigen binding fragment thereof, capable of binding to IGF-1R and, by inducing internalization of IGF-1R, being internalized into the cell. The invention also comprises the use of said antibody as an addressing product or vehicle in conjugation with other anti-cancer compounds such as toxins, radio-elements or drugs, and the use of same for the treatment of certain cancers.

The insulin-like growth factor 1 receptor called IGF-1R (also called IGF1R or IGF-1R) is a receptor with tyrosine kinase activity having 70% homology with the insulin receptor IR. IGF-1R is a glycoprotein of molecular weight approximately 350,000. It is a hetero-tetrameric receptor of which each half-linked by disulfide bridges—is composed of an extracellular α-subunit and of a transmembrane β-subunit. IGF-1R binds IGF1 and IGF2 with a very high affinity (Kd #1 nM) but is equally capable of binding to insulin with an affinity 100 to 1000 times lower. Conversely, the IR binds insulin with a very high affinity although the IGFs only bind to the insulin receptor with a 100 times lower affinity. The tyrosine kinase domains of IGF-1R and of IR have a very high sequence homology although the zones of weaker homology respectively concern the cysteine-rich region situated on the α-subunit and the C-terminal part of the β-subunit. The sequence differences observed in the α-subunit are situated in the binding zone of the ligands and are therefore at the origin of the relative affinities of IGF-1R and of IR for the IGFs and insulin respectively. The differences in the C-terminal part of the β-subunit result in a divergence in the signalling pathways of the two receptors; IGF-1R mediating mitogenic, differentiation and anti-apoptosis effects, while the activation of the IR principally involves effects at the level of the metabolic pathways.

The cytoplasmic tyrosine kinase proteins are activated by the binding of the ligand to the extracellular domain of the receptor. The activation of the kinases in its turn involves the stimulation of different intra-cellular substrates, including IRS-1, IRS-2, Shc and Grb 10. The two major substrates of IGF-1R are IRS and Shc which mediate, by the activation of numerous effectors downstream, the majority of the growth and differentiation effects connected with the attachment of the IGFs to this receptor. The availability of substrates can consequently dictate the final biological effect connected with the activation of the IGF-1R. When IRS-1 predominates, the cells tend to proliferate and to transform. When Shc dominates, the cells tend to differentiate. It seems that the route principally involved for the effects of protection against apoptosis is the phosphatidyl-inositol 3-kinases (PI 3-kinases) route.

The role of the IGF system in carcinogenesis has become the subject of intensive research in the last ten years. This interest followed the discovery of the fact that in addition to its mitogenic and antiapoptotic properties, IGF-1R seems to be required for the establishment and the maintenance of a transformed phenotype. In fact, it has been well established that an overexpression or a constitutive activation of IGF-1R leads, in a great variety of cells, to a growth of the cells independent of the support in media devoid of foetal calf serum, and to the formation of tumors in nude mice. This in itself is not a unique property since a great variety of products of overexpressed genes can transform cells, including a good number of receptors of growth factors. However, the crucial discovery which has clearly demonstrated the major role played by IGF-1R in the transformation has been the demonstration that the IGF-1R⁻ cells, in which the gene coding for IGF-1R has been inactivated, are totally refractory to transformation by different agents which are usually capable of transforming the cells, such as the E5 protein of bovine papilloma vin's, an overexpression of EGFR or of PDGFRS, the T antigen of SV 40, activated ras or the combination of these two last factors.

IGF-1R is expressed in a great variety of tumors and of tumor lines and the IGFs amplify the tumor growth via their attachment to IGF-1R. Other arguments in favor of the role of IGF-1R in carcinogenesis come from studies using murine monoclonal antibodies directed against the receptor or using negative dominants of IGF-1R. Actually, murine monoclonal antibodies directed against IGF-1R inhibit the proliferation of numerous cell lines in culture and the growth of tumor cells in vivo. It has likewise been shown that a negative dominant of IGF-1R is capable of inhibiting tumor proliferation.

In such a context IGF-1R has been considered for a long time as an interesting target in oncology. A large number of projects targeting IGF-1R (humanized or human antibodies or small molecules) have been initiated to develop IGF-1R antibodies for the treatment of cancers and more than 70 clinical trials have been performed in various indications. Nevertheless, at this date, none of these projects have been successful and there are no IGF-1R antibodies on the market despite the frequent overexpression of this target described for many patients in a wide series of indications.

Moreover, a series of clinical trials involving anti-IGF-1R antibodies combined to anti-EGFR antibodies in order to target both EGFR and IGF-1R, have failed as none of these antibodies were able to treat KRAS mutant patients.

As a consequence, IGF-1R is not considered now as a major target and, in the research of potential therapeutic antibodies, IGF-1R appears no longer considered as of particular interest.

Nevertheless, it must also be noticed that endeavors to generate IGF-1R antibodies were focused on naked antibodies, i.e. antibodies useful by their intrinsic properties. In this sense, IGF-1R is considered as a target not suitable for the generation of an immunoconjugate such as an antibody-drug conjugate (referred as "ADC") as IGF-1R is described as a target also widely expressed by normal cells, including blood vessels. In this sense, it can be noticed that the most recent IGF-1R antibody, i.e. AVE1642, is developed as a naked antibody not armed with a drug. It is the same with the other IGF-1R antibodies currently in development and with all those which failed in clinical trials.

In one aspect, the present invention tends to remedy these issues and is describing an IGF-1R antibody capable of binding to IGF-1R in a specific manner such as it is suitable to be used armed with a drug. More particularly, the invention relates to an IGF-1R antibody presenting particular properties such as it is a perfect candidate for being used armed in the context of an immunoconjugate.

In a first embodiment, the invention relates to an antibody, or an antigen binding fragment thereof, which i) binds to human IGF-1R, and ii) is internalized following its binding to said human IGF-1R.

The terms "antibody", "antibodies", "ab", "Ab" or "immunoglobulin" are used interchangeably in the broadest sense and include monoclonal antibodies, isolated, engineered, chemically synthesized, or recombinant antibodies (e.g., full length or intact monoclonal antibodies), polyclonal antibodies, multivalent antibodies or multispecific antibodies (e.g., bispecific antibodies) and also antibody fragment, so long as they exhibit the desired biological activity. In an embodiment, the invention relates to a recombinant antibody.

More particularly, such a molecule consists of a glycoprotein comprising at least two heavy (H) chains and two light (L) chains inter-connected by disulfide bonds. Each heavy chain comprises a heavy chain variable region (or domain) (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g. effector cells) and the first component (Clq) of the classical complement system.

By "IGF-1R binding fragment" or "antigen binding fragment" of an antibody according to the invention, it is intended to indicate any peptide, polypeptide, or protein retaining the ability to bind to the target (also generally referred as antigen) of the antibody.

In an embodiment, such "antigen binding fragments" are selected in the group consisting of Fv, scFv (sc for single chain), Fab, F(ab')2, Fab', scFv-Fc fragments or diabodies, or any fragment of which the half-life time would have been increased by chemical modification, such as the addition of poly(alkylene) glycol such as poly(ethylene) glycol ("PEGylation") (pegylated fragments called Fv-PEG, scFv-PEG, Fab-PEG, F(ab')$_2$-PEG or Fab'-PEG) ("PEG" for Poly(Ethylene) Glycol), or by incorporation into a liposome, said fragments having at least one of the characteristic CDRs of the antibody according to the invention. Preferably, said "antigen binding fragments" will be constituted or will comprise a partial sequence of the heavy or light variable chain of the antibody from which they are derived, said partial sequence being sufficient to retain the same specificity of binding as the antibody from which it is descended and a sufficient affinity, preferably at least equal to 1/100, in a more preferred manner to at least 1/10, of the affinity of the antibody from which it is descended, with respect to the target. More preferably, said "antigen binding fragments" will be constituted of or will comprise at least the three CDRs CDR-H1, CDR-H2 and CDR-H3 of the heavy variable chain and the three CDRs CDR-L1, CDR-L2 and CDR-L3 of the light variable chain of the antibody from which they are derived.

By "binding", "binds", or the like, it is intended that the antibody, or any antigen binding fragment thereof, forms a complex with an antigen that is relatively stable under physiologic conditions. Specific binding can be characterized by an equilibrium dissociation constant of at least about $1\times10^{-6}$ M or less. Methods for determining whether two molecules bind are well known in the art and include, for example, equilibrium dialysis, surface plasmon resonance, and the like. For the avoidance of doubt, it does not mean that the said antibody could not bind or interfere, at a low level, to another antigen. Nevertheless, as an embodiment, the said antibody binds only to the said antigen.

As used in the present specification, the expression "IGF-1R antibody" should be interpreted as similar to "anti-IGF-1R antibody" and means an antibody capable of binding to IGF-1R.

In an embodiment of the present application, the epitope of the antibody is localized into the extracellular domain of the human IGF-1R (also referred as IGF-1R ECD).

In a particular embodiment, the antibody, or any antigen binding fragment thereof, is capable of binding to IGF-1R with an $EC_{50}$ comprised between $10\times10^{-10}$ to $1\times10^{-10}$, and more preferentially between $8\times10^{-10}$ to $2\times10^{-10}$M.

In this sense, "$EC_{50}$" refers to 50% effective concentration. More precisely the term half maximal effective concentration ($EC_{50}$) corresponds to the concentration of a drug, antibody or toxicant which induces a response halfway between the baseline and maximum after some specified exposure time. It is commonly used as a measure of drug's potency. The $EC_{50}$ of a graded dose response curve therefore represents the concentration of a compound where 50% of its maximal effect is observed. The $EC_{50}$ of a quantal dose response curve represents the concentration of a compound where 50% of the population exhibits a response, after specified exposure duration. Concentration measures typically follow a sigmoidal curve, increasing rapidly over a relatively small change in concentration. This can be determined mathematically by derivation of the best-fit line.

As a preferred embodiment, the $EC_{50}$ determined in the present invention characterized the potency of antibody binding on the IGF-1R ECD exposed on human tumor cells. The $EC_{50}$ parameter is determined using FACS analysis. The $EC_{50}$ parameter reflects the antibody concentration for which 50% of the maximal binding on the human IGF-1R expressed on human tumor cells is obtained. Each $EC_{50}$ value was calculated as the midpoint of the dose response curve using a four-parameter regression curve fitting program (Prism Software). This parameter has been selected as to be representative of physiological/pathological conditions.

The term "epitope" is a region of an antigen that is bound by an antigen binding protein, including antibodies. Epitopes may be defined as structural or functional. Functional epitopes are generally a subset of the structural epitopes and have those residues that directly contribute to the affinity of the interaction. Epitopes may also be conformational, that is, composed of non-linear amino acids, in other words conformational epitopes are composed of non-sequential amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

In a particular embodiment, the present invention relates to a method for selecting an internalizing antibody, or an internalizing IGF-1R binding fragment thereof, which binds to the human Insulin like Growth Factor 1 Receptor (IGF-1R) and is internalized following to its binding to IGF-1R, said method comprising the step of selecting an antibody:
  i) which binds to an IGF-1R of SEQ ID No 52, and
  ii) which does not bind to an IGF-1R of SEQ ID No 52 with an amino acid other than Histidine at position 494 of SEQ ID No 52 or with an Aspartic acid (ASP) at position 491, preferably which does not bind to an IGF-1R of SEQ ID No 52 with an amino acid other than Histidine at position 494 of SEQ ID No 52 and Aspartic acid (ASP) at position 491.

In a more particular embodiment, the present invention relates to a method for selecting an internalizing antibody, or an internalizing IGF-1R binding fragment thereof, which binds to the human Insulin like Growth Factor 1 Receptor (IGF-1R) and is internalized following to its binding to IGF-1R, said method comprising the steps of: 1) selecting an antibody:
  i) that binds to an IGF-1R of SEQ ID No 52, and
  ii) that does not bind to an IGF-1R of SEQ ID No 52 with an amino acid other than Histidine at position 494 of SEQ ID No 52, or with an Aspartic acid (ASP) at position 491, preferably which does not bind to an IGF-1R of SEQ ID No 52 with an amino acid other than Histidine at position 494 of SEQ ID No 52 and Aspartic acid (ASP) at position 491, and, then, from such an antibody,
2) selecting an internalizing antibody, or an IGF-1R binding fragment thereof, which percentage of internalization following to its binding to IGF-1R is at least of 40%, preferably at least 50%, at least 60%, at least 70%, or at least 80%.

In another particular embodiment, the present invention relates to a method for selecting an internalizing antibody, or an internalizing IGF-1R binding fragment thereof, which binds to the human Insulin like Growth Factor 1 Receptor (IGF-1R) and is internalized following to its binding to IGF-1R, said method comprising the steps of:
  1) selecting an internalizing antibody, or an IGF-1R binding fragment thereof, which percentage of internalization following to its binding to IGF-1R is at least of 40%, preferably at least 50%, at least 60%, at least 70%, or at least 80%,
  2) and, then, from such an antibody, selecting an antibody:
    i) that binds to an IGF-1R of SEQ ID No 52, and
    ii) that does not bind to an IGF-1R of SEQ ID No 52 with an amino acid other than Histidine at position 494 of SEQ ID No 52, or with an Aspartic acid (ASP) at position 491, preferably which does not bind to an IGF-1R of SEQ ID No 52 with an amino acid other than Histidine at position 494 of SEQ ID No 52 and Aspartic acid (ASP) at position 491.

In a method according to the invention, the step of selecting an antibody upon its characteristics of internalization and of binding, or not binding, to IGF-1R may be performed in any successive order.

According to a particular embodiment, the present invention relates to an internalizing antibody, or an internalizing IGF-1R binding fragment thereof, which binds to the human Insulin like Growth Factor 1 Receptor (IGF-1R), such as obtained by one of the above cited methods according to the invention.

In another particular embodiment, the present invention relates to an internalizing antibody, or an internalizing IGF-1R binding fragment thereof, which binds to the human Insulin like Growth Factor 1 Receptor (IGF-1R) of SEQ ID No 52 and is internalized following to its binding to IGF-1R, and which does not bind to an IGF-1R of SEQ ID No 82 or 92, preferably SEQ ID No 82 and 92.

For an antibody according to the present invention, SEQ ID No 52 corresponds to the amino acid sequence of the human IGF-1R receptor, wherein there is a Histidine at position 494, i.e. wild-type IGF-1R, whereas SEQ ID No 82 corresponds to the mutated amino acid sequence of the human IGF-1R receptor, wherein there is an Arginine at position 494, and whereas SEQ ID No 92 corresponds to the mutated amino acid sequence of the human IGF-1R receptor, wherein there is an Alanine at position 491.

In a more particular embodiment, the present invention relates to an internalizing antibody, or an internalizing IGF-1R binding fragment thereof, wherein the epitope of said internalizing antibody comprises the Histidine amino acid at position 494 of SEQ ID No 52.

In a more particular embodiment, the present invention relates to an internalizing antibody, or an internalizing IGF-1R binding fragment thereof, wherein the epitope of said internalizing antibody comprises the Histidine amino acid at position 494 of SEQ ID No 52, with said epitope comprising an amino acid sequence of at least 8 amino acids.

In a more particular embodiment, the present invention relates to an internalizing antibody, or an internalizing IGF-1R binding fragment thereof, wherein the epitope of said internalizing antibody comprises the Aspartic acid amino acid at position 491 of SEQ ID No 52, with said epitope comprising an amino acid sequence of at least 8 amino acids.

In a more particular embodiment, the present invention relates to an internalizing antibody, or an internalizing IGF-1R binding fragment thereof, wherein the epitope of said internalizing antibody comprises the Histidine amino acid at position 494 and the Aspartic acid amino acid at position 491 of SEQ ID No 52, with said epitope comprising an amino acid sequence of at least 8 amino acids.

In a more particular embodiment, the present invention relates to an internalizing antibody, or an internalizing IGF-1R binding fragment thereof, wherein the epitope of said internalizing antibody comprises the Histidine amino acid at position 494 of SEQ ID No 52, with said epitope comprising an amino acid sequence of 9, 10, 11, 12, 13, 14, 15, 16, 17, 18, 19 or 20 amino acids.

In a more particular embodiment, the present invention relates to an internalizing antibody, or an internalizing IGF-1R binding fragment thereof, wherein the epitope of said internalizing antibody comprises Histidine amino acid at position 494 of SEQ ID No 52, with said epitope comprising an amino acid sequence of at least 8 amino acids, wherein said epitope comprises an amino acid sequence chosen in the group consisting of:
  an amino acid sequence identical to, or exhibiting at least 80% identity with, the amino acid sequence from the amino acid at position 487 to the amino acid at position 494 of SEQ ID No 52,
  an amino acid sequence identical to, or exhibiting at least 80% identity with, the amino acid sequence from the amino acid at position 488 to the amino acid at position 495 of SEQ ID No 52,
  an amino acid sequence identical to, or exhibiting at least 80% identity with, the amino acid sequence from the amino acid at position 489 to the amino acid at position 496 of SEQ ID No 52,
  an amino acid sequence identical to, or exhibiting at least 80% identity with, the amino acid sequence from the amino acid at position 490 to the amino acid at position 497 of SEQ ID No 52, an amino acid sequence identical to, or exhibiting at least 80% identity with, the amino acid sequence from the amino acid at position 491 to the amino acid at position 498 of SEQ ID No 52, an amino acid sequence identical to, or exhibiting at least 80% identity with, the amino acid sequence from the amino acid at position 492 to the amino acid at position 499 of SEQ ID No 52, and an amino acid sequence identical to, or exhibiting at least 80% identity with, the amino acid sequence from the amino acid at position 493 to the amino acid at position 500 of SEQ ID No 52.

In a more particular embodiment, the present invention relates to an internalizing antibody, or an internalizing IGF-1R binding fragment thereof, wherein the epitope of said internalizing antibody comprises the Aspartic acid amino acid at position 491 of SEQ ID No 52, with said epitope comprising an amino acid sequence of 9, 10, 11, 12, 13, 14, 15, 16, 17, 18, 19 or 20 amino acids.

In a more particular embodiment, the present invention relates to an internalizing antibody, or an internalizing IGF-1R binding fragment thereof, wherein the epitope of said internalizing antibody comprises Aspartic acid amino acid at position 491 of SEQ ID No 52, with said epitope comprising an amino acid sequence of at least 8 amino acids, wherein said epitope comprises an amino acid sequence chosen in the group consisting of:

an amino acid sequence identical to, or exhibiting at least 80% identity with, the amino acid sequence from the amino acid at position 484 to the amino acid at position 491 of SEQ ID No 52, an amino acid sequence identical to, or exhibiting at least 80% identity with, the amino acid sequence from the amino acid at position 485 to the amino acid at position 492 of SEQ ID No 52, an amino acid sequence identical to, or exhibiting at least 80% identity with, the amino acid sequence from the amino acid at position 486 to the amino acid at position 493 of SEQ ID No 52, an amino acid sequence identical to, or exhibiting at least 80% identity with, the amino acid sequence from the amino acid at position 487 to the amino acid at position 494 of SEQ ID No 52, an amino acid sequence identical to, or exhibiting at least 80% identity with, the amino acid sequence from the amino acid at position 488 to the amino acid at position 495 of SEQ ID No 52, an amino acid sequence identical to, or exhibiting at least 80% identity with, the amino acid sequence from the amino acid at position 489 to the amino acid at position 496 of SEQ ID No 52, and an amino acid sequence identical to, or exhibiting at least 80% identity with, the amino acid sequence from the amino acid at position 490 to the amino acid at position 497 of SEQ ID No 52.

In a more particular embodiment, the present invention relates to an internalizing antibody, or an internalizing IGF-1R binding fragment thereof, wherein the epitope of said internalizing antibody comprises the Histidine amino acid at position 494 and the Aspartic acid at position 491 of SEQ ID No 52, with said epitope comprising an amino acid sequence of 9, 10, 11, 12, 13, 14, 15, 16, 17, 18, 19 or 20 amino acids.

In a more particular embodiment, the present invention relates to an internalizing antibody, or an internalizing IGF-1R binding fragment thereof, wherein the epitope of said internalizing antibody comprises the Histidine amino acid at position 494 and the Aspartic acid at position 491 of SEQ ID No 52, with said epitope comprising an amino acid sequence of at least 8 amino acids, wherein said epitope comprises an amino acid sequence chosen in the group consisting of:

an amino acid sequence identical to, or exhibiting at least 80% identity with, the amino acid sequence from the amino acid at position 487 to the amino acid at position 494 of SEQ ID No 52, an amino acid sequence identical to, or exhibiting at least 80% identity with, the amino acid sequence from the amino acid at position 488 to the amino acid at position 495 of SEQ ID No 52, an amino acid sequence identical to, or exhibiting at least 80% identity with, the amino acid sequence from the amino acid at position 489 to the amino acid at position 496 of SEQ ID No 52, an amino acid sequence identical to, or exhibiting at least 80% identity with, the amino acid sequence from the amino acid at position 490 to the amino acid at position 497 of SEQ ID No 52 and an amino acid sequence identical to, or exhibiting at least 80% identity with, the amino acid sequence from the amino acid at position 491 to the amino acid at position 498 of SEQ ID No 52.

In another particular embodiment, the present invention relates to an internalizing antibody, or an internalizing IGF-1R binding fragment thereof, which binds to the human Insulin like Growth Factor 1 Receptor (IGF-1R) of SEQ ID No 52 and is internalized following to its binding to IGF-1R, and which does not bind to an IGF-1R of SEQ ID No 82, or wherein the epitope of said internalizing antibody comprises the Histidine amino acid at position 494 and/or the Aspartic acid amino acid at position 491 of SEQ ID No 52, wherein the percentage of internalization of said antibody following to its binding to IGF-1R is of at least 40%, at least 50%, at least 60%, at least 70%, or at least 80%. The percentage of internalization of an antibody, or of an antigen-binding fragment thereof, may be determined by any method known by a person skilled in the art, such as, for example, a method described in the present specification.

In a particular embodiment, the present invention relates to an internalizing antibody, or an internalizing IGF-1R binding fragment thereof, according to the invention, wherein said amino acid other than Histidine at position 494 of SEQ ID No 52 is Arginine (SEQ ID No 82).

In a particular embodiment, the present invention relates to an internalizing antibody, or an internalizing IGF-1R binding fragment thereof, according to the invention, wherein said amino acid other than Aspartic acid at position 491 of SEQ ID No 52 is Alanine (SEQ ID No 92) According to an embodiment, the invention relates to an antibody, or an antigen binding fragment thereof, which binds to the human Insulin like Growth Factor 1 Receptor (IGF-1R) and which is internalized following its binding to IGF-1R, wherein said antibody is selected from:

i) an antibody comprising three heavy chain CDRs with CDR-H2 of sequence SEQ ID No. 2 and CDR-H3 of sequence SEQ ID No. 3, and three light chain CDRs with CDR-L2 of sequence SEQ ID No. 5;

ii) an antibody which competes for binding to IGF-1R with the antibody of i); and iii) an antibody which binds to the same epitope of IGF-1R as does the antibody of i).

The competition for binding to IGF-1R can be determined by any methods or techniques known by the person skilled in the art such as, without limitation, radioactivity, Biacore, ELISA, Flow cytometry, etc, or according to a method such as described in the present specification.

The determination of the binding to the same epitope can be determined by any methods or techniques known by the person skilled in the art such as, without limitation, radioactivity, Biacore, ELISA, Flow cytometry, etc, or according to a method such as described in the present specification.

As above mentioned, and contrary to the general knowledge, the present invention focuses on specific IGF-1R antibodies presenting a high ability to be internalized following IGF-1R binding. As used herein, an antibody that "is internalized" or that "internalized" (the two expressions being similar) is one that is taken up by (meaning it "enters") the cell upon binding to IGF-1R on a mammalian cell. Such an antibody is interesting as one of the immuno-drug-conjugate components, so it addresses or directs the linked cytotoxic into the targeted cells, preferably cancer cells. Once internalized the cytotoxic triggers cancer cell death.

Preferably, the antibodies according to the invention are all presenting the same sequences for the CDR-H2, CDR-H3 and CDR-L2, the other 3 CDRs being different. This observation seems coherent as it is part of the general knowledge that, regarding the binding specificity of an antibody, the CDR-H3 is described as being the most important and the most implicated with the recognition of the epitope.

Important keys to success with immunoconjugate therapy are thought to be the target antigen specificity and the internalization of the antigen-binding protein complexes into the cancer cells. Obviously non-internalizing antigens are less effective than internalizing antigens to delivers cytotoxic agents. Internalization processes are variable across antigens and depend on multiple parameters that can be influenced by antibodies.

In the immunoconjugate, the cytotoxic brings the cytotoxic activity and the used antibody brings its specificity against cancer cells, as well as a vector for entering within the cells to correctly address the cytotoxic. Thus to improve the immunoconjugate, the antibody can exhibit high ability to internalize into the targeted cancer cells. The efficiency with which the antibody mediated internalisation differs significantly depending on the epitope targeted. Selection of potent internalizing IGF-1R antibodies requires various experimental data studying not only IGF-1R downregulation but also following IGF-1R antibody internalization into the cells.

In one embodiment, the internalization of the antibody according to the invention can be evaluated by immunofluorescence (as exemplified hereinafter in the present application) or any method or process known by the person skilled in the art specific for the internalization mechanism.

The complex IGF-1R/antibody is internalized after the binding of the antibody to the ECD of said IGF-1R, a reduction in the quantity of IGF-1R at the surface of the cells is induced. This reduction can be quantified by any method known by the person skilled in the art such as, as non limitative examples, western-blot, FACS, immunofluorescence and the like.

In one embodiment, this reduction, thus reflecting the internalization, can be preferably measured by FACS and expressed as the difference or delta between the Mean Fluorescence Intensity (MFI) measured at 4° C. with the MFI measured at 37° C. after 4 hours incubation with the antibody.

As non limitative example, this delta is determined based on MFIs obtained with untreated cells and cells treated with the antibody using i) breast cancer cells MCF7 after a 4 hour incubation period with the antibody herein described and ii) a secondary antibody labelled with Alexa488. This parameter is defined as calculated with the following formula: $\Delta(MFI_{4° C.} - MFI_{37° C.})$.

This difference between MFIs reflects the IGF-1R downregulation as MFIs are proportional of IGF-1R expressed on the cell-surface.

In an advantageous aspect, the antibodies, or any antigen binding fragment thereof, consist of monoclonal antibodies triggering a $\Delta(MFI_{4° C.} - MFI_{37° C.})$ on MCF7 of at least 280, preferably of at least 400.

In more details, the above mentioned delta can be measured according to the following process, which must be considered as an illustrative and non limitative example:
a) Treating and incubating tumoral cells of interest with the antibody of the invention in either cold (4° C.) or warm (37° C.) complete culture medium;
b) Treating the treated cells of step a) and, in parallel, untreated cells with a secondary antibody,
c) Measuring the MFI (representative of the quantity of IGF-1R present at the surface) for the treated and the non treated cells with a secondary labeled antibody capable of binding to the antibody of the invention, and
d) Calculating the delta as the subtraction of the MFI obtained with the treated cells from the MFI obtained with the non treated cells.

From this delta MFI, an internalization percentage can be determined as: $100 \times (MFI_{4° C.} - MFI_{37° C.})/MFI_{4° C.}$.

The antibodies, or any antigen binding fragment thereof, according to the invention, present on MCF7 a internalization percentage comprised between 70% and 90%, preferentially between 75% and 87%.

A particular advantage of the antibodies herein described relies on their rate of internalization.

It is generally known that, for an immunoconjugate, it is desirable that the used antibodies exhibit a rapid rate of internalization, preferably within 24 hours from administration of the antibody in vivo and, more preferably within 12 hours and, even more preferably within 6 hours.

In the present invention, the internalization rate, also referred as cell surface bound antibody decrease or cell surface antibody decay, is expressed as t½ (half life) and corresponds as the time necessary to obtain a decrease of 50% of the ΔMFI (this aspect will be clearly understood regarding the following examples).

A particular advantage is that the antibodies of the invention have a t½ comprised between 5 and 25 minutes, and preferentially between 10 and 20 minutes.

A particular embodiment of the invention relates to an antibody comprising the three heavy chain CDRs of sequences SEQ ID Nos. 1, 2 and 3 and the three light chain CDRs of sequences SEQ ID Nos. 4, 5 and 6.

An embodiment is an antibody, or an antigen binding fragment thereof, comprising the three heavy chain CDRs comprising, or consisting of, the sequences SEQ ID Nos. 1, 2 and 3, or any sequence exhibiting at least 80%, preferably 85%, 90%, 95% or 98% identity with SEQ ID Nos. 1, 2 and 3; and the three light chain CDRs comprising or consisting of the sequences SEQ ID Nos. 4, 5 and 6, or any sequence exhibiting at least 80%, preferably 85%, 90%, 95% or 98% identity with SEQ ID Nos. 4, 5 and 6.

In another embodiment, the antibody, or any antigen binding fragment thereof, comprises the three heavy chain CDRs comprising or consisting of the sequences SEQ ID Nos. 1, 2 and 3; and the three light chain CDRs comprising or consisting of the sequences SEQ ID Nos. 4, 5 and 6.

By CDR regions or CDR(s), it is intended to indicate the hypervariable regions of the heavy and light chains of the immunoglobulins as defined by IMGT.

The IMGT unique numbering has been defined to compare the variable domains whatever the antigen receptor, the chain type, or the species [Lefranc M.-P., Immunology Today 18, 509 (1997)/Lefranc M.-P., The Immunologist, 7, 132-136 (1999)/Lefranc, M.-P., Pommié, C., Ruiz, M., Giudicelli, V., Foulquier, E., Truong, L., Thouvenin-Contet, V. and Lefranc, Dev. Comp. Immunol., 27, 55-77 (2003)]. In the IMGT unique numbering, the conserved amino acids always have the same position, for instance cystein 23 (1st-CYS), tryptophan 41 (CONSERVED-TRP), hydrophobic amino acid 89, cystein 104 (2nd-CYS), phenylalanine or tryptophan 118 (J-PHE or J-TRP). The IMGT unique numbering provides a standardized delimitation of the framework regions (FR1-IMGT: positions 1 to 26, FR2-IMGT: 39 to 55, FR3-IMGT: 66 to 104 and FR4-IMGT: 118 to 128) and of the complementarity determining regions: CDR1-IMGT: 27 to 38, CDR2-IMGT: 56 to 65 and CDR3-IMGT: 105 to 117. As gaps represent unoccupied positions, the CDR-IMGT lengths (shown between brackets and separated by dots, e.g. [8.8.13]) become crucial information. The IMGT unique numbering is used in 2D graphical representations, designated as IMGT Colliers de Perles [Ruiz, M. and Lefranc, M.-P., Immunogenetics, 53, 857-883 (2002)/Kaas, Q. and Lefranc, M.-P., Current Bioinformatics, 2, 21-30 (2007)], and in 3D structures in IMGT/3Dstructure-DB [Kaas, Q., Ruiz, M. and Lefranc, M.-P., T cell receptor and MHC structural data. Nucl. Acids. Res., 32, D208-D210 (2004)].

It must be understood that, without contradictory specification in the present specification, complementarity-determining regions or CDRs, mean the hypervariable regions of the heavy and light chains of immunoglobulins as defined according to the IMGT numbering system.

Nevertheless, CDRs can also be defined according to the Kabat numbering system (Kabat et al., Sequences of proteins of immunological interest, 5$^{th}$ Ed., U.S. Department of Health and Human Services, NIH, 1991, and later editions). There are three heavy-chain CDRs and three light-chain CDRs. Here, the terms "CDR" and "CDRs" are used to indicate, depending on the case, one or more, or even all, of the regions containing the majority of the amino acid residues responsible for the antibody's binding affinity for the antigen or epitope it recognizes. In order to simplify the reading of the present application, the CDRs according to Kabat are not defined. Nevertheless, it would be obvious for the person skilled in that art, using the definition of the CDRs according to IMGT, to define the CDRs according to Kabat.

In the sense of the present invention, the "percentage identity" between two sequences of nucleic acids or amino acids means the percentage of identical nucleotides or amino acid residues between the two sequences to be compared, obtained after optimal alignment, this percentage being purely statistical and the differences between the two sequences being distributed randomly along their length. The comparison of two nucleic acid or amino acid sequences is traditionally carried out by comparing the sequences after having optimally aligned them, said comparison being able to be conducted by segment or by using an "alignment window". Optimal alignment of the sequences for comparison can be carried out, in addition to comparison by hand, by means of the local homology algorithm of Smith and Waterman (1981) [Ad. App. Math. 2:482], by means of the local homology algorithm of Neddleman and Wunsch (1970) [J. Mol. Biol. 48:443], by means of the similarity search method of Pearson and Lipman (1988) [Proc. Natl. Acad. Sci. USA 85:2444] or by means of computer software using these algorithms (GAP, BESTFIT, FASTA and TFASTA in the Wisconsin Genetics Software Package, Genetics Computer Group, 575 Science Dr., Madison, Wis., or by the comparison software BLAST NR or BLAST P).

The percentage identity between two nucleic acid or amino acid sequences is determined by comparing the two optimally-aligned sequences in which the nucleic acid or amino acid sequence to compare can have additions or deletions compared to the reference sequence for optimal alignment between the two sequences. Percentage identity is calculated by determining the number of positions at which the amino acid nucleotide or residue is identical between the two sequences, preferably between the two complete sequences, dividing the number of identical positions by the total number of positions in the alignment window and multiplying the result by 100 to obtain the percentage identity between the two sequences.

For example, the BLAST program, "BLAST 2 sequences" (Tatusova et al., "Blast 2 sequences—a new tool for comparing protein and nucleotide sequences", FEMS Microbiol., 1999, Lett. 174:247-250) available on the site http://www.ncbi.nlm.nih.gov/gorf/bl2.html, can be used with the default parameters (notably for the parameters "open gap penalty": 5, and "extension gap penalty": 2; the selected matrix being for example the "BLOSUM 62" matrix proposed by the program); the percentage identity between the two sequences to compare is calculated directly by the program.

For the amino acid sequence exhibiting at least 80%, preferably 85%, 90%, 95% or 98% identity with a reference amino acid sequence, preferred examples include those containing the reference sequence, certain modifications, notably a deletion, addition or substitution of at least one amino acid, truncation or extension. In the case of substitution of one or more consecutive or non-consecutive amino acids, substitutions are preferred in which the substituted amino acids are replaced by "equivalent" amino acids. Here, the expression "equivalent amino acids" is meant to indicate any amino acids likely to be substituted for one of the structural amino acids without however modifying the biological activities of the corresponding antibodies and of those specific examples defined below.

Equivalent amino acids can be determined either on their structural homology with the amino acids for which they are substituted or on the results of comparative tests of biological activity between the various antigen binding proteins likely to be generated.

As a non-limiting example, table 1 below summarizes the possible substitutions likely to be carried out without resulting in a significant modification of the biological activity of the corresponding modified antigen binding protein; inverse substitutions are naturally possible under the same conditions.

TABLE 1

| Original residue | Substitution(s) |
| --- | --- |
| Ala (A) | Val, Gly, Pro |
| Arg (R) | Lys, His |
| Asn (N) | Gln |
| Asp (D) | Glu |
| Cys (C) | Ser |
| Gln (Q) | Asn |
| Glu (E) | Asp |

TABLE 1-continued

| Original residue | Substitution(s) |
|---|---|
| Gly (G) | Ala |
| His (H) | Arg |
| Ile (I) | Leu |
| Leu (L) | Ile, Val, Met |
| Lys (K) | Arg |
| Met (M) | Leu |
| Phe (F) | Tyr |
| Pro (P) | Ala |
| Ser (S) | Thr, Cys |
| Thr (T) | Ser |
| Trp (W) | Tyr |
| Tyr (Y) | Phe, Trp |
| Val (V) | Leu, Ala |

A particular aspect of the invention is that the antibody, or any antigen binding fragment thereof, does not bind to the Insulin receptor (IR). This aspect is of interest as the antibody herein described will not have any negative impact on the IR, meaning the Insulin metabolism.

In another embodiment, still another advantageous aspect of the antibody of the invention is that it is capable of binding not only to the human IGF-1R but also to the monkey IGF-1R, and more particularly to the cynomolgus IGF-1R. This aspect is also of interest as it will facilitate the toxicity and clinical trials.

In another embodiment, the antibody of the invention consists of a monoclonal antibody.

The term "monoclonal antibody" or "Mab" as used herein refers to an antibody obtained from a population of substantially homogeneous antibodies, i.e. the individual antibodies of the population are identical except for possible naturally occurring mutations that may be present in minor amounts. Monoclonal antibodies are highly specific, being directed against a single epitope. Such monoclonal antibody may be produced by a single clone of B cells or hybridoma. Monoclonal antibodies may also be recombinant, i.e. produced by protein engineering. Monoclonal antibodies may also be isolated from phage antibody libraries. In addition, in contrast with preparations of polyclonal antibodies which typically include various antibodies directed against various determinants, or epitopes, each monoclonal antibody is directed against a single epitope of the antigen. The invention relates to an antibody isolated or obtained by purification from natural sources or obtained by genetic recombination or chemical synthesis.

In one embodiment, the monoclonal antibody herein includes murine, chimeric and humanized antibody, such as described after.

The antibody can be derived from an hybridoma of murine origin filed within the French collection for microorganism cultures (CNCM, Pasteur Institute, Paris, France), said hybridoma being obtained by the fusion of Balb/C immunized mice splenocytesilymphocytes and cells of the myeloma Sp 2/O-Ag 14 cell line.

In another embodiment, the antibody of the invention consists of a recombinant antibody. The term "recombinant antibody" refers to an antibody that results from the expression of recombinant DNA within living cells. A recombinant antibody of the invention is obtained by using laboratory methods of genetic recombination, well known by a person skilled in the art, creating DNA sequences that would not be found in biological organisms.

In another embodiment, the antibody of the invention consists of a chemically synthesized antibody.

In an embodiment, the IGF-1R antibody of the invention consists of a murine antibody, then referred as m[name of the antibody].

In an embodiment, the IGF-1R antibody consists of a chimeric antibody, then referred as c[name of the antibody].

In an embodiment, the IGF-1R antibody consists of a humanized antibody, then referred as hz[name of the antibody].

For the avoidance of doubt, in the following specification, the expressions "IGF-1R antibody" and "[name of the antibody]" are similar and include (without contrary specification) the murine, the chimeric and the humanized versions of the said IGF-1R antibody and said "[name of the antibody]". When necessary, the prefix m- (murine), c- (chimeric) or hz- (humanized) is used.

In another embodiment, the antibody of the invention is selected from:

a) an antibody comprising the three heavy chain CDRs of sequences SEQ ID Nos. 7, 2 and 3 and the three light chain CDRs of sequences SEQ ID Nos. 9, 5 and 11;

b) an antibody comprising the three heavy chain CDRs of sequences SEQ ID Nos. 7, 2 and 3 and the three light chain CDRs of sequences SEQ ID Nos. 10, 5 and 11, c) an antibody comprising the three heavy chain CDRs of sequences SEQ ID Nos. 7, 2 and 3 and the three light chain CDRs of sequences SEQ ID Nos. 9, 5 and 12; and d) an antibody comprising the three heavy chain CDRs of sequences SEQ ID Nos. 8, 2 and 3 and the three light chain CDRs of sequences SEQ ID Nos. 9, 5 and 11.

For more clarity, the following table 2 illustrates the CDR sequences, defined according to IMGT, for the preferred antibodies.

TABLE 2

|  | Heavy chain | Light chain | SEQ ID No. |
|---|---|---|---|
| Consensus | CDR-H1 |  | 1 |
|  | CDR-H2 |  | 2 |
|  | CDR-H3 |  | 3 |
|  |  | CDR-L1 | 4 |
|  |  | CDR-L2 | 5 |
|  |  | CDR-L3 | 6 |
| 208F2 | CDR-H1 |  | 7 |
|  | CDR-H2 |  | 2 |
|  | CDR-H3 |  | 3 |
|  |  | CDR-L1 | 9 |
|  |  | CDR-L2 | 5 |
|  |  | CDR-L3 | 11 |
| 212A11 | CDR-H1 |  | 7 |
|  | CDR-H2 |  | 2 |
|  | CDR-H3 |  | 3 |
|  |  | CDR-L1 | 10 |
|  |  | CDR-L2 | 5 |
|  |  | CDR-L3 | 11 |
| 214F8 & 213B10 | CDR-H1 |  | 7 |
|  | CDR-H2 |  | 2 |
|  | CDR-H3 |  | 3 |
|  |  | CDR-L1 | 9 |
|  |  | CDR-L2 | 5 |
|  |  | CDR-L3 | 12 |
| 219D6 | CDR-H1 |  | 8 |
|  | CDR-H2 |  | 2 |
|  | CDR-H3 |  | 3 |
|  |  | CDR-L1 | 9 |
|  |  | CDR-L2 | 5 |
|  |  | CDR-L3 | 11 |

It will be obvious for the man skilled in the art that any combination of the 6 CDRs as above described should be considered as part of the present invention.

As can be observed from this table 2, all the antibodies described in the table have the same sequences for the CDR-H2, CDR-H3 and CDR-L2, this property being of particular interest as above described.

A specific aspect relates to a murine (m) antibody, or any antigen binding fragments, characterized in that said antibody also comprises light-chain and heavy-chain constant regions derived from an antibody of a species heterologous with the mouse, notably man.

Another specific aspect relates to a chimeric (c) antibody, or any antigen binding fragments, characterized in that said antibody also comprises light-chain and heavy-chain constant regions derived from an antibody of a species heterologous with the mouse, notably human.

In an embodiment of the invention, the antibody consists of a chimeric antibody.

A chimeric antibody is one containing a natural variable region (light chain and heavy chain) derived from an antibody of a given species in combination with constant regions of the light chain and the heavy chain of an antibody of a species heterologous to said given species.

The antibodies, or chimeric fragments of same, can be prepared by using the techniques of recombinant genetics. For example, the chimeric antibody could be produced by cloning recombinant DNA containing a promoter and a sequence coding for the variable region of a nonhuman monoclonal antibody of the invention, notably murine, and a sequence coding for the human antibody constant region. A chimeric antibody according to the invention coded by one such recombinant gene could be, for example, a mouse-human chimera, the specificity of this antibody being determined by the variable region derived from the murine DNA and its isotype determined by the constant region derived from human DNA.

In a preferred, but not limitative, embodiment, the antibody of the invention is selected from:
a) an antibody comprising a heavy chain variable domain of sequence SEQ ID No. 13 or any sequence exhibiting at least 80% identity with SEQ ID No. 13 and the three light chain CDRs of sequences SEQ ID Nos. 9, 5 and 11;
b) an antibody comprising, or consisting of, a heavy chain variable domain of sequence SEQ ID No. 14 or any sequence exhibiting at least 80%, 85%, 90%, 95% or 98% identity with SEQ ID No. 14 and the three light chain CDRs of sequences SEQ ID Nos. 10, 5 and 11;
c) an antibody comprising, or consisting of, a heavy chain variable domain of sequence SEQ ID No. 15 or any sequence exhibiting at least 80%, 85%, 90%, 95% or 98% identity with SEQ ID No. 15 and the three light chain CDRs of sequences SEQ ID Nos. 9, 5 and 12;
d) an antibody comprising, or consisting of, a heavy chain variable domain of sequence SEQ ID No. 16 or any sequence exhibiting at least 80%, 85%, 90%, 95% or 98% identity with SEQ ID No. 16 and the three light chain CDRs of sequences SEQ ID Nos. 9, 5 and 11; and
e) an antibody comprising, or consisting of, a heavy chain variable domain of sequence SEQ ID No. 17 or any sequence exhibiting at least 80%, 85%, 90%, 95% or 98% identity with SEQ ID No. 17 and the three light chain CDRs of sequences SEQ ID Nos. 9, 5 and 12.

By "any sequence exhibiting at least 80%, preferably 85%, 90%, 95% or 98% identity with SEQ ID No. 13 to 17", its is intended to designate, respectively, a sequence exhibiting the three heavy chain CDRs SEQ ID Nos. 1, 2 and 3 and, in addition, exhibiting at least 80%, preferably 85%, 90%, 95% or 98%, identity with the full sequence SEQ ID Nos. 13 to 17 outside the sequences corresponding to the CDRs (i.e. SEQ ID No. 1, 2 and 3), wherein "outside the sequences corresponding to the CDRs" is intended for "excepting the sequences corresponding to the CDRs".

In another preferred, but not limitative, embodiment, the antibody of the invention is selected from:
a) an antibody comprising a light chain variable domain of sequence SEQ ID No. 18 or any sequence exhibiting at least 80%, 85%, 90%, 95% or 98% identity with SEQ ID No. 18 and the three heavy chain CDRs of sequences SEQ ID Nos. 7, 2 and 3;
b) an antibody comprising a light chain variable domain of sequence SEQ ID No. 19 or any sequence exhibiting at least 80%, 85%, 90%, 95% or 98% identity with SEQ ID No. 19 and the three heavy chain CDRs of sequences SEQ ID Nos. 7, 2 and 3;
c) an antibody comprising a light chain variable domain of sequence SEQ ID No. 20 or any sequence exhibiting at least 80%, 85%, 90%, 95% or 98% identity with SEQ ID No. 20 and the three heavy chain CDRs of sequences SEQ ID Nos. 7, 2 and 3;
d) an antibody comprising a light chain variable domain of sequence SEQ ID No. 21 or any sequence exhibiting at least 80%, 85%, 90%, 95% or 98% identity with SEQ ID No. 21 and the three heavy chain CDRs of sequences SEQ ID Nos. 8, 2 and 3; and
e) an antibody comprising a light chain variable domain of sequence SEQ ID No. 22 or any sequence exhibiting at least 80%, 85%, 90%, 95% or 98% identity with SEQ ID No. 22 and the three heavy chain CDRs of sequences SEQ ID Nos. 7, 2 and 3.

By "any sequence exhibiting at least 80%, preferably 85%, 90%, 95% or 98% identity with SEQ ID No. 18 to 22", its is intended to designate the sequences exhibiting the three light chain CDRs SEQ ID Nos. 4, 5 and 6 and, in addition, exhibiting at least 80%, preferably 85%, 90%, 95% or 98%, identity with the full sequence SEQ ID No. 18 to 22 outside the sequences corresponding to the CDRs (i.e. SEQ ID No. 4, 5 and 6).

An embodiment of the invention relates to an antibody selected from:
a) an antibody comprising a heavy chain variable domain of sequence SEQ ID No. 13 or any sequence exhibiting at least 80%, 85%, 90%, 95% or 98% identity with SEQ ID No. 13 and a light chain variable domain of sequence SEQ ID No. 18 or any sequence exhibiting at least 80%, 85%, 90%, 95% or 98% identity with SEQ ID No. 18;
b) an antibody comprising a heavy chain variable domain of sequence SEQ ID No. 14 or any sequence exhibiting at least 80%, 85%, 90%, 95% or 98% identity with SEQ ID No. 14 and a light chain variable domain of sequence SEQ ID No. 19 or any sequence exhibiting at least 80%, 85%, 90%, 95% or 98% identity with SEQ ID NO. 19;
c) an antibody comprising a heavy chain variable domain of sequence SEQ ID No. 15 or any sequence exhibiting at least 80%, 85%, 90%, 95% or 98% identity with SEQ ID No. 15 and a light chain variable domain of sequence SEQ ID No. 20 or any sequence exhibiting at least 80%, 85%, 90%, 95% or 98% identity with SEQ ID No. 20;
d) an antibody comprising a heavy chain variable domain of sequence SEQ ID No. 16 or any sequence exhibiting at least 80%, 85%, 90%, 95% or 98% identity with SEQ ID No. 16 and a light chain variable domain of sequence SEQ ID No. 21 or any sequence exhibiting at least 80%, 85%, 90%, 95% or 98% identity with SEQ ID No. 21; and
e) an antibody comprising a heavy chain variable domain of sequence SEQ ID No. 17 or any sequence exhibiting at least 80%, 85%, 90%, 95% or 98% identity with SEQ ID No. 17 and a light chain variable domain of sequence SEQ ID No.

22 or any sequence exhibiting at least 80%, 85%, 90%, 95% or 98% identity with SEQ ID No. 22.

Chimeric antibodies herein described can be also characterized by the constant domain and, more particularly, said chimeric antibodies can be selected or designed such as, without limitation, IgG1, IgG2, IgG3, IgM, IgA, IgD or IgE. More preferably, in the context of the present invention, said chimeric antibodies are IgG1 or IgG4.

An embodiment of the invention relates to a chimeric antibody comprising variable domains VH and VL as above described in the format IgG1. More preferably, said chimeric antibody comprises a constant domain for the VH of sequence SEQ ID No. 43 and a Kappa domain for the VL of sequence SEQ ID No. 45.

An embodiment of the invention relates to a chimeric antibody comprising variable domains VH and VL as above described in the format IgG4. More preferably, said chimeric antibody comprises a constant domain for the VH of sequence SEQ ID No. 44 and a Kappa domain for the VL of sequence SEQ ID No. 45.

In another preferred, but not limitative, embodiment, the antibody of the invention is selected from:
a) an antibody comprising, or consisting of, a heavy chain of sequence SEQ ID No. 23 or any sequence exhibiting at least 80%, 85%, 90%, 95% or 98% identity with SEQ ID No. 23 and a light chain of sequence SEQ ID No. 28 or any sequence exhibiting at least 80%, 85%, 90%, 95% or 98% identity with SEQ ID No. 28;
b) an antibody comprising, or consisting of, a heavy chain of sequence SEQ ID No. 24 or any sequence exhibiting at least 80%, 85%, 90%, 95% or 98% identity with SEQ ID No. 24 and a light chain of sequence SEQ ID No. 29 or any sequence exhibiting at least 80%, 85%, 90%, 95% or 98% identity with SEQ ID No. 29;
c) an antibody comprising, or consisting of, a heavy chain of sequence SEQ ID No. 25 or any sequence exhibiting at least 80%, 85%, 90%, 95% or 98% identity with SEQ ID No. 25 and a light chain of sequence SEQ ID No. 30 or any sequence exhibiting at least 80%, 85%, 90%, 95% or 98% identity with SEQ ID No. 30;
d) an antibody comprising, or consisting of, a heavy chain of sequence SEQ ID No. 26 or any sequence exhibiting at least 80%, 85%, 90%, 95% or 98% identity with SEQ ID No. 26 and a light chain of sequence SEQ ID No. 31 or any sequence exhibiting at least 80%, 85%, 90%, 95% or 98% identity with SEQ ID No. 31; and
e) an antibody comprising, or consisting of, a heavy chain of sequence SEQ ID No. 27 or any sequence exhibiting at least 80%, 85%, 90%, 95% or 98% identity with SEQ ID No. 27 and a light chain of sequence SEQ ID No. 32 or any sequence exhibiting at least 80%, 85%, 90%, 95% or 98% identity with SEQ ID No. 32.

For more clarity, the following table 3 illustrates the sequences of the VH and VL, respectively, for the preferred chimeric antibodies.

TABLE 3

| | Heavy Chain | Light chain | SEQ ID No. |
|---|---|---|---|
| c208F2 | Variable domain (VH) | | 13 |
| | | Variable domain (VL) | 18 |
| | Full length | | 23 |
| | | Full length | 28 |
| c212A11 | Variable domain (VH) | | 14 |
| | | Variable domain (VL) | 19 |
| | Full length | | 24 |
| | | Full length | 29 |

TABLE 3-continued

| | Heavy Chain | Light chain | SEQ ID No. |
|---|---|---|---|
| c214F8 | Variable domain (VH) | | 15 |
| | | Variable domain (VL) | 20 |
| | Full length | | 25 |
| | | Full length | 30 |
| c219D6 | Variable domain (VH) | | 16 |
| | | Variable domain (VL) | 21 |
| | Full length | | 26 |
| | | Full length | 31 |
| c213B10 | Variable domain (VH) | | 17 |
| | | Variable domain (VL) | 22 |
| | Full length | | 27 |
| | | Full length | 32 |

Yet another specific aspect of the present invention relates to a humanized antibody, or an antigen binding fragment thereof, characterized in that the constant regions of the light-chain and the heavy-chain derived from human antibody are, respectively, the lambda or kappa region and the gamma-1, gamma-2 or gamma-4 region.

In an embodiment of the invention, the antibody consists of a humanized antibody.

"Humanized antibodies" means an antibody that contains CDR regions derived from an antibody of nonhuman origin, the other parts of the antibody molecule being derived from one (or several) human antibodies. In addition, some of the skeleton segment residues (called FR) can be modified to preserve binding affinity.

The humanized antibodies or fragments of same can be prepared by techniques known to a person skilled in the art. Such humanized antibodies are preferred for their use in methods involving in vitro diagnoses or preventive and/or therapeutic treatment in vivo. Other humanization techniques, also known to a person skilled in the art, such as, for example, the "CDR grafting" technique described by PDL in patents EP 0 451 216, EP 0 682 040, EP 0 939 127, EP 0 566 647 or U.S. Pat. Nos. 5,530,101, 6,180,370, 5,585,089 and 5,693,761. U.S. Pat. No. 5,639,641 or 6,054,297, 5,886,152 and 5,877,293 can also be cited.

As a particular embodiment of the invention, and as it will be explicated in more details in the following examples, it is herein described an antibody consisting of the hz208F2. Such humanization can also be applied to the other antibodies part of the present invention.

In a preferred embodiment, the antibody according to the present invention comprises a heavy chain variable domain (VH) having:
i) the CDR-H1, CDR-H2 and CDR-H3 of sequences SEQ ID Nos. 7, 2 and 3, respectively,
ii) the FR1, FR2 and FR3 derived from the human germline IGHV1-46*01 (SEQ ID No. 46), and
iii) the FR4 derived from the human germline IGHJ4*01 (SEQ ID No. 48).

In a preferred embodiment, the antibody according to the present invention comprises a light chain variable domain (VL) having:
i) the CDR-L1, CDR-L2 and CDR-L3 of sequences SEQ ID Nos. 9, 5 and 11, respectively,
ii) the FR1, FR2 and FR3 derived from the human germline IGKV1-39*01 (SEQ ID No. 47), and
iii) the FR4 derived from the human germline IGKJ4*01 (SEQ ID No. 49).

In a preferred, but not limitative, embodiment of the invention, the antibody comprises:
a) a heavy chain having CDR-H1, CDR-H2 and CDR-H3 of sequences SEQ ID Nos. 7, 2 and 3, respectively, and FR1, FR2 and FR3 derived from the human germline IGHV1-46*01 (SEQ ID No. 46), and the FR4 derived from the human germline IGHJ4*01 (SEQ ID No. 48); and b) a light chain having CDR-L1, CDR-L2 and CDR-L3 of sequences SEQ ID Nos. 9, 5 and 11, respectively, and FR1, FR2 and FR3 derived from the human germline IGKV1-39*01 (SEQ ID No. 47), and the FR4 derived from the human germline IGKJ4*01 (SEQ ID No. 49).

In an embodiment, the antibody according to the invention comprises a heavy chain variable domain (VH) of sequence SEQ ID No. 33 and a light chain variable domain (VL) of sequence SEQ ID No. 35. Said humanized antibody will be called thereinafter hz208F2 ("Variant" or "Var." 1).

In another embodiment, the antibody according to the present invention comprises a heavy chain variable domain (VH) of sequence SEQ ID No. 33 wherein said sequence SEQ ID No. 33 comprises at least 1 back-mutation selected from the residues 20, 34, 35, 38, 48, 50, 59, 61, 62, 70, 72, 74, 76, 77, 79, 82 and 95.

By the expressions "back-mutation" or "back mutation" it is meant a mutation or replacement of the human residue present in the germline by the corresponding residue initially present in the murine sequence.

In another embodiment, the antibody according to the present invention comprises a heavy chain variable domain (VH) of sequence SEQ ID No. 33 wherein said sequence SEQ ID No. 33 comprises 2, 3, 4, 5, 6, 7, 8, 9, 10, 11, 12, 13, 14, 15, 16 or 17 back-mutations selected from the residues 20, 34, 35, 38, 48, 50, 59, 61, 62, 70, 72, 74, 76, 77, 79, 82 and 95.

For more clarity, the following table 4 illustrates the preferred back-mutations.

TABLE 4

| | Amino acid N° | | | | | | | |
|---|---|---|---|---|---|---|---|---|
| | 20 | 34 | 35 | 38 | 48 | 50 | 59 | 61 |
| Murine | M | I | Y | K | L | W | K | N |
| Human | V | M | H | R | M | I | S | A |

| | Amino acid N° | | | | | | | |
|---|---|---|---|---|---|---|---|---|
| | 62 | 70 | 72 | 74 | 76 | 77 | 79 | 82 | 95 |
| Murine | E | L | A | K | S | N | A | F | F |
| Human | Q | M | R | T | T | S | V | E | Y |

In an embodiment, the antibody according to the present invention comprises a light chain variable domain (VL) of sequence SEQ ID No. 35, wherein said sequence SEQ ID No. 35 comprises at least 1 back-mutation selected from the residues 22, 53, 55, 65, 71, 72, 77 and 87.

In an embodiment, the antibody according to the present invention comprises a light chain variable domain (VL) of sequence SEQ ID No. 35, wherein said sequence SEQ ID No. 35 comprises 2, 3, 4, 5, 6, 7 or 8 back-mutations selected from the residues 22, 53, 55, 65, 71, 72, 77 and 87.

In another embodiment, the antibody according to the present invention comprises:

a) a heavy chain variable domain (VH) of sequence SEQ ID No. 33 wherein said sequence SEQ ID No. 33 comprises at least 1 back-mutation selected from the residues 20, 34, 35, 38, 48, 50, 59, 61, 62, 70, 72, 74, 76, 77, 79, 82 and 95; and b) a light chain variable domain (VL) of sequence SEQ ID No. 35, wherein said sequence SEQ ID No. 35 comprises at least 1 back-mutation selected from the residues 22, 53, 55, 65, 71, 72, 77 and 87.

For more clarity, the following table 5 illustrates the preferred back-mutations.

TABLE 5

| | Amino acid N° | | | | | | | |
|---|---|---|---|---|---|---|---|---|
| | 22 | 53 | 55 | 65 | 71 | 72 | 77 | 87 |
| Murine | S | R | H | R | Y | S | N | F |
| Human | T | S | Q | S | F | T | S | Y |

In such an embodiment, the antibody according to the invention comprises all the back-mutations above mentioned and corresponds to an antibody comprising a heavy chain variable domain (VH) of sequence SEQ ID No. 34 and a light chain variable domain (VL) of sequence SEQ ID No. 36. Said humanized antibody will be called thereinafter hz208F2 ("Variant" or "Var." 3).

In another embodiment, all the humanized forms comprised between the Variant 1 and the Variant 3 are also encompassed by the present invention. In other words, the antibody according to the invention corresponds to an antibody comprising a heavy chain variable domain (VH) of "consensus" sequence SEQ ID No. 41 and a light chain variable domain (VL) of "consensus" sequence SEQ ID No. 42. Said humanized antibody, as a whole, will be called thereinafter hz208F2 ("Variant" or "Var." 2).

In a preferred, but not limitative, embodiment, the antibody of the invention is selected from:

a) an antibody comprising a heavy chain variable domain of sequence SEQ ID No. 33 or any sequence exhibiting at least 80%, 85%, 90%, 95% or 98% identity with SEQ ID No. 33 and the three light chain CDRs of sequences SEQ ID Nos. 9, 5 and 11;

b) an antibody comprising a heavy chain variable domain of sequence SEQ ID No. 34 or any sequence exhibiting at least 80%, 85%, 90%, 95% or 98% identity with SEQ ID No. 34 and the three light chain CDRs of sequences SEQ ID Nos. 9, 5 and 11; and c) an antibody comprising a heavy chain variable domain of sequence selected from SEQ ID Nos. 56, 62, 64, 66, 68, 70, 72, 74, 76, 78 and 80 or any sequence with at least 80%, 85%, 90%, 95% or 98% identity with SEQ ID No. 56, 62, 64, 66, 68, 70, 72, 74, 76, 78 80; and the three light chain CDRs of sequences SEQ ID Nos. 9, 5 and 11.

By "any sequence exhibiting at least 80%, preferably 85%, 90%, 95% or 98% identity with SEQ ID No. 33, 34, 56, 62, 64, 66, 68, 70, 72, 74, 76, 78 or 80", its is intended to designate the sequences exhibiting the three heavy chain CDRs SEQ ID Nos. 1, 2 and 3 and, in addition, exhibiting at least 80%, preferably 85%, 90%, 95% or 98%, identity with the full sequence SEQ ID No. 33, 34, 56, 62, 64, 66, 68, 70, 72, 74, 76, 78 80 outside the sequences corresponding to the CDRs (i.e. SEQ ID Nos. 1, 2 and 3).

In a preferred, but not limitative, embodiment, the antibody of the invention is selected from:

a) an antibody comprising a light chain variable domain of sequence SEQ ID No. 35 or any sequence exhibiting at least 80%, 85%, 90%, 95% or 98% identity with SEQ ID No. 35 and the three heavy chain CDRs of sequences SEQ ID Nos. 7, 2 and 3; and b) an antibody comprising a light chain variable domain of sequence SEQ ID No. 36 or any sequence exhibiting at least 80%, 85%, 90%, 95% or 98% identity with SEQ ID No. 36 and the three heavy chain CDRs of sequences SEQ ID Nos. 7, 2 and 3; and c) an antibody comprising a light chain variable domain of sequence selected from SEQ ID Nos. 57 and 60 or any sequence with at least 80%, 85%, 90%, 95% or 98% identity with SEQ ID No. 57 or 60; and the three heavy chain CDRs of sequences SEQ ID Nos. 7, 2 and 3.

By "any sequence exhibiting at least 80%, preferably 85%, 90%, 95% or 98% identity with SEQ ID No. 35, 36, 57 or 60", its is intended to designate the sequences exhibiting the three light chain CDRs SEQ ID Nos. 4, 5 and 6 and, in addition, exhibiting at least 80%, preferably 85%, 90%, 95% or 98%, identity with the full sequence SEQ ID Nos. 35, 36, 57 or 60 outside the sequences corresponding to the CDRs (i.e. SEQ ID Nos. 4, 5 and 6).

Humanized antibodies herein described can be also characterized by the constant domain and, more particularly, said humanized antibodies can be selected or designed such as, without limitation, IgG1, IgG2, IgG3, IgM, IgA, IgD or IgE. More preferably, in the context of the present invention, said humanized antibodies are IgG1 or IgG4.

An embodiment of the invention relates to a humanized antibody comprising variable domains VH and VL as above described in the format IgG1. More preferably, said humanized antibody comprises a constant domain for the VH of sequence SEQ ID No. 43 and a Kappa domain for the VL of sequence SEQ ID No. 45.

An embodiment of the invention relates to a humanized antibody comprising variable domains VH and VL as above described in the format IgG4. More preferably, said humanized antibody comprises a constant domain for the VH of sequence SEQ ID No. 44 and a Kappa domain for the VL of sequence SEQ ID No. 45.

Still another embodiment of the invention relates to an antibody selected from:
a) an antibody comprising, or consisting of, a heavy chain of sequence SEQ ID No. 37 or any sequence exhibiting at least 80%/o, 85%, 90%, 95%, or 98% identity with SEQ ID No. 37 and a light chain comprising, or consisting of, sequence SEQ ID No. 39 or any sequence exhibiting at least 80%, 85%, 90%, 95%, or 98% identity with SEQ ID No. 39;
b) an antibody comprising, or consisting of, a heavy chain of sequence SEQ ID No. 38 or any sequence exhibiting at least 80%, 85%, 90%, 95%, or 98% identity with SEQ ID No. 38 and a light chain comprising, or consisting of, sequence SEQ ID No. 40 or any sequence exhibiting at least 80%, 85%, 90%, 95%, or 98% identity with SEQ ID No. 40; and
c) an antibody comprising a heavy chain variable domain of sequence selected from SEQ ID Nos. 56, 62, 64, 66, 68, 70, 72, 74, 76, 78 and 80 or any sequence with at least 80%, 85%, 90%, 95%, or 98% identity with SEQ ID No. 56, 62, 64, 66, 68, 70, 72, 74, 76, 78 or 80 and a light chain variable domain of sequence selected from SEQ ID Nos. 57 60 or any sequence with at least 80%, 85%, 90%, 95%, or 98% identity with SEQ ID No. 57 or 60. For more clarity, the following table 6a illustrates non limitative examples of sequences of the VH and VL for the variant 1 (Var. 1) and the variant 3 (Var. 3) of the humanized antibody hz208F2. It also comprises the consensus sequence for the variant 2 (Var. 2).

TABLE 6a

| | Heavy Chain | Light chain | SEQ ID No. |
|---|---|---|---|
| hz208F2 (var. 1) | Variable domain (VH) | | 33 |
| | | Variable domain (VL) | 35 |
| | Full length | | 37 |
| | | Full length | 39 |

TABLE 6a-continued

| | Heavy Chain | Light chain | SEQ ID No. |
|---|---|---|---|
| hz208F2 (Var. 3) | Variable domain (VH) | | 34 |
| | | Variable domain (VL) | 36 |
| | Full length | | 38 |
| | | Full length | 40 |
| hz208F2 (Var. 2) | Variable domain (VH) | | 41 |
| | | Variable domain (VL) | 42 |

In another preferred, but not limitative, embodiment, the antibody of the invention is selected from:
a) an antibody comprising a heavy chain variable domain of sequence selected from SEQ ID Nos. 56, 62, 64, 66, 68, 70, 72, 74, 76, 78 and 80 or any sequence with at least 80%, 85%, 90%, 95%, or 98% identity with SEQ ID No. 56, 62, 64, 66, 68, 70, 72, 74, 76, 78 or 80; and the three light chain CDRs of sequences SEQ ID Nos. 9, 5 and 11;
b) an antibody comprising a light chain variable domain of sequence selected from SEQ ID Nos. 57 and 60 or any sequence with at least 80%, 85%, 90%, 95%, or 98% identity with SEQ ID No. 57 or 60; and the three heavy chain CDRs of sequences SEQ ID Nos. 7, 2 and 3; and
c) an antibody comprising a light chain variable domain of sequence selected from SEQ ID Nos. 57 and 60 or any sequence with at least 80%, 85%, 90%, 95%, or 98% identity with SEQ ID No. 57 or 60; and a heavy chain variable domain of sequence selected from SEQ ID Nos. 56, 62, 64, 66, 68, 70, 72, 74, 76, 78 and 80 or any sequence with at least 80%, 85%, 90%, 95%, or 98% identity with SEQ ID No. 56, 62, 64, 66, 68, 70, 72, 74, 76, 78 or 80.

Still another embodiment of the invention relates to an antibody selected from an antibody comprising or consisting of:
a) a heavy chain of sequence selected from SEQ ID Nos. 58, 63, 65, 67, 69, 71, 73, 75, 77, 79 and 81 or any sequence with at least 80%, preferably 85%, 90%, 95% or 98% identity with SEQ ID Nos. 58, 63, 65, 67, 69, 71, 73, 75, 77, 79 or 81; and
b) a light chain of sequence selected from SEQ ID Nos. 59 and 61 or any sequence with at least 80%, preferably 85%, 90%, 95% or 98% identity with SEQ ID Nos. 59 or 61.

Still another embodiment of the invention relates to an antibody selected from: a) an antibody comprising a heavy chain variable domain of sequence selected from SEQ ID Nos. 56, 62, 64, 66, 68, 70, 72, 74, 76, 78 and 80 or any sequence exhibiting at least 80%, 85%, 90%, 95%, or 98% identity with SEQ ID No. 56, 62, 64, 66, 68, 70, 72, 74, 76, 78 or 80; and a light chain variable domain of sequence SEQ ID No. 57 or any sequence exhibiting at least 80%, 85%, 90%, 95%, or 98% identity with SEQ ID No. 57; and
b) an antibody comprising a heavy chain variable domain of sequence selected from SEQ ID Nos. 56, 64, 68 and 78 or any sequence exhibiting at least 80%, 85%, 90%, 95%, or 98% identity with SEQ ID No. 56, 64, 68 or 78 and a light chain variable domain of sequence SEQ ID No. 60 or any sequence exhibiting at least 80% identity with SEQ ID No. 60

Still another embodiment of the invention relates to an antibody selected from:
a) an antibody comprising, or consisting of, a heavy chain of sequence SEQ ID No. 58 or any sequence exhibiting at least 80%, 85%, 90%, 95%, or 98% identity with SEQ ID No. 58 and a light chain comprising, or consisting of, sequence SEQ ID No. 59 or any sequence exhibiting at least 80%, 85%, 90%, 95%, or 98% identity with SEQ ID No. 59;

b) an antibody comprising or consisting of a heavy chain of sequence SEQ ID No. 58 or any sequence exhibiting at least 80%, 85%, 90%, 95%, or 98% identity with SEQ ID No. 58 and a light chain of sequence SEQ ID No. 61 or any sequence exhibiting at least 80%, 85%, 90%, 95%, or 98% identity with SEQ ID No. 61;

c) an antibody comprising, or consisting of, a heavy chain of sequence SEQ ID No. 63 or any sequence exhibiting at least 80%, 85%, 90%, 95%, or 98% identity with SEQ ID No. 63 and a light chain comprising, or consisting of, sequence SEQ ID No. 59 or any sequence exhibiting at least 80%, 85%, 90%, 95%, or 98% identity with SEQ ID No. 59;

d) an antibody comprising, or consisting of, a heavy chain of sequence SEQ ID No. 65 or any sequence exhibiting at least 80%, 85%, 90%, 95%, or 98% identity with SEQ ID No. 65 and a light chain comprising, or consisting of, sequence SEQ ID No. 59 or any sequence exhibiting at least 80%, 85%, 90%, 95%, or 98% identity with SEQ ID No. 59;

e) an antibody comprising, or consisting of, a heavy chain of sequence SEQ ID No. 65 or any sequence exhibiting at least 80%, 85%, 90%, 95%, or 98% identity with SEQ ID No. 65 and a light chain comprising, or consisting of, sequence SEQ ID No. 61 or any sequence exhibiting at least 80%, 85%, 90%, 95%, or 98% identity with SEQ ID No. 61;

f) an antibody comprising, or consisting of, a heavy chain of sequence SEQ ID No. 67 or any sequence exhibiting at least 80%, 85%, 90%, 95%, or 98% identity with SEQ ID No. 67 and a light chain comprising, or consisting of, sequence SEQ ID No. 59 or any sequence exhibiting at least 80%, 85%, 90%, 95%, or 98% identity with SEQ ID No. 59;

g) an antibody comprising, or consisting of, a heavy chain of sequence SEQ ID No. 69 or any sequence exhibiting at least 80%, 85%, 90%, 95%, or 98% identity with SEQ ID No. 69 and a light chain comprising, or consisting of, sequence SEQ ID No. 59 or any sequence exhibiting at least 80%, 85%, 90%, 95%, or 98% identity with SEQ ID No. 59;

h) an antibody comprising, or consisting of, a heavy chain of sequence SEQ ID No. 69 or any sequence exhibiting at least 80%, 85%, 90%, 95%, or 98% identity with SEQ ID No. 69 and a light chain comprising, or consisting of, sequence SEQ ID No. 61 or any sequence exhibiting at least 80%, 85%, 90%, 95%, or 98% identity with SEQ ID No. 61;

i) an antibody comprising, or consisting of, a heavy chain of sequence SEQ ID No. 71 or any sequence exhibiting at least 80%, 85%, 90%, 95%, or 98% identity with SEQ ID No. 71 and a light chain comprising, or consisting of, sequence SEQ ID No. 59 or any sequence exhibiting at least 80%, 85%, 90%, 95%, or 98% identity with SEQ ID No. 59;

j) an antibody comprising, or consisting of, a heavy chain of sequence SEQ ID No. 73 or any sequence exhibiting at least 80%, 85%, 90%, 95%, or 98% identity with SEQ ID No. 73 and a light chain comprising, or consisting of, sequence SEQ ID No. 59 or any sequence exhibiting at least 80%, 85%, 90%, 95%, or 98% identity with SEQ ID No. 59;

k) an antibody comprising, or consisting of, a heavy chain of sequence SEQ ID No. 75 or any sequence exhibiting at least 80%, 85%, 90%, 95%, or 98% identity with SEQ ID No. 75 and a light chain comprising, or consisting of, sequence SEQ ID No. 59 or any sequence exhibiting at least 80%, 85%, 90%, 95%, or 98% identity with SEQ ID No. 59;

l) an antibody comprising, or consisting of, a heavy chain of sequence SEQ ID No. 77 or any sequence exhibiting at least 80%, 85%, 90%, 95%, or 98% identity with SEQ ID No. 77 and a light chain comprising, or consisting of, sequence SEQ ID No. 59 or any sequence exhibiting at least 80%, 85%, 90%, 95%, or 98% identity with SEQ ID No. 59;

m) an antibody comprising, or consisting of, a heavy chain of sequence SEQ ID No. 79 or any sequence exhibiting at least 80%, 85%, 90%, 95%, or 98% identity with SEQ ID No. 79 and a light chain comprising, or consisting of, sequence SEQ ID No. 59 or any sequence exhibiting at least 80%, 85%, 90%, 95%, or 98% identity with SEQ ID No. 59;

n) an antibody comprising, or consisting of, a heavy chain of sequence SEQ ID No. 79 or any sequence exhibiting at least 80%, 85%, 90%, 95%, or 98% identity with SEQ ID No. 79 and a light chain comprising, or consisting of, sequence SEQ ID No. 61 or any sequence exhibiting at least 80%, 85%, 90%, 95%, or 98% identity with SEQ ID No. 61; and o) an antibody comprising, or consisting of, a heavy chain of sequence SEQ ID No. 81 or any sequence exhibiting at least 80%, 85%, 90%, 95%, or 98% identity with SEQ ID No. 81 and a light chain comprising, or consisting of, sequence SEQ ID No. 59 or any sequence exhibiting at least 80%, 85%, 90%, 95%, or 98% identity with SEQ ID No. 59.

For more clarity, the following table 6b illustrates non limitative examples of sequences of the VH and VL (variable domain and full length) for different variants of the humanized antibody hz208F2.

TABLE 6b

|  | Heavy Chain | Light chain | SEQ ID NO. |
|---|---|---|---|
| hz208F2 H037/L018 | Variable domain (VH) |  | 56 |
|  |  | Variable domain (VL) | 57 |
|  | Full length |  | 58 |
|  |  | Full length | 59 |
| Hz208F2 H037/L021 | Variable domain (VH) |  | 56 |
|  |  | Variable domain (VL) | 60 |
|  | Full length |  | 58 |
|  |  | Full length | 61 |
| Hz208F2 H047/L018 | Variable domain (VH) |  | 62 |
|  |  | Variable domain (VL) | 57 |
|  | Full length |  | 63 |
|  |  | Full length | 59 |
| Hz208F2 H049/L018 | Variable domain (VH) |  | 64 |
|  |  | Variable domain (VL) | 57 |
|  | Full length |  | 65 |
|  |  | Full length | 59 |
| Hz208F2 H049/L021 | Variable domain (VH) |  | 64 |
|  |  | Variable domain (VL) | 60 |
|  | Full length |  | 65 |
|  |  | Full length | 61 |
| Hz208F2 H051/L018 | Variable domain (VH) |  | 66 |
|  |  | Variable domain (VL) | 57 |
|  | Full length |  | 67 |
|  |  | Full length | 59 |
| Hz208F2 H052/L018 | Variable domain (VH) |  | 68 |
|  |  | Variable domain (VL) | 57 |
|  | Full length |  | 69 |
|  |  | Full length | 59 |
| Hz208F2 H052/L021 | Variable domain (VH) |  | 68 |
|  |  | Variable domain (VL) | 60 |
|  | Full length |  | 69 |
|  |  | Full length | 61 |
| Hz208F2 H057/L018 | Variable domain (VH) |  | 70 |
|  |  | Variable domain (VL) | 57 |
|  | Full length |  | 71 |
|  |  | Full length | 59 |
| Hz208F2 H068/L018 | Variable domain (VH) |  | 72 |
|  |  | Variable domain (VL) | 57 |
|  | Full length |  | 73 |
|  |  | Full length | 59 |
| Hz208F2 H070/L018 | Variable domain (VH) |  | 74 |
|  |  | Variable domain (VL) | 57 |
|  | Full length |  | 75 |
|  |  | Full length | 59 |

TABLE 6b-continued

| | Heavy Chain | Light chain | SEQ ID NO. |
|---|---|---|---|
| Hz208F2 H071/L018 | Variable domain (VH) | | 76 |
| | | Variable domain (VL) | 57 |
| | Full length | | 77 |
| | | Full length | 59 |
| Hz208F2 H076/L018 | Variable domain (VH) | | 78 |
| | | Variable domain (VL) | 57 |
| | Full length | | 79 |
| | | Full length | 59 |
| Hz208F2 H076/L021 | Variable domain (VH) | | 78 |
| | | Variable domain (VL) | 60 |
| | Full length | | 79 |
| | | Full length | 61 |
| Hz208F2 H077/L018 | Variable domain (VH) | | 80 |
| | | Variable domain (VL) | 57 |
| | Full length | | 81 |
| | | Full length | 59 |

Another aspect of the present invention is an antibody selected from:
i) an antibody produced by the hybridoma 1-4757, 1-4773, 1-4775, 1-4736 or 1-4774 deposited at the CNCM, Collection Nationale de Culture de Microorganismes, Institut Pasteur, 25, rue du Docteur Roux, 75724 Paris, France on the 30 May 2013, 26 Jun. 2013, 26 Jun. 2013, 24 Apr. 2013 and 26 Jun. 2013, respectively,
ii) an antibody which competes for binding to IGF-1R with the antibody of i); and
iii) an antibody which binds to the same epitope of IGF-1R as does the antibody of i).

According to another aspect, the invention relates to a murine hybridoma selected from the hybridoma I-4757, I-4773, I-4775, I-4736 and I-4774 deposited at the CNCM, Institut Pasteur France on the 30 May 2013, 26 Jun. 2013, 26 Jun. 2013, 24 Apr. 2013 and 26 Jun. 2013, respectively.

A novel aspect of the present invention relates to an isolated nucleic acid coding for an antibody, or for an antigen binding fragment thereof, according to the invention.

The terms "nucleic acid", "nucleic sequence", "nucleic acid sequence", "polynucleotide", "oligonucleotide", "polynucleotide sequence" and "nucleotide sequence", used interchangeably in the present description, mean a precise sequence of nucleotides, modified or not, defining a fragment or a region of a nucleic acid, containing unnatural nucleotides or not, and being either a double-strand DNA, a single-strand DNA or transcription products of said DNAs.

The sequences of the present invention have been isolated and/or purified, i.e., they were sampled directly or indirectly, for example by a copy, their environment having been at least partially modified. Isolated nucleic acids obtained by recombinant genetics, by means, for example, of host cells, or obtained by chemical synthesis should also be mentioned here.

The invention also relates to a vector comprising a nucleic acid coding for an antibody, or for an antigen binding fragment thereof, according to the invention.

The invention notably targets cloning and/or expression vectors that contain such a nucleotide sequence.

The vectors preferably contain elements which allow the expression and/or the secretion of nucleotide sequences in a given host cell. The vector thus must contain a promoter, translation initiation and termination signals, as well as suitable transcription regulation regions. It must be able to be maintained in a stable manner in the host cell and may optionally have specific signals which specify secretion of the translated protein. These various elements are selected and optimized by a person skilled in the art according to the host cell used. For this purpose, the nucleotide sequences can be inserted in self-replicating vectors within the chosen host or be integrative vectors of the chosen host.

Such vectors are prepared by methods typically used by a person skilled in the art and the resulting clones can be introduced into a suitable host by standard methods such as lipofection, electroporation, heat shock or chemical methods.

The vectors are, for example, vectors of plasmid or viral origin. They are used to transform host cells in order to clone or express the nucleotide sequences of the invention.

The invention also relates to isolated host cells transformed by or comprising a vector as above described.

The host cell can be selected among prokaryotic or eukaryotic systems such as bacterial cells, for example, but also yeast cells or animal cells, notably mammal cells (with the exception of human). Insect or plant cells can also be used.

The invention also relates to animals, other than human, that have a transformed cell.

Another aspect relates to a method for the production of an antibody according to the invention, or an antigen binding fragment thereof, characterized in that said method comprises the following steps:
a) the culture in a medium with the suitable culture conditions for a host cell according to the invention; and
b) the recovery of the antibody, or one of its antigen binding fragments, thus produced from the culture medium or from said cultured cells.

The transformed cells are of use in methods for the preparation of recombinant antibodies according to the invention. Methods for the preparation of antibodies in recombinant form using a vector and/or a cell transformed by a vector according to the invention, are also comprised in the present specification. Preferably, a cell transformed by a vector as above described is cultured under conditions that allow the expression of the aforesaid antibody and recovery of said antibody.

As already mentioned, the host cell can be selected among prokaryotic or eukaryotic systems. In particular, it is possible to identify the nucleotide sequences that facilitate secretion in such a prokaryotic or eukaryotic system. A vector according to the invention carrying such a sequence can thus be used advantageously for the production of recombinant proteins to be secreted. Indeed, the purification of these recombinant proteins of interest will be facilitated by the fact that they are present in the supernatant of the cellular culture rather than inside host cells.

The antibody can also be prepared by chemical synthesis. One such method of preparation is also an object of the invention. A person skilled in the art knows methods for chemical synthesis, such as solid-phase techniques or partial solid-phase techniques, by condensation of fragments or by conventional synthesis in solution. Polypeptides obtained by chemical synthesis and capable of containing corresponding unnatural amino acids are also comprised in the invention.

The antibody, or any antigen binding fragments of same, likely to be obtained by the method above described are also comprised in the present invention.

According to a particular aspect, the invention concerns an antibody, or an antigen binding fragment thereof, as above described for use as an addressing vehicle for delivering a cytotoxic agent at a host target site, said host target site consisting of an epitope localized into IGF-1R, preferably the IGF-1R extracellular domain, more preferably the human IGF-1R (SEQ ID No. 50) and still more preferably the human IGF-1R extracellular domain (SEQ ID No. 51), and still more preferably to the N-terminal of the human IGF-1R extracellular domain (SEQ ID No. 52), or any natural variant sequence thereof.

In a preferred embodiment, said host target site is a target site of a mammalian cell, more preferably of a human cell, more preferably cells which naturally or by way of genetic recombination, express IGF-1R.

Another aspect of the invention is an antibody-drug conjugate comprising the antibody, or an antigen binding fragment thereof, as above described, conjugated to a cytotoxic agent.

The invention relates to an immunoconjugate comprising the antibody as described in the present specification conjugated to a cytotoxic agent.

The expressions "immunoconjugate" or "immuno-conjugate" refer generally to a compound comprising at least an addressing product, such as an antibody, physically linked with a one or more therapeutic agent(s), thus creating a highly targeted compound.

In a preferred embodiment, such therapeutic agents consist of cytotoxic agents.

By "cytotoxic agent" or "cytotoxic", it is intended an agent which, when administered to a subject, treats or prevents the development of abnormal cell proliferation, preferably the development of cancer in the subject's body, by inhibiting or preventing a cellular function and/or causing cell death.

Many cytotoxic agents have been isolated or synthesized and make it possible to inhibit the cells proliferation, or to destroy or reduce, if not definitively, at least significantly the tumour cells. However, the toxic activity of these agents is not limited to tumour cells, and the non-tumour cells are also affected and can be destroyed. More particularly, side effects are observed on rapidly renewing cells, such as haematopoietic cells or cells of the epithelium, in particular of the mucous membranes. By way of illustration, the cells of the gastrointestinal tract are largely affected by the use of such cytotoxic agents.

One of the aims of the present invention is also to be able to provide a cytotoxic agent which makes it possible to limit the side effects on normal cells while at the same time conserving a high cytotoxicity on tumour cells.

More particularly, the cytotoxic agent may preferably consist of, without limitation, a drug (i.e. "antibody-drug conjugate"), a toxin (i.e. "immunotoxin" or "antibody-toxin conjugate"), a radioisotope (i.e. "radioimmunoconjugate" or "antibody-radioisotope conjugate"), etc.

In a first preferred embodiment, the immunoconjugate consists of an antibody linked to at least a drug or a medicament. Such an immunoconjugate is referred as an antibody-drug conjugate (or "ADC").

In a first embodiment, such drugs can be described regarding their mode of action. As non limitative example, it can be mentioned alkylating agents such as nitrogen mustard, alkyle-sulfonates, nitrosourea, oxazophorins, aziridines or imine-ethylenes, anti-metabolites, anti-tumor antibiotics, mitotic inhibitors, chromatin function inhibitors, anti-angiogenesis agents, anti-estrogens, anti-androgens, chelating agents, Iron absorption stimulant, Cyclooxygenase inhibitors, Phosphodiesterase inhibitors, DNA inhibitors, DNA synthetis inhibitors, Apopstotis stimulants, Thymidylate inhibitors, T cell inhibitors, Interferon agonists, Ribonucleoside triphosphate reductase inhibitors, Aromatase inhibitors, Estrogen receptor antagonists, Tyrosine kinase inhibitors, Cell cycle inhibitors, Taxane, Tubulin inhibitors, angiogenesis inhibitors, macrophage stimulants, Neurokinin receptor antagonists, Cannabinoid receptor agonists, Dopamine receptor agonists, granulocytes stimulating factor agonists, Erythropoietin receptor agonists, somatostatin receptor agonists, LHRH agonists, Calcium sensitizers, VEGF receptor antagonists, interleukin receptor antagonists, osteoclast inhibitors, radical formation stimulants, endothelin receptor antagonists, Vinca alkaloid, anti-hormone or immunomodulators or any other new drug that fullfills the activity criteria of a cytotoxic or a toxin.

Such drugs are, for example, cited in the VIDAL 2010, on the page devoted to the compounds attached to the cancerology and hematology column "Cytotoxics", these cytotoxic compounds cited with reference to this document are cited here as preferred cytotoxic agents.

More particularly, without limitation, the following drugs or medicaments are preferred according to the invention: mechlorethamine, chlorambucol, melphalen, chlorydrate, pipobromen, prednimustin, disodic-phosphate, estramustine, cyclophosphamide, altretamine, trofosfamide, sulfofosfamide, ifosfamide, thiotepa, triethylenamine, altetramine, carmustine, streptozocin, fotemustin, lomustine, busulfan, treosulfan, improsulfan, dacarbazine, cis-platinum, oxaliplatin, lobaplatin, heptaplatin, miriplatin hydrate, carboplatin, methotrexate, pemetrexed, 5-fluoruracil, floxuridine, 5-fluorodeoxyuridine, capecitabine, cytarabine, fludarabine, cytosine arabinoside, 6-mercaptopurine (6-MP), nelarabine, 6-thioguanine (6-TG), chlorodesoxyadenosine, 5-azacytidine, gemcitabine, cladribine, deoxycoformycin, tegafur, pentostatin, doxorubicin, daunorubicin, idarubicin, valrubicin, mitoxantrone, dactinomycin, mithramycin, plicamycin, mitomycin C, bleomycin, procarbazine, paclitaxel, docetaxel, vinblastine, vincristine, vindesine, vinorelbine, topotecan, irinotecan, etoposide, valrubicin, amrubicin hydrochloride, pirarubicin, elliptinium acetate, zorubicin, epirubicin, idarubicin and teniposide, razoxin, marimastat, batimastat, prinomastat, tanomastat, ilomastat, CGS-27023A, halofuginon, COL-3, neovastat, thalidomide, CDC 501, DMXAA, L-651582, squalamine, endostatin, SU5416, SU6668, interferon-alpha, EMD121974, interleukin-12, IM862, angiostatin, tamoxifen, toremifene, raloxifene, droloxifene, iodoxyfene, anastrozole, letrozole, exemestane, flutamide, nilutamide, sprironolactone, cyproterone acetate, finasteride, cimitidine, bortezomid, Velcade, bicalutamide, cyproterone, flutamide, fulvestran, exemestane, dasatinib, erlotinib, gefitinib, imatinib, lapatinib, nilotinib, sorafenib, sunitinib, retinoid, rexinoid, methoxsalene, methylaminolevulinate, aldesleukine, OCT-43, denileukin diflitox, interleukin-2, tasonermine, lentinan, sizofilan, roquinimex, pidotimod, pegademase, thymopentine, poly I:C, procodazol, Tic BCG, *Corynebacterium parvum*, NOV-002, ukrain, levamisole, 1311-chTNT, H-101, celmoleukin, interferon alfa2a, interferon alfa2b, interferon gamma1a, interleukin-2, mobenakin, Rexin-G, teceleukin, aclarubicin, actinomycin, arglabin, asparaginase, carzinophilin, chromomycin, daunomycin, leucovorin, masoprocol, neocarzinostatin, peplomycin, sarkomycin, solamargine, trabectedin, streptozocin, testosterone, kunecatechins, sinecatechins, alitretinoin, belotecan hydrocholoride, calusterone, dromostanolone, elliptinium acetate, ethinyl estradiol, etoposide, fluoxymesterone, formestane, fosfetrol, goserelin acetate, hexyl aminolevulinate, histrelin, hydroxyprogesterone, ixabepilone, leuprolide, medroxyprogesterone acetate, megesterol acetate, methylprednisolone, methyltestosterone, miltefosine, mitobronitol, nadrolone phenylpropionate, norethindrone acetate, prednisolone, prednisone, temsirrolimus, testolactone, triamconolone, triptorelin, vapreotide acetate, zinostatin stimalamer, amsacrine, arsenic trioxide, bisantrene hydrochloride, chlorambucil, chlortrianisene, cis-diamminedichloroplatinium, cyclophosphamide, diethylstilbestrol, hexamethylmelamine, hydroxyurea, lenalidomide, lonidamine, mechlorethanamine, mitotane, nedaplatin, nimustine hydrochloride, pamidronate, pipobroman, porfumer sodium, ranimustine, razoxane, semustine, sobuzoxane, mesylate, triethylenemelamine, zoledronic acid, camostat mesylate, fadrozole HCl, nafoxidine, aminoglutethimide, carmofur, clofarabine, cytosine arabinoside, decitabine, doxifluridine, enocitabine, fludarabne phosphate, fluorouracil, ftorafur, uracil mustard, abarelix, bexarotene, raltiterxed, tamibarotene, temozolomide, vorinostat, megastrol, clodronate disodium, levamisole, ferumoxytol, iron isomaltoside, celecoxib, ibudilast, bendamustine, altretamine, mitolactol, temsirolimus, pralatrexate, TS-1, decitabine, bicalutamide, flutamide, letrozole, clodronate disodium, degarelix, toremifene citrate, histamine dihydrochloride, DW-166HC, nitracrine, decitabine, irinoteacn hydrochloride, amsacrine, romidepsin, tretinoin, cabazitaxel, vandetanib, lenalidomide, ibandronic acid, miltefosine, vitespen, mifamurtide, nadroparin, granisetron, ondansetron, tropisetron, alizapride, ramosetron, dolasetron mesilate, fosaprepitant dimeglumine, nabilone, aprepitant, dronabinol, TY-10721, lisuride hydrogen maleate, epiceram, defibrotide, dabigatran etexilate, filgrastim, pegfilgrastim, reditux, epoetin, molgramostim, oprelvekin, sipuleucel-T, M-Vax, acetyl L-carnitine, donepezil hydrochloride, 5-aminolevulinic acid, methyl aminolevulinate, cetrorelix acetate, icodextrin, leuprorelin, metbylphenidate, octreotide, amlexanox, plerixafor, menatetrenone, anethole dithiolethione, doxercalciferol, cinacalcet hydrochloride, alefacept, romiplostim, thymoglobulin, thymalfasin, ubenimex, imiquimod, everolimus, sirolimus, H-101, lasofoxifene, trilostane, incadronate, gangliosides, pegaptanib octasodium, vertoporfin, minodronic acid, zoledronic acid, gallium nitrate, alendronate sodium, etidronate disodium, disodium pamidronate, dutasteride, sodium stibogluconate, armodafinil, dexrazoxane, amifostine, WF-10, temoporfin, darbepoetin alfa, ancestim, sargramostim, palifermin, R-744, nepidermin, oprelvekin, denileukin diftitox, crisantaspase, buserelin, deslorelin, lanreotide, octreotide, pilocarpine, bosentan, calicheamicin, maytansinoids, ciclonicate and pyrrolobenzodiazepines, particularly those disclosed in the PCT application published under number WO2011/130598.

In another embodiment, the immunoconjugate consists of an antibody linked to at least a radioisotope. Such an immunoconjugate is referred as an antibody-radioisotope conjugate (or "ARC").

For selective destruction of the tumor, the antibody may comprise a highly radioactive atom. A variety of radioactive isotopes are available for the production of ARC such as, without limitation, $At^{211}$, $C^{13}$, $N^{15}$, $O^{17}$, $Fl^{19}$, $I^{123}$, $I^{131}$, $I^{125}$, $In^{111}$, $Y^{90}$, $Re^{186}$, $Re^{188}$, $Sm^{153}$, $tc^{99}m$, $Bi^{212}$, $P^{32}$, $Pb^{212}$, radioactive isotopes of Lu, gadolinium, manganese or iron.

Any methods or processes known by the person skilled in the art can be used to incorporate such radioisotope in the ARC. As non limitative example, $tc^{99}m$ or $I^{123}$, $Re^{186}$, $Re^{188}$ and $In^{111}$ can be attached via a cysteine residue. $Y^{90}$ can be attached via a lysine residue. $I^{123}$ can be attached using the IODOGEN method.

Several examples can be mentioned to illustrate the knowledge of the person skilled in the art in the field of ARC such as Zevalin® which is an ARC composed of an anti-CD20 monoclonal antibody and $In^{111}$ or $Y^{90}$ radioisotope bound by a thiourea linker-chelator; or Mylotarg® which is composed of an anti-CD33 antibody linked to calicheamicin, (U.S. Pat. Nos. 4,970,198; 5,079,233; 5,585,089; 5,606,040; 5,693,762; 5,739,116; 5,767,285; 5,773,001). More recently, it can also be mentioned the ADC referred as Adcetris (corresponding to the Brentuximab vedotin) which has been recently accepted by the FDA in the treatment of Hodgkin's lymphoma.

In another embodiment, the immunoconjugate consists of an antibody linked to at least a toxin. Such an immunoconjugate is referred as an antibody-toxin conjugate (or "ATC").

Toxins are effective and specific poisons produced by living organisms. They usually consist of an amino acid chain which can vary in molecular weight between a couple of hundred (peptides) and one hundred thousand (proteins). They may also be low-molecular organic compounds. Toxins are produced by numerous organisms, e.g., bacteria, fungi, algae and plants. Many of them are extremely poisonous, with a toxicity that is several orders of magnitude greater than the nerve agents.

Toxins used in ATC can include, without limitation, all kind of toxins which may exert their cytotoxic effects by mechanisms including tubulin binding, DNA binding, or topoisomerase inhibition.

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

Small molecule toxins, such as dolastatins, auristatins, particularly the monomethylauristatine E (MMAE), a trichothecene, and CC 1065, and the derivatives of these toxins that have toxin activity, are also contemplated herein. Dolastatins and auristatins have been shown to interfere with microtubule dynamics, GTP hydrolysis, and nuclear and cellular division and have anticancer and antifungal activity.

"Linker", "Linker Unit", or "link" means a chemical moiety comprising a covalent bond or a chain of atoms that covalently attaches an antibody to at least one cytotoxic agent.

Linkers may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Carbon-14-labeled 1-isothiocyanatobenzyl-3-methyldiethylene triaminepentaacetic acid (MX-DTPA) is an exemplary chelating agent for conjugation of cyctotoxic agents to the addressing system. Other cross-linker reagents may be BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

The linker may be a "non cleavable" or "cleavable".

In a preferred embodiment, it consists in a "cleavable linker" facilitating release of the cytotoxic agent in the cell. For example, an acid-labile linker, peptidase-sensitive linker, photolabile linker, dimethyl linker or disulfide-containing linker may be used. The linker is, in a preferred embodiment, cleavable under intracellular conditions, such that cleavage of the linker releases the cytotoxic agent from the antibody in the intracellular environment.

For example, in some embodiments, the linker is cleavable by a cleaving agent that is present in the intracellular environment (e.g., within a lysosome or endosome or caveolea). The linker can be, for example, a peptidyl linker that is cleaved by an intracellular peptidase or protease enzyme, including, but not limited to, a lysosomal or endosomal protease. Typically, the peptidyl linker is at least two amino acids long or at least three amino acids long. Cleaving agents can include cathepsins B and D and plasmin, all of which are known to hydrolyze dipeptide drug derivatives resulting in the release of active drug inside target cells. For example, a peptidyl linker that is cleavable by the thiol-dependent protease cathepsin-B, which is highly expressed in cancerous tissue, can be used (e.g., a Phe-Leu or a Gly-Phe-Leu-Gly linker). In specific embodiments, the peptidyl linker cleavable by an intracellular protease is a Val-Cit linker or a Phe-Lys linker. One advantage of using intracellular proteolytic release of the cytotoxic agent is that the agent is typically attenuated when conjugated and the serum stabilities of the conjugates are typically high.

In other embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond.

In yet other embodiments, the linker is cleavable under reducing conditions (e.g., a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT.

As non limitative example of non-cleavable or "non reductible" linkers, it can be mentioned the immunoconjugate Trastuzumab-DM1 (TDM1) which combines trastuzumab with a linked chemotherapy agent, maytansine.

In a preferred embodiment, the immunoconjugate of the invention may be prepared by any method known by the person skilled in the art such as, without limitation, i) reaction of a nucleophilic group of the antibody with a bivalent linker reagent followed by reaction with the cytotoxic agent or ii) reaction of a nucleophilic group of a cytotoxic agent with a bivalent linker reagent followed by reaction with the nucleophilic group of the antibody.

Nucleophilic groups on antibody include, without limitation, N-terminal amine groups, side chain amine groups, e.g. lysine, side chain thiol groups, and sugar hydroxyl or amino groups when the antigen binding protein is glycosylated. Amine, thiol, and hydroxyl groups are nucleophilic and capable of reacting to form covalent bonds with electrophilic groups on linker moieties and linker reagents including, without limitation, active esters such as NHS esters, HOBt esters, haloformates, and acid halides; alkyl and benzyl halides such as haloacetamides; aldehydes, ketones, carboxyl, and maleimide groups. The antibody may have reducible interchain disulfides, i.e. cysteine bridges. The antibody may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into the antibody through any reaction known by the person skilled in the art. As non limitative example, reactive thiol groups may be introduced into the antibody by introducing one or more cysteine residues.

Immunoconjugates may also be produced by modification of the antibody to introduce electrophilic moieties, which can react with nucleophilic substituents on the linker reagent or cytotoxic agent. The sugars of glycosylated antibody may be oxidized to form aldehyde or ketone groups which may react with the amine group of linker reagents or cytotoxic agent. The resulting imine Schiff base groups may form a stable linkage, or may be reduced to form stable amine linkages. In one embodiment, reaction of the carbohydrate portion of a glycosylated antibody with either galactose oxidase or sodium meta-periodate may yield carbonyl (aldehyde and ketone) groups in the antibody that can react with appropriate groups on the drug. In another embodiment, antibodies containing N-terminal serine or threonine residues can react with sodium meta-periodate, resulting in production of an aldehyde in place of the first amino acid.

In certain preferred embodiments, the linker unit may have the following general formula:

-Ta-Ww-Yywherein:
-T- is a stretcher unit;
a is 0 or 1;
—W— is an amino acid unit;
w is independently an integer ranging from 1 to 12;
—Y— is a spacer unit;
y is 0, 1 or 2.

The stretcher unit (-T-), when present, links the antibody to an amino acid unit (—W—). Useful functional groups that can be present on the antibody, either naturally or via chemical manipulation, include sulfhydryl, amino, hydroxyl, the anomeric hydroxyl group of a carbohydrate, and carboxyl. Suitable functional groups are sulfhydryl and amino. Sulfhydryl groups can be generated by reduction of the intramolecular disulfide bonds of the antibody, if present. Alternatively, sulfhydryl groups can be generated by reaction of an amino group of a lysine moiety of the antibody with 2-iminothiolane or other sulfhydryl generating reagents. In specific embodiments, the antibody is a recombinant antibody and is engineered to carry one or more lysines. More preferably, the antibody can be engineered to carry one or more Cysteines (cf. ThioMabs).

In certain specific embodiments, the stretcher unit forms a bond with a sulfur atom of the antibody. The sulfur atom can be derived from a sulfhydryl (—SH) group of a reduced antibody.

In certain other specific embodiments, the stretcher unit is linked to the antibody via a disulfide bond between a sulfur atom of the antibody and a sulfur atom of the stretcher unit.

In other specific embodiments, the reactive group of the stretcher contains a reactive site that can be reactive to an amino group of the antibody. The amino group can be that of an arginine or a lysine. Suitable amine reactive sites include, but are not limited to, activated esters such as succinimide esters, 4-nitrophenyl esters, pentafluorophenyl esters, anhydrides, acid chlorides, sulfonyl chlorides, isocyanates and isothiocyanates.

In yet another aspect, the reactive function of the stretcher contains a reactive site that is reactive to a modified carbohydrate group that can be present on the antibody. In a specific embodiment, the antibody is glycosylated enzymatically to provide a carbohydrate moiety. The carbohydrate may be mildly oxidized with a reagent such as sodium periodate and the resulting carbonyl unit of the oxidized carbohydrate can be condensed with a stretcher that contains a functionality such as a hydrazide, an oxime, a reactive amine, a hydrazine, a thiosemicarbazide, a hydrazine carboxylate, or an arylhydrazide.

The amino acid unit (—W—) links the stretcher unit (-T-) to the Spacer unit (—Y—) if the spacer unit is present, and links the stretcher unit to the cytotoxic agent if the spacer unit is absent.

As above mentioned, -Ww- may be a dipeptide, tripeptide, tetrapeptide, pentapeptide, hexapeptide, heptapeptide, octapeptide, nonapeptide, decapeptide, undecapeptide or dodecapeptide unit In some embodiments, the amino acid unit may comprise amino acid residues such as, without limitation, alanine, valine, leucine, isoleucine, methionine, phenylalanine, tryptophan, proline, lysine protected with acetyl or formyl, arginine, arginine protected with tosyl or nitro groups, histidine, ornithine, ornithine protected with acetyl or formyl and citrulline. Exemplary amino acid linker components include preferably a dipeptide, a tripeptide, a tetrapeptide or a pentapeptide.

Exemplary dipeptides include: Val-Cit, Ala-Val, Ala-Ala, Val-Ala, Lys-Lys, Cit-Cit, Val-Lys, Ala-Phe, Phe-Lys, Ala-Lys, Phe-Cit, Leu-Cit, Ile-Cit, Trp-Cit, Phe-Ala, Phe-N$^9$-tosyl-Arg, Phe-N$^9$-Nitro-Arg.

Exemplary tripeptides include: Val-Ala-Val, Ala-Asn-Val, Val-Leu-Lys, Ala-Ala-Asn, Phe-Phe-Lys, Gly-Gly-Gly, D-Phe-Phe-Lys, Gly-Phe-Lys.

Exemplary tetrapeptide include: Gly-Phe-Leu-Gly (SEQ ID NO. 53), Ala-Leu-Ala-Leu (SEQ ID NO. 54).

Exemplary pentapeptide include: Pro-Val-Gly-Val-Val (SEQ ID NO. 55).

Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzyme, for example, a tumor-associated protease, cathepsin B, C and D, or a plasmin protease.

The amino acid unit of the linker can be enzymatically cleaved by an enzyme including, but not limited to, a tumor-associated protease to liberate the cytotoxic agent.

The amino acid unit can be designed and optimized in its selectivity for enzymatic cleavage by a particular tumor-associated protease. The suitable units are those whose cleavage is catalyzed by the proteases, cathepsin B, C and D, and plasmin.

The spacer unit (—Y—), when present, links an amino acid unit to the cytotoxic agent. Spacer units are of two general types: self-immolative and non self-immolative. A non self-immolative spacer unit is one in which part or all of the spacer unit remains bound to the cytotoxic agent after enzymatic cleavage of an amino acid unit from the immunoconjugate. Examples of a non self-immolative spacer unit include, but are not limited to a (glycine-glycine) spacer unit and a glycine spacer unit. To liberate the cytotoxic agent, an independent hydrolysis reaction should take place within the target cell to cleave the glycine-drug unit bond.

In another embodiment, a non self-immolative the spacer unit (—Y—) is -Gly-.

In one embodiment, the immunoconjugate lacks a spacer unit (y=0). Alternatively, an imunoconjugate containing a self-immolative spacer unit can release the cytotoxic agent without the need for a separate hydrolysis step. In these embodiments, —Y— is a p-aminobenzyl alcohol (PAB) unit that is linked to -Ww- via the nitrogen atom of the PAB group, and connected directly to -D via a carbonate, carbamate or ether group.

Other examples of self-immolative spacers include, but are not limited to, aromatic compounds that are electronically equivalent to the PAB group such as 2-aminoimidazol-5-methanol derivatives and ortho or para-aminobenzylacetals. Spacers can be used that undergo facile cyclization upon amide bond hydrolysis, such as substituted and unsubstituted 4-aminobutyric acid amides, appropriately substituted bicyclo[2.2.1] and bicyclo[2.2.2] ring systems and 2-aminophenylpropionic acid amides.

In an alternate embodiment, the spacer unit is a branched bis(hydroxymethyl)styrene (BHMS) unit, which can be used to incorporate additional cytotoxic agents.

The drug loading also referred as the Drug-Antibody ratio (DAR) is the average number of PBD drugs per cell binding agent.

In the case of an antibody IgG1 isotype, where the drugs are bound to cysteines after partial antibody reduction, drug loading may range from 1 to 8 drugs (D) per antibody, i.e. where 1, 2, 3, 4, 5, 6, 7, and 8 drug moieties are covalently attached to the antibody.

In the case of an antibody IgG2 isotype, where the drugs are bound to cysteines after partial antibody reduction, drug loading may range from 1 to 12 drugs (D) per antibody, i.e. where 1, 2, 3, 4, 5, 6, 7, 8, 9, 10, 11 and 12 drug moieties are covalently attached to the antibody.

Compositions of ADC include collections of cell binding agents, e.g. antibodies, conjugated with a range of drugs, from 1 to 8 or 1 to 12.

Where drugs are bound to lysines, drug loading may range from 1 to 80 drugs (D) per cell antibody, although an upper limit of 40, 20, 10 or 8 may be preferred.

Compositions of ADC include collections of cell binding agents, e.g. antibodies, conjugated with a range of drugs, from 1 to 80, 1 to 40, 1 to 20, 1 to 10 or 1 to 8.

The average number of drugs per antibody in preparations of ADC from conjugation reactions may be characterized by conventional means. The quantitative distribution of ADC in terms of drug ratio may also be determined. For some antibody-drug conjugates, drug ratio may be limited by the number of attachment sites on the antibody. For example, an antibody may have only one or several cysteine thiol groups, or may have only one or several sufficiently reactive thiol groups through which a linker may be attached. Higher drug loading, e.g. drug ratio >5, may cause aggregation, insolubility, toxicity, or loss of cellular permeability of certain antibody-drug conjugates.

Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by engineering one, two, three, four, or more cysteine residues (e.g., preparing mutant antibodies comprising one or more non-native cysteine amino acid residues). U.S. Pat. No. 7,521,541 teaches engineering antibodies by introduction of reactive cysteine amino acids.

Cysteine amino acids may be engineered at reactive sites in an antibody and which do not form intrachain or intermolecular disulfide linkages (Junutula, et al., 2008b Nature Biotech., 26(8):925-932; Doman et al (2009) Blood 114(13): 2721-2729; U.S. Pat. Nos. 7,521,541; 7,723,485; WO2009/052249). The engineered cysteine thiols may react with linker reagents or the drug-linker reagents of the present invention which have thiol-reactive, electrophilic groups such as maleimide or alpha-halo amides to form ADC with cysteine engineered antibodies and the PBD drug moieties. The location of the drug moiety can thus be designed, controlled, and known. The drug loading can be controlled since the engineered cysteine thiol groups typically react with thiol-reactive linker reagents or drug-linker reagents in high yield. Engineering an IgG antibody to introduce a cysteine amino acid by substitution at a single site on the heavy or light chain gives two new cysteines on the symmetrical antibody. A drug loading near 2 can be achieved with near homogeneity of the conjugation product ADC.

In addition, the invention also relates to an immunoconjugate or an antibody-drug conjugate as above described for use as a medicament.

Also, the invention further relates to an immunoconjugate or an antibody-drug conjugate as above described for use in the treatment of cancer.

The invention relates to antibody-drug conjugate as above described for use as a medicament. In a particular embodiment, the invention relates to antibody-drug conjugate as above described for use in the treatment of cancer. In a more particular embodiment, the invention relates to antibody-drug conjugate as above described for use in the treatment of IGF-1R expressing cancer, or IGF-1R related cancers.

IGF-1R related cancers include tumoral cells expressing or over-expressing whole or part of the IGF-1R at their surface.

More particularly, said cancers are breast, colon, esophageal carcinoma, hepatocellular, gastric, glyoma, lung, melanoma, osteosarcoma, ovarian, prostate, rhabdomyosarcoma, renal, thyroid, uterine endometrial cancer and any drug resistance phenomena.

In another aspect, the present invention relates to the use of an antibody-drug conjugate according to the invention for the treatment of an IGF-1R expressing cancer.

Another object of the invention is a pharmaceutical composition comprising an antibody according to the invention or an antibody-drug conjugate, or immunoconjugate, as described in the specification.

More particularly, the invention relates to a pharmaceutical composition comprising an antibody according to the invention or an antibody-drug conjugate, or the immunoconjugate above described and at least an excipient and/or a pharmaceutically acceptable vehicle.

The invention concerns a pharmaceutical composition comprising the antibody or the antibody-drug conjugate above described, and at least an excipient and/or a pharmaceutical acceptable vehicle.

In the present description, the expression "pharmaceutically acceptable vehicle" or "excipient" is intended to indicate a compound or a combination of compounds entering into a pharmaceutical composition not provoking secondary reactions and which allows, for example, facilitation of the administration of the active compound(s), an increase in its lifespan and/or in its efficacy in the body, an increase in its solubility in solution or else an improvement in its conservation. These pharmaceutically acceptable vehicles and excipients are well known and will be adapted by the person skilled in the art as a function of the nature and of the mode of administration of the active compound(s) chosen.

Preferably, these immunoconjugates will be administered by the systemic route, in particular by the intravenous route, by the intramuscular, intradermal, intraperitoneal or subcutaneous route, or by the oral route. In a more preferred manner, the composition comprising the immunoconjugates will be administered several times, in a sequential manner.

Their modes of administration, dosages and optimum pharmaceutical forms can be determined according to the criteria generally taken into account in the establishment of a treatment adapted to a patient such as, for example, the age or the body weight of the patient, the seriousness of his/her general condition, the tolerance to the treatment and the secondary effects noted.

In another aspect, the present invention relates to a pharmaceutical composition comprising an antibody according to the invention or an antibody-drug conjugate, or the immunoconjugate above described and at least an excipient and/or a pharmaceutically acceptable vehicle for use in the treatment of cancer. In a more particular aspect, the present invention relates to a pharmaceutical composition comprising an antibody according to the invention or an antibody-drug conjugate, or the immunoconjugate above described and at least an excipient and/or a pharmaceutically acceptable vehicle for use in the treatment of an IGF-1R expressing cancer.

The invention also relates to a method for the treatment of cancer in a subject, and in particular for the treatment of an IGF-1R expressing cancer, comprising administering to said subject an effective amount of at least an antibody-drug conjugate according to the invention. The present invention further relates to a method for the treatment of cancer in a subject, and in particular for the treatment of an IGF-1R expressing cancer, comprising administering to said subject an effective amount of a pharmaceutical composition according to the invention.

In another embodiment, the present invention relates to a method of delivering a drug or a medicament to an IGF-1R expressing cancer cell in a subject, comprising administering to said subject an effective amount of at least the antibody-drug conjugate according to the invention or a pharmaceutical composition according to the invention.

Other characteristics and advantages of the invention appear in the continuation of the description with the examples and the figures whose legends are represented below.

BRIEF DESCRIPTION OF THE DRAWINGS

FIG. 3A, FIG. 3B, and FIG. 3C: Antibody binding to the human native IGF-1R by FACS analyses. FIG. 3A represents the titration curve, on MCF-7 cell line, of one chimeric anti-IGF-1R Ab representative for each epitope clustering group. MFI represents the mean of fluorescent intensity. FIG. 3B represents the $EC_{50}$ of both murine and chimeric anti-IGF-1R antibodies on the MCF-7 cell line. FIG. 3C represents the $B_{max}$ of chimeric anti-IGF-1R antibodies on MCF-7 cell line.

FIG. 4A represents titration curves of one chimeric anti-IGF-1R Ab representative of each epitope clustering group on IGF-1R cell line. MFI represents the mean of fluorescent intensity. FIG. 4B represents the binding of one chimeric anti-IGF-1R Ab representative of each epitope clustering group on the human IGF-1R⁻ cell line. MFI represents the mean of fluorescent intensity FIG. 5A represents the binding of murine anti-IGF-1R Ab on the hIR⁺ transfected cell line. FIG. 5B represents the binding of chimeric anti-IGF-1R Ab on the IR+ cell line. MFI represents the mean of fluorescent intensity. In panel A and B the commercially available anti-hIR antibody described as GRO5 (Calbiochem) has been introduced as a positive control.

FIG. 7A represents the titration curves of one chimeric anti-IGF-1R Ab representative of each epitope clustering group on the COS-7 cell line. MFI represents the mean of fluorescent intensity. FIG. 7B represents the $EC_{50}$ of both murine and chimeric anti-IGF-1R antibodies on COS-7 cell line. FIG. 7C represents the $EC_{50}$ of chimeric anti-IGF-1R antibodies on both hIGF-1R transfected cells and COS-7 cells. GR11L (Calbiochem) was introduced as a positive control.

FIG. 11: Cell surface binding of anti-IGF-1R antibodies is down-regulated at 37° C. MCF-7 cells were incubated at 4° C. or 37° C. for 4 h with 10 µg/ml of each Ab. The figure represents the ΔMFI.

FIG. 12A and FIG. 12B: Antibody surface decay. Cell surface bound antibody was assessed after 10, 20, 30, 60 and 120 min at 37° C. FIG. 12A represents the % of remaining IGF-1R in comparison to the signal intensity measured at 4° C. FIG. 12B represents Half Life calculation using Prims Software and using exponential decay fitting.

FIG. 14A: MCF-7 cells incubated with m208F2 for 20 min. at 4° C. and washed before incubation [a] at 37° C. for 15 [b)], 30 [c)] and 60 [d)] min. Cells were fixed and permeabilized. The m208F2 Ab was revealed using an anti-mouse IgG Alexa488 and Lamp-1 was revealed with a rabbit anti-Lamp-1 antibody and with a secondary anti-rabbit IgG Alexa 555. FIG. 14B, FIG. 14C, and FIG. 14D: MCF-7 cells were incubated for 30 minutes at 37° C. with each of the other anti-hIGF-1R murine antibody to be tested and then stained as described above. Colocalization was identified using the colocalization highliter plug-in of the Image J software.

FIG. 17A: MCF-7 cells were incubated with increasing concentrations of the chimeric anti-IGF-1R antibodies in combination with the human Fab-ZAP kit. Cell viability was measured using CellTiter-Glo® luminescent cell viability assay. The c9G4 chimeric antibody was used as irrelevant antibody. FIG. 17B: $IC_{50}$s from results depicted in FIG. 17A.

FIG. 19A, FIG. 19B, FIG. 19C, and FIG. 19D: Binding characteristic of the first humanized form of the c208F2 Mab. Binding properties of the hz208F2 VH3/VL3 mAb was evaluated on the human cell line MCF-7 (FIG. 19A), on the monkey cell line COS-7 (FIG. 19B) and on the transfected murine cell line expressing the human insulin receptor (FIG. 19C). The binding of both the murine and the chimeric 208F2 mAbs was evaluated in parallel. The anti-hIR antibody clone GRO5 was used to verify the expression of the hIR on the transfected cell line (FIG. 19D).

FIG. 20A: Binding to hIGF-1R, FIG. 20B: Binding to human recombinant IR. No recognition of hIR EDC and of cellular IR expressed by transfected cells (FIG. 20D) compared to the control Ab GRO5 on these hIR transfected cells (FIG. 20C).

1—Injection during one minute of a solution of recombinant h-IGF-1R (10 μg/ml) on the second flowcell.
2—For the first sensorgramme: 5 injections of running buffer during 90 s each
For the second sensorgramme: five injections in the growing range of concentrations of the anti-IGF-1R c208F2 antibody solutions during 90 s each.
3—A delay of 300 s for the determination of the dissociation kinetic rates.
4—A regeneration of the surface by an injection during 45 s of a 10 mM Glycine, HCl pH 1.5 buffer.

Figure 27:
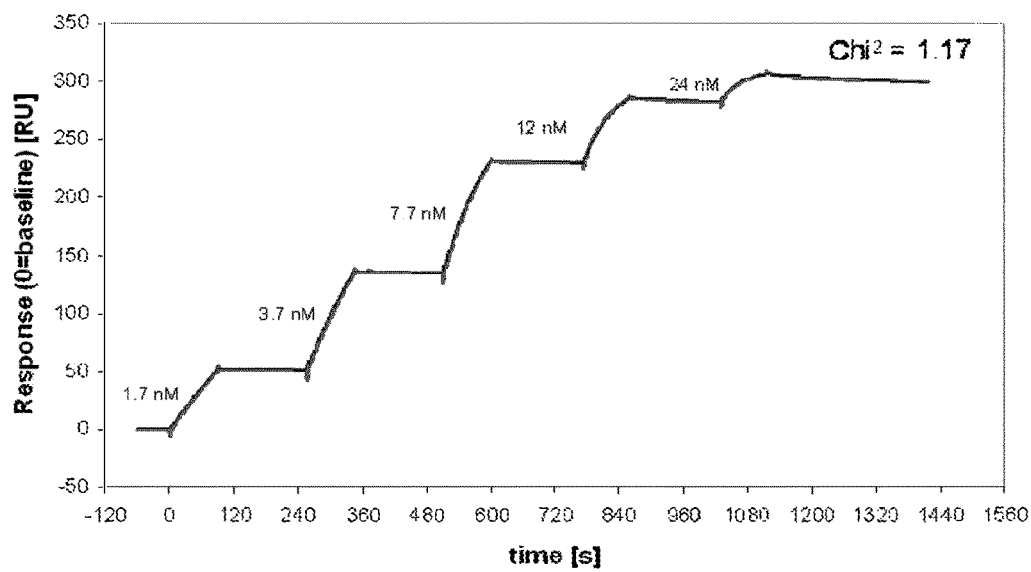

FIG. 27: The sensorgramme corresponding to the subtraction of the blank sensorgramme (5 injections of HBS-EP+) to the sensorgramme obtained with the growing range of concentrations of the anti-IGF-1R c208F2 solutions is presented in grey. The theoretical sensorgramme corresponding to the 1:1 model with the following parameters: $k_{on}=(1.206\pm0.036)\times10^6$ $M^{-1}\cdot s^{-1}$, $k_{off}=(7.81\pm0.18)\times10^{-5}\cdot s^{-1}$, Rmax=307.6±0.3 RU is presented by a thin black line. The calculated concentrations of c208F2 are reported on the graph: only the highest concentration (24 nM) is considered as a constant).

Figure 28:
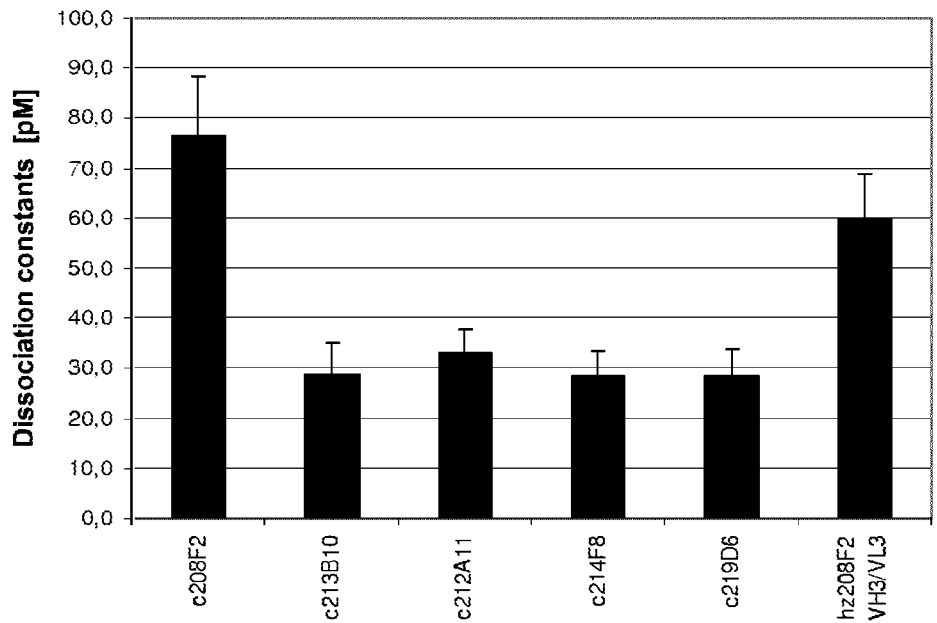

FIG. 28: The dissociation constants correspond to the mean of the four experiments run for each antibody and correspond to the ratio: $k_{off}/k_{on}\times10^{12}$ to be express in the pM unit. The error bars correspond to the standard error (n=4).

Figure 29:
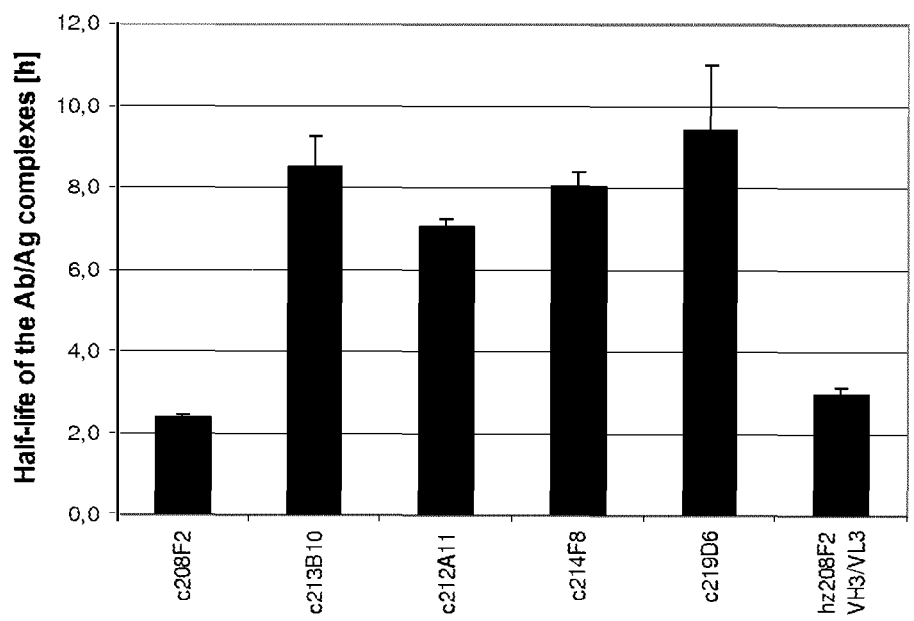

FIG. 29: The half-lives correspond to the mean of the four experiments run for each antibody and correspond to the ratio: $Ln(2)/k_{off}/3600$ to be express in the h unit. The error bars correspond to the standard error (n=4).

Figure 30:
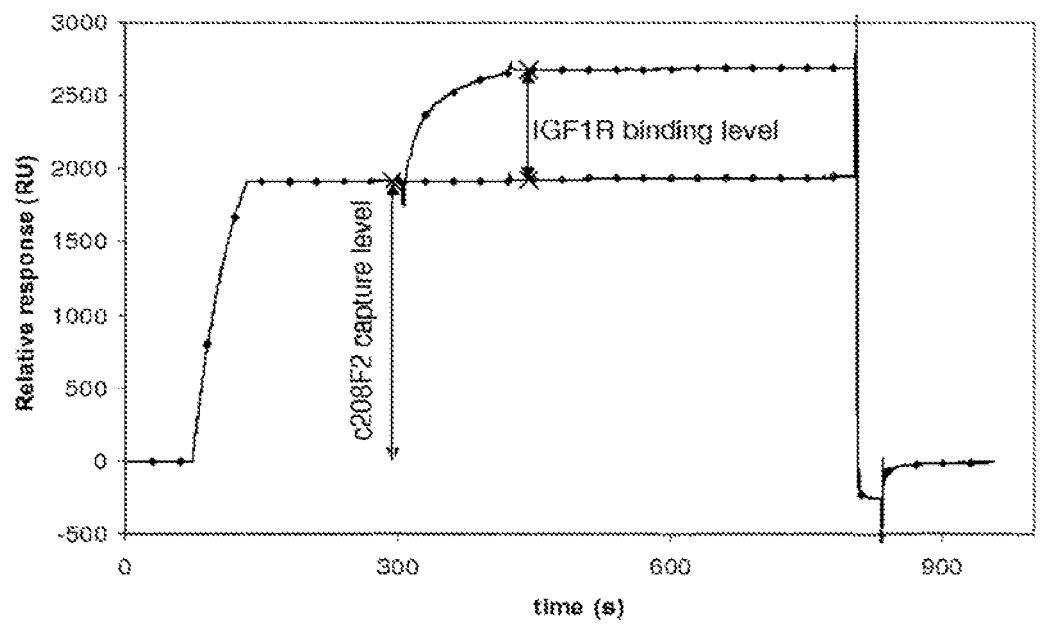

FIG. 30: Superposition of two sensorgrams corresponding to two cycle of an experiment running on a Biacore X100 device at a flow rate of 30 l/min and at 25° C.

The first step of the cycle correspond the injection of a solution of c208F2 antibody at the concentration of 10 μg/ml during 60 s on the second flowcell of a CM5 sensor chip activated by the grafting of more than 10,500 RU of a mouse anti-human IgG Fc monoclonal antibody chemically linked to the carboxymethyldextran matrix by its amine functions. The second step correspond to the injection of the extracellular domain of either h-IGF-1R (plain diamonds) or m-IGF-1R (empty diamonds) solutions of crude cell medium culture supernatants during 120 s with a delay of 120 s. The double headed arrows indicate the positions of measure of the antibody capture level and the IGF-1R binding level used in this study.

Figure 31:
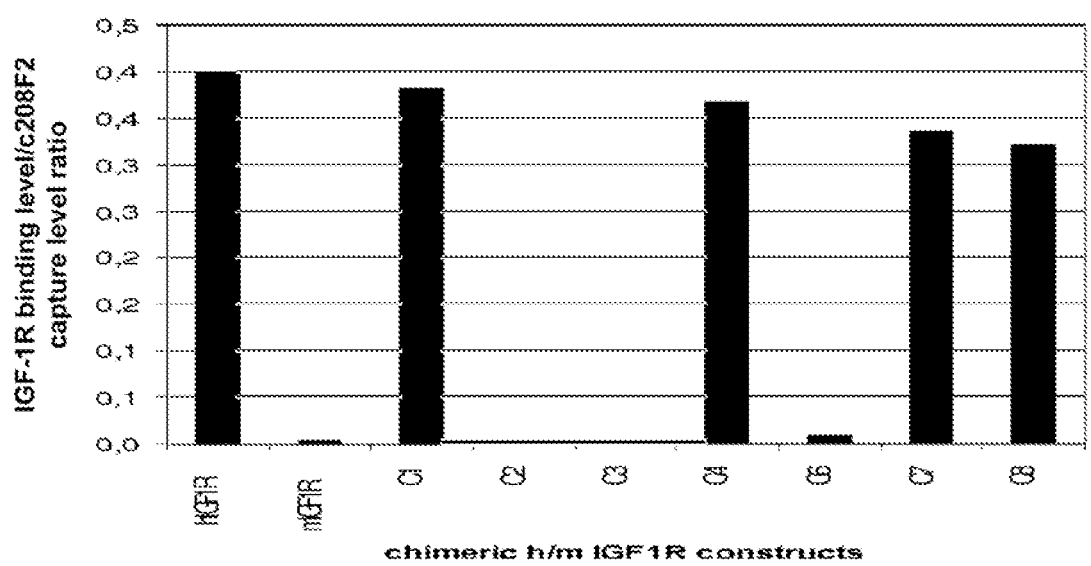

FIG. 31: Histograms representing the ratio between IGF-1R binding level obtained for each chimerical h/m IGF-1R constructs and the level of c208F2 captured on second flowcell of the sensorchip during the corresponding cycle.

Figure 32A:
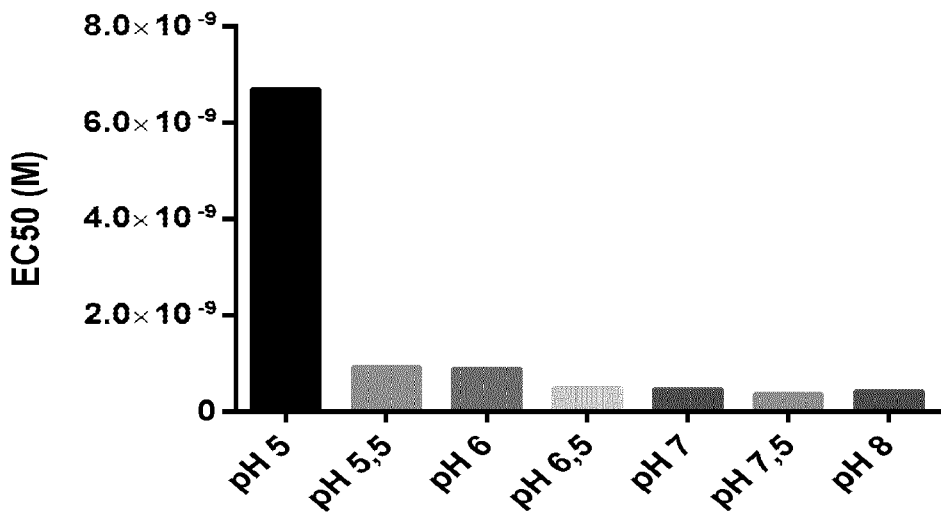
Figure 32B:
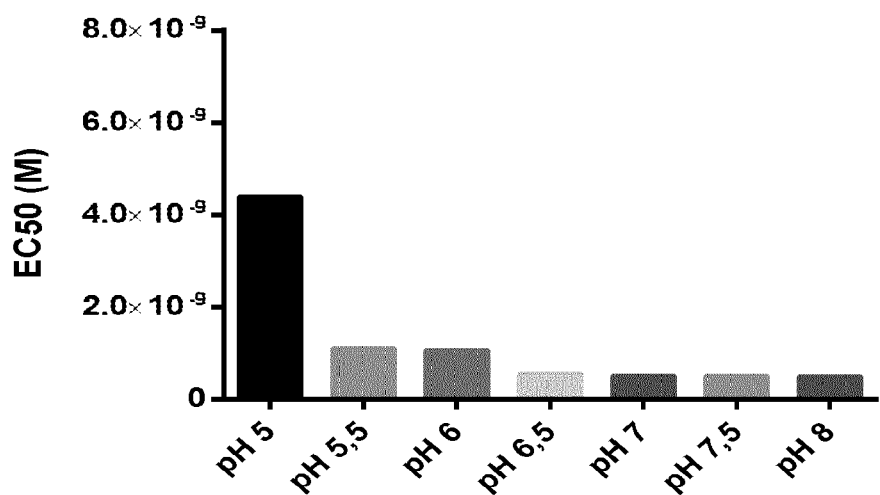

FIG. 32A and FIG. 32B: Histograms representing the EC50 of hz208F2 H076/L024 for pH 5 to pH 8, Acidic pH decreases binding capacity of the humanized IGF-1R antibodies hz208F2 H076/L024 (A) and hz208F2 (H077/L018 (B).

Figure 33:
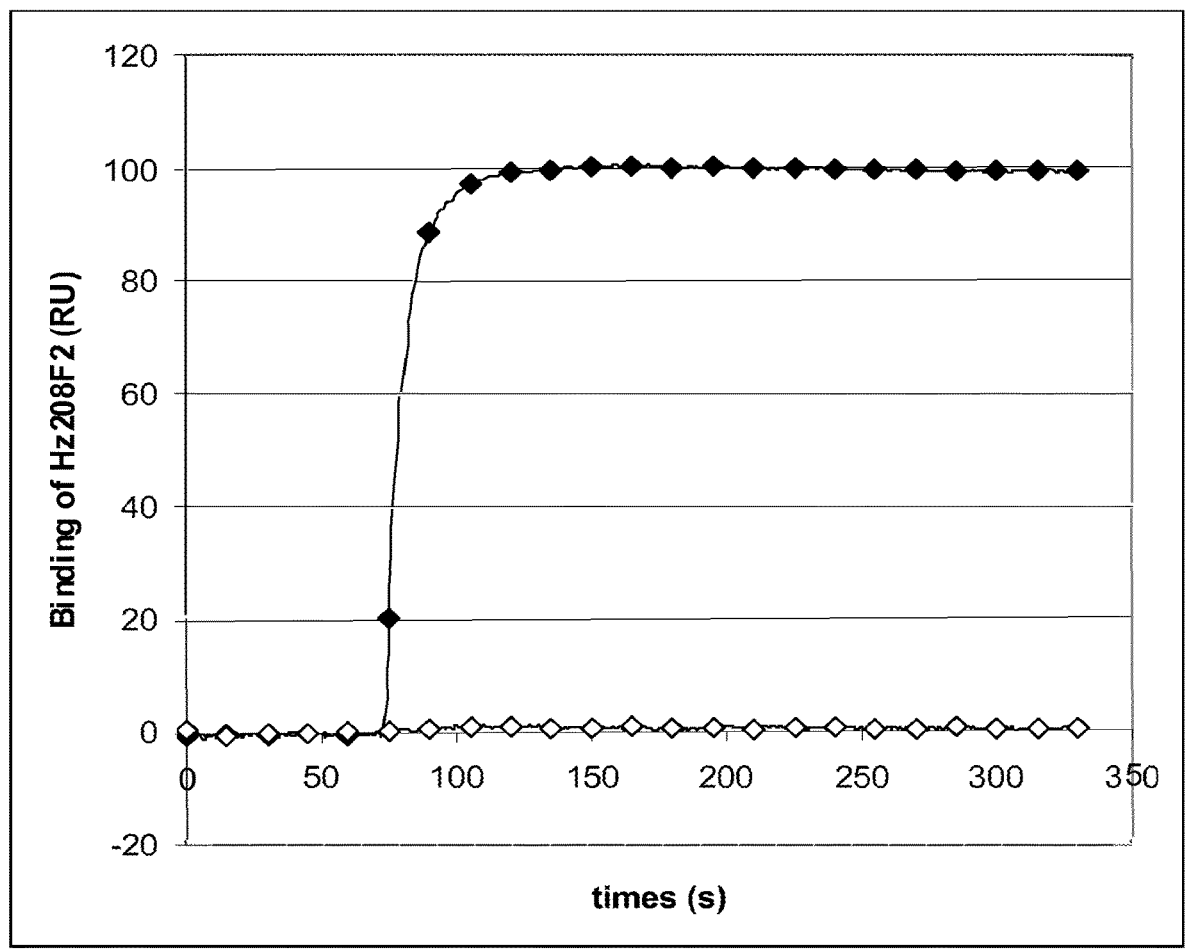

FIG. 33: Binding of Hz208F2 (10 g/ml) on either 170 RU of the wild-type of a soluble version of the h-IGF1R (black diamond) or on 120 RU of the mutant C29 (Asp491>Ala) of this receptor. Each receptor is captured by their C-terminal 66His Tag on a CM5 sensor chip. The experiment was run with a Biacore X100 device at 25° C. at a flow rate of 30 μl/min using the classical HBS-EP+ as the running buffer.

EXAMPLES

All hybridomas mentioned in the present invention have been deposited at the CNCM (Institut Pasteur, France) and are identified in the following table 7.

TABLE 7

| Hybridoma name | CNCM ref. | Filing date |
|---|---|---|
| 101H8 | I-4733 | 24 Apr. 2013 |
| 201F1 | I-4769 | 26 Jun. 2013 |
| 208F2 | I-4757 | 30 May 2013 |
| 212A11 | I-4773 | 26 Jun. 2013 |
| 214F8 | I-4775 | 26 Jun. 2013 |
| 219D6 | I-4736 | 24 Apr. 2013 |
| 213B10 | I-4774 | 26 Jun. 2013 |
| 102H8 | I-4767 | 26 Jun. 2013 |
| 110G9 | I-4768 | 26 Jun. 2013 |
| 415A8 | I-4778 | 26 Jun. 2013 |
| 410G4 | I-4777 | 26 Jun. 2013 |
| 414E1 | I-4738 | 24 Apr. 2013 |
| 433H9 | I-4780 | 26 Jun. 2013 |
| 105G2 | I-4735 | 24 Apr. 2013 |
| 832E5 | I-4765 | 30 May 2013 |

Example 1: Generation of IGF-1R Antibodies

To generate murine monoclonal antibodies (Mabs) against human extracellular domain (ECD) of the human IGF-1 receptor (hIGF-1R), 5 BALB/c mice were immunized 3-times s.c. with 10 μg of the rhIGF-1R protein (R&D Systems, Cat No 391-GR). As an alternative, three additional immunizations with 10 μg of the murine extracellular domain (ECD) of IGF-1R (R&D Systems, Cat No 6630-GR/Fc) were performed on some animals. The first immunization was done in presence of Complete Freund Adjuvant (Sigma, St Louis, Md., USA). Incomplete Freund adjuvant (Sigma) was added for following immunizations. Three days prior to the fusion, immunized mice were boosted with 10 μg of the rhIGF-1R protein. Then splenocytes and lymphocytes were prepared by perfusion of the spleen and by mincing of the proximal lymph nodes, respectively, harvested from 1 out of the 5 immunized mice (selected after sera titration of all mice) and fused to SP2/0-Ag14 myeloma cells (ATCC, Rockville, Md., USA). The fusion protocol is described by Kohler and Milstein (Nature, 256:495-497, 1975). Fused cells are then subjected to HAT selection. In general, for the preparation of monoclonal antibodies or their functional fragments, especially of murine origin, it is possible to refer to techniques which are described in particular in the manual "Antibodies" (Harlow and Lane, Antibodies: A Laboratory Manual, Cold Spring Harbor Laboratory, Cold Spring Harbor N.Y., pp. 726, 1988). Approximately 10 days after the fusion, colonies of hybrid cells were screened. For the primary screen, supernatants of hybridomas were evaluated for the secretion of Mabs raised against the rhIGF-1R ECD protein by FACS analysis using human breast MCF7 tumor cells (ATCC) and/or monkey COS7 cells (African green monkey kidney-SV40 transformed) which express monkey IGF-1R on their cell surface. More precisely, for the selection by flow cytometry, $10^5$ cells (either MCF7 or COS7) were plated in each well of a 96 well-plate in PBS containing 1% BSA and 0.01% sodium azide (FACS buffer) at 4° C. After a 2 min centrifugation at 2000 rpm, the buffer was removed and hybridoma supernatants to be tested were added. After 20 min of incubation at 4° C., cells were washed twice and an Alexa 488-conjugated goat anti-mouse antibody 1/500° diluted in FACS buffer (#A11017, Molecular Probes Inc., Eugene, USA) was added and incubated for 20 min at 4° C. After a final wash with FACS buffer, cells were analyzed by FACS (Facscalibur, Becton-Dickinson) after addition of propidium iodide to each tube at a final concentration of 40 μg/ml. Wells containing cells alone and cells incubated with the secondary Alexa 488-conjugated antibody were included as negative controls. Isotype controls were used in each experiment (Sigma, ref M90351MG). At least 5000 cells were assessed to calculate the mean value of fluorescence intensity (MFI).

Additionally an internalization assay was performed in order to select only internalizing antibodies. For this assay, the MCF7 tumor cell line was cultured in RMPI 1640 without phenol red with 1% L-glutamine and 10% of FACS for 3 days before experiment. Cells were then detached using trypsin and 100 μl of a cell suspension at 4·10 cell/ml are plated in 96-multiwell plates in RPMI1640 without phenol red with 1% L-glutamine and 5% FBS. After a 2 min centrifugation at 2000 rpm, cells were resuspended in 50 μl of hybridoma supernatant or control antibody solutions (positive and isotype controls at 1 μg/ml). After a 20 min incubation time at 4° C., cells were centrifuged 2 min at 2000 rpm and resuspended in either cold (4° C.) or warm (37° C.) complete culture medium. Cells were then incubated for 2 hours either at 37° C. or at 4° C. Then cells were washed three times with FACS buffer. An Alexa 488-labeled goat anti-mouse IgG antibody was incubated for 20 minutes and cells were washed three times before FACS analysis on propidium iodide negative cell population.

Following the FACS analysis, two parameters were determined: (i) the difference of the fluorescent signal detected on the surface of cells incubated at 4° C. with those obtained with the cells incubated at 37° C. with one hybridoma supernatant and (ii) the percentage of remaining IGF-1R on the cell surface.

The percentage of remaining hIGF-1R is calculated as follows:

$$\% \text{ remaining IGF-1R} = (\text{MFI}_{Ab\ 37°\ C.}/\text{MFI}_{Ab\ 4°\ C.}) \times 100$$

In addition three ELISA were performed (either before or after cloning) to study the binding of antibodies on the recombinant human (hIGF-1R) and murine (mIGF-1R) proteins, and on the recombinant human Insulin Receptor (hIR) protein. Hybridoma secreting antibody showing binding on rh- and/or rm-IGF-1R and no binding on rhIR were retained. Briefly, 96-well ELISA plates (Costar 3690, Corning, N.Y., USA) were coated with 100 μl/well of either the rhIGF-1R protein (R&D Systems, cat No 391-GR) at 0.6 μg/ml or rmIGF-1R protein (R&D Systems, cat No 6630-GRiFc) at 1 μg/ml or rhIR protein (R&D Systems, cat No 1544-IR/CF) at 1 μg/ml in PBS overnight at 4° C. The plates were then blocked with PBS containing 0.5% gelatin (#22151, Serva Electrophoresis GmbH, Heidelberg, Germany) for 2 h at 37° C. Once the saturation buffer discarded by flicking plates, 100 μl of each supernatant dilution were added to the wells (either undiluted hybridoma supernatant either supernatant serial dilutions) and incubated for 1 h at 37° C. After three washes, 100 μl horseradish peroxidase-conjugated polyclonal goat anti-mouse IgG (#115-035-164, Jackson Immuno-Research Laboratories, Inc., West Grove, Pa., USA) was added at a 1/5000 dilution in PBS containing 0.1% gelatin and 0.05% Tween 20 (w:w) for 1 h at 37° C. Then, ELISA plates were washed 3-times and the TMB (#UP664782, Uptima, Interchim, France) substrate is added. After a 10 min incubation time at room temperature, the reaction was stopped using 1 M sulfuric acid and the optical density at 450 nm is measured.

Hybridoma secreting antibody of interest were expanded and cloned by limit dilution. Once isotyped, one clone of each code was expanded and frozen. Each antibody of interest was produced in in vitro production systems named CellLine (Integra Biosciences) for further characterization.

Additional assays to address binding specificity by FACS analyses were performed on IM9 cells (human IR expressing B lymphoblasts) as well as on hIGF-1R transfected cells versus non transfected cells.

All the data corresponding to the selected antibodies were summarized in Table 8. It is interesting to notice that among the antibodies selected i) on the bases of their selectivity for hIGF-1R vs hIR and ii) on their capacity of inducing IGF-1R internalization, some are able to recognize their target both in ELISA and FACS setting while other were very good binders when studied by cytometry and very poor binders when evaluated by ELISA. m280F2, m212A11, m213B10, m214F8 and m219D6 belong to this latter group that did not well recognize the coated protein

TABLE 8

| | | ELISA (SNT at 5 µg/ml) | | | Internalisation Assay (Ab at 5 µg/ml) | | | FACS (Ab at 5 µg/ml) | | | |
|---|---|---|---|---|---|---|---|---|---|---|---|
| | | D.O 450 nm | | | | | | MFI | | | |
| | hybridoma name | rh IGF-1R | rm IGF-1R | rh Insulin R | MFI 4° C. | MFI 37° C. | % remaining rh IGF1R | Δ (MFI 4° C. − MFI 37° C.) | IM9 (h IR+) | Cos-7 (monkey IGF1R+) | Tf hIGF1R+ | non Tf cells (h IGF1R−) |
| 1 | 101H8 | 1.552 | 0.115 | 0.125 | 373 | 128 | 34 | 246 | 9 | 145 | 1902 | 10 |
| 2 | 102H8 | 1.988 | 0.136 | 0.130 | 360 | 140 | 39 | 220 | 10 | 136 | 2026 | 10 |
| 3 | 105G2 | 2.409 | 0.166 | 0.205 | 301 | 114 | 38 | 187 | 9 | 114 | 1673 | 11 |
| 4 | 110G9 | 1.989 | 0.133 | 0.153 | 396 | 126 | 32 | 270 | 10 | 146 | 2208 | 7 |
| 5 | 201F1 | 1.756 | 0.165 | 0.156 | 357 | 81 | 23 | 276 | 8 | 119 | 1987 | 15 |
| 6 | 208F2 | 0.163 | 0.099 | 0.140 | 355 | 94 | 27 | 261 | 4 | 106 | 2197 | 22 |
| 7 | 212A11 | 0.232 | 0.102 | 0.141 | 390 | 106 | 27 | 284 | 7 | 125 | 2187 | 23 |
| 8 | 213B10 | 0.399 | 0.127 | 0.110 | 386 | 115 | 30 | 271 | 7 | 122 | 2055 | 23 |
| 9 | 214F8 | 0.349 | 0.102 | 0.115 | 386 | 111 | 29 | 275 | 7 | 132 | 2137 | 20 |
| 10 | 219D6 | 0.329 | 0.112 | 0.106 | 349 | 106 | 30 | 243 | 7 | 114 | 2110 | 21 |
| 11 | 410G4 | 2.937 | 0.135 | 0.095 | 619 | 229 | 37 | 390 | 11 | 158 | 2260 | 34 |
| 12 | 414E1 | 3.009 | 0.099 | 0.093 | 729 | 188 | 26 | 540 | 13 | 204 | 2740 | 36 |
| 13 | 415A8 | 3.044 | 0.107 | 0.089 | 727 | 174 | 24 | 553 | 12 | 188 | 2960 | 32 |
| 14 | 433H9 | 3.104 | 0.154 | 0.131 | 617 | 153 | 25 | 464 | 13 | 206 | 2590 | 24 |
| 15 | 832E5 | 1.854 | 0.107 | 0.048 | 134 | 82 | 61 | 52 | 5 | 24* | nd | nd |
| 15 | mIgG1 | 0.093 | 0.116 | 0.127 | 9 | 8 | 94 | 1 | 5 | 14 | 24 | 22 |

*FACS realized using purified antibody

Example 2: Characterization of Anti-IGF-1R Antibodies Epitope Clustering by Mapping Experiments Using Biacore's SPR Based Technology In order to study the diversity of the response against IGF-1R, the selected antibodies have been mapped by Biacore and a clustering of these antbodies according to competition properties has been performed.

Briefly, the epitope mapping experiments were run on a Biacore X device using a CM5 sensor chip activated by an anti-Tag His antibody (His capture kit GE Healthcare catalogue number 28-9950-56). More than 11000 RU of antibodies are chemically grafted on the carboxymethyldextan matrix using the amine kit chemistry. The experiments were carried out at 25° C. with a flow rate of 1 µl/min using the HBS-EP buffer (GE Healthcare) as both the running and sample dilution buffer.

The epitope mapping experiment followed the same scheme:

1—A solution of a soluble version of the hIGF-1R heterotetramere (2α chains and the extracellular domains of the 2β chains expressed with an additional c-terminal 10-His tag (R&D Systems catalog number 305-GR)) is injected at the concentration of 5 µg/ml on both flowcells during 1 minute.

2—A solution of an anti-hIGF-1R antibody (classically 50 µg/ml) to be tested is then injected only on the flowcell 1 during between 60 to 90 s in order to reach (or at least to be closed to) a saturation of the hIGF-1R binding sites.

3—A solution of a second antibody, used as a potential competitor, is either injected in the same conditions on both flowcells or only on the second flowcell 4—Eventually, a solution of a third antibody may be injected in the same conditions on both flowcells.

5—The surface is then regenerated with an injection of a 10 mM Glycine, HCl pH 1.5 buffer during 30 s.

This kind of experiment shows clearly if two antibodies may bind simultaneously on the same molecule of hIGF-1R demonstrating that the binding regions (epitopes) of each antibody are distant enough to allow this. In contrast, if the binding of an antibody to hIGF-1R prevents the binding of a second antibody that suggested that the same epitope was recognize by both antibodies. Finally, in case of partial competition, one can suspect an overlap of the epitopes recognized by the two tested antibodies. Epitope region groups are thus defined. The complexity of the result generally increases with size of the panel of antibodies used in the experiment.

Figure 1:
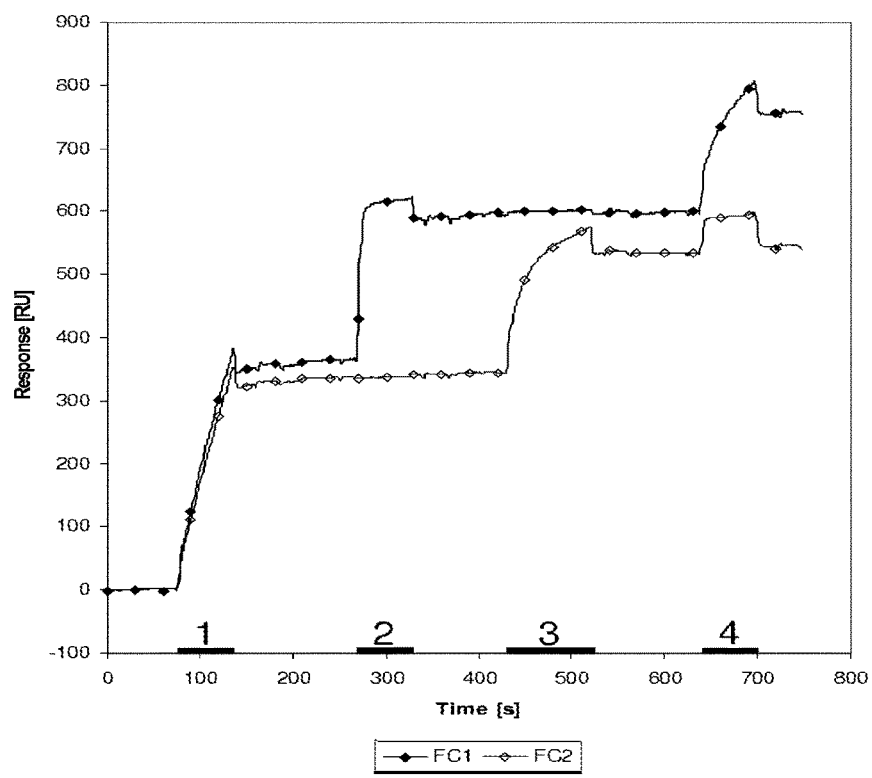
FIG. 1: Example of Biacore binding profile obtained with 3 antibodies on hIGF-1R ECD captured by an anti-His-Tag antibody.

FIG. 1 describes an example of a typical cycle of an epitope mapping experiment using a SPR based Biacore X device The sensorgrams show the response (RU) as function to the time (seconds) of the flowcells 1 (black diamonds) and 2 (white diamonds). In phase 1, a solution of the antigen: a soluble recombinant hIGF-1R with two C-term 10-His Tag is injected on both flowcells of a CM5 sensorchip with an anti-His Tag mouse antibody chemically linked to the carboxymethyldextran matrix at the concentration of 5 µg/ml at a flow rate of 10 µl/min.

Figure 2:
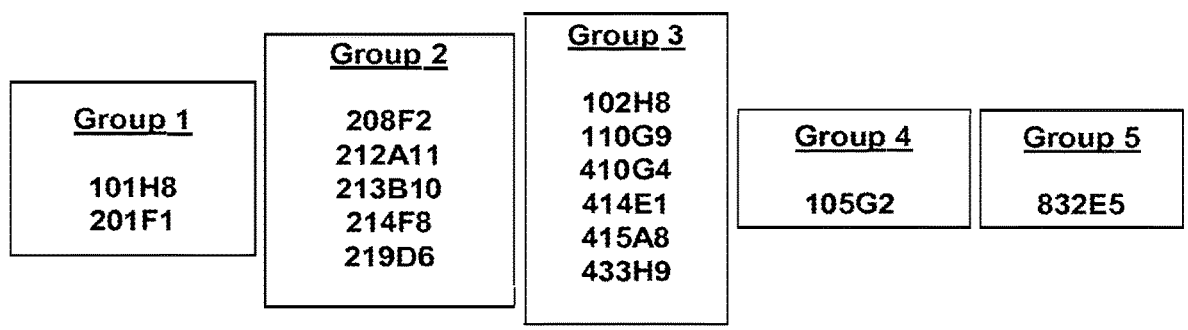
FIG. 2: Epitope mapping scheme defined from the panel of 15 anti-hIGF-1R monoclonal antibodies witch defined 5 epitope groups. The numbering of the groups is not linked to a position regarding the sequence nor the 3D structure of the antigen.

In phase 2, a solution of a first antibody to be tested (219D6) at the concentration of 50 µg/ml is injected on the flowcell 1. Then in phase 3, a solution of a second antibody (101H8) at the concentration of 50 µg/ml is injected on the flowcell 2, followed in phase 4, by the injection of a solution of a third antibody (201F1) at the concentration of 50 µg/ml on both flowcells. The response of this injection clearly shows that the binding of 201F1 on the IGF-1R is prevented by 101H8 but not by 219D6. Antibodies 201F1 and 219D6 clearly belong to different epitope groups. The clustering resulting to the whole analysis of the 15 selected candidates is described in FIG. 2 and demonstrated that the immunization of mice with hIGF-1R give raise of a series of antibodies displaying a good diversity. Indeed. 5 different groups of Mabs recognizing different epitopes were generated.

Example 3: Antibody Binding to the Human Native IGF-1R by FACS Analyses

The binding properties of a series of anti-IGF-1R antibodies were evaluated by FACS analyses on the human MCF-7 breast adenocarcinoma cell line (ATCC#HTB-22) using increasing antibody concentrations. For that purpose, cells ($1 \times 10^6$ cells/ml) were incubated with anti-IGF-1R antibodies for 20 min. at 4° C. in FACS buffer (PBS, 0.1% BSA, 0.01% $NaN_3$). They were then washed 3 times and incubated with the appropriate secondary antibody coupled with Alexa 488 for 20 additional minutes at 4° C. in the dark before being washed 3 times in FACS buffer. The binding of anti-IGF-1R antibodies was immediately performed on viable cells which were identified using propidium iodide (that stains dead cells). The maximum of signal intensity obtained with each antibody was designed as $B_{max}$ and expressed in mean of fluorescence intensity (MFI). The $EC_{50}$ of binding expressed in molarity (M) was calculated using a nonlinear regression analysis (GraphPad Prims 4.0).

The titration curve of each murine or chimeric Ab demonstrated that all generated antibodies are capable of recognizing the native IGF-1R form with a typical saturation profile (FIG. 3A). In order to rank antibodies and to compare the binding properties of both murine and chimeric Abs, the binding $EC_{50}$ of each compound was determined using a non linear regression analysis. The comparison of the $EC_{50}$ of each murine Ab with its corresponding chimeric form showed that the 2 forms displayed the same binding properties demonstrating that the Ab chimerization did not affect IGF-1R recognition (FIG. 3B). $EC_{50}$s ranged between $1.2 \times 10^{-8}$ and $4.4 \times 10^{-10}$. Antibodies belonging to Group 2 and c102H8 belonging to group 3a showed the better $EC_{50}$. Regarding to B, analyses (FIG. 3C), three Abs (414E1 (G3b), 105G2 (G4) and 832E5 (G5) had a lower $B_{max}$ compared to the other one. $EC_{50}$ and $B_{max}$ values were summarized in Table 9.

TABLE 9

| Group | Ac | $B_{max}$ | $EC_{50}$(M) |
| --- | --- | --- | --- |
| G1 | c101H8 | 905 | 2.8E−09 |
| G3a | c102H8 | 951 | 8.5E−10 |
| G4 | c105G2 | 805 | 4.9E−09 |
| G3a | c110G9 | 992 | 1.4E−09 |
| G1 | c201F1 | 936 | 1.5E−08 |
| G2 | c208F2 | 981 | 6.7E−10 |
| G2 | c212A11 | 991 | 6.7E−10 |
| G2 | c214F8 | 1069 | 5.0E−10 |
| G2 | c219D6 | 993 | 4.7E−10 |
| G2 | c213B10 | 1103 | 4.4E−10 |
| G3b | c410G4 | 1020 | 2.6E−09 |
| G3b | c414E1 | 795 | 6.0E−09 |
| G3a | c415A8 | 1142 | 1.6E−09 |
| G3b | c433H9 | 1032 | 1.7E−09 |
| G5 | c832E5 | 691 | 1.2E−08 |

Example 4: Confirmation of Antibody Specificity by Using Either IGF-1R or IR Transfected Cells or IM9 Cells That Naturally Express Significant Levels of IR In order to confirm the specificity of the generated antibodies for hIGF-1R versus hIR, stable transfectants expressing either hIGF-1R or hIR were evaluated by FACS analyses. Briefly, increasing concentrations of chimeric mAbs were incubated with cells for 20 min at 4° C. in FACS buffer (PBS. 0.1% BSA, 0.01% $NaN_3$). Cells were then washed 3 times and incubated with the appropriate secondary antibody coupled with Alexa 488 before being incubated for 20 additional minutes at 4° C. in the dark and then washed 3 times in FACS buffer. The binding of anti-IGF-1R antibodies was immediately performed on viable cells which were identified using propidium iodide (that stains dead cells). The binding $EC_{50}$ expressed in molarity (M) was calculated using a nonlinear regression analysis (GraphPad Prims 4.0).

Figure 4A:
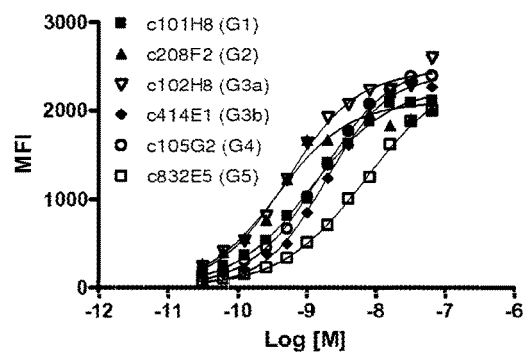
FIG. 4A and FIG. 4B: Evaluation of hIGF-1R recognition using transfected vs non transfected cells.
Figure 4B:
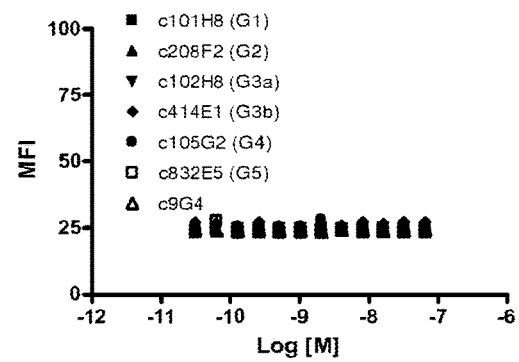

Titration curves obtained on the hIGF-1R transfected cell line (FIG. 4A) versus untransfected cells (FIG. 4B) confirmed the binding specificity of chimeric Abs for the human IGF-1R. $EC_{50}$ and B, values were summarized in Table 10. In this assay antibodies from G2 and G3a groups showed the best $EC_{50}$.

TABLE 10

| Group | Ac | $B_{max}$ | $EC_{50}$ (M) |
| --- | --- | --- | --- |
| G1 | c101H8 | 2107 | 1.2E−09 |
| G1 | c201F1 | 2500 | 1.1E−08 |
| G2 | c208F2 | 2008 | 3.2E−10 |
| G2 | c212A11 | 2513 | 4.4E−10 |
| G2 | c214F8 | 2094 | 2.7E−10 |
| G2 | c219D6 | 2521 | 5.5E−10 |
| G2 | c213B10 | 2029 | 3.3E−10 |
| G3a | c102H8 | 2594 | 5.4E−10 |
| G3a | c110G9 | 2189 | 5.2E−10 |
| G3a | c415A8 | 2728 | 7.0E−10 |
| G3b | c410G4 | 1667 | 7.1E−10 |
| G3b | c414E1 | 2265 | 1.9E−09 |
| G3b | c433H9 | 2165 | 6.5E−10 |
| G4 | c105G2 | 2396 | 1.7E−09 |
| G5 | c832E5 | 1998 | 7.3E−09 |

In order to verify the absence of binding of both murine and chimeric antibodies on hIR, a stable cell line expressing the human IR was used. The recognition of human cell surface hIR by both murine and chimeric Ab was performed by FACS analyses. Increasing concentrations of either the murine or the chimeric mAbs were incubated on the $hIR^+$ transfected cell line for 20 minutes at 4° C. in FACS buffer (PBS, 0.1% BSA, 0.01% $NaN_3$). Cells were then washed 3 times and incubated with the appropriate secondary antibody coupled with Alexa 488 before being incubated for 20 additional minutes at 4° C. in the dark and then washed 3 times in FACS buffer. The binding of anti-IGF-1R antibodies was immediately performed on viable cells which were identified using propidium iodide (that stains dead cells). The binding $EC_{50}$ expressed in molarity (M) was calculated using a nonlinear regression analysis (GraphPad Prims 4.0). A commercial specific anti-IGF-1R antibody, clone GR11L and the anti-hIR antibody clone GRO5 were used as positive controls. The c9G4 was introduced as an irrelevant antibody (isotype control).

Figure 5A:
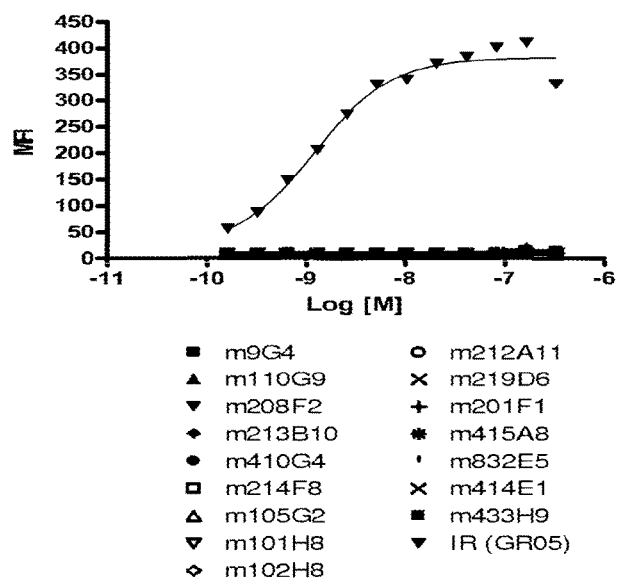
FIG. 5A and FIG. 5B: Evaluation of the specificity of Abs to hIGF-1R vs hIR using transfected cells.
Figure 5B:
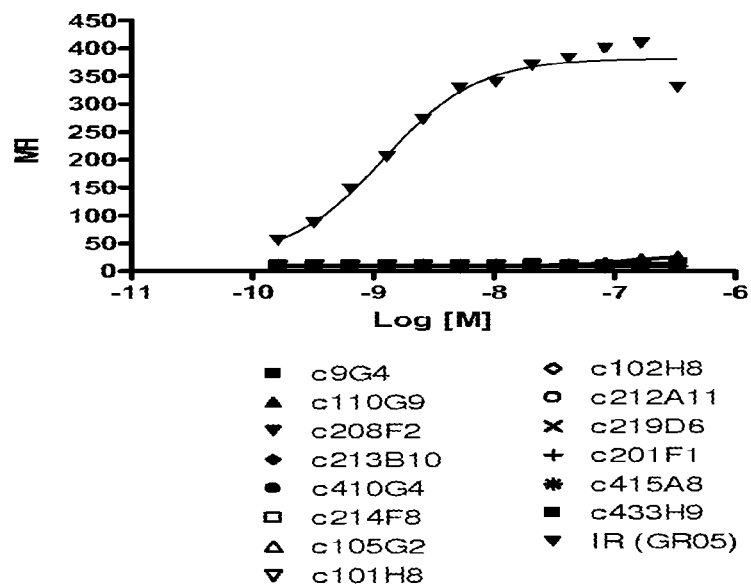

The high level of expression of hIR on cell surface of the transfected cells was confirmed using the commercial anti-hIR antibody GRO5. Even using high concentrations of either the murine (FIG. 5A) or the chimeric (FIG. 5B) anti-hIGF-1R Abs, no binding on cell surface of hIR* transfected cells was observed. These results demonstrated that neither murine nor chimeric anti-hIGF-1R Abs did recognized the hIR.

Figure 6:
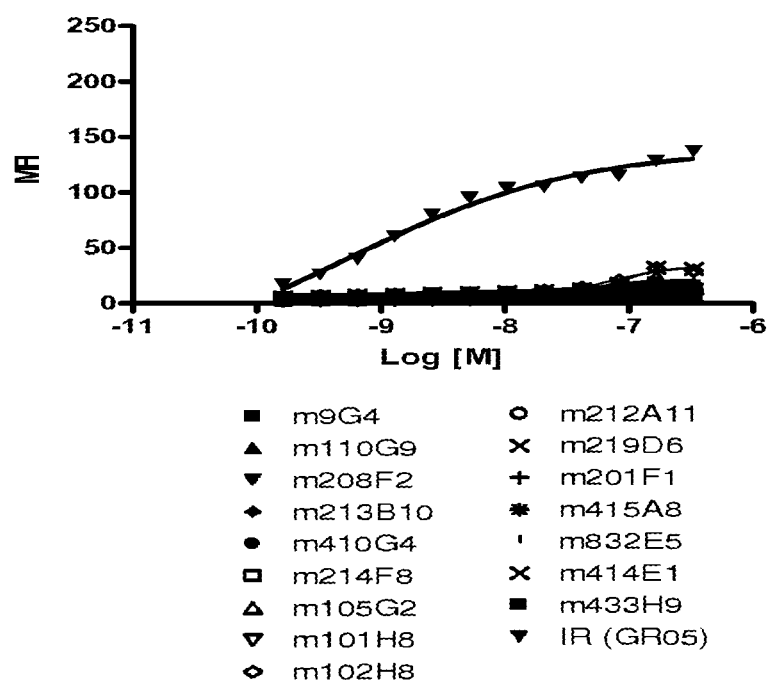
FIG. 6: Binding of murine anti-IGF-1R Ab on the IM-9 cell line. MFI represents the mean of fluorescent intensity. The GRO5 anti-hIR Mab was introduced as a positive control.

This specificity of recognition of hIGF-1R versus IR has also been demonstrated using IM9 cells, a B-lymphoma cell line that express hIR (FIG. 6). For this FACS analysis, the protocol was the same as the one described previously and murine anti-IGF-1R antibodies were used in order to prevent the cross reactivity of the secondary anti-human Ab (IM9 cells express human Ig on their cell surface). Results presented in FIG. 6 demonstrated once again that the expected signal was observed using the GRO5 anti-hIR antibody while none of the murine antibody evaluated displayed any significant binding signal on this cell line.

Example 5: Antibody Binding to the Monkey Native IGF-1R by FACS and Biacore Analyses One of the first pre-requisite for regulatory toxicology studies is to identify a relevant animal specie to evaluate the selected compound. As the series of antibodies described herein is not able to recognize murine IGF-1R, the most likely specie for toxicological evaluation is the non human primate (NHP).

In order to evaluate the binding of anti-IGF-1R antibodies on monkey IGF-1R, the binding of both murine and chimeric anti-hIGF-1R antibodies was evaluated by FACS analyses on COS-7 cell line using increasing antibody concentrations. Cells ($1 \times 10^6$ cells/ml) were incubated with anti-IGF-1R antibodies for 20 minutes at 4° C. in FACS buffer (PBS, 0.1% BSA, 0.01% $NaN_3$). Then, cells were washed 3 times and incubated with the appropriate secondary antibody coupled with Alexa 488 before being incubated for 20 additional minutes at 4° C. in the dark and finally washed 3 times in FACS buffer. The binding of anti-IGF-1R antibodies was immediately evaluated on viable cells identified using propidium iodide (that stains dead cells). The binding $EC_{50}$ expressed in molarity (M) was calculated using a nonlinear regression analysis (GraphPad Prims 4.0).

Figure 7A:
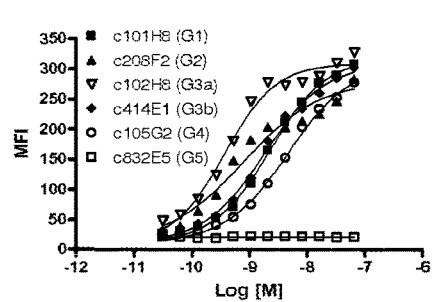
FIG. 7A, FIG. 7B, and FIG. 7C: Evaluation of recognition of the monkey IGF-1R.
Figure 7B:
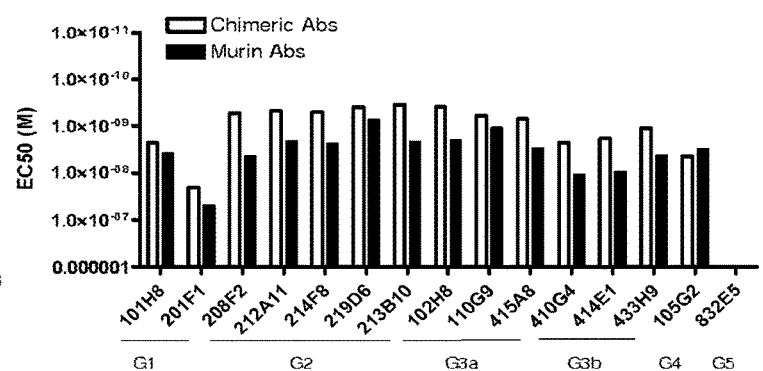
Figure 7C:
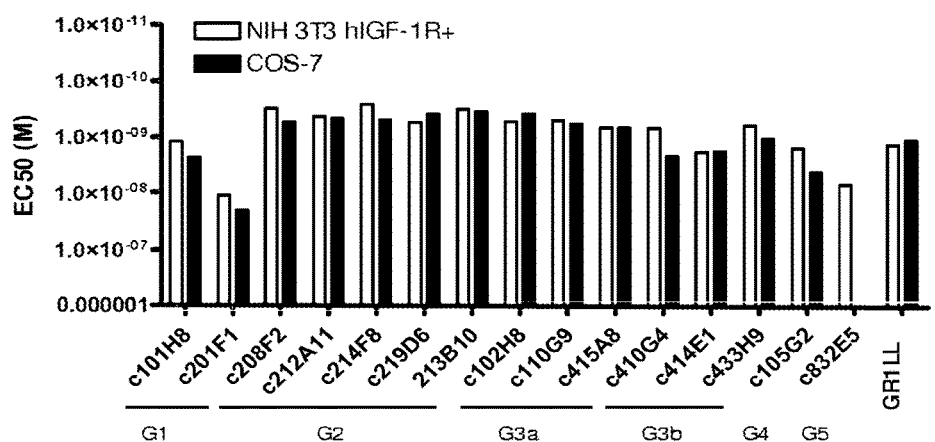

The titration curves obtained on the COS-7 monkey cell line showed that, excepted for the 832E5 mAb, all the anti-hIGF-1R Abs recognized specifically the IGF-1R expressed on the surface of the monkey cell line (FIG. 7A). Determination of the $EC_{50}$ for each murine and chimeric Abs showed that the 2 forms compared well regarding to their binding properties on monkey IGF-1R (FIG. 7B). Those results showed that all the generated anti-hIGF-1R except the mAb 832E5 recognized the monkey IGF-1R.

A comparison of binding $EC_{50}$ on COS-7 cells versus transfected IGF-1R cells was performed in order to verify the magnitude of chimeric antibody recognition on human versus monkey IGF-1R. Results shown in FIG. 7B demonstrated a similar recognition of human and monkey IGF-1Rs by all antibodies except the 832E5 mAb.

In order to confirm the recognition on another type of monkey, cells were transfected with the IGF-1R form Cynomolgus monkey to produce soluble monkey IGF-1R ECD and Biacore experiments were performed with one of the chimeric antibodies (c208F2) in order to compare its binding properties either the hIGF-1R or the Cynomolgus IGF-1R.

The recognition experiments were run on a Biacore X100 device using a CM5 sensor chip activated by an anti-Tag His antibody (His capture kit GE Healthcare catalogue number 28-9950-56). More than 11000 RU of antibodies are chemically grafted on the carboxymethyldextan matrix using the amine kit chemistry. The experiments were carried out at 25° C. with a flow rate of 30 µl/min using the HBS-EP buffer (GE Healthcare) as the running and sample dilution buffer. The single cycle kinetic scheme was used to defined the kinetic parameters of the binding of the chimeric form of the 208F2 anti-IGF-1R antibody (c208F2) on hIGF-1R compared to Macaca IGF-1R A solution of a soluble recombinant version of the IGF-1R hetero-tetramere composed of 2β chains and the extracellular domains of 2a chains expressed with an additional C-terminal 10-His tag, based either on the sequence of the human (R&D Systems catalogue number 305-GR-50) or of the one of cynomolgus (produced in house) was injected 1 minute on the second flowcell at a dilution defined to capture around 160 RU of antigen. Solution of a second antibody is either injected in the same conditions on both flowcells or only on the second flowcell. After the capture phase, either the running buffer was injected 5 times (90 s each injection) or a growing range of 5 concentrations of c208F2 were injected (90 s each injection) on both flowcells. At the end of the fifth injection the running buffer was passed in order to define the dissociation rate. The surface was then regenerated with an injection of a 10 mM Glycine, HCl pH 1.5 buffer during 30 s.

Figure 8:
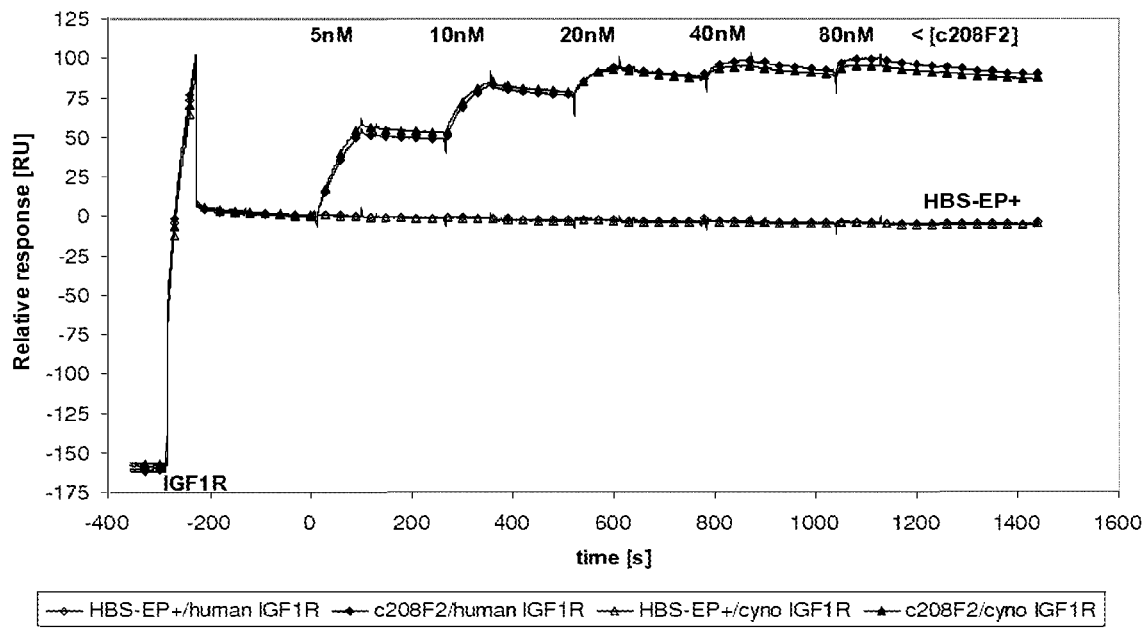
FIG. 8: Comparison of c208F2 binding on either hIGF-1R ECD or Cynomolgus monkey IGF-1R ECD using a Biacore assay. Sensorgrams obtained on a SPR technology based Biacore X100 using a CM5 sensorchip activated with more the 11000 RU of mouse anti-Tag His antibody chemically grafted to the carboxymethyl dextran matrix. The experiment is run at a flow rate of 30 µl/min at 25° C. using the HBS-EP+ as the running and samples diluting buffer. The figure shows the superposition of 4 independent sensorgrams aligned on the x-axis at the beginning of the first injection of the analytes and on the y-axis by the baseline defined just before this first injection. The sensorgrams obtained with the capture of the human based sequence of the recombinant soluble IGF-1R are marked by diamonds. The sensorgrams obtained with the capture of the cynomolgus based sequence of the recombinant soluble IGF-1R are marked by triangles. White symbols correspond to the blank cycles (5 injections of the running buffer) and black symbols correspond to the injections of the growing range of concentrations of c208F2 (5, 10, 20, 40 and 80 nM).

The computed signal corresponds to the difference between the response of the flowcell 2 (with captured IGF-1R) and the response of the flowcell 1 (without any IGF-1R molecules) (FIG. 8).

For each IGF-1R molecule (human or cyno), the signal due to the injections of the growing range of concentrations of c208F2 was corrected by subtraction of the signal obtained with the 5 injections of the buffer (double reference). The resulting sensorgrams were analysed using the Biaevaluation software with a 1:1 model. The kinetic rates are evaluated either independently (2 kinetics rates of the binding of c208F2 on each IGF-1R) or commonly (the same kinetic rates of the binding of c208F2 on the human and the cynomolgus IGF-1R). The quality of the fitting was assessed by a Chi2/Rmax ratio lower than 0.05 RU.

The kinetics rates of the binding (see Table 11) defined separately for each IGF-1R are close and a fitting of both sensorgrams with the same kinetic rates is of good quality. The c208F2 antibody recognizes as well the recombinant human and cynomolgus IGF-1Rs with a dissociation constant (KD) about 0.2 nM. The affinities defined in this study correspond to the functional affinities (or avidities) of the antibodies for a level of captured human and cynomolgus IGF-1R around 160 RU.

TABLE 11

| IGF1R | kon [1/M · s] | koff [1/s] | Kd [nM] | Chi2/Rmax |
|---|---|---|---|---|
| human | 1.52E+06 | 3.40E−04 | 0.23 | 0.045 |
| cynomogus | 1.85E+06 | 3.10E−04 | 0.17 | 0.032 |
| Hum. & Cyno. | 1.52E+06 | 3.33E−04 | 0.22 | 0.039 |

Example 6: Intrinsic Effect of Generated Antibodies on IGF-1R Phosphorylation It is well known that antibodies could induce an agonistic effect when they bind to tyrosine kinase receptors. As we would not like to select such agonist antibodies, the evaluation of hIGF-1R phosphorylation was studied using the chimeric antibodies.

For that purpose, MCF-7 cells were incubated in serum-free medium overnight. Then, either IGF-1 (100 nM) or Abs to be tested were added (10 µg/ml) for 10 minutes at 37° C. Medium was discarded and cells were scraped in a lysis buffer (pH 7.5) containing 10 mM Tris HCl buffer (pH 7.5). 15% NaCl (IM), 10% detergent mix (10 mM Tris-HCl, 10% Igepal lysis buffer) (Sigma Chemical Co.), 5% sodium deoxycholate (Sigma Chemical Co.), 1 protease inhibitor cocktail complete TM tablet (Roche), 1% phosphatase inhibitor Cocktail Set II (Calbiochem), for 90 min at 4° C. The lysates were clarified by centrifugation at 4° C., heated for 5 min at 100° C. and kept at −20° C. or directly loaded on 4-12% SDS-PAGE gels. Incubation of the primary antibody was performed for 2 hr at room temperature and then incubation with HRP-linked secondary antibodies was done for 1 hr at room temperature. Membranes were washed in TBST prior to visualization of proteins with ECL. Blots were quantified using Image J software. Phospho-protein values were normalized with GAPDH. Phosphorylation of hIGF-1R in response to IGF-1 was considered as 100% of stimulation. The effect of anti-hIGF-1R Abs on the phosphorylation of hIGF-1R was determined as % of phosphorylation induced by IGF-1.

Figure 9:
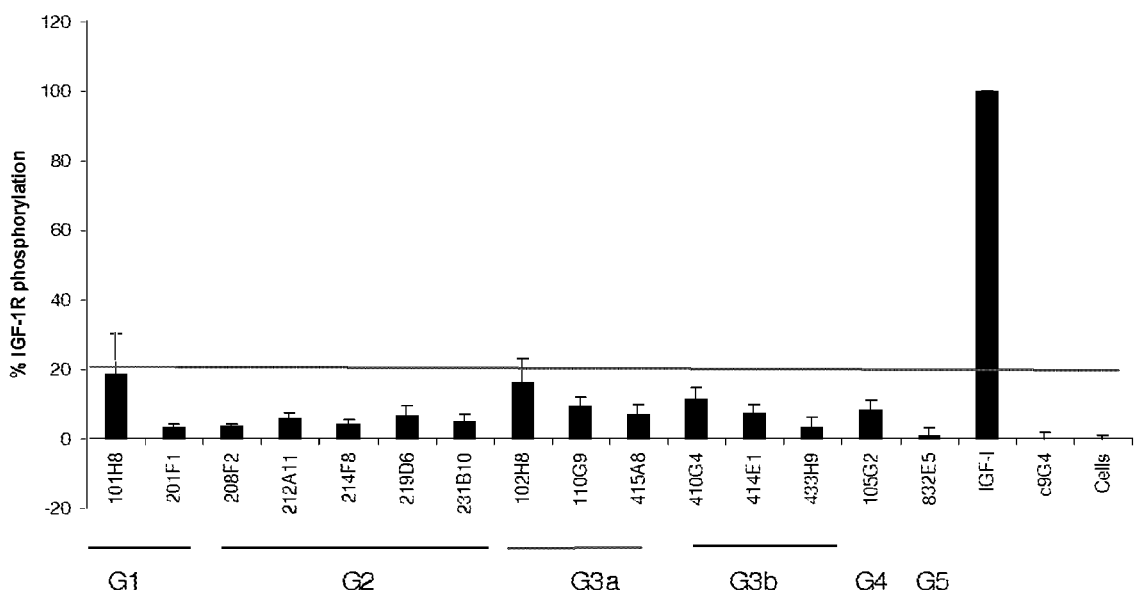
FIG. 9: Evaluation of the intrinsic effect of anti-hIGF-1R antibodies on the receptor phosphorylation compared to IGF1.

The results described in FIG. 9 represent the mean of the % of pIGF-1R in response to the chimeric anti-IGF-1R Abs of 3 independent experiments+/−S.D. compared to IGF-1. As illustrated no significant or minor (<20%) phosphorylation of hIGF-1R was detected when MCF-7 cells were incubated with 10 μg of anti-IGF-1R Abs.

Example 7: Inhibition of IGF-1R Phosphorylation in Response to IGF-1 by Murine Anti-hIGF-1R Antibodies In order to characterize the selected antibodies, their ability to inhibit IGF1-induced phosphorylation was studied. For that purpose, MCF-7 cells were incubated in serum-free medium overnight. Then, cells were incubated for 5 minutes with murine anti-hIGF-1R Abs before addition of IGF-1 for 2 minutes at 37° C. Medium was discarded and cells were scraped in a lysis buffer (pH 7.5) containing 10 mM Tris HCl buffer (pH 7.5), 15% NaCl (1M), 10% detergent mix (10 mM Tris-HCl, 10% Igepal lysis buffer) (Sigma Chemical Co.), 5% sodium deoxycholate (Sigma Chemical Co.), 1 protease inhibitor cocktail complete TM tablet (Roche). 1% phosphatase inhibitor Cocktail Set II (Calbiochem), for 90 min at 4° C. The lysates were clarified by centrifugation at 4° C., heated for 5 min at 100° C. and kept at −20° C. or directly loaded on 4-12% SDS-PAGE gels. Incubation of the primary antibody was performed for 2 hr at room temperature and then incubation with HRP-linked secondary antibodies was performed for 1 hr at room temperature. Membranes were washed in TBST prior to visualization of proteins with ECL. Blots were quantified using Image J software. Phospho-protein values were normalized with GAPDH. Phosphorylation of hIGF-1R in response to IGF-1 was considered as 100% of stimulation. The effect of anti-hIGF-1R Abs on the phosphorylation of hIGF-1R was determined as % of phosphorylation induced by IGF-1.

Figure 10:
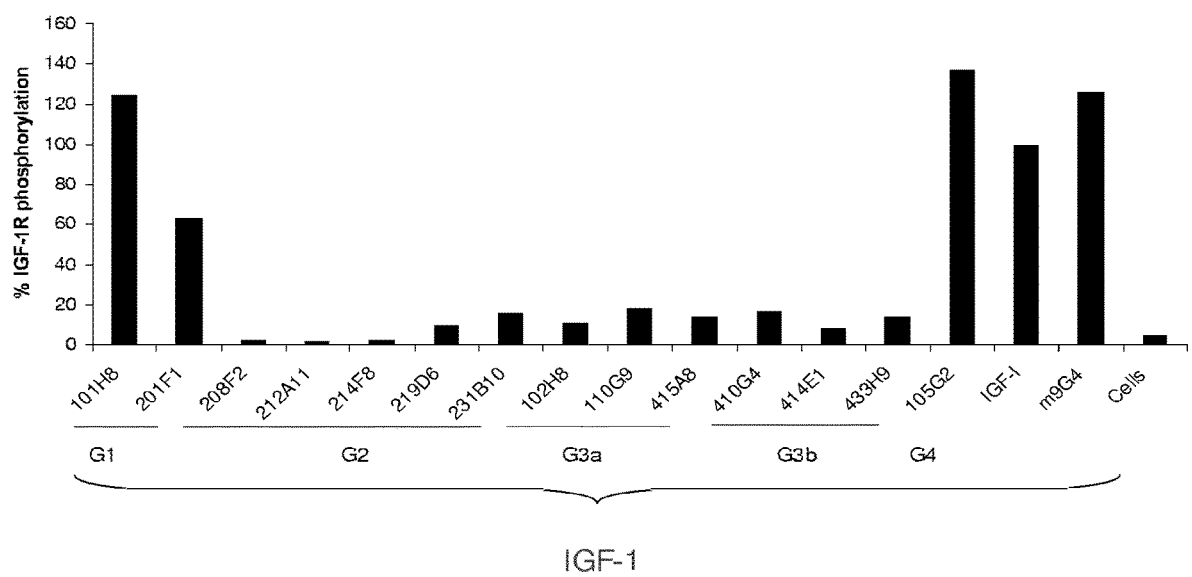
FIG. 10: Inhibition of IGF-1R phosphorylation in response to IGF-1 by murine anti-hIGF-1R.

Addition of either m105G2, m101H8 or m9G4, an irrelevant murine antibody, did not inhibit hIGF-1R phosphorylation in response to IGF-1 (FIG. 10). Addition of m201F1 decreased moderately hIGF-1R phosphorylation in response to IGF-1 (~40% of decrease). All other anti-IGF-1R Abs inhibited strongly hIGF-1R phosphorylation in response to IGF-1 (decrease >80%). The best inhibitors of IGF1-induced phosphorylation of hIGF-1R are the m208F2, m212A11 and m214F8 Mabs.

Example 8: Study of IGF-1R Internalization after Binding of the Generated Anti-IGF-1R Antibodies by FACS Analyses MCF-7 cells were incubated with 10 μg/ml of chimeric antibodies at 4° C. for 20 min. Then, cells were washed and incubated at 4° C. or 37° C. for 4 h. The quantity of cell-surface bound antibody was determined using a secondary antibody on a FacsCalibur Flow cytometer (Becton Dickinson). The ΔMFI defined as the difference between MFI measured at 4° C. and MFI measured at 37° C. after a 4 hour incubation time corresponded to the quantity of internalized Ab. The ΔMFI was presented in FIGS. 11A and 11B and Table 12. The percentage of internalization at 10 μg/ml of Ab were calculated as followed 100*(MFI at 4° C. −MFI at 37° C.)/MFI at 4° C. and presented in Table 11. The maximum of ΔMFI calculated for each chimeric antibody (FIGS. 11A and 11B) showed no correlation between the group and the maximum of internalisation.

TABLE 12

| Group | Abs | % Internalization | ΔMFI | $EC_{50}$ |
|---|---|---|---|---|
| G1 | c101H8 | 75 | 254 | 4.2E−09 |
| G1 | c201F1 | 75 | 277 | 8.4E−08 |
| G2 | c208F2 | 83 | 288 | 1.8E−10 |
| G2 | c212A11 | 80 | 377 | 2.7E−10 |
| G2 | c214F8 | 87 | 403 | 2.2E−10 |
| G2 | c219D6 | 80 | 353 | 4.4E−10 |
| G2 | c213B10 | 85 | 369 | 2.3E−10 |
| G3a | c102H8 | 71 | 262 | 7.9E−10 |
| G3a | c110G9 | 79 | 309 | 1.2E−09 |
| G3a | c415A8 | 78 | 327 | 1.2E−09 |
| G3b | c410G4 | 82 | 321 | 3.7E−09 |
| G3b | c414E1 | 68 | 229 | 3.1E−09 |
| G3b | c433H9 | 79 | 323 | 1.1E−09 |
| G4 | c105G2 | 81 | 260 | 7.2E−09 |
| G5 | c832E5 | 40 | 92 | 2.0E−08 |

In order to determine whether antibodies that also recognized the monkey IGF-1R were able to internalize this receptor, the same internalization experiment was performed. Results summarized in Table 13 demonstrated that all tested antibodies were able to mediate monkey IGF-1R internalization.

TABLE 13

| | | Murine Abs | | Chimeric Abs | |
|---|---|---|---|---|---|
| Group | Abs | ΔMFI | % internalisation | ΔMFI | % internalisation |
| G1 | 101H8 | 73 | 73 | 85 | 73 |
| G1 | 201F1 | 66 | 65 | 76 | 60 |
| G2 | 208F2 | 53 | 74 | 52 | 67 |
| G2 | 212A11 | 83 | 73 | 98 | 75 |
| G2 | 214F8 | 76 | 71 | 98 | 72 |
| G2 | 219D6 | 80 | 71 | 102 | 74 |
| G2 | 213B10 | 84 | 74 | 101 | 73 |
| G3a | 102H8 | 60 | 55 | 74 | 54 |
| G3a | 110G9 | 69 | 59 | 93 | 61 |
| G3a | 415A8 | 89 | 65 | 121 | 68 |
| G3b | 410G4 | 51 | 49 | 87 | 58 |
| G3b | 414E1 | 93 | 67 | 59 | 54 |
| G3b | 433H9 | 80 | 61 | 98 | 63 |
| G4 | 105G2 | 68 | 67 | 94 | 72 |

The kinetic of cell surface bound antibody decrease was further evaluated. For that purpose, MCF-7 cells were seeded in 96-well plates and incubated with 10 μg/ml of murine for 20 min at 4° C. Cells were then washed to remove unbound antibody and in media at 37° C. for 10, 20, 30, 60 or 120 min. At each time point, cells were centrifuged and then surface labelled on ice with a secondary anti-mouse IgG-Alexa488 to determine the amount of antibody remaining on the cell surface. The fluorescence intensity for each murine Ab and for each time point was normalized by the signal at 4° C. (% remaining IGF-1R) and fit to an exponential decay to determine the half life (t½). t½ was considered as the time needed to obtain a decrease of 50% of the signal measured at 4° C. As illustrated in FIGS. 12A and 12B, the surface level of all murine Abs dropped rapidly over the first 30 min and the decrease was almost maximum after 60 min of incubation (FIG. 12A). The calculated half life was comprised between 10 to 18 min regarding to the murine Ab (FIG. 12B). There was no correlation between the antibody surface decay and the group of Abs.

Figure 13A:
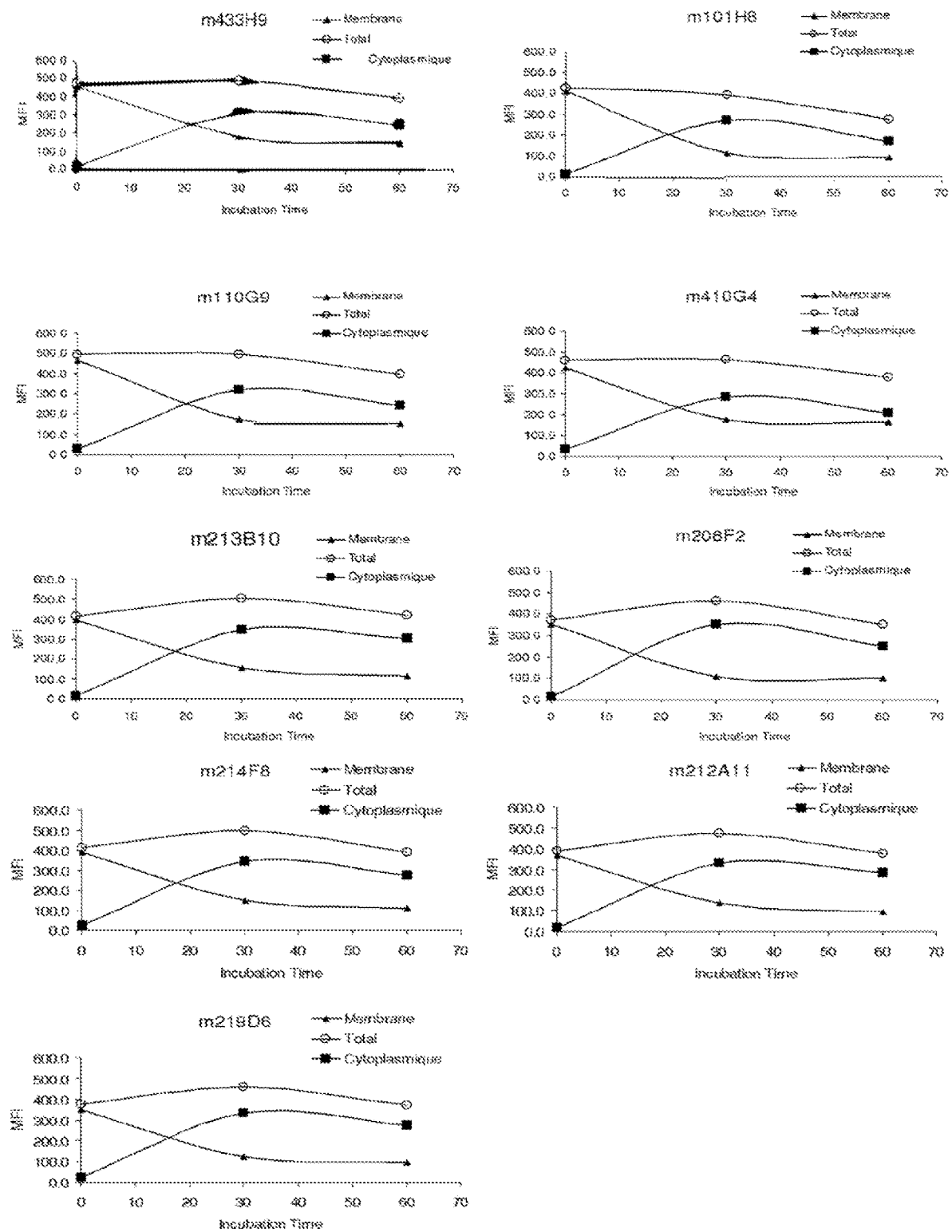
FIG. 13A and FIG. 13B: Kinetic of antibody internalization evaluated by FACS analyses. Cells were incubated with 10 µg/ml of murine Abs for 0, 30 or 60 min at 37° C. Cells were permeabilized or not and incubated with a secondary anti-mouse IgG-Alexa 488. Membrane corresponds to the signal intensity w/o permeabilization. Total correspond to the signal intensity after cell permeabilization and cytoplasmic corresponds to internalized Ab. The name of each evaluated antibody is depicted on the top of each graph.
Figure 13B:
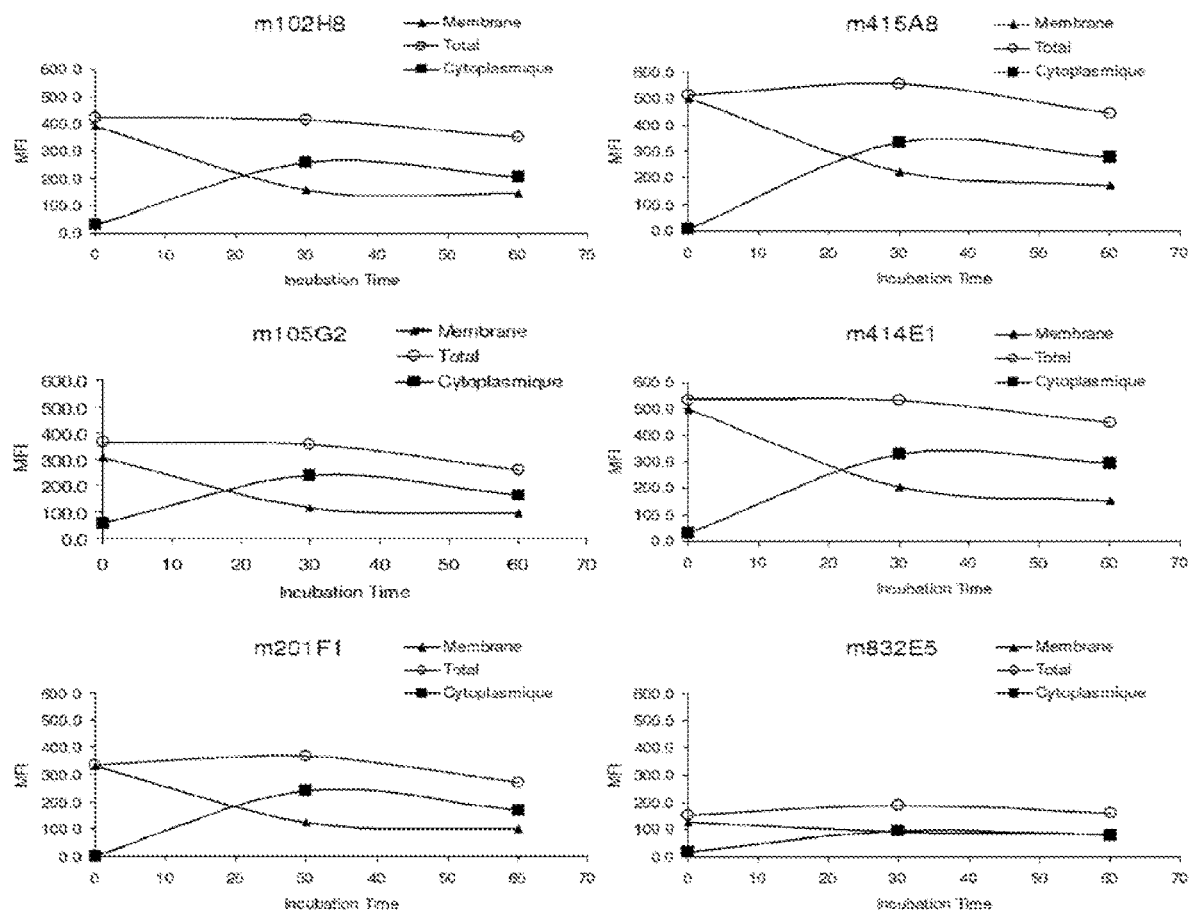

In order to validate that the decrease of the cell surface signal was due to Ab internalization and not due to receptor shedding, cells were incubated with murine Abs for 0, 30 and 60 min à 37° C. (FIG. 13). Cells were then fixed and permeabilized or not in order to determine cell surface bound antibody (w/o permeabilization) and total antibody signal corresponding to cell-surface bound+internalized Ab (with permeabilization). The quantity of internalized Ab (cytoplasmic) was determined as follow: MFI after permabilization−MFI w/o permeabilization. This experiment showed that the decrease of cell-surface bound Ab was due to an increase of cytoplasmic Abs demonstrating that Abs were internalized (FIG. 13). In addition, the degradation of the Abs started after 1 h of incubation as indicated by the decrease of the signal after permeabilization (Total).

Figure 14A:
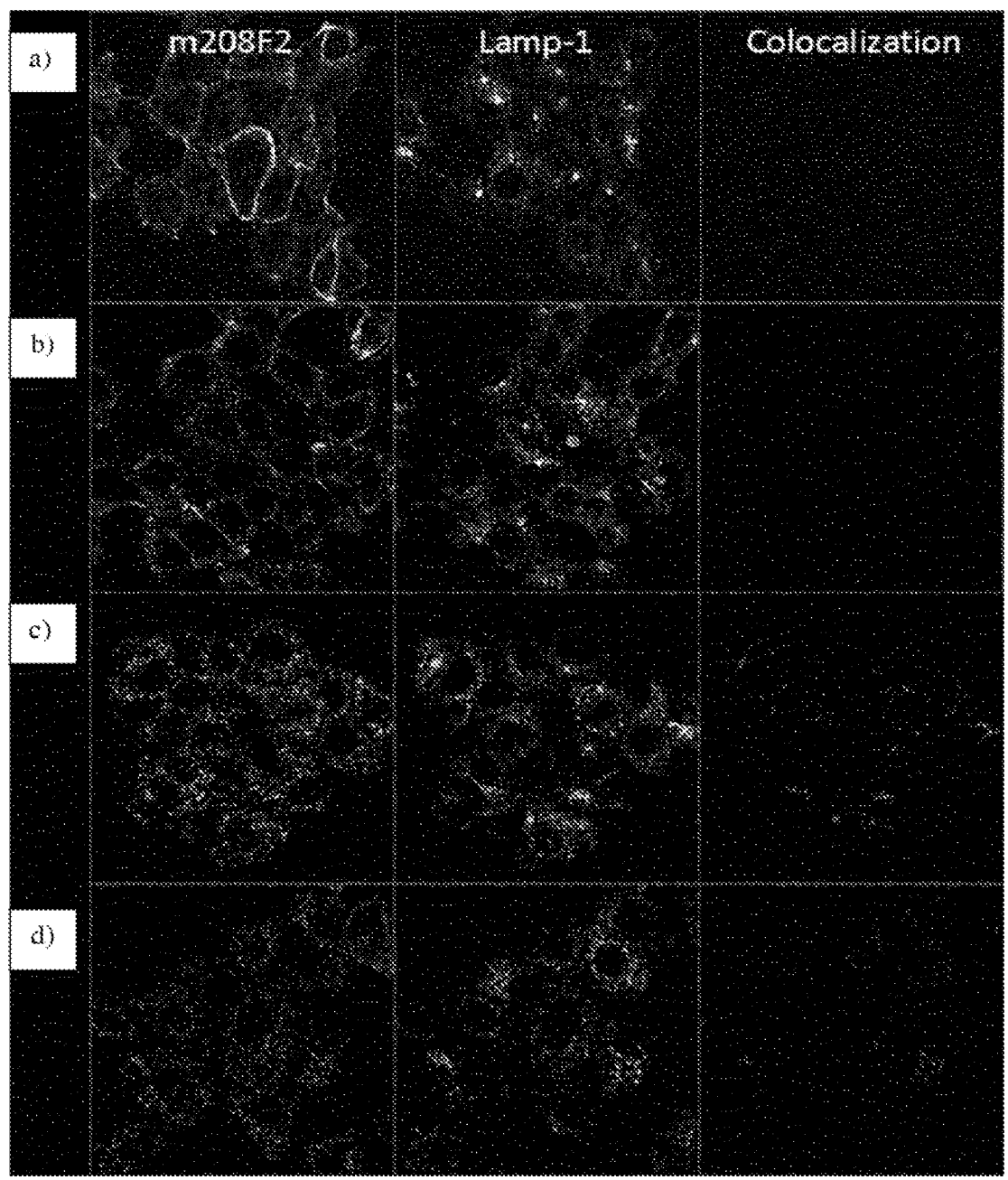
FIG. 14A, FIG. 14B, FIG. 14C, and FIG. 14D: Imaging Ab internalization.

Example 9: Study of IGF-1R Internalization after Binding of the Generated Anti-IGF-1R Antibodies by Confocal Analyses To further confirm antibodies internalization, confocal microscopy was done to assess the subcellular distribution of antibodies following cellular trafficking. Cells were incubated with anti-hIGF-1R Abs 37° C. fixed and permeabilized. Therefore, cells were stained using a secondary antibody Alexa-488 and with rabbit anti-lLamp-1 antibody that was revealed using a secondary anti-Rabbit IgG Alexa 555. Before incubation at 37° C. the murine 208F2 Ab was localized on the membrane of MCF-7 cells (FIG. 14A) and no colocalization with the lysosome marker, lamp-1 was noted using the colocalization highliter plug-in of the ImageJ software. The cell surface bound antibody decreased dramatically after 15 min of incubation. Concomitantly to the decrease of the cell surface bound antibody, intracellular antibody was detected into vesicles. Rare colocalization with lamp-1 could be observed. After 30 min of incubation, the cell surface bound antibody was hardly detected. However, the colocalization of the Ab into lysosome increased. After 1 h of incubation, the intracellular Ab staining decreased as well as the number of colocalization with lamp-1. This kinetic of cell surface bound antibody and its intracellular accumulation correlated with the kinetic of antibody surface decay measure by FACS. In addition, as already described with FACS studies, the degradation of murine Abs started after 1 h of incubation by confocal microscopy.

Figure 14B:
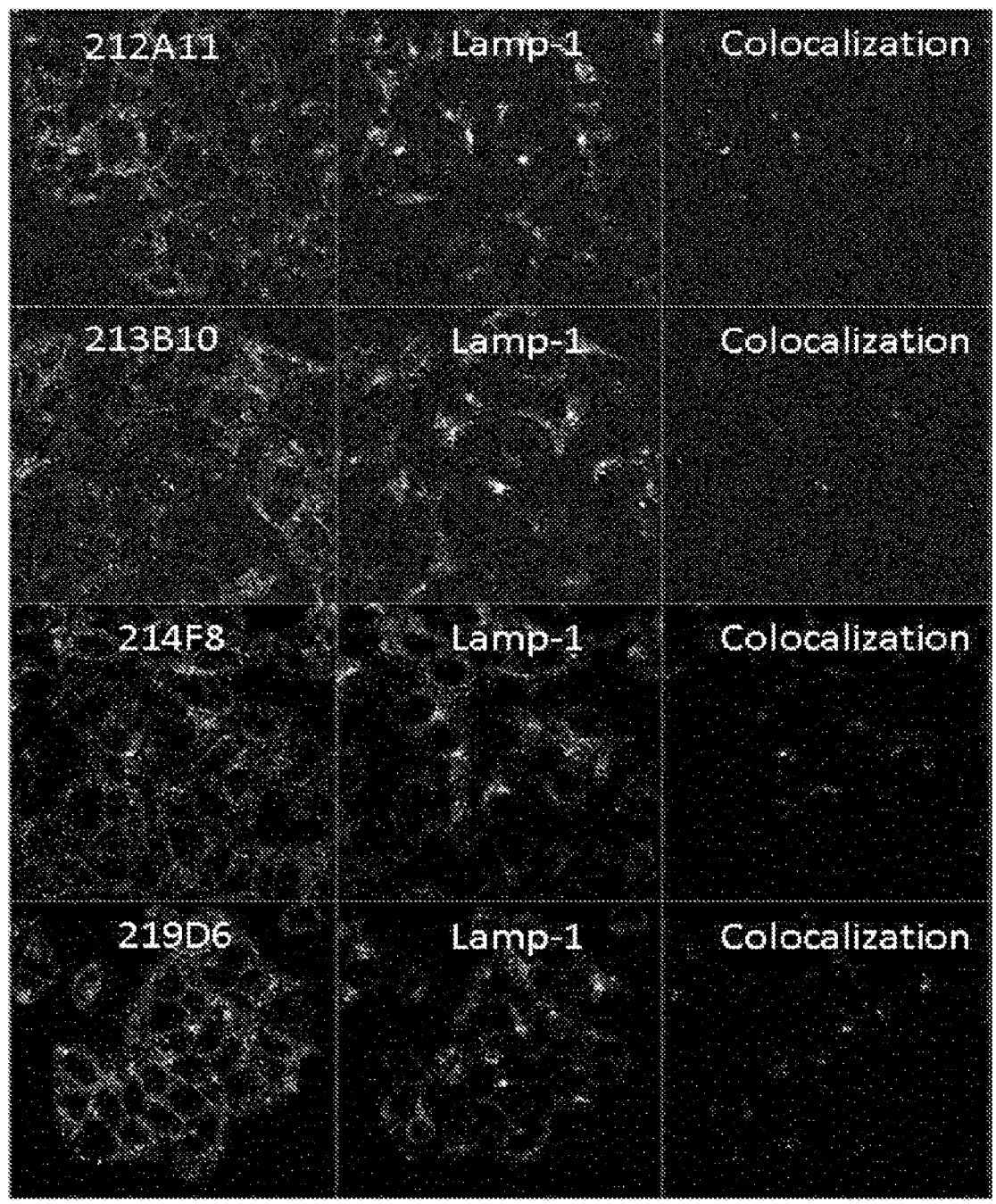
Figure 14C:
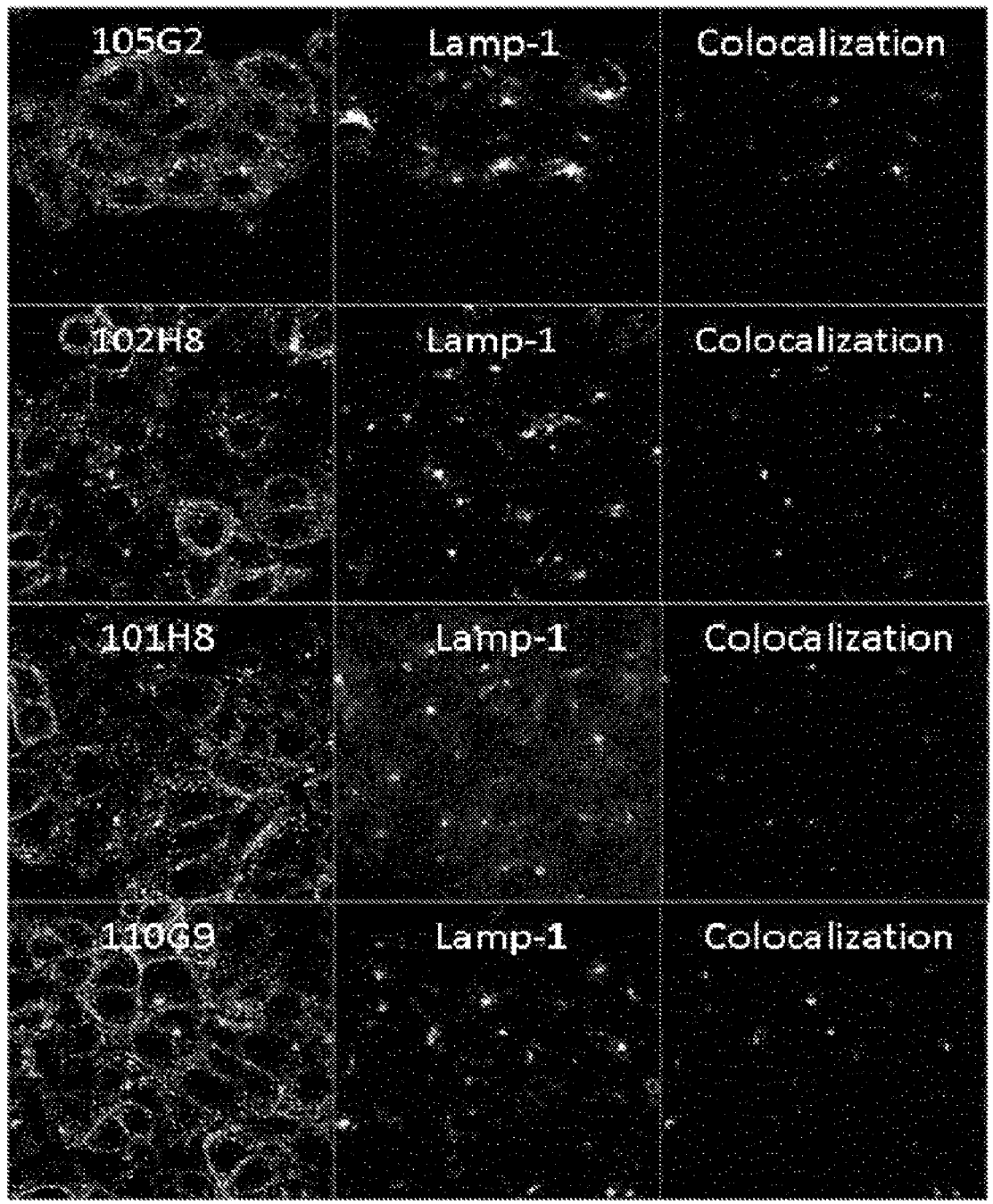
Figure 14D:
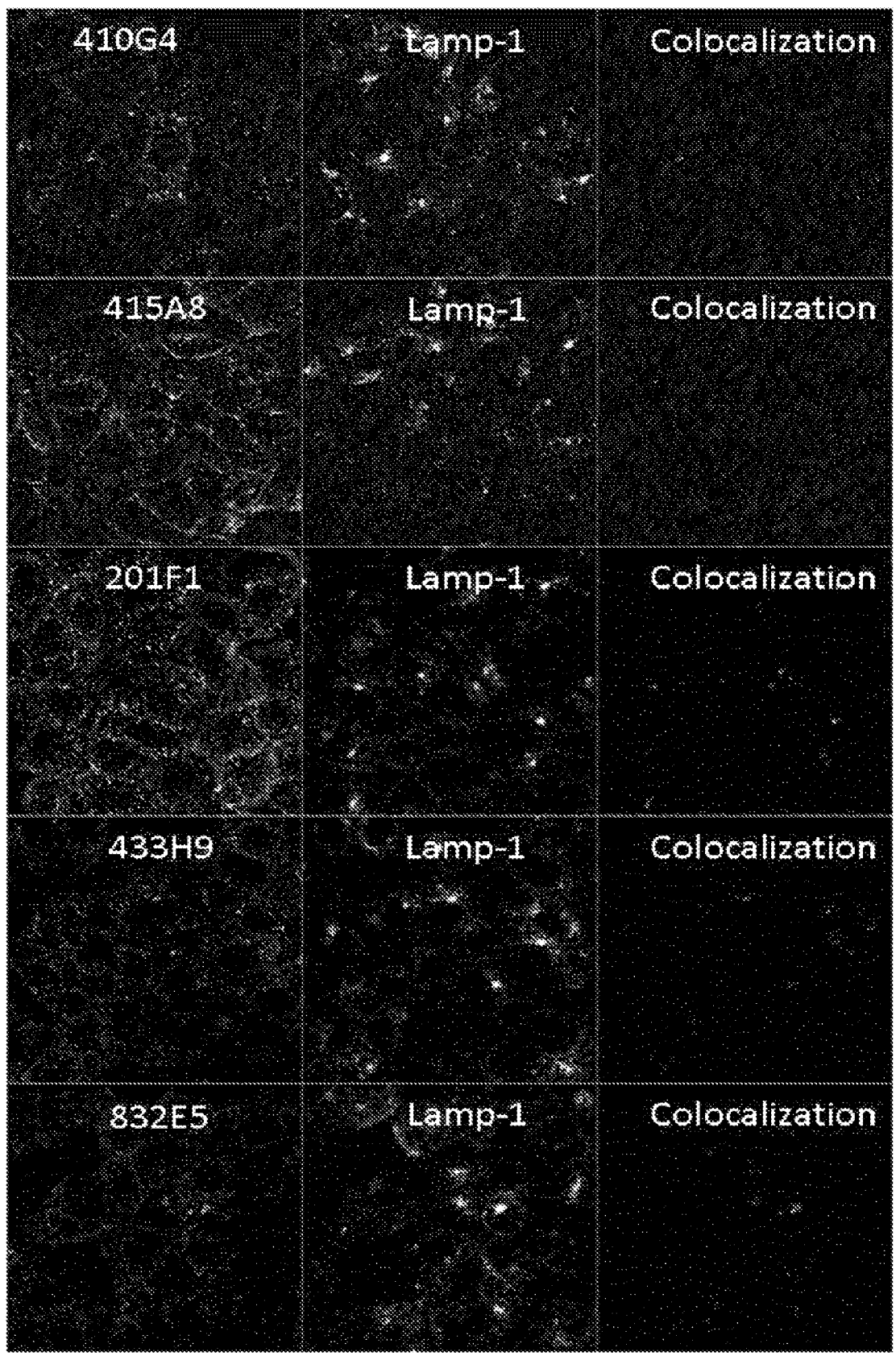

The internalization of all other anti-hIGF-1R murine antibodies and their colocalization with Lamp-1 was also assessed (FIG. 14B).

Example 10: Inhibition of Abs Degradation Using Lysosome Inhibitor, Bafilomycin A1

Figure 15:
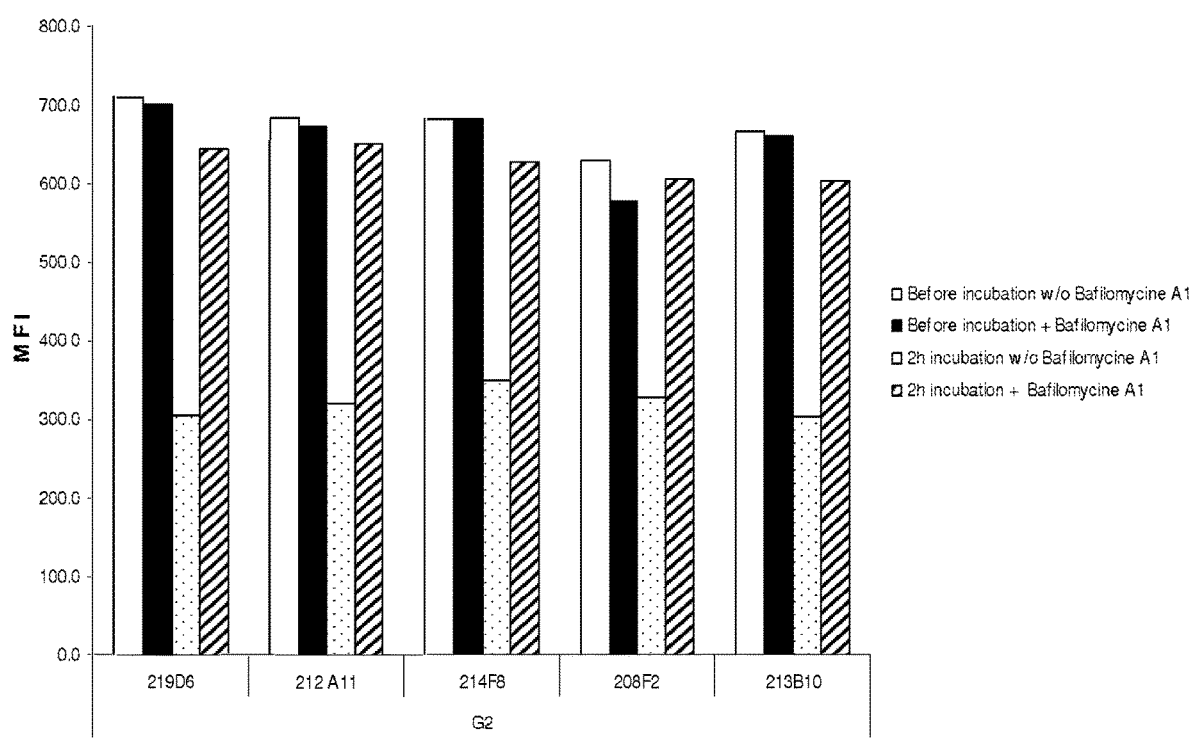
FIG. 15: Involvement of the lysosome pathway in antibody degradation

In order to confirm that antibodies reached the lysosome were they are degraded, cells were treated or not with bafilomycine A1, a potent inhibitor of lysosome functions. Cells were then incubated with 10 µg/ml of Ab to be tested at 4° C., washed and incubated for 2 h at 37° C. The internalized Ab was detected after cell permeabilisation using a secondary anti-mouse IgG-Alexa 488 Ab. Addition of bafilomycine A1 prevented the degradation of intracellular Ab (FIG. 15) indicating that Abs were effectively internalized and degraded into lysosomes.

Example 11: Effect of pH on Antibody-IGF-1R Binding and Correlation with Cytotoxicity Potency As antibodies were selected on the bases of their internalizing potential and shown above to co-localize with early endosomes before entering into the lysosomal compartment, an interesting approach consisted in selecting antibodies for which the stability of the Ab-hIGF-1R binding was modulated regarding to pH environment and preferentially antibodies that dissociated preferentially from IGF-1R when the pH environment became acid. Indeed, the primary difference between early endosomes and lysosomes is their luminal pH: in the endosome compartment the pH is approximately 6 while in the lysosomal compartment the pH is about 4.5.

It is well known that once internalized after ligand binding (IGF1), hIGF-1R returns back to the cell surface through a recycling pathway.

Without being linked by a theory, a hypothesis herein described is that antibodies more prone to be released from their target early at acidic pH will probably favour target recycling to the membrane and consequently could be considered as better candidates for immunoconjugate approaches. In order to investigate whether some of our antibodies display such a property and to correlate this property to cytotoxic activity, the binding of the murine anti-hIGF-1R Mabs on MCF-7 cell line was done in buffers at different pH. Increasing concentration of murine mAbs were incubated on MCF-7 cell line for 20 min at 4° C. in different pH ranging from 5 to 8. Cells were then washed 3 times and incubated with the appropriate secondary antibody coupled with Alexa 488 in FACS buffer. Cells were incubated for 20 additional minutes at 4° C. in the dark and then washed 3 times in FACS buffer. The binding of anti-hIGF-1R antibodies was immediately performed on viable cells which were identified using propidium iodide that stained dead cells. The binding $EC_{50}$ expressed in molarity (M) was calculated using a nonlinear regression analysis (GraphPad Prims 4.0).

Figure 16A:
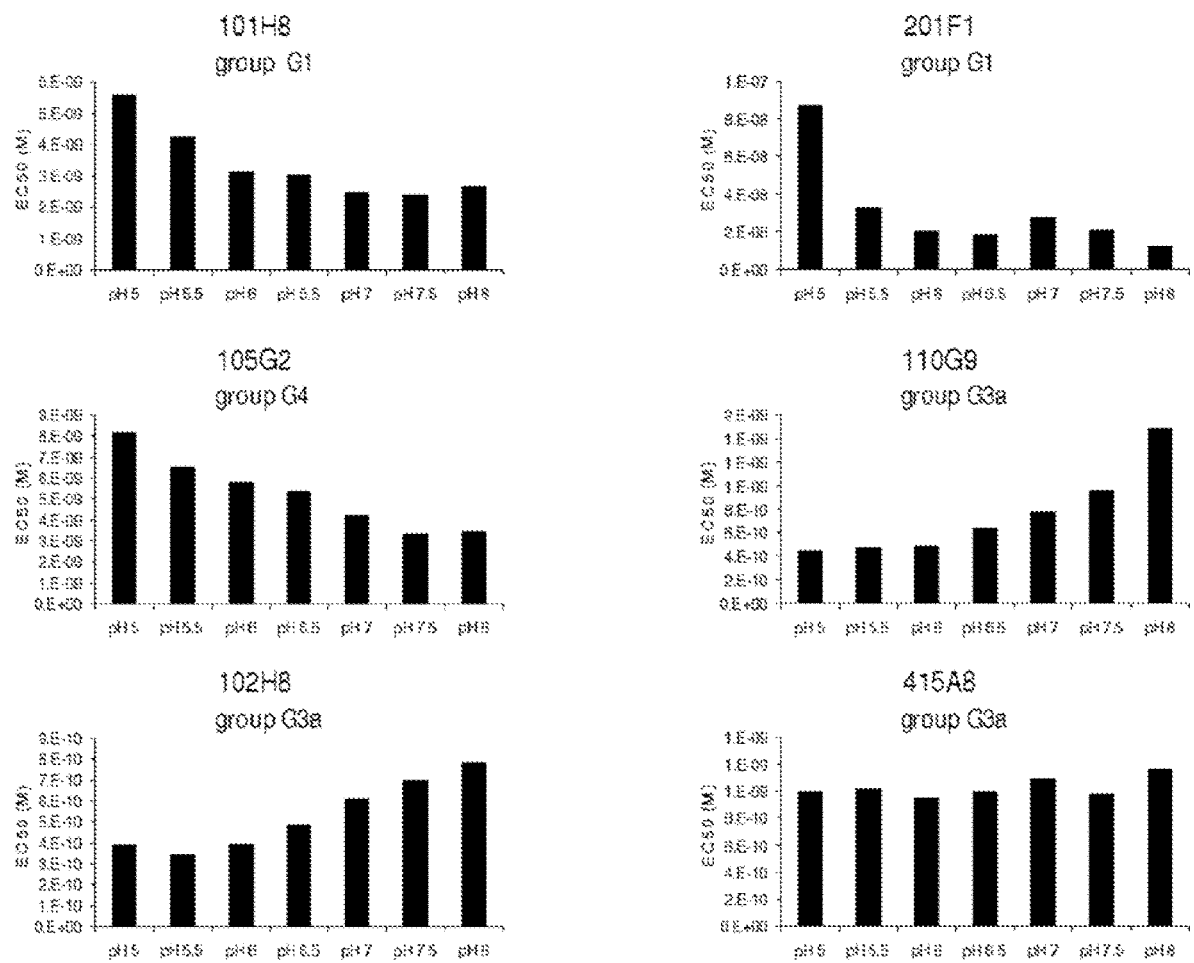
FIG. 16A and FIG. 16B: Evaluation of the binding of anti-hIG-1R murine antibodies at different pH. The EC50s of the binding of the different antibodies was evaluated on MCF-7 using buffer with different pH ranging from 5 to 8.
Figure 16B:
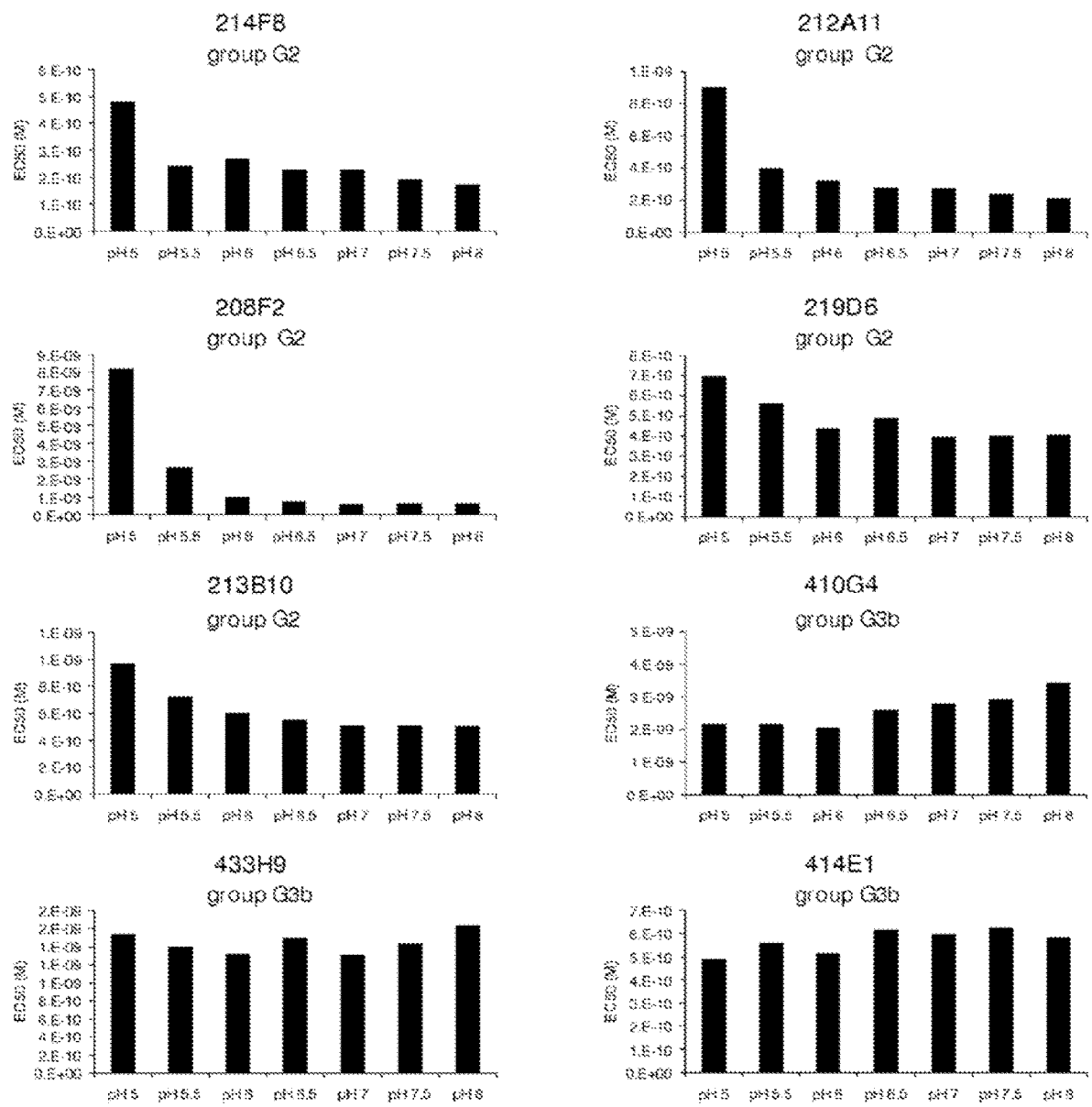

The $EC_{50}$ of the anti-hIGF-1R belonging to the epitope cluster group 3B was not significantly affected by the pH (FIG. 16). The binding capacity of the anti-hIGF-1R Abs belonging to the epitope cluster group 3a was often enhanced at acidic pH. On the contrary, the binding capacity of anti-hIGF-1R Abs belonging to the epitope cluster groups 1, 2 and 4 was decreased at acidic pH.

Figure 17A:
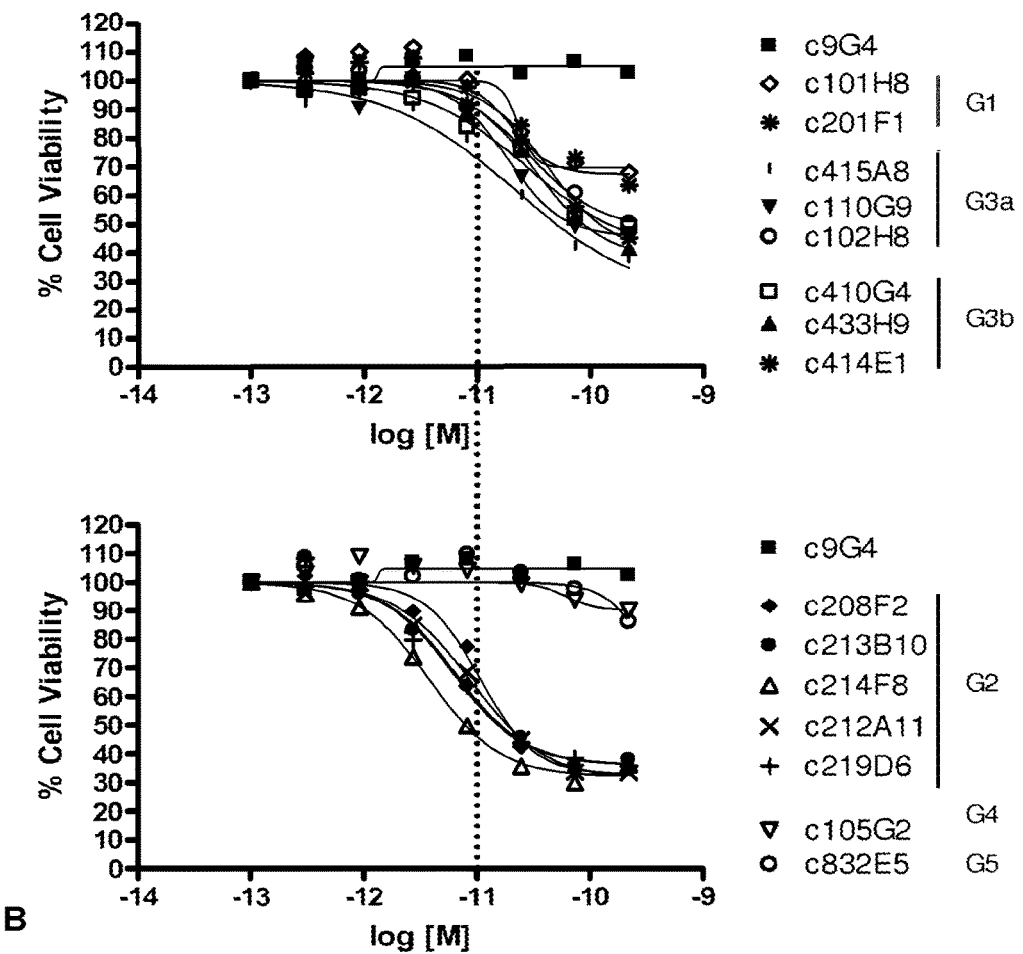
FIG. 17A and FIG. 17B: Evaluation of the ability of the selected anti-IGF-1R Abs to induce cytotoxicity on a Fab-ZAP assay.
Figure 17B:
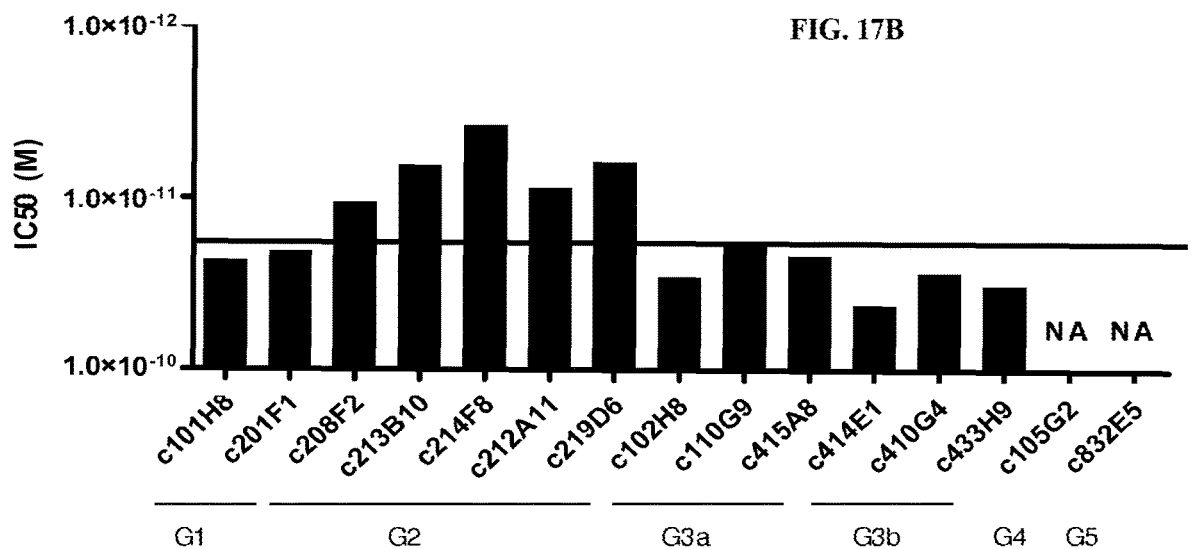

In the aim of determining if acidic pH has a positive impact on cytotoxicity induced by an immunoconjugate, the commercially available Fab-ZAP human assay (ATS BIO) was used. Briefly, MCF7 cells were seeded at 2000 cells/well on 96 well plates and left overnight to adhere. The day after, cells were treated with 0.45 µg/mL of Fab-ZAP and increasing concentrations of chimeric anti-IGF-1R Abs, c9G4 monoclonal antibody which does not bind cell surface was used as a negative control. On day 6, cell viability was measured using CellTiter Glo Luminesence Cell Viability assay from Promega (Madison, Wi). As illustrated in FIG. 17A, the anti-IGF-1R Abs of groups 4 and 5 did not induced induced any cytotoxicity on MCF-7, whereas moderate cytotoxicity (groups 1, 3a and 3b) to high cytotoxicity (group 2) was measured with the other groups. In the FIG. 17B, determination of the $IC_{50}$ confirmed that the group 2 have the highest cytotoxic potency suggesting that these antibodies will be the most suitable for an ADC (Antibody Drug Conjugate) or an ATC approach.

Figure 18:
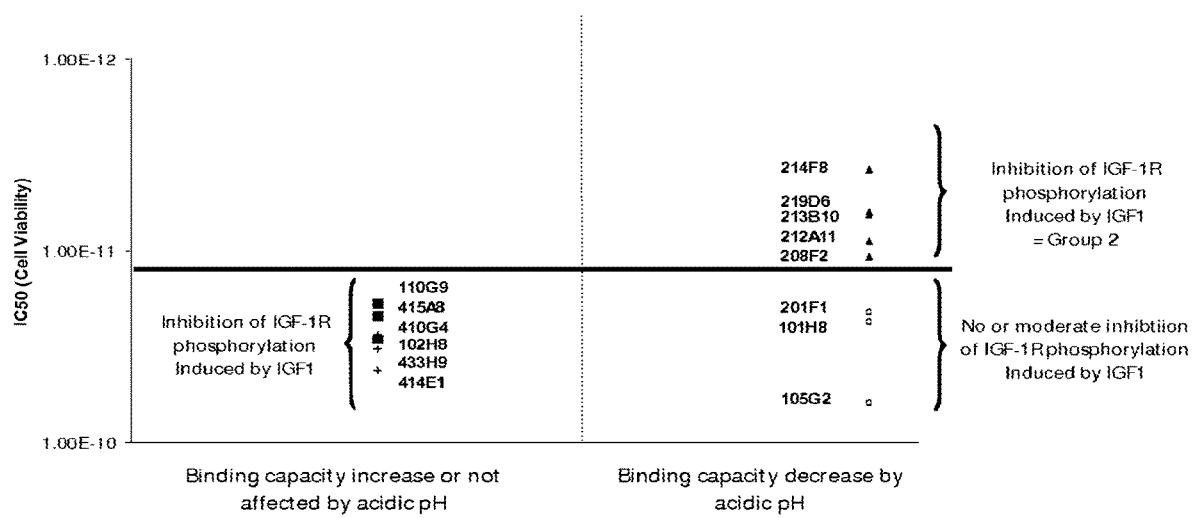
FIG. 18: Correlation between i) cytotoxic potency, ii) influence of pH on the Ab/IGF-1R binding, iii) effect of Abs on the IGF-1-induced phosphorylation of IGF-1R and iv) antibody clustering.

The results summarized in FIG. 17 showed that among the 15 chimeric mabs evaluated the best cytotoxic effect was reached with c208F2, c219D5, c212A11, c213B10 and c214F8 that all belong to group 2. However other antibodies from group 1 and 4 also that also display a sensitivity to acidic pH for IGF-1R binding, were not clustered as the best candidates for cytotoxicity suggesting that this property could be required but not sufficient to explain the particular properties of antibodies from the group 2. In order to better understand the particular characteristics of this set of antibodies correlations studies were performed regarding to the data available for all the generated antibodies. The results of this analysis suggested that both inhibition of phosphorylation and decrease capacity of binding to hIGF-1R in an acidic pH environment are required to get the best cytotoxic activity (FIG. 18). Indeed 101H8 (G1), 201F1 (G1) and 105G2 (G4) whose binding was decreased in acidic pH environment, but that were poor phosphorylation inhibitors, showed low cytotoxic activities. On the other hand, 102H8 (G3a), 110G9 (G3a), 415A8 (G3a), 410G4 (G3b), 414E1 (G3b) and 433H9 (G3b) were potent inhibitors of IGF1-induced phosphorylation but not sensitive to pH variation or whose binding was enhanced at acidic pH, demonstrated only moderate cytotoxic activities in the Fab-ZAP human assay.

The binding of the humanized anti-IGF-1R Mabs on MCF-7 cell line was done in buffers at different pH. Increasing concentrations of humanized mAbs were incubated on MCF-7 cell line for 20 min at 4° C. in different pH ranging from 5 to 8. Cells were then washed 3 times and incubated with the appropriate secondary antibody coupled with Alexa 488 in FACS buffer. Cells were incubated for 20 additional minutes at 4° C. in the dark and then washed 3 times in FACS buffer. The binding of anti-IGF-1R antibodies was immediately performed on viable cells which were identified using propidium iodide that stained dead cells. The binding $EC_{50}$ expressed in molarity (M) was calculated using a nonlinear regression analysis (GraphPad Prims 4.0). The humanized anti-IGF-1R-antibodies showed a lower binding capacity at acidic pH as illustrated in FIGS. 32A and 32B.

Example 12: Evaluation of the Humanized Forms of the 208F2 Mab 12.1 Evaluation of the Binding and Internalization of the First Humanized Form hz208F2 VH3/VL3 (Also Referred as hz208F2 H026/L024)

The binding of the first humanized form of the c208F2 mAb was evaluated on MCF-7. COS-7 and NIH 3T3 IR$^+$ cell lines. Increasing concentrations of the m208F2, the c208F2 or the hz208F2 VH3VL3 were added on each cell line for 20 min. at 4° C. Cells were then washed and the binding of the tested mAb was revealed using the corresponding secondary antibody. In order to validate the expression of the human IR on the transfected cell line, the commercial anti-hIR antibody clone GRO5 was used and its recognition profile exemplified on (FIG. 19D).

Comparison of the humanized form with either murin or chimeric ones on MCF-7 (FIG. 19A) or monkey COS-7 (FIG. 19B) cells showed close profiles for the 3 tested forms. The humanisation process did not modify the specificity of recognition of the antibody that is perfectly comparable to the murin and chimeric forms regarding to the absence of cross reactivity on the human insulin receptor (FIG. 19C).

The calculated $EC_{50s}$ of the first humanized form of c208F2 on the human cell line MCF-7 and the monkey cell line COS-7 were similar to the one determined with either the murine or the chimeric form of the 208F2.

The capacity of the mAb hz208F2 VH3/VL3 to be internalized was assessed by flow cytometry. MCF-7 cells were incubated with 10 µg/ml of antibodies at 4° C. for 20 min. Then, cells were washed and incubated at 4° C. or 37° C. for 4 h. The quantity of cell-surface bound antibody was determined using a secondary antibody. The ΔMFI defined as the difference between MFI measured at 4° C. and MFI measured at 37° C. after a 4 hour incubation time corresponded to the quantity of internalized Ab. The ΔMFI was presented in Table 14a. The percentage of internalization at 10 µg/ml of Ab were calculated as followed 100*(MFI at 4° C. −MFI at 37° C.)/MFI at 4° C. and presented in Table 14a. Therefore, the humanized hz208F2 VH3/VL3 had similar binding and internalization properties as the one measured with the corresponding murine and chimeric 208F2 antibodies.

TABLE 14a

|  | ΔMFI | % internalization |
|---|---|---|
| m208F2 | 294 | 88 |
| c208F2 | 278 | 82 |
| Hz208F2 VH3/VL3 | 344 | 87 |

12.2 Evaluation of the Binding of Subsequent hz208F2 Humanized Forms

The mAb 208F2 was humanized and the binding properties of sixteen humanized variants (including the first form described in 12.1) were evaluated. The binding properties of the humanized variants were evaluated by FACS analyses on the human MCF-7 breast adenocarcinoma cell line and the monkey cell line Cos-7 using increasing antibody concentrations. For that purpose, cells (1×10$^6$ cells/ml) were incubated with anti-IGF-1R humanized antibodies for 20 min. at 4° C. in FACS buffer (PBS, 0.1% BSA, 0.01% NaN$_3$). They were then washed 3 times and incubated with the appropriate secondary antibody coupled with Alexa 488 for 20 additional minutes at 4° C. in the dark before being washed 3 times in FACS buffer. The binding of anti-IGF-1R antibodies was immediately performed on viable cells which were identified using propidium iodide (that stains dead cells). The $EC_{50}$ of binding expressed in molarity (M) was calculated using a nonlinear regression analysis (GraphPad Prims 4.0).

The $EC_{50}$ of humanized variants showed that all the humanized variants displayed the equivalent binding properties on both human and monkey cell lines.

$EC_{50}$ of humanized antibodies were summarized in Table 14b.

TABLE 14b

|  |  | EC50 (M) | |
|---|---|---|---|
|  |  | MCF-7 | Cos-7 |
| Humanized variants | hz208F2 H026/L024 | 7.09E−10 | 5.1E−10 |
|  | hz208F2 H037/L018 | 4.9E−10 | 7.4E−10 |
|  | hz208F2 H047/L018 | 7.7E−10 | 9.2E−10 |
|  | hz208F2 H049/L018 | 4.9E−10 | 6.9E−10 |
|  | hz208F2 H051/L018 | 5.7E−10 | 7.2E−10 |
|  | hz208F2 H052/L018 | 8.4E−10 | 9.9E−10 |
|  | hz208F2 H057/L018 | 5.8E−10 | 8.3E−10 |
|  | hz208F2 H068/L018 | 1.1E−09 | 1.2E−09 |
|  | hz208F2 H070/L018 | 4.6E−10 | 7.3E−10 |
|  | hz208F2 H071/L018 | 5.5E−10 | 1.1E−09 |
|  | hz208F2 H076/L018 | 6.5E−10 | 1.1E−09 |
|  | hz208F2 H077/L018 | 7.7E−10 | 1.1E−09 |
|  | hz208F2 H037/L021 | 4.8E−10 | 8.2E−10 |
|  | hz208F2 H049/L021 | 6.6E−10 | 8.5E−10 |
|  | hz208F2 H052/L021 | 5.7E−10 | 1.2E−09 |
|  | hz208F2 H076/L021 | 5.8E−10 | 1.1E−09 |

12.3 Evaluation of the Internalization of Another hz208F2 Humanized Form

MCF-7 cells were incubated with 10 µg/ml of humanized antibodies at 4° C. for 20 min. Then, cells were washed and incubated at 4° C. or 37° C. for 4 h. The quantity of cell-surface bound antibody was determined using a secondary antibody on a FacsCalibur Flow cytometer (Becton Dickinson). The ΔMFI defined as the difference between MFI measured at 4° C. and MFI measured at 37° C. after a 4 hour incubation time corresponded to the quantity of internalized Ab. The ΔMFI was presented in Table 14c. The percentage of internalization at 10 µg/ml of Ab was calculated as followed 100*(MFI at 4° C.−MFI at 37° C.)/MFI at 4° C. The humanized antibody hz208F2 H077/L018 is able to induce a significant internalization of IGF-1R.

TABLE 14c

|  | ΔMFI | % Internalization |
|---|---|---|
| hz208F2 H077/L018 | 468 | 88 |

Example 13: IGF-1R as a Target for an Immunoconjugate Approach

IHC studies were set up in order to validate hIGF-1R as a target for an immunoconjugate approach. Indeed a useful target for such an approach requires a significant over expression on tumor cells compared to normal cells. Another property of an appropriate target for an immunoconjugate approach is its prevalence of overexpression on a significant percentage of the patient population in many indications.

In order to evaluate whether hIGF-1R could be considered as an appropriate target for an immunoconjugate approach, a commercially available polyclonal antibody (AF305-NA from R&D Systems) described as being specific of hIGF-1R extracellular domain (EDC) versus hIR was selected. The first step of our process was to verify the specificity of AF305-NA for hIGF-1R ECD and its absence of recognition of hIR. For that purpose, a series of ELISA tests were performed on both human IGF-1R and hIR ECD proteins using protocols already detailed above.

Figure 20A:
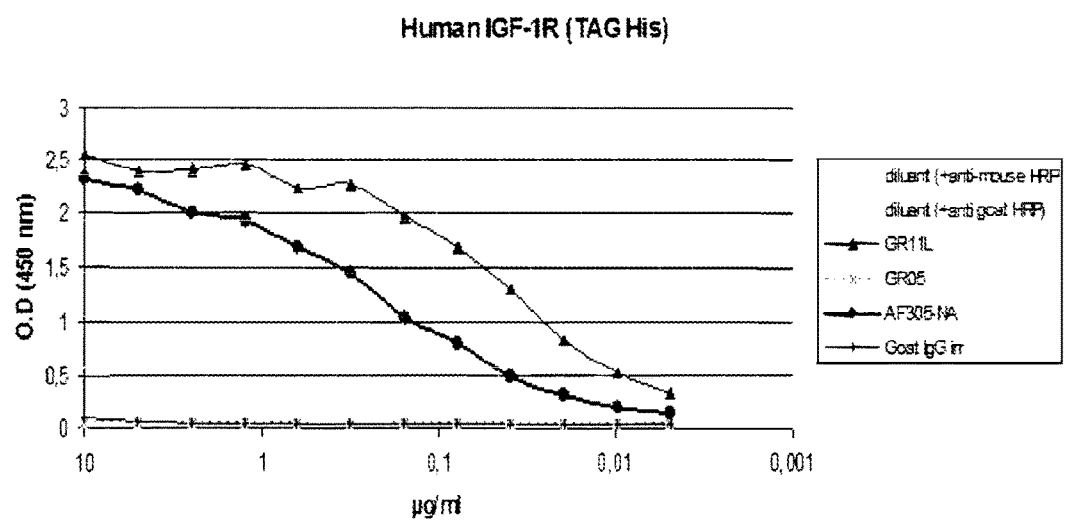
FIG. 20A, FIG. 20B, FIG. 20C, and FIG. 20D: ELISA validation of the AF305-NA polyclonal antibody that has been used for IHC assays.
Figure 20B:
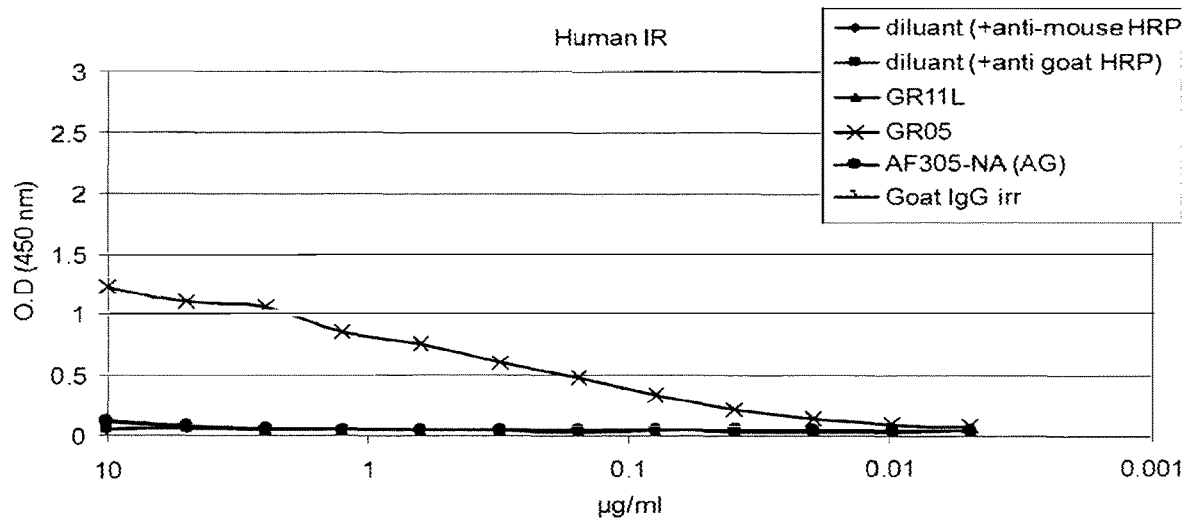
Figure 20C:
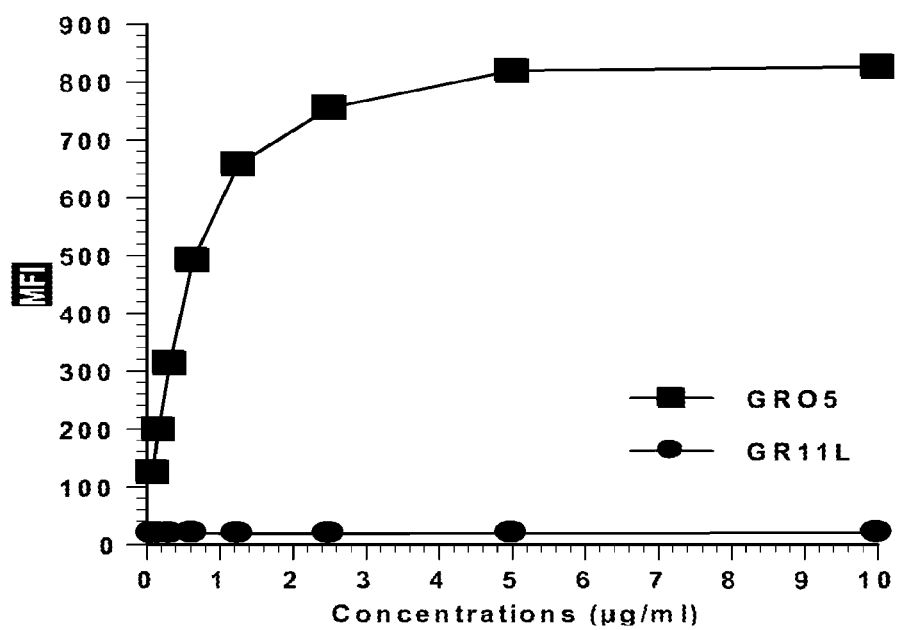
Figure 20D:
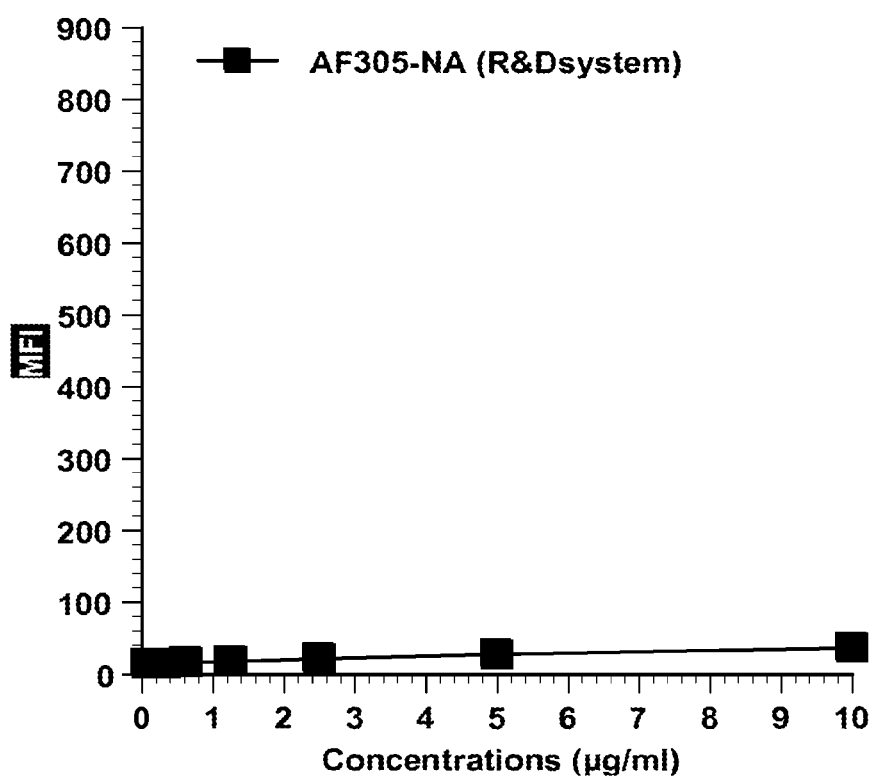

Results described in FIG. 20A demonstrated that the polyclonal anti-hIGF-1R antibody efficiently recognized the hIGF-1R ECD. The GR11L antibody (Calbiochem) that was used as a positive control gave the expected profile. As described by the provider. FIG. 20B showed that AF305-NA does not recognize the hIR in contrast to the anti-hIR GRO5 Mab (Calbiochem) used as a positive control in the ELISA. Likewise, a binding evaluation of the polyclonal AF305-NA on hIR+ transfected cells by FACS analyses confirmed that it does not recognize the cellular form of hIR (FIG. 20D) while the anti-hIR GRO5 antibody (FIG. 20C) presented the expected profile on the transfected cells demonstrating that they express a high level of hIR. As expected, the GR11L, recognizing the hIGF-1R, and introduced in the experiment as an negative control does not show any signal on hIR+ transfected cells (FIG. 20C)

Figure 21:
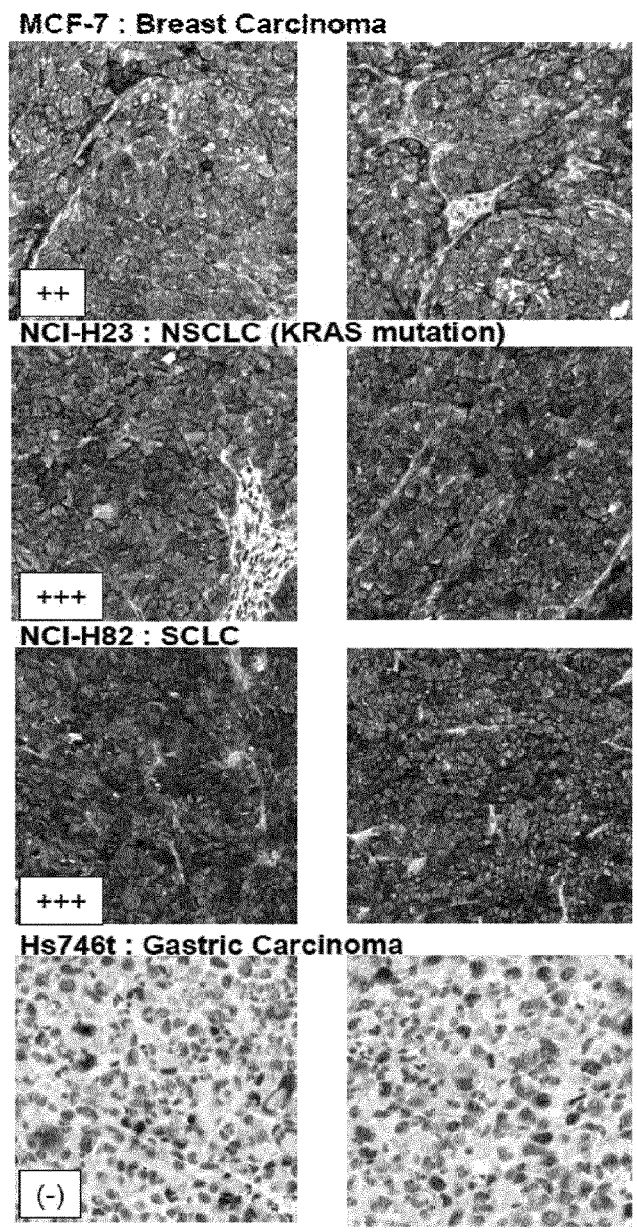
FIG. 21: Validation of hIGF-1R staining on FFPE sections from xenografts expressing various levels of hIGF-1R. Hs746T was introduced as a negative control

As the AF305-NA antibody was fully validated for a hIGF-1R distribution study, an IHC protocol was set up on the Discovery Ultra autostainer Ventana. Briefly, after dewax, antigen retrieval was performed using CCI corresponding to EDTA pH8 buffer for 32 minutes at 96° C. Primary antibody (AF305-NA) was incubated for 1 h at 37° C. After washing, polymer HRP-OMap anti-goat IgG (Ventana) was incubated for 16 minutes at 37° C. and then revealed using DAB chromogen. Finally, tissues were counterstaining using Hematoxilin. Slides were then mounted in Eukitt medium. In order to validate the IHC staining, a panel of tumor tissues from xenograft was selected regarding their in vitro expression of hIGF-1R. As showed in FIG. 21, strong membranous staining is observed on the 3 positive tissues (MCF-7. NCI-H23 and NCI-H82). No membranous staining was observed on the Hs746t selected as a negative tumor. For staining analysis, slides were scanned using HT scanner form Roche Ventana and IGF-1R staining was quantified using Virtuoso software (Roche Ventana). For tissue analysis 4 fields of view (FOVs) per tumors were scored, when possible, with more than 50 cells in order to increase the statistical accuracy of the algorithm. Tissues were scored +++ (also described as 3+), ++ to +++ (also described as 2+ to 3+ or as ++/+++). ++ (also described as 2+), + (also described as 1+) according to HER2 membranous algorithm. Scoring was defined following CAP/ASCO Testing guideline as (+) for weak or incomplete membrane staining or weak, complete membrane staining in less than 10% of cells in the sample. A score of (++) described as a complete membrane staining that is non-uniform or weak but with obvious circumferential distribution in at least 10% of cells, or intense complete membrane staining in 30% or less of tumor cells. A score of (+++) corresponds to a uniform intense membrane staining of more that 30% of invasive tumor cells. When tumors were scored (++) to (+++), it traduces heterogeneity in the tumoral analyzed tissue (−) means that no expression of hIGF-1R was detected and (c) means that the staining is exclusively cytoplasmic. Cytoplasmic staining is characterized by the absence of membranous staining that make isolated cells.

Figure 22A:
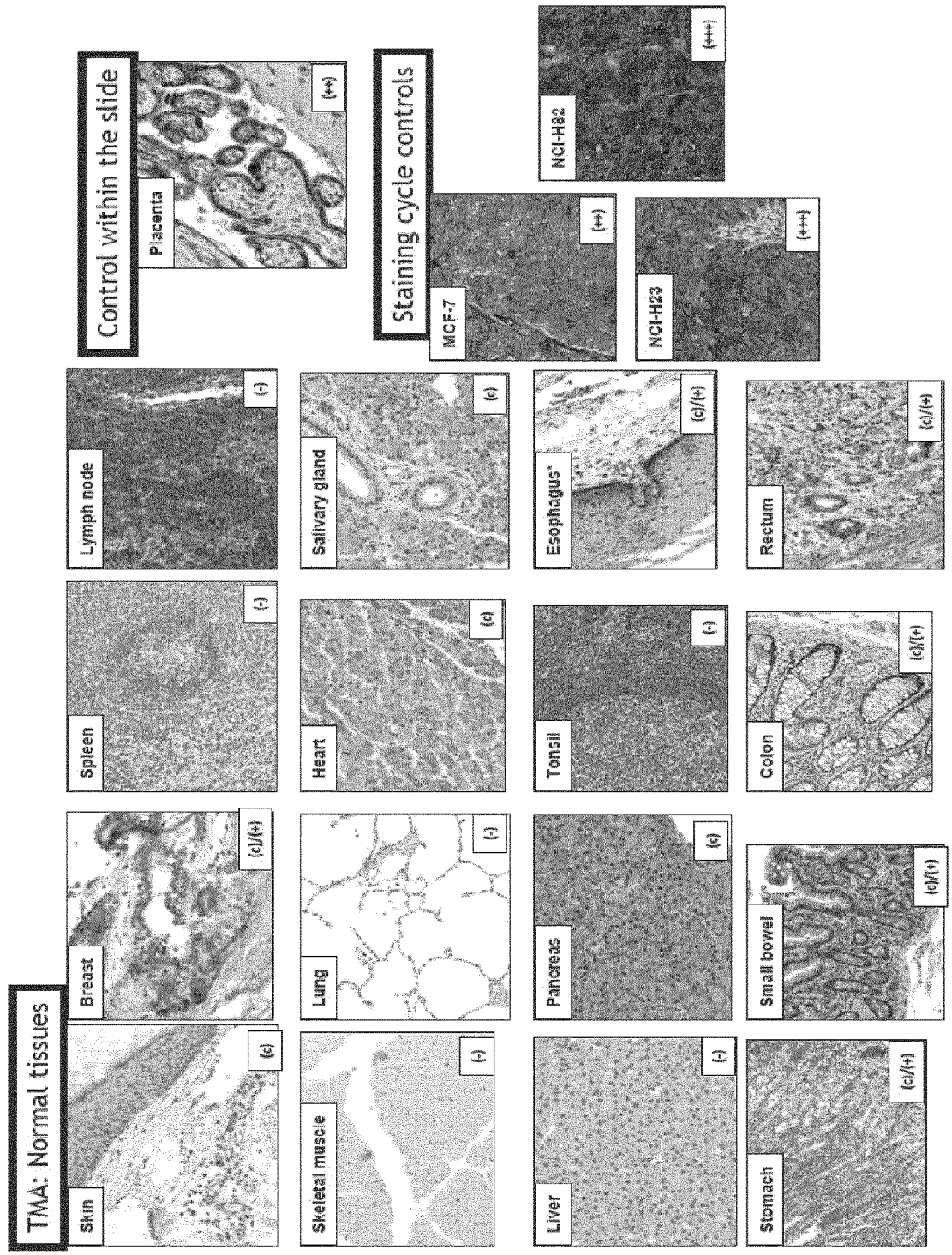
FIG. 22A and FIG. 22B: Evaluation of hIGF-1R expression on normal FFPE tissue sections. Placenta sections were used as a positive control for normal tissues while positive tumor xenograft tissues were introduced in each run in order to calibrate hIGF-1R expression.

An extended study was then performed on normal and tumor tissues using the above protocol (FIGS. 22A and B).

For these studies, human normal and tumor TMA from Superbiochips were used to perform distribution and prevalence studies. Two different controls were introduced in each autostainer cycle. One control consisted on placenta sections known to be a positive control for its IGF-1R expression and provided with the normal TMA tissues. A second series of controls consisted on 3 slides of tumor xenograft tissues presenting score 2+ or 3+(MCF-7 and NCI-H23. NCI-H82 respectively). This latter control is added in each staining run order to calibrate the expression.

Figure 22B:
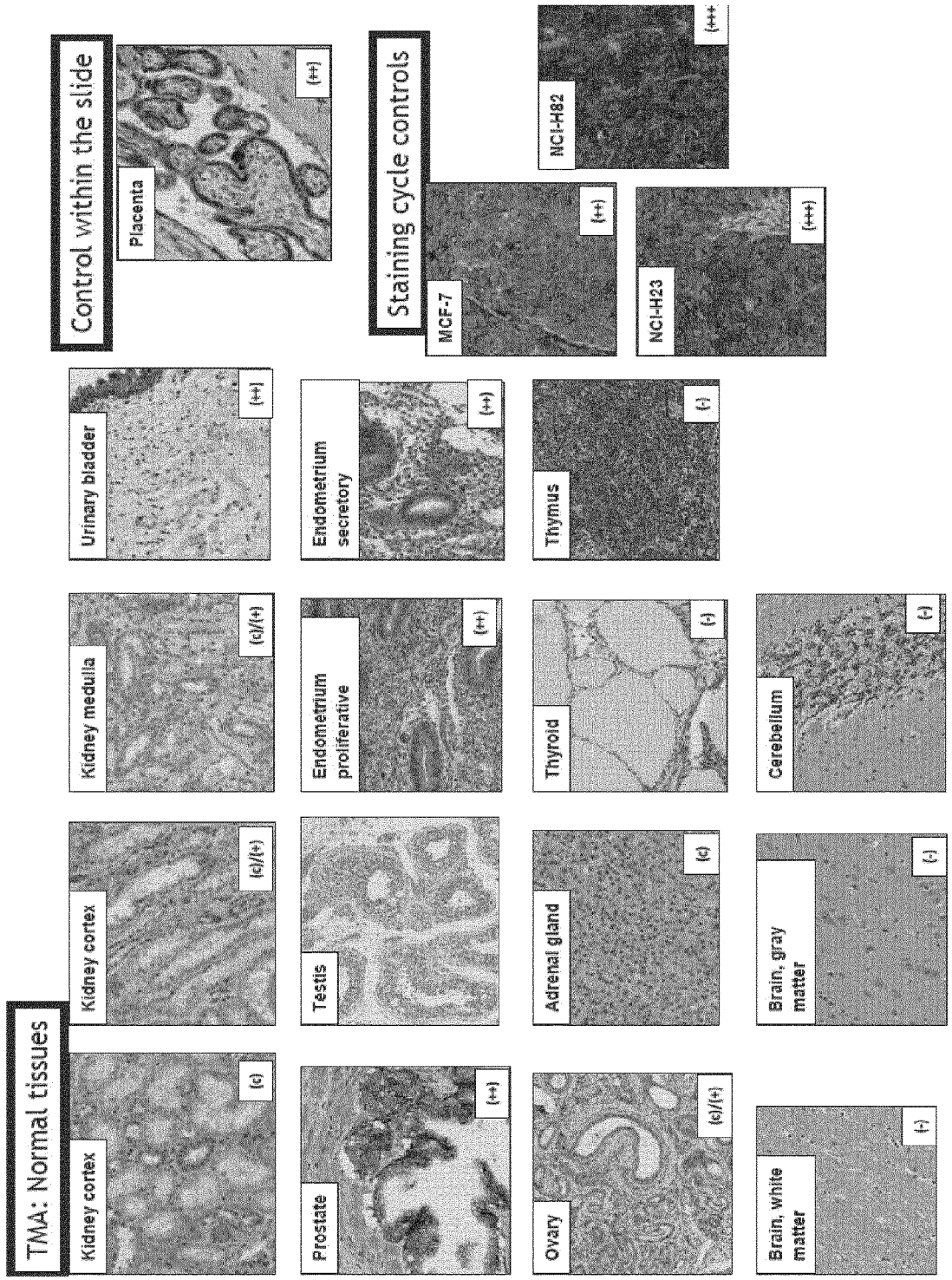

As expected, placenta and tissue from xenograft were, positive for hIGF-1R. A strong membranous staining was observed in these 4 controls. In the first panel of human normal tissues (FIG. 22A), slight membranous detection of IGF-1R that never exceeded 1+ was observed in the gastric tract (esophagus, small bowel, colon and rectum). For all other analyzed tissues, no membranous expression of IGF-1R was observed. In the second panel of normal human tissues (FIG. 22B), slight membranous detection of IGF-1R never exceeding 1+ was observed in kidney structures. Strong membranous staining (++) was observed on the epithelium of the prostate and on urothelium. Excepted for these both tissues, no strong membranous staining was observed. This pattern of expression strongly suggested that hIGF-1R could be a good target for ADC or ATC approaches.

In order to determine the potential indications for an immunoconjugate targeting IGF-1R, lung, breast, head and neck, bladder and kidney tumor samples from patient were analyzed for their expression of IGF-1R using the protocol described above.

Figure 23:
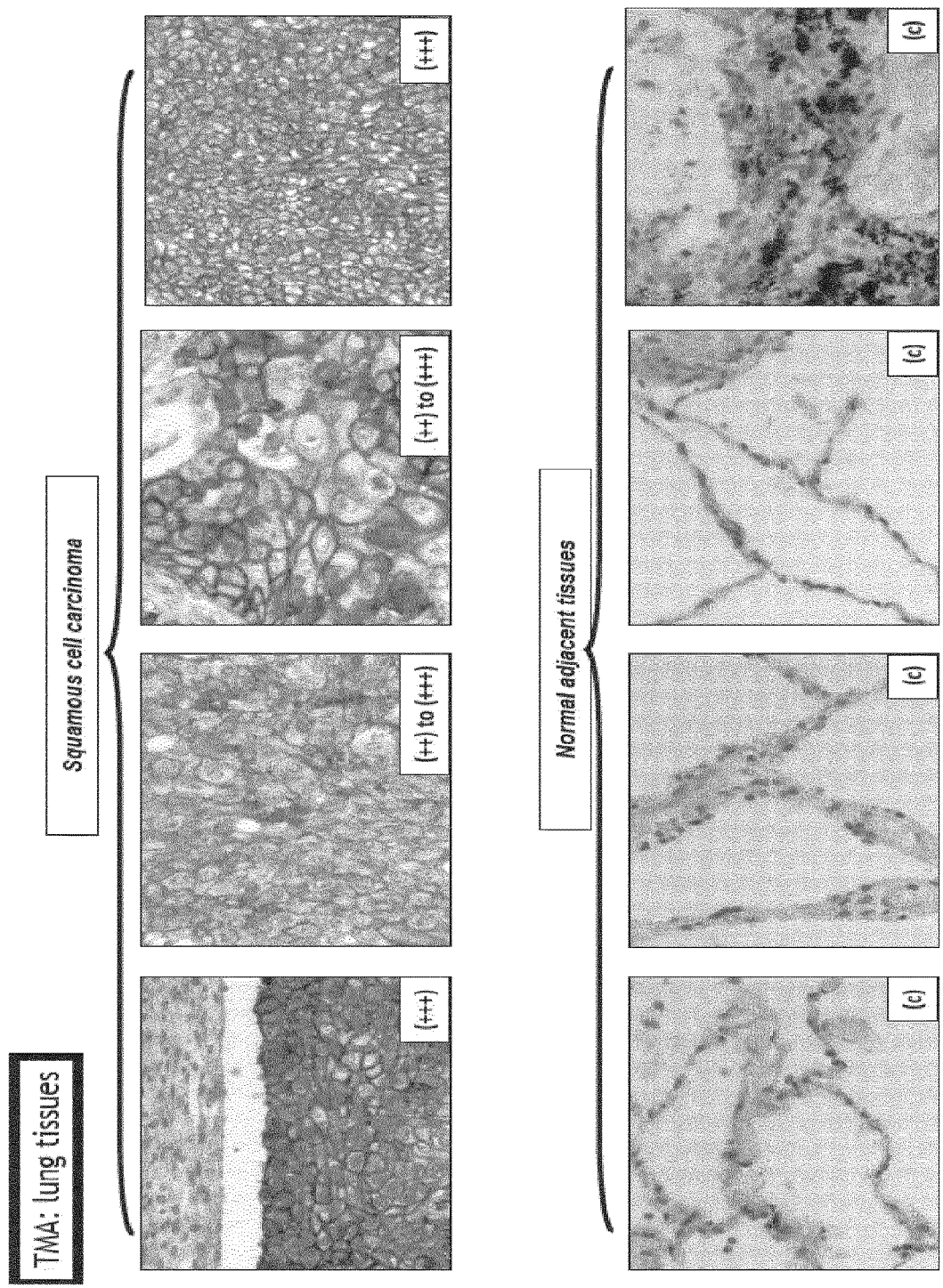
FIG. 23: Evaluation of hIGF-1R expression on NSCL FFPE tissue sections. Four cases which are representative for the strong staining observed in the large panel of tissue analyzed.

Among the 69 lung samples studied, 67 cases were interpretable. IGF-1R expression was quantified as described above. As shown in FIG. 23, strong membranous expression is detected on many carcinomas compared to normal adjacent tissues that are negatives in agreement with what we have already described above on normal tissues. All analyzed cases were summarized in Table 15. 55% of either ++ or +++ cases are observed including all subtypes of lung cancer. Squamous cell lung carcinomas were the most expressive hIGF-1R tumors with 70% ++, ++/+++, or +++ cases and 43% keeping only +++ and ++/+++ tumors. These results are in agreement with published data that described frequent high polysomies or hIGF-1R amplifications in squamous cell lung carcinoma patients.

Figure 24:
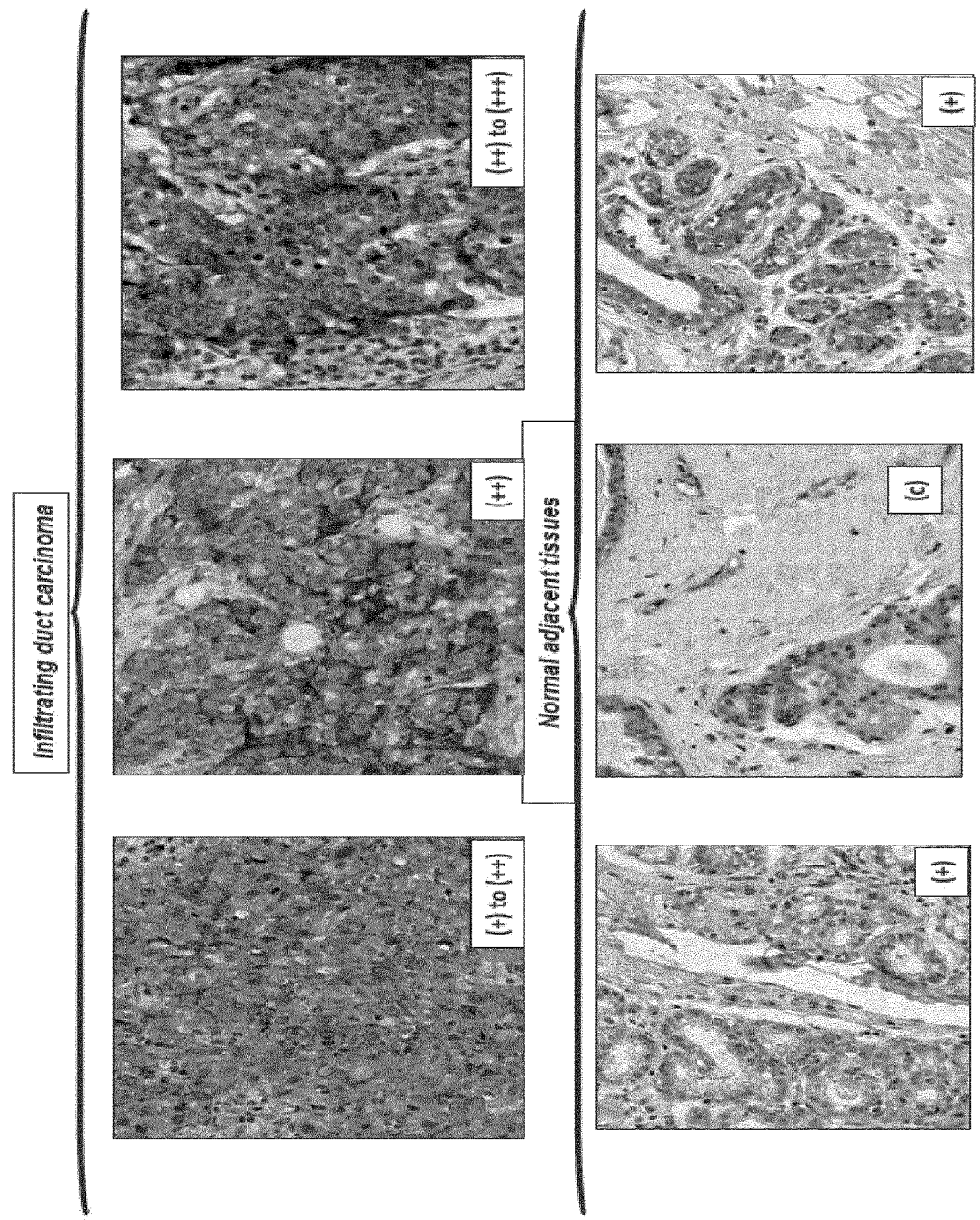
FIG. 24: Evaluation of hIGF-1R expression on breast cancer FFPE tissue sections. Three cases which are representative for the strong staining observed in the tested panel of tissue analyzed.

Another study of IGF-1R expression has been performed on a series of 10 breast cancer samples. Results shown in FIG. 24 demonstrated that IGF-1R is highly expressed on cancer tissues compared to the adjacent normal tissues. Staining data summarized in Table 16 demonstrated that 66% of analyzed cases were ++, ++/+++ or +++ and 22% of the analyzed case were +++ or ++/+++.

TABLE 15

|  | IGF-1R EXPRESSION | NORMAL TISSUE |
|---|---|---|
| Lung adenocarcinoma, well differentiated 18/30 T2bN2M0 IIIA 103 6 | (−) | (−) |
| Lung adenocarcinoma, well differentiated 0/15 T2aN0M0 IB 104 6 | (−) | (−) |
| Lung adenocarcinoma, well differentiated 0/39 T2aN0M0 IB 108 6 | (+) | (−) |
| Lung adenocarcinoma, well differentiated 22/22 T3N2M0 IIIA 157 6 | (−) | (−) |
| Lung adenocarcinoma, moderately differentiated 0/6 T2aN0M0 IB 156 6 | (+) | (−) |
| Lung adenocarcinoma, moderately differentiated 0/30 T2aN0M0 IB 102 6 | (+) | (−) |
| Lung adenocarcinoma, moderately differentiated 0/12 T2aN0M0 IB 158 6 | (+) | (−) |
| Lung adenocarcinoma, moderately differentiated 2/15 T3N2M0 IIIA 159 6 | (−) | (−) |
| Lung squamous cell carcinoma, well differentiated 5/43 T2aN1M0 IIA 101 6 | (+) to (++) | (−) |
| Lung squamous cell carcinoma, well differentiated 0/15 T2aN0M0 IB 109 6 | (+) to (++) | (−) |
| Lung squamous cell carcinoma, well differentiated 2/20 T3N2M0 IIIA 113 6 | (+++) | (−) |
| Lung squamous cell carcinoma, well differentiated 4/61 T2aN1M0 IIA 115 6 | (++) to (+++) | (−) |
| Lung squamous cell carcinoma, well differentiated 0/17 T2aN0M0 IB 120 6 | (++) to (+++) | (−) |
| Lung squamous cell carcinoma, well differentiated 1/46 T2bN1M0 IIB 121 6 | (++) to (+++) | (−) |
| Lung squamous cell carcinoma, well differentiated 1/43 T2aN1M0 IIA 123 6 | (++) to (+++) | (−) |
| Lung squamous cell carcinoma, well differentiated 8/28 T2aN2M0 II1A 136 6 | (++) | (−) |
| Lung squamous cell carcinoma, well differentiated 0/17 T2aN0M0 IB 137 6 | (++) | (−) |
| Lung squamous cell carcinoma, well differentiated 0/19 T2aN0M0 IB 139 6 | (++) | (−) |
| Lung squamous cell carcinoma, well differentiated 4/32 T2aN2M0 IIIA 144 6 | (++) | (−) |
| Lung squamous cell carcinoma, well differentiated 0/24 T2bN0M0 IIA 148 6 | (+++) | (−) |
| Lung squamous cell carcinoma, well differentiated 5/40 T2bN1M0 IIB 150 6 | (+++) | (−) |
| Lung squamous cell carcinoma, moderately differentiated 0/20 T2aN0M0 IB 155 6 | (+++) | (−) |
| Lung squamous cell carcinoma, moderately differentiated 1/15 T2bN1M0 IIB 105 6 | (+) | (−) |
| Lung squamous cell carcinoma, moderately differentiated 0/8 T2aN0M0 IB 106 6 | (+) to (++) | (−) |
| Lung squamous cell carcinoma, moderately differentiated 0/16 T3N0M0 IIB 110 6 | (+++) | (−) |
| Lung squamous cell carcinoma, moderately differentiated 0/16 T2aN0M0 IB 118 6 | (−) | (−) |
| Lung squamous cell carcinoma, moderately differentiated 0/34 T2bN0M0 IIA 119 6 | (++) | (−) |
| Lung squamous cell carcinoma, moderately differentiated 5/18 T2aN2M0 IIIA 126 6 | (+++) | (−) |
| Lung squamous cell carcinoma, moderately differentiated 1/25 T2aN1M0 IIA 129 6 | (+++) | (−) |
| Lung squamous cell carcinoma, moderately differentiated 0/22 T2bN0M0 IIA 130 6 | (++) to (+++) | (−) |
| Lung squamous cell carcinoma, moderately differentiated 3/21 T2aN1M0 IIA 131 6 | (−) | (−) |
| Lung squamous cell carcinoma, moderately differentiated 2/18 T1bN1M0 IIA 134 6 | (+) to (++) | (−) |
| Lung squamous cell carcinoma, moderately differentiated 1/33 T2aN1M0 IIA 138 6 | (++) | (−) |
| Lung squamous cell carcinoma, moderately differentiated 1/25 T2aN1M0 IIA 145 6 | (+++) | (−) |
| Lung squamous cell carcinoma, moderately differentiated 0/21 T2aN0M0 IB 146 6 | (++) to (+++) | (−) |
| Lung squamous cell carcinoma, moderately differentiated 0/28 T3N0M0 IIB 151 6 | (++) | (−) |
| Lung squamous cell carcinoma, poorly differentiated 0/50 T4N0M0 II1A 132 6 | (+++) | (−) |
| Lung squamous cell carcinoma, poorly differentiated 1/3 T2aN2M0 IIIA 135 6 | (−) | (−) |
| Lung squamous cell carcinoma, poorly differentiated 0/22 T3N0M0 IIB 140 6 | (+) to (++) | (−) |
| Lung squamous cell carcinoma, poorly differentiated 0/22 T2aN0M0 IB 141 6 | (+++) | (−) |
| Lung squamous cell carcinoma, poorly differentiated 0/18 T2bN0M0 IIA 128 6 | (++) | (−) |
| Lung squamous cell carcinoma, poorly differentiated 0/11 T2aN0M0 IB 147 6 | (+) to (++) | (−) |
| Lung squamous cell carcinoma, poorly differentiated 0/12 T2aN0M0 IB 152 6 | (++) | (−) |
| Lung squamous cell carcinoma, poorly differentiated 0/14 T3N0M0 IIB 153 6 | (−) | (−) |
| Lung squamous cell carcinoma, spindle cell 0/10 T1bN0M0 IA 122 6 | (++) | (−) |
| Lung carcinosarcoma 0/6 T3N0M0 IIB 111 6 | (−) | (−) |
| Lung carcinosarcoma 0/14 T2aN0M0 IB 154 6 | (+++) | (−) |
| Lung large cell neuroendocrine carcinoma 0/7 T2aN0M0 IB 112 6 | (+++) | (−) |
| Lung large cell neuroendocrine carcinoma 0/38 T3N0M0 IIB 133 6 | (+) | (−) |
| Lung large cell carcinoma 0/9 T2aN0M0 IB 114 6 | (++) to (+++) | (−) |
| Lung large cell carcinoma 0/14 T1bN0M0 IA 125 6 | (+) | (−) |
| Lung large cell carcinoma 0/33 T2aN0M0 IB 142 6 | (++) | (−) |
| Lung bronchioloalveolar carcinoma, non-mucinous 7/17 T3N2M0 IIIA 107 6 | (−) | (−) |
| Lung bronchioloalveolar carcinoma, non-mucinous 0/8 T2bN0M0 IIA 116 6 | (−) | (−) |
| Lung bronchioloalveolar carcinoma, non-mucinous 2/24 T1aN1M0 IIA 149 6 | (+) | (−) |
| Lung bronchioloalveolar carcinoma, mucinous 0/8 T2aN0M0 IB 117 6 | (−) | (−) |
| Lung bronchioloalveolar carcinoma, mucinous 0/24 T2aN0M0 IB 124 6 | (++) | (−) |
| Lung bronchioloalveolar carcinoma, mucinous 0/9 T3N0M0 IIB 127 6 | n/a | (−) |
| Lung bronchioloalveolar carcinoma, mucinous 1/11 T1bN1M0 IIA 143 6 | (+) | (−) |

TABLE 16

|  | EXPRESSION (membranous staining) | NORMAL TISSUE |
|---|---|---|
| Breast infiltrating duct carcinoma T2N0M0 | (+++) | (+) |
| Breast infiltrating duct carcinoma T3N2aM0 | (+) | c |
| Breast infiltrating duct carcinoma T2N3aM0 | n/a | n/a |
| Breast infiltrating duct carcinoma T3N1aM0 | (+) | (+) |
| Breast infiltrating papillary carcinoma with signet ring cell carcinoma T3N1aM0* | (++) to (+++) | (+) |
| Breast infiltrating duct carcinoma T3N3aM0 | (++) | (+) |
| Breast mixed infiltrating duct and lobular carcinoma T3N2aM0 | c (++) |  |
| Breast medullary carcinoma T3N0M0* | (+) to (++) | 0 to (+) |
| Breast atypical medullary carcinoma T2N1aM0 | (++) | 0 to (+) |
| Breast infiltrating ductal carcinoma T2N0M0* | (++) | 0 to (+) |

*Cases illustrated

Figure 25:
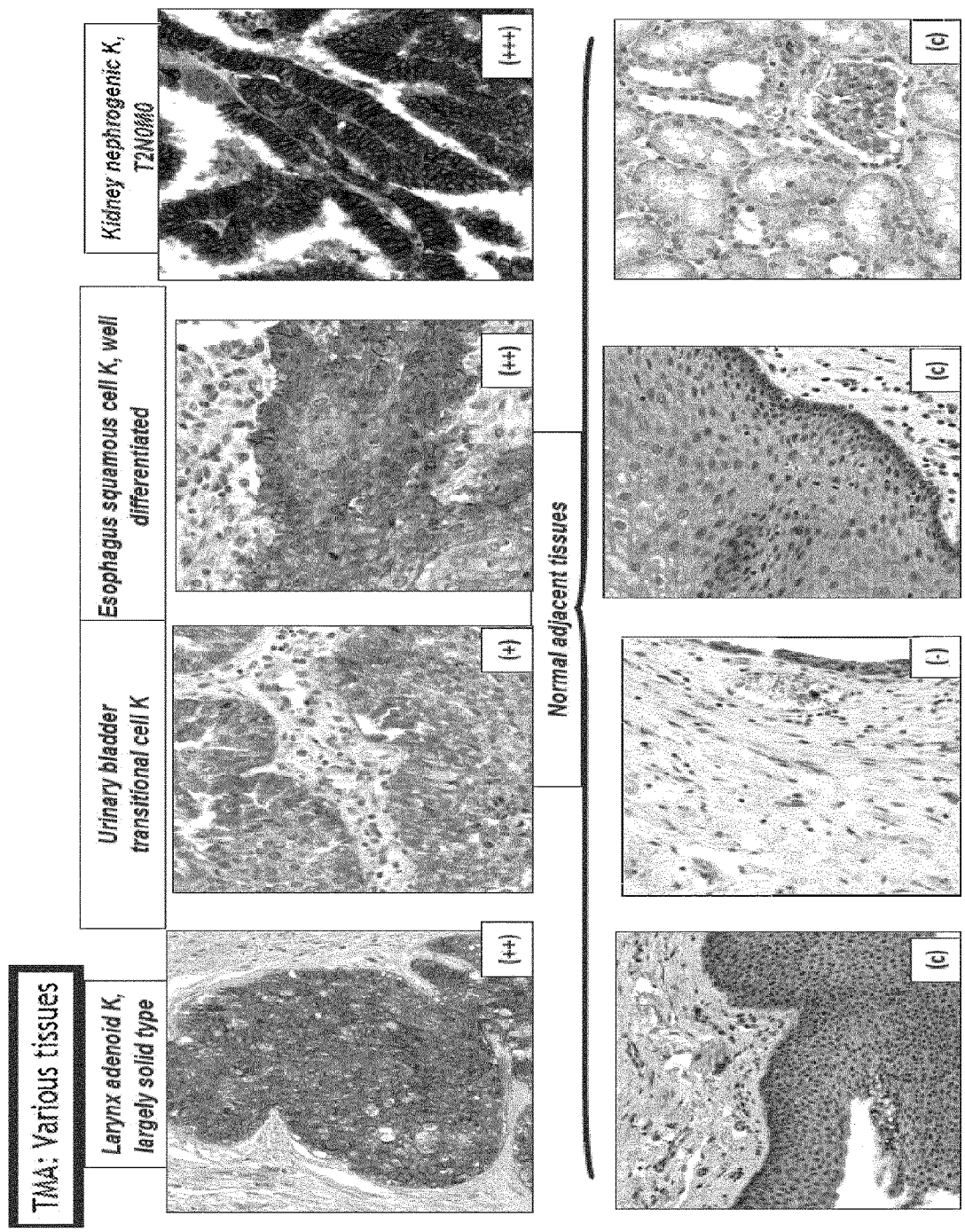
FIG. 25: Evaluation of hIGF-1R expression on FFPE tissue sections from various tumors.

Finally overexpression of IGF-1R was shown in a series of tumors including Head and Neck, urinary bladder and kidney (FIG. 25). Once again a high overexpression of IGF-1R was noticed on tumor samples versus normal adjacent tissues.

Taken together, these results are in agreement with an immunoconjugate approach to treat many tumors IGF-1R positives including lung, breast, head and neck, urinary bladder and kidney.

Example 14: Definition of the Dissociation Constant (Kn) of the Binding of Five Chimeric Anti-IGF-1R Antibodies (c208F2, c213B10, c212A11, c214F8 and c219D6) and a Humanized Version (VH3/VL3) of the 208F2 Antibody on a Soluble Recombinant Human IGF-1R The dissociation constants ($K_D$) of the binding of the antibodies on a recombinant soluble human-IGF-1R were defined by the ratio between the dissociation rate ($k_{off}$) and the association rate ($k_{on}$). The kinetic experiments were run on a Biacore X100 device using a CM5 sensor chip activated by a mouse anti-Tag His monoclonal antibody. Around 12000 RU of antibodies are chemically grafted on the carboxymethyldextan matrix using the amine kit chemistry.

The experiments were carried out at 25° C. with a flow rate of 30 µl/min using the HBS-EP+ buffer (GE Healthcare) as the running and sample dilution buffer.

The single cycle kinetic scheme was used to define the kinetic parameters of the binding of the anti-IGF-1R antibodies on a soluble recombinant human IGF-1R captured by its two C-terminal 10 Histidine-tag.

1—A solution of a soluble recombinant version of the human IGF-1R hetero-tetramere: 2a chains and the extracellular domains of 2P chains expressed with an additional C-terminal 10-His tag (R&D Systems catalogue number 305-GR-50) was injected during one minute on the second flowcell at a concentration of 10 µg/ml. A mean of 587 RU (with a standard deviation 24 RU) of the soluble receptor were captured at each of the 24 cycles realised for this study.

2—After the capture phase, either the running buffer was injected 5 times (90 s each injection) or a growing range of 5 concentrations of one of the six antibodies was injected (90s each injection) on both flowcells. At the end of the fifth injection the running buffer was passed during 5 minutes in order to define the dissociation rate.

3—The surface was then generated with an injection of a 10 mM Glycine, HCl pH 1.5 buffer during 45 s.

The computed signal corresponds to the difference between the response of the flowcell 2 (with captured IGF-1R) and the response of the flowcell 1 (without any IGF-1R molecules).

Figure 26:
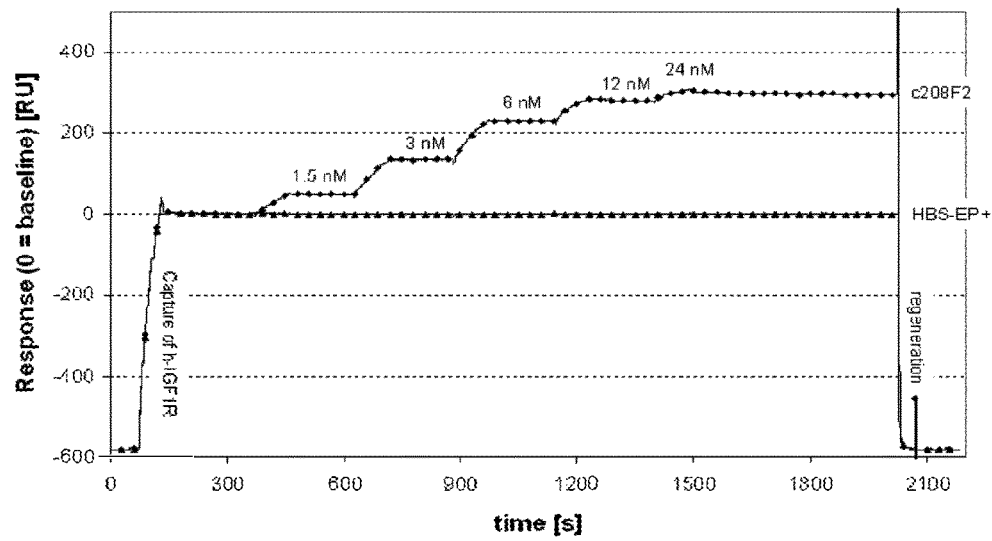
FIG. 26: Superposition of sensorgrammes obtained with a SPR based Biacore X100 device at a temperature of 25° C. with a CM5 sensor chip activated on both flowcells with around 12.000 RU of a mouse anti-TagHis monoclonal antibodies chemically grafted to the carboxymethyldextran matrix using a HBS-EP+ as the running buffer at a flow rate of 30 μl/min. Each sensorgrammes (the first one marked by triangles and the second one marked by diamonds) correspond to a complete cycle.

For each IGF-1R the signal due to the injections the growing range of concentrations of one antibody was corrected by subtraction of the signal obtained with the 5 injections of the buffer (double reference) see FIG. 26.

The resulting sensorgrams were analysed by the Biaevaluation software with a 1:1 model.

Four experiences were run for each antibody using two different ranges of concentrations: 40, 20, 10, 5 and 2.5 nM for the two first experiments and: 24, 12, 6, 3 and 1.5 nM for the two last experiments run for each antibody.

For the 6 antibodies tested in this experiment the experimental data fitted well with an 1:1 model with significant $k_{off}$ values when the higher concentration was defined as a constant and the other four concentrations are calculated (see FIG. 27).

The dissociation constants ($K_D$) calculated as the ratio: $k_{off}/k_{on}$ and the half-live of the complexes calculated as the ratio: $Ln(2)/k_{off}$ are represented in the FIGS. 28 and 29. They correspond to the mean of the four independent experiments run for each antibodies. The error bars correspond to the standard errors (n=4) of the values.

The dissociation constants are in the range of 10 to 100 pM. The c208F2 antibody presents the weaker affinity (higher dissociation constant value) for the h-IGF-1R (with a $K_D$ around 75 pM) and its humanized version is at least as good as the chimeric version (with a $K_D$ around 60 pM). The four other anti-IGF-1R chimeric antibodies present a quite similar affinity for the hIGF1-R (with a $K_D$ around 30 pM). The difference of the affinities is principally linked to the dissociation rate or the resultant half life of the complexes. With 208F2 the half-life of the complex is between 2 and 3 hour with the chimeric and the humanized (VH3/VL3) versions. For the four other chimeric antibodies the means half lives are between 7.0 and 9.4 h.

These very slow dissociation kinetics are clearly linked to the bivalent structure of the antibodies which are able to bind simultaneously by both of their Fab arms to two adjacent h-IGF-1R molecules. In this case the level of captured IGF-1R molecules may have an impact on the dissociation rate. The affinities defined in this study correspond to the functional affinities (or avidities) of the antibodies for a level of captured h-IGF-1R around 600 RU. The 3 fold difference of KD observed between data shown above (table 10) and values presented in example 13 is linked to a change of the level of capture of hIGF-1R (600 RU versus 160 RU in example 5).

Example 15: Definition of Mouse IGF-1R Specific Residues which Prevent the Binding of c208F2 Using Soluble Forms of Chimerical h/m IGF-1R Recombinant Proteins The binding of the soluble forms of chimerical h/m IGF-1R recombinant proteins on the c208F2 antibody experiments were run on a Biacore X100 device using a CM5 sensor chip activated by a mouse anti-human IgG Fc monoclonal antibody. More than 10,500 RU of the anti-Fc antibody are chemically grafted on the carboxymethyldextan matrix of both flowcells using the amine kit chemistry.

The experiments were carried out at 25° C. with a flow rate of 30 µl/min using the HBS-EP+ buffer as the running and sample dilution solution.

The set up of the experiment was as follow:
1—A solution of c208F2 at the concentration of 10 µg/ml was injected during 60 s on the second flowcell.
2—The IGF-1R constructs tested corresponds to concentrated supernatants of culture medium diluted 10 times in the running buffer. One construction was injected at each cycle during 120 s with a delay of 120 s.
3—Both flowcells were regenerated by an injection of 10 mM Glycine, HCl pH 1.7 buffer during 30 s.

FIG. 30 shows the superposition of two cycles, h-IGF-1R and m-IGF-1R supernatants were injected during the first and the second cycle respectively. This experiment shows clearly the inability of the m-IGF-1R to bind to the c208F2 antibody the positions used for the determination of the c208F2 capture level and of the IGF-1R binding level are indicated by double headed arrows.

The extracellular domains of IGFR (without the signal peptide) are composed of 805 and 806 amino acid for the human and mouse sequence respectively. 869 residues (96%) are identical in both structures. 37 residues of the mouse sequence are different from the corresponding human sequence. One difference corresponds to a gap.

As shown on FIG. 31, among the 7 chimerical constructs tested 4 (C1 (SEQ ID No. 83), C4 (SEQ ID No. 86), C7 (SEQ ID No. 88) and C8 (SEQ ID No. 89)) bind as well as the h-IGF-1R to c208F2, 3 constructs (C2 (SEQ ID No. 84), C3 (SEQ ID No. 85) and C6 (SEQ ID No. 87)) as the mIGF-1R (SEQ ID No. 91) do not bind to c208F2.

The binding of C1 and the lack of binding of C2 suggest that the mouse specific residues blocking the binding of c208F2 are located in the N-terminal half of the protein. So the last eleven specific mouse amino acids located in the C-terminal half have no influence on the binding of c208F2.

The lack of binding of C3 demonstrates a major contribution of one mouse specific residue the Arg instead of the His at position 494. This result is confirmed by the lack of binding of C6 which contains two mouse specific residues: His494>Arg and Ser501>Trp.

The binding of C4 suggests that the only mouse specific residue Trp at the position 501 of this chimerical IGF-1R is not responsible of the lack of binding of the C2 and C6.

The binding of C7 suggests that none of the 17 mouse specific residues present in this constructs have any weight in the blocking of the binding of c208F2.

Likewise, the binding of C8 excludes 4 other mouse specific residues.

The C12 mutant of the human IGF1R which presents the three mouse residues in the L1 domain ie Phe at position 28 instead of Tyr, Ile at the position 125 instead of Val and Leu at the position 156 instead of Met binds c208F2 at a sub nanomolar dissociation constant. This experiment confirms that the L1 domain is not involved in the binding of the antibody or at least that the 3 positions which differentiated the mouse and the human sequences are not responsible of the absence of binding of the antibody on the murin form of the IGF1R.

As shown on the FIG. 33, the hz208F2 is not able to bind to 120 RU of the C29 mutant (Asp491>Ala) of the soluble form of the h-IGF1R captured on a CM5 sensorchip by its 6His C-terminal tag (white diamonds) whereas the same solution of the antibody clearly binds (black diamonds) to 170 RU of the wild type form of the soluble receptor. As the His 494, the Asp 491 is critical for the affinity of the hz208F2 for the IGF1R. Crystallographic data show that both residues are exposed at the surface of the receptor in the FnR3 domain.

Taken together these results demonstrated that hz208F2 binds to the FnR3 domain of IGF-1R and that the epitope recognized by this antibody contains the His 494 and the Asp 491 that are crucial for antibody binding.

The invention claimed is:

1. A humanized anti-IGF-1R antibody, or an IGF-1R binding fragment thereof, said antibody being selected from:

a) an antibody comprising three heavy chain CDRs of sequences SEQ ID Nos. 7, 2 and 3 and three light chain CDRs of sequences SEQ ID Nos. 9, 5 and 11;

b) an antibody comprising three heavy chain CDRs of sequences SEQ ID Nos. 7, 2 and 3 and three light chain CDRs of sequences SEQ ID Nos. 10, 5 and 11;

c) an antibody comprising three heavy chain CDRs of sequences SEQ ID Nos. 7, 2 and 3 and three light chain CDRs of sequences SEQ ID Nos. 9, 5 and 12; and d) an antibody comprising three heavy chain CDRs of sequences SEQ ID Nos. 8, 2 and 3 and three light chain CDRs of sequences SEQ ID Nos. 9, 5 and 11.

2. The humanized anti-IGF-1R antibody or an IGF-1R binding fragment thereof of claim 1, said antibody comprising:

a) a heavy chain having CDR-H1, CDR-H2 and CDR-H3 of sequences SEQ ID Nos. 7, 2 and 3, respectively, and FR1, FR2 and FR3 derived from the human germline IGHV1-46*01 (SEQ ID No. 46), and the FR4 derived from the human germline IGHJ4*01 (SEQ ID No. 48); and b) a light chain having CDR-L1, CDR-L2 and CDR-L3 of sequences SEQ ID Nos. 9, 5 and 11, respectively, and FR1, FR2 and FR3 derived from the human germline IGKV1-39*01 (SEQ ID No. 47), and the FR4 derived from the human germline IGKJ4*01 (SEQ ID No. 49).

3. The humanized anti-IGF-1R antibody or an IGF-1R binding fragment thereof of claim 1, wherein said antibody comprises a heavy chain variable domain (VH) of sequence SEQ ID No. 33 and a light chain variable domain (VL) of sequence SEQ ID No. 35.

4. The humanized anti-IGF-1R antibody or an IGF-1R binding fragment thereof of claim 1, wherein said antibody comprises a heavy chain variable domain (VH) of sequence SEQ ID No. 33, wherein said sequence SEQ ID No. 33 comprises at least one back-mutation selected from the residues 20, 34, 35, 38, 48, 50, 59, 61, 62, 70, 72, 74, 76, 77, 79, 82 and 95.

5. The humanized anti-IGF-1R antibody or an IGF-1R binding fragment thereof of claim 1, wherein said antibody comprises a light chain variable domain (VL) of sequence SEQ ID No. 35, wherein said sequence SEQ ID No. 35 comprises at least 1 back-mutation selected from the residues 22, 53, 55, 65, 71, 72, 77 and 87.

6. The humanized anti-IGF-1R antibody or an IGF-1R binding fragment thereof of claim 1, wherein said antibody comprises:

a) a heavy chain variable domain (VH) of sequence SEQ ID No. 33 wherein said sequence SEQ ID No. 33 comprises at least one back-mutation selected from the residues 20, 34, 35, 38, 48, 50, 59, 61, 62, 70, 72, 74, 76, 77, 79, 82 and 95, and b) a light chain variable domain (VL) of sequence SEQ ID No. 35, wherein said sequence SEQ ID No. 35 comprises at least 1 back-mutation selected from the residues 22, 53, 55, 65, 71, 72, 77 and 87.

7. The humanized anti-IGF-1R antibody or an IGF-1R binding fragment thereof of claim 1, wherein said antibody is selected from:

a) an antibody comprising a heavy chain variable domain of sequence SEQ ID No. 33 and the three light-chain CDRs of sequences SEQ ID NOs 9, 5, and 11;

b) an antibody comprising a heavy chain variable domain of sequence SEQ ID No. 34 and the three light-chain CDRs of sequences SEQ ID NOs 9, 5, and 11; and c) an antibody comprising a heavy chain variable domain of a sequence selected from SEQ ID No. 56, 62, 64, 66, 68, 70, 72, 74, 76, 78 and 80, and the three light-chain CDRs of sequences SEQ ID NOs 9, 5, and 11.

8. The humanized anti-IGF-1R antibody or an IGF-1R binding fragment thereof of claim 1, wherein said antibody is selected from:

a) an antibody comprising a light chain variable domain of sequence SEQ ID No. 35 and the three heavy-chain CDRs of sequences SEQ ID Nos. 7, 2 and 3;

b) an antibody comprising a light chain variable domain of sequence SEQ ID No. 36 and the three heavy-chain CDRs of sequences SEQ ID Nos. 7, 2 and 3; and c) an antibody comprising a light chain variable domain of sequence selected from SEQ ID Nos. 57 and 60, and the three heavy-chain CDRs of sequences SEQ ID Nos. 7, 2 and 3.

9. The humanized anti-IGF-1R antibody or an IGF-1R binding fragment thereof of claim 1, wherein said antibody is selected from:

a) an antibody comprising a heavy chain of sequence SEQ ID No. 37 and a light chain of sequence SEQ ID No. 39;

b) an antibody comprising a heavy chain of sequence SEQ ID No. 38 and a light chain of sequence SEQ ID No. 40; and c) an antibody comprising a heavy chain variable domain of sequence selected from SEQ ID Nos. 56, 62, 64, 66, 68, 70, 72, 74, 76, 78 and 80, and a light chain variable domain of sequence selected from SEQ ID Nos. 57 and 60.

10. The humanized anti-IGF-1R antibody or an IGF-1R binding fragment thereof of claim 1, wherein said antibody is selected in the group consisting of:

a) an antibody comprising a heavy chain variable domain (VH) of sequence SEQ ID No. 34 and a light chain variable domain (VL) of sequence SEQ ID No. 36;

b) an antibody comprising a heavy chain variable domain (VH) of sequence SEQ ID No. 41 and a light chain variable domain (VL) of sequence SEQ ID No. 42;

c) an antibody comprising a heavy chain variable domain (VH) of sequence SEQ ID No. 56 and a light chain variable domain (VL) of sequence SEQ ID No. 57;

d) an antibody comprising a heavy chain variable domain (VH) of sequence SEQ ID No. 56 and a light chain variable domain (VL) of sequence SEQ ID No. 60;

e) an antibody comprising a heavy chain variable domain (VH) of sequence SEQ ID No. 62 and a light chain variable domain (VL) of sequence SEQ ID No. 57;

f) an antibody comprising a heavy chain variable domain (VH) of sequence SEQ ID No. 64 and a light chain variable domain (VL) of sequence SEQ ID No. 57;

g) an antibody comprising a heavy chain variable domain (VH) of sequence SEQ ID No. 64 and a light chain variable domain (VL) of sequence SEQ ID No. 60;

h) an antibody comprising a heavy chain variable domain (VH) of sequence SEQ ID No. 66 and a light chain variable domain (VL) of sequence SEQ ID No. 57;

i) an antibody comprising a heavy chain variable domain (VH) of sequence SEQ ID No. 68 and a light chain variable domain (VL) of sequence SEQ ID No. 57;

j) an antibody comprising a heavy chain variable domain (VH) of sequence SEQ ID No. 68 and a light chain variable domain (VL) of sequence SEQ ID No. 60;

k) an antibody comprising a heavy chain variable domain (VH) of sequence SEQ ID No. 70 and a light chain variable domain (VL) of sequence SEQ ID No. 57;

l) an antibody comprising a heavy chain variable domain (VH) of sequence SEQ ID No. 72 and a light chain variable domain (VL) of sequence SEQ ID No. 57;

m) an antibody comprising a heavy chain variable domain (VH) of sequence SEQ ID No. 74 and a light chain variable domain (VL) of sequence SEQ ID No. 57;

n) an antibody comprising a heavy chain variable domain (VH) of sequence SEQ ID No. 76 and a light chain variable domain (VL) of sequence SEQ ID No. 57;

o) an antibody comprising a heavy chain variable domain (VH) of sequence SEQ ID No. 78 and a light chain variable domain (VL) of sequence SEQ ID No. 57;

p) an antibody comprising a heavy chain variable domain (VH) of sequence SEQ ID No. 78 and a light chain variable domain (VL) of sequence SEQ ID No. 60; and q) an antibody comprising a heavy chain variable domain (VH) of sequence SEQ ID No. 80 and a light chain variable domain (VL) of sequence SEQ ID No. 57.

11. The humanized anti-IGF-1R antibody or an IGF-1R binding fragment thereof of claim 1, wherein said antibody comprises:
   a) a heavy chain of sequence selected from SEQ ID Nos. 58, 63, 65, 67, 69, 71, 73, 75, 77, 79 and 81; and
   b) a light chain of sequence selected from SEQ ID Nos. 59 and 61.

12. The humanized anti-IGF-1R antibody or an IGF-1R binding fragment thereof of claim 1, wherein said antibody is selected in the group consisting of:
   a) an antibody comprising a heavy chain of sequence SEQ ID No. 58 and a light chain of sequence SEQ ID No. 59;
   b) an antibody comprising a heavy chain of sequence SEQ ID No. 58 and a light chain of sequence SEQ ID No. 61;
   c) an antibody comprising a heavy chain of sequence SEQ ID No. 63 and a light chain of sequence SEQ ID No. 59;
   d) an antibody comprising a heavy chain of sequence SEQ ID No. 65 and a light chain of sequence SEQ ID No. 59;
   e) an antibody comprising a heavy chain of sequence SEQ ID No. 65 and a light chain of sequence SEQ ID No. 61;
   f) an antibody comprising a heavy chain of sequence SEQ ID No. 67 and a light chain of sequence SEQ ID No. 59;
   g) an antibody comprising a heavy chain of sequence SEQ ID No. 69 and a light chain of sequence SEQ ID No. 59;
   h) an antibody comprising a heavy chain of sequence SEQ ID No. 69 and a light chain of sequence SEQ ID No. 61;
   i) an antibody comprising a heavy chain of sequence SEQ ID No. 71 and a light chain of sequence SEQ ID No. 59;
   j) an antibody comprising a heavy chain of sequence SEQ ID No. 73 and a light chain of sequence SEQ ID No. 59;
   k) an antibody comprising a heavy chain of sequence SEQ ID No. 75 and a light chain of sequence SEQ ID No. 59;
   l) an antibody comprising a heavy chain of sequence SEQ ID No. 77 and a light chain of sequence SEQ ID No. 59;
   m) an antibody comprising a heavy chain of sequence SEQ ID No. 79 and a light chain of sequence SEQ ID No. 59;
   n) an antibody comprising a heavy chain of sequence SEQ ID No. 79 and a light chain of sequence SEQ ID No. 61; and
   o) an antibody comprising a heavy chain of sequence SEQ ID No. 81 and a light chain of sequence SEQ ID No. 59.

13. An antibody-drug conjugate comprising the humanized antibody, or an antigen binding fragment thereof, according to claim 1, conjugated to a cytotoxic agent.

14. A pharmaceutical composition comprising the humanized antibody of claim 4 and at least an excipient and/or a pharmaceutical acceptable vehicle.

15. A method for the treatment of an IGF-1R expressing cancer in a subject, comprising administering to said subject an effective amount of at least the antibody-drug conjugate of claim 13.

16. A method of delivering a drug or a medicament to an IGF-1R expressing cancer cell in a subject, comprising administering to said subject an effective amount of at least the antibody-drug conjugate of claim 13.

17. A method for delivering a cytotoxic agent at a host target site, said host target site consisting of an epitope localized within the IGF-1R extracellular domain, said method comprising administering the humanized antibody, or an antigen binding fragment thereof of claim 1 as an addressing vehicle.

18. The method of claim 17, wherein said IGF-1R extracellular domain is the human IGF-1R extracellular domain of SEQ ID No. 51.

19. The method of claim 17, wherein the IGF-1R extracellular domain is the human IGF-1R extracellular domain N terminus region of SEQ ID No. 52.

20. A method of treating cancer, comprising administering the antibody-drug conjugate of claim 13 to a patient in need thereof.

21. The method of claim 20, wherein said cancer is an IGF-1R expressing cancer.

22. A pharmaceutical composition comprising the antibody-drug conjugate of claim 13 and at least an excipient and/or a pharmaceutical acceptable vehicle.

23. A method for the treatment of an IGF-1R expressing cancer in a subject, comprising administering to said subject an effective amount of the pharmaceutical composition of claim 14.

24. A method of delivering a drug or a medicament to an IGF-1R expressing cancer cell in a subject, comprising administering to said subject an effective amount of the pharmaceutical composition of claim 14.

25. A method of treating cancer, comprising administering the pharmaceutical composition of claim 14 to a patient in need thereof.

26. The method of claim 25, wherein said cancer is an IGF-1R expressing cancer.

* * * * *